(12) United States Patent
Goldberg et al.

(10) Patent No.: US 10,413,612 B2
(45) Date of Patent: Sep. 17, 2019

(54) METHOD OF TREATING CANCER WITH A BIOMATERIAL AND A TOLL-LIKE RECEPTOR AGONIST

(71) Applicant: Dana-Farber Cancer Institute, Inc., Boston, MA (US)

(72) Inventors: Michael Solomon Goldberg, Brookline, MA (US); Chun Gwon Park, Suwon-si (KR)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/192,663

(22) Filed: Nov. 15, 2018

(65) Prior Publication Data

US 2019/0083626 A1    Mar. 21, 2019

Related U.S. Application Data

(63) Continuation of application No. PCT/US2017/049424, filed on Aug. 30, 2017.

(60) Provisional application No. 62/501,464, filed on May 4, 2017, provisional application No. 62/486,814, filed on Apr. 18, 2017, provisional application No. 62/381,456, filed on Aug. 30, 2016.

(51) Int. Cl.

| | |
|---|---|
| *A61K 47/36* | (2006.01) |
| *A61K 31/47* | (2006.01) |
| *C07K 16/28* | (2006.01) |
| *A61K 38/19* | (2006.01) |
| *A61K 39/395* | (2006.01) |
| *A61K 9/00* | (2006.01) |
| *A61K 9/06* | (2006.01) |
| *A61K 38/17* | (2006.01) |
| *A61P 35/04* | (2006.01) |
| *A61K 31/4745* | (2006.01) |
| *A61K 45/06* | (2006.01) |
| *A61K 38/20* | (2006.01) |
| *C07H 21/04* | (2006.01) |
| *C07K 16/30* | (2006.01) |
| *A61K 31/444* | (2006.01) |
| *A61K 31/635* | (2006.01) |
| *A61K 39/00* | (2006.01) |
| *A61K 35/17* | (2015.01) |
| *A61L 27/52* | (2006.01) |

(52) U.S. Cl.
CPC .......... *A61K 47/36* (2013.01); *A61K 9/0019* (2013.01); *A61K 9/0024* (2013.01); *A61K 9/06* (2013.01); *A61K 31/444* (2013.01); *A61K 31/4745* (2013.01); *A61K 31/635* (2013.01); *A61K 38/1793* (2013.01); *A61K 38/19* (2013.01); *A61K 38/2086* (2013.01); *A61K 39/3955* (2013.01); *A61K 39/39541* (2013.01); *A61K 45/06* (2013.01); *A61P 35/04* (2018.01); *C07H 21/04* (2013.01); *C07K 16/2818* (2013.01); *C07K 16/2878* (2013.01); *C07K 16/2896* (2013.01); *C07K 16/30* (2013.01); *A61K 35/17* (2013.01); *A61K 2039/505* (2013.01); *A61L 27/52* (2013.01); *C07K 2317/75* (2013.01)

(58) Field of Classification Search
CPC .......................... A61K 47/36; A61K 31/4745
See application file for complete search history.

(56) References Cited

U.S. PATENT DOCUMENTS

| | | | |
|---|---|---|---|
| 4,689,338 | A | 8/1987 | Gerster et al. |
| 5,446,153 | A | 8/1995 | Lindstrom et al. |
| 5,714,608 | A | 2/1998 | Gerster et al. |
| 6,039,969 | A | 3/2000 | Tomai et al. |
| 6,110,929 | A | 8/2000 | Gerster et al. |
| 6,194,425 | B1 | 2/2001 | Gerster et al. |
| 6,200,592 | B1 | 3/2001 | Tomai et al. |
| 9,364,545 | B2 | 6/2016 | Jhan et al. |
| 9,394,315 | B2 | 7/2016 | Aicher et al. |
| 9,695,212 | B2 | 7/2017 | Dubensky et al. |
| 9,770,467 | B2 | 9/2017 | Dubensky et al. |
| 9,840,533 | B2 | 12/2017 | Patel et al. |
| 10,106,574 | B2 | 10/2018 | Altman et al. |
| 2007/0213393 | A1 | 9/2007 | Hunter et al. |
| 2011/0262485 | A1 | 10/2011 | Barber et al. |

(Continued)

FOREIGN PATENT DOCUMENTS

| | | |
|---|---|---|
| WO | WO 2005/079195 | 9/2005 |
| WO | WO 2011/078990 A1 | 6/2011 |

(Continued)

OTHER PUBLICATIONS

International Search Report and Written Opinion for PCT/US2017/049424, dated Dec. 21, 2017.
Ali et al., in Situ Regulation of DC Subsets and T Cells Mediates Tumor Regression in Mice. Science Translational Medicine Nov. 25, 2009;1(8):8ra19. Doi: 10.1126/scitranslmed.3000359.

(Continued)

*Primary Examiner* — Prema M Mertz
(74) *Attorney, Agent, or Firm* — Wolf, Greenfield & Sacks, P.C.

(57) ABSTRACT

Provided are drug delivery compositions and devices useful for the treatment and/or prevention of cancer and metastatic tumors. For example, a drug delivery device is provided that comprises a biodegradable scaffold carrying one or more anti-cancer therapeutic agents that activate the innate immune system (e.g., STING agonists) and/or the adaptive immune system (e.g., anti-PD-1 antibodies). The compositions and devices may include a cytokine (e.g., IL-15 superagonist). The drug delivery device can be implanted in the void volume of a resected tumor to prevent tumor regrowth and tumor metastasis. Also provided are methods of making the drug delivery compositions and devices as well as kits containing materials to provide the compositions and devices.

28 Claims, 120 Drawing Sheets

(56) References Cited

U.S. PATENT DOCUMENTS

| | | |
|---|---|---|
| 2014/0329889 A1 | 11/2014 | Vance et al. |
| 2015/0343056 A1 | 12/2015 | Chen et al. |
| 2016/0210400 A1 | 7/2016 | Patel et al. |
| 2016/0287623 A1 | 10/2016 | Gajewski et al. |
| 2017/0007686 A1 | 1/2017 | Glick et al. |

FOREIGN PATENT DOCUMENTS

| | | |
|---|---|---|
| WO | WO 2014/189805 | 11/2014 |
| WO | WO 2016/004213 A2 | 1/2016 |
| WO | WO 2016/119308 A1 | 8/2016 |
| WO | WO 2016/123573 A1 | 8/2016 |
| WO | WO 2017/093933 | 6/2017 |
| WO | WO 2017/123657 | 7/2017 |
| WO | WO 2017/123669 | 7/2017 |

OTHER PUBLICATIONS

Ali et al., Infection-mimicking materials to program dendritic cells in situ. Nat Mater. Feb. 2009;8(2):151-8. doi: 10.1038/nmat2357. Epub Jan. 11, 2009.

Hori et al., Modular injectable matrices based on alginate solution/microsphere mixtures that gel in situ and co-deliver immunomodulatory factors. Acta Biomater. May 2009;5(4):969-82. doi: 10.1016/j.actbio.2008.11.019. Epub Dec. 10, 2008.

Hori et al., Engulfing tumors with synthetic extracellular matrices for cancer immunotherapy. Biomaterials. Dec. 2009; 30(35): 6757-6767.

Kim et al., Resorbable polymer microchips releasing BCNU inhibit tumor growth in the rat 9L flank model. J Control Release. Nov. 6, 2007;123(2):172-8. Epub Aug. 15, 2007.

Kirman et al., Combined whole tumor cell and monophosphoryl lipid A vaccine improved by encapsulation in murine colorectal cancer. Surg Endosc. Apr. 2002;16(4):654-8. Epub Dec. 10, 2001.

Langer, Biodegradable polymers for drug delivery to the brain. ASAIO Trans. Oct.-Dec. 1988;34(4):945-6.

Lee et al., Percutaneous Coronary Intervention at Centers With and Without On-Site Surgical Backup: An Updated Meta-Analysis of 23 Studies. Circulation. 2015;132:388-401.

Li et al., Hydrogel dual delivered celecoxib and anti-PD-1 synergistically improve antitumor immunity. OncoImmunology, 2015;5:2. DOI: 10.1080/2162402X.2015.1074374.

Peattie et al., Stimulation of in vivo angiogenesis by cytokine-loaded hyaluronic acid hydrogel implants. Biomaterials. Jun. 2004;25(14):2789-98.

Peattie, Release of growth factors, cytokines and therapeutic molecules by hyaluronan-based hydrogels. Curr Pharm Biotechnol. Jun. 2012;13(7):1299-305.

Singh et al., Hydrogels and scaffolds for immunomodulation. Adv Mater. Oct. 2014;26(38):6530-41. doi: 10.1002/adma.201402105. Epub Aug. 25, 2014.

Smyth et al., Combination cancer immunotherapies tailored to the tumour microenvironment. Nat Rev Clin Oncol. Mar. 2016;13(3):143-58. doi: 10.1038/nrclinonc.2015.209. Epub Nov. 24, 2015.

Stephan et al., Biopolymer implants enhance the efficacy of adoptive T-cell therapy. Nat Biotechnol. Jan. 2015;33(1):97-101. doi: 10.1038/nbt.3104. Epub Dec. 15, 2014.

Verma et al., Activated dendritic cells delivered in tissue compatible biomatrices induce in-situ anti-tumor CTL responses leading to tumor regression. Oncotarget. Jun. 28, 2016;7(26):39894-39906. doi: 10.18632/oncotarget.9529.

Xu et al., Injectable hyaluronic acid-tyramine hydrogels incorporating interferon-α2a for liver cancer therapy. Journal of Controlled Release Mar. 2013;166(3):203-210.

Yang et al., Controlled delivery of 1,3-bis(2-chloroethyl)-1-nitrosourea from ethylene-vinyl acetate copolymer. Cancer Res. Sep. 15, 1989;49(18):5103-7.

Dowling et al., Recent Advances in the Discovery and Delivery of TLR7/8 Agonists as Vaccine Adjuvants. ImmunoHorizons Jul. 1, 2018;2(6):185-197. DOI: https://doi.org/10.4049/immunohorizons.1700063.

Hori et al. "Injectable dendritic cell-carrying alginate gels for immunization and immunotherapy" Biomaterials (2008) 29: 3671-82. https://www.ncbi.nlm.nih.gov/pubmed/18565578/.

Liu et al. "Improved Efficacy of Neoadjuvant Compared to Adjuvant Immunotherapy to Eradicate Metastatic Disease." Cancer Discovery (2016) 6(12): 1382-99.

Smith et al., "Biopolymers codelivering engineered T cells and STING agonists can eliminate heterogeneous tumors" J Clin Invest (2017) 127:2176-2191.

2'3'-cGAMP was conjugated with FITC

IL-15sa was conjugated with Vivotag 680

Anti-PD-1 was conjugated with AF405

Diameter = 9 mm
Height = 3~3.2 mm
Storage modulus = 1380 Pa

Fluorescent image (Ex/Em=745/780 nm)
Dye loaded (left) or unloaded control (right)

Day 28

Tumor recurrence

Lung metastasis

STING-RR, LLC

B16-BL6

METHOD OF TREATING CANCER WITH A BIOMATERIAL AND A TOLL-LIKE RECEPTOR AGONIST

RELATED APPLICATIONS

This application claims priority under 35 U.S.C. §§ 120 and 365(c) to and is a continuation of international PCT Application, PCT/US2017/049424, filed Aug. 30, 2017, which claims priority under 35 U.S.C. § 119(e) to U.S. Provisional Application Ser. No. 62/381,456, filed Aug. 30, 2016; U.S. Ser. No. 62/486,814, filed Apr. 18, 2017; and U.S. Ser. No. 62/501,464, filed May 4, 2017, each of which is incorporated herein by reference.

STATEMENT OF GOVERNMENT INTEREST

This invention was made with government support under grant number P50CA168504 awarded by the National Cancer Institute of the National Institutes of Health. The government has certain rights in the invention.

FIELD OF THE INVENTION

The present invention relates to implantable drug delivery compositions and devices that provide local administration of therapeutic agents (e.g., activators of the innate immune response system and/or activators of the adaptive immune response system) and methods of treating diseases, such as cancer, using such compositions and devices.

BACKGROUND OF THE INVENTION

Systemic administration of medication, nutrition, or other substances into the circulatory system affects the entire body. Systemic routes of administration include enteral (e.g., oral dosage resulting in absorption of the drug through the gastrointestinal tract) and parenteral (e.g., intravenous, intramuscular, and subcutaneous injections) administration. Administration of immunotherapeutics typically relies on these systemic administration routes. However, immunotherapeutics often induce toxicities that are undesirable for non-diseased tissues, thus systemic administration can lead to unwanted side effects. In some instances, certain promising therapeutics are extremely difficult to develop due to associated toxicities and the limitations of current administration methods and systems. For example, systemic administration of immunotherapeutic agents for the treatment of cancer is often associated with immune-related adverse events (e.g., skin rashes, hepatitis, diarrhea, colitis, hypophysitis, thyroiditis, and adrenal insufficiency). These adverse events may in part be attributable to the exposure of non-tumor-specific immune cells to drug, as well as the higher doses required by systemic administration to achieve sufficient concentration in the tumor to induce a desired response. In addition to enhancing safety, localizing delivery of immunotherapeutic agents can improve efficacy by concentrating the action of the drug where it is needed.

Surgery is often the first-line of treatment for solid tumor cancers and is generally used in combination with systemic administration of anti-cancer therapy. However, surgery-induced immunosuppression has been implicated in the development of postoperative septic complications and tumor metastasis due to changes in a variety of metabolic and endocrine responses, ultimately resulting in the death of many patients (Smyth, M. J. et al. *Nature Reviews Clinical Oncology*, 2016, 13, 143-158). Accordingly, there is a need to effectively and safely administer immunotherapies in combination with surgical approaches to achieve antimetastatic efficacy and reduction in tumor regrowth.

SUMMARY OF THE INVENTION

Systemic administration of immunotherapies can result in adverse side effects, and surgical resection of tumors can result in immunosuppression, as described above. However, the present invention provides targeted drug delivery systems (e.g., targeted to a particular tissue or cell type or targeted to a specific diseased tissue, but not normal tissue) that can reduce the amount of a drug present in tissues of the body that are not targeted (e.g., non-diseased tissue) and be particularly useful when treating cancer, where it is desirable that an effective dose of the drug be delivered to cancerous tissue while minimally affecting the surrounding non-cancerous tissue. In particular, the drug delivery systems deliver one or more therapeutic agents that act on the immune system for the treatment of cancer and prevention of tumor recurrence and/or metastasis while minimizing adverse side effects.

In one aspect, provided are drug delivery compositions and devices comprising a biomaterial (e.g., a hydrogel) and an activator of innate immune response (e.g., a STING agonist). In certain embodiments, the activator of innate immune response is a stimulator of interferon genes (STING) agonist, a cytosolic DNA sensor (CDS) agonist, a Toll-like receptor (TLR) agonist, a C-type lectin receptor (CLR) agonist, a NOD-like receptor (NLR) agonist, a RIG-I-like receptor (RLR) agonist, or an inflammasome inducer. Certain activators of innate immune response can trigger antitumor responses.

In another aspect, provided are drug delivery compositions and devices comprising a biomaterial, an activator of innate immune response, and a cytokine (e.g., an IL-15 superagonist). Certain cytokines act as immunomodulating agents and, for example, can activate T cells and NK cells and induce their proliferation, can cause T cells and NK cells to secrete interferon-γ, and can confer upon T cells and NK cells the ability to kill malignant cells in the absence of antigenic stimulation. In other aspects, provided are drug delivery compositions and devices comprising a biomaterial and a cytokine (e.g., an IL-15 superagonist).

In certain embodiments, provided are drug delivery compositions and devices comprising a biomaterial, an activator of innate immune response, and a chemokine (e.g., CXCL9). Certain chemokines can control cells of the immune system during processes of immune surveillance and may recruit immune cells to the site of tumor burden. They can serve to guide cells of both the innate immune system and adaptive immune system. In other embodiments, provided are drug delivery compositions and devices comprising a biomaterial and a chemokine (e.g., CXCL9).

In certain embodiments, the drug delivery compositions and devices further comprise an activator of adaptive immune response (e.g., anti-PD-1 antibody, anti-CTLA-4 antibody, agonist anti-CD137 antibody). Certain activators of adaptive immune response can activate therapeutic antitumor immunity, including the blockade of immune checkpoints or the activation of co-stimulatory molecules.

In another aspect, provided are drug delivery compositions and devices comprising a biomaterial and an activator of adaptive immune response (e.g., anti-PD-1 antibody, anti-CTLA-4 antibody, agonist anti-CD137 antibody).

In certain embodiments, the drug delivery compositions and devices further comprise one or more additional activators of adaptive immune response. In certain embodiments, the activator of adaptive immune response is an antibody (e.g., anti-PD-1 antibody, anti-PD-L1 antibody, anti-CTLA-4 antibody, agonist anti-CD137 antibody), a bispecific antibody (e.g., a bi-functional fusion-protein targeting PD-L1 and TGFβ), an antibody-drug conjugate (e.g., trastuzumab emtansine, inotuzumab ozogamicin), or a small molecule (e.g., celecoxib, bortezomib).

In certain embodiments, the biomaterial is a hydrogel. Hydrogels can provide a scaffold that allows the components of the composition or device to be combined effectively and form a drug delivery system that is implantable in a surgical setting. In certain embodiments, the hydrogel is prepared from hyaluronic acid. Hyaluronic acid is a biocompatible material that biodegrades over time in vivo, allowing for release of drug from the drug delivery system.

In certain embodiments, the drug delivery compositions and devices further comprise an oncolytic virus, a radioactive isotope, a chemotherapeutic agent, or a combination thereof. In certain embodiments, the drug delivery compositions and devices comprise at least one excipient.

In certain embodiments, the drug delivery compositions and devices further comprise an oncolytic virus, a radioactive isotope, an immunomodulatory chemotherapeutic agent, a targeted agent, or a combination thereof.

In certain embodiments, the drug delivery compositions and devices comprise at least one excipient.

In certain embodiments, the biomaterial (e.g., hydrogel) of the drug delivery compositions and devices are biodegradable in viva. In certain embodiments, the drug delivery devices have a storage modulus of about 500 Pa to about 3000 Pa.

In another aspect, provided are methods for treating and/or preventing cancer by surgically implanting the drug delivery composition or device. In certain embodiments, the cancer is a sarcoma, carcinoma, lymphoma, germ cell tumor, or blastoma. In another aspect, provided are methods of preventing primary tumor regrowth by surgically implanting the drug delivery compositions. In another aspect, provided are methods of preventing tumor recurrence and/or metastasis by surgically implanting the drug delivery compositions. In certain embodiments, the methods further comprise implanting the drug delivery compositions after surgical resection of a tumor. In certain embodiments, the methods further comprise implanting the drug delivery compositions at the site of tumor resection.

Also provided are uses and methods of preparing the drug delivery compositions and devices, as well as kits providing the drug delivery compositions and devices.

The details of certain embodiments of the invention are set forth herein. Other features, objects, and advantages of the invention will be apparent from the Detailed Description, Figures, Examples, and Claims.

DEFINITIONS

As used herein, the term "salt" refers to any and all salts and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, non-toxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_1\text{-}C_4 \text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "polymer" is given its ordinary meaning as used in the art, i.e., a molecular structure comprising one or more repeat units (monomers), connected by covalent bonds. The repeat units may all be identical, or, in some cases, there may be more than one type of repeat unit present within the polymer. In certain embodiments, a polymer is a compound comprising eleven or more covalently connected repeating units. In certain embodiments, a polymer is naturally occurring, in certain embodiments, a polymer is synthetic (i.e., not naturally occurring).

The term "cross-linker" refers to compounds that link one polymer chain to another, for example, by covalent bonds or ionic bonds.

The term "solvate" refers to forms of a compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x \text{ H}_2\text{O}$, wherein R is the compound and x is a number greater than 0. A given compound may form more than one type of hydrate, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2H$_2$O) and hexahydrates (R·6 H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol, amide-to-imide, lactam-to-lactam, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal contains a compound of the present invention and one or more other component, including, but not limited to, atoms, ions, molecules, or solvent molecules. In certain embodiments, a co-crystal contains a compound of the present invention and one or more solvent molecules. In certain embodiments, a co-crystal contains a compound of the present invention and one or more acid or base. In certain embodiments, a co-crystal contains a compound of the present invention and one or more components related to said compound, including, but not limited to, an isomer, tautomer, salt, solvate, hydrate, synthetic precursor, synthetic derivative, fragment, or impurity of said compound.

The term "prodrugs" refers to compounds that have cleavable groups and become by solvolysis or under physiological conditions the compounds described herein, which are pharmaceutically active in vivo. Such examples include, but are not limited to, choline ester derivatives and the like as well as N-alkylmorpholine esters and the like. Other derivatives of the compounds described herein have activity in both their acid and acid-derivative forms, but often offer advantages in the acid-sensitive form of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, amides prepared by reaction of the parent acid compound with a substituted or unsubstituted amine, acid anhydrides, or mixed anhydrides. Simple aliphatic or aromatic esters, amides, and anhydrides derived from acidic groups pendant on the compounds described herein are particular prodrugs. In some cases, it is desirable to prepare double ester-type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

A "subject" to which administration is contemplated includes, but is not limited to, humans a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, dogs, and/or birds (e.g., commercially relevant birds such as chickens, ducks, geese, and/or turkeys). In certain embodiments, the animal is a mammal. The animal may be a male or female and at any stage of development. A non-human animal may be a transgenic or genetically engineered animal.

The term "biological sample" refers to any sample, including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refer to implanting, absorbing, ingesting, injecting, inhaling, or otherwise introducing a drug delivery composition as described herein.

The terms "treatment," "treat," and "treating" refer to reversing, alleviating, delaying the onset of, or inhibiting the progress of a "pathological condition" (e.g., a disease, disorder, or condition, including one or more signs or symptoms thereof) described herein. In some embodiments, treatment may be administered after one or more signs or symptoms have developed or have been observed. Treatment may also be continued after symptoms have resolved, for example, to delay or prevent recurrence and/or spread.

The terms "condition," "disease," and "disorder" are used interchangeably.

An "effective amount" is an amount sufficient to elicit a desired biological response, i.e., treating the condition. As will be appreciated by those of ordinary skill in this art, the effective amount of drug delivery composition may vary depending on such factors as the desired biological endpoint, the pharmacokinetics of the therapeutic agents in the composition, the condition being treated, and the age and health of the subject. An effective amount encompasses therapeutic and prophylactic treatment. For example, in treating cancer, an effective amount of an inventive composition may prevent tumor regrowth, reduce the tumor burden, or stop the growth or spread of a tumor.

A "therapeutically effective amount" is an amount sufficient to provide a therapeutic benefit in the treatment of a condition or to delay or minimize one or more symptoms associated with the condition. A therapeutically effective amount of an inventive composition means an amount of therapeutic agent(s), alone or in combination with other therapies, that provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" is an amount sufficient to prevent a condition, or one or more symptoms associated with the condition or prevent its recurrence. A prophylactically effective amount of a composition means an amount of therapeutic agent(s), alone or in combination with other agents, that provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bile duct cancer; bladder cancer; bone cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cardiac tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ductal carcinoma in situ; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis funinodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; multiple myeloma; heavy chain disease (e.g., alpha chain disease, gamma chain disease, mu chain disease); hemangioblastoma; histiocytosis; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinorna, small cell lung cancer (SCLC), non-small cell lung cancer (NSCLC), adenocarcinoma of the lung); leiomyosarcoma (LMS); mastocytosis (e.g., systemic mastocytosis); melanoma; midline tract carcinoma; multiple endocrine neoplasia syndrome; muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) myelofibrosis (MF), chronic idiopathic myelofibrosis, chronic myelocytic leukemia (CML), chronic neutrophilic leukemia (CNL), hypereosinophilic syndrome (HES)); nasopharynx cancer; neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); parathyroid cancer; papillary adenocarcinoma; penile cancer (e.g., Paget's disease of the penis and scrotum); pharyngeal cancer; pinealoma; pituitary cancer; pleuropulmonary blastoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; retinoblastoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; stomach cancer; small intestine cancer; sweat gland carcinoma; synovioma; testicular cancer (e.g., seminoma, testicular embryonal carcinoma); thymic cancer; thyroid cancer (e.g., papillary carcinoma of the thyroid, papillary thyroid carcinoma (PTC), medullary thyroid cancer); urethral cancer; uterine cancer; vaginal cancer; and vulvar cancer (e.g., Paget's disease of the vulva).

The term "immunotherapy" refers to a therapeutic agent that promotes the treatment of a disease by inducing, enhancing, or suppressing an immune response. Immunotherapies designed to elicit or amplify an immune response are classified as activation immunotherapies, while immunotherapies that reduce or suppress an immune response are classified as suppression immunotherapies. Immunotherapies are typically, but not always, biotherapeutic agents. Numerous immunotherapies are used to treat cancer. These include, but are not limited to, monoclonal antibodies, adoptive cell transfer, cytokines, chemokines, vaccines, small molecule inhibitors, and small molecule agonists. For example, useful immunotherapies may include, but are not limited to, inducers of type interferon, interferons, stimulator of interferon genes (STING) agonists, TLR7/8 agonists, IL-15 superagonists, anti-PD-1 antibodies, anti-CD137 antibodies, and anti-CTLA-4 antibodies.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities such as cells and tissues. Biologics may be isolated from a variety of natural sources (e.g., human, animal, microorganism) and may be produced by biotechnological methods and other technologies.

The term "antibody" refers to a functional component of serum and is often referred to either as a collection of molecules (antibodies or immunoglobulin) or as one molecule (the antibody molecule or immunoglobulin molecule). An antibody is capable of binding to or reacting with a specific antigenic determinant (the antigen or the antigenic epitope), which in turn may lead to induction of immunological effector mechanisms. An individual antibody is usually regarded as monospecific, and a composition of antibodies may be monoclonal (i.e., consisting of identical antibody molecules) or polyclonal (i.e., consisting of two or more different antibodies reacting with the same or different epitopes on the same antigen or even on distinct, different antigens). Each antibody has a unique structure that enables it to bind specifically to its corresponding antigen, and all natural antibodies have the same overall basic structure of two identical light chains and two identical heavy chains. Antibodies are also known collectively as immunoglobulins.

The terms "antibody" or "antibodies" as used herein are also intended to include chimeric and single chain antibodies (e.g., a nanobody or Fcab), as well as binding fragments of antibodies, such as Fab, Fv fragments or single chain Fv (say) fragments, as well as multimeric forms such as dimeric IgA molecules or pentavalent IgM molecules. Also included are bispecific antibodies, bispecific T cell engagers (BiTEs), immune mobilixing monoclonal T cell receptors against cancer (ImmTACs), dual-affinity re-targeting (DART); alternative scaffolds or antibody mimetics (e.g., anticalins, FN3 monobodies, DARPins, Affibodies, Affilins, Affimers, Affitins, Alphabodies, Avimers, Fynomers, Im7, VLR, VNAR, Trimab, CrossMab, Trident); nanobodies, binanobodies, F(ab')2, Fab', di-sdFv, single domain antibodies, trifunctional antibodies, diabodies, and minibodies. An antibody may be of human or non-human origin, for example a murine or other rodent-derived antibody, or a chimeric, humanized, or reshaped antibody based e.g., on a murine antibody.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "chemotherapeutic agent" refers to a therapeutic agent known to be of use in chemotherapy for cancer.

The term "targeted agent" refers to an anticancer agent that blocks the growth and spread of cancer by interfering with specific molecules ("molecular targets") that are involved in the growth, progression, and spread of cancer. Targeted agents are sometimes called "targeted cancer therapies," "molecularly targeted drugs," "molecularly targeted therapies," or "precision medicines." Targeted agents differ from standard chemotherapy in that targeted agents act on specific molecular targets that are associated with cancer, whereas most standard chemotherapies act on all rapidly dividing normal and cancerous cells. Targeted agents are deliberately chosen or designed to interact with their target, whereas many standard chemotherapies are identified because they kill cells.

The term "biomaterial" refers to any biocompatible substance that has been engineered to interact with biological systems for a medical purpose (e.g., therapeutic, diagnostic). Biomaterials can be either derived from nature or synthesized.

The term "hydrogel" is a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility similar to natural tissue, due to their significant water content.

The terms "implantable," "implantation," "implanting," and "implant" refer to positioning a drug delivery composition at a specific location in a subject, such as within a tumor resection site or in a sentinel lymph node, and typically by general surgical methods.

The term "biocompatible" refers to a material that is substantially non-toxic in the in vivo environment of its intended use and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, and/or immunogenicity. A biocompatible structure or material, when introduced into a majority of patients, will not cause an undesirably adverse, long-lived, or escalating biological reaction or response and is distinguished from a mild, transient inflammation, which typically accompanies surgery or implantation of foreign objects into a living organism.

The term "inhibit" or "inhibition" in the context of enzymes refers to a reduction in the activity of the enzyme. In some embodiments, the term refers to a reduction of the level of enzyme activity to a level that is statistically significantly lower than an initial level, which may, for example, be a baseline level of enzyme activity. In some embodiments, the term refers to a reduction of the level of enzyme activity to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

The term "activator of innate immune response" refers to an agent that activates the innate immune system. Such activation can stimulate the expression of molecules that initiate an inflammatory response and/or help to induce adaptive immune responses, leading to the development of antigen-specific acquired immunity. Activation of the innate immune system can lead to cytokine production, proliferation, and survival as well as improved T cell priming by enhancing presentation of antigens and expression of co-stimulatory molecules by antigen-presenting cells.

The term "activator of adaptive immune response" refers to an agent that activates the adaptive immune system. Such activation can restore antitumor function by neutralizing inhibitory immune checkpoints or by triggering co-stimulatory receptors, ultimately generating helper and/or effector T cell responses against immunogenic antigens expressed by cancer cells and producing memory B cell and/or T cell populations. In certain embodiments, the activator of adaptive immune response involves modulation of adaptive immune response and/or leukocyte trafficking.

The term "modulator of macrophage effector function" refers to an agent that activates macrophage effector function or depletes immunosuppressive macrophages or macrophage-derived suppressor cells. Such potentiation can mobilize macrophage and myeloid components to destroy the tumor and its stroma, including the tumor vasculature. Macrophages can be induced to secrete antitumor cytokines and/or to perform phagocytosis, including antibody-dependent cellular phagocytosis.

As used herein, the terms "sustained release" and "extended release" are equivalent terms. The compositions and devices of the present disclosure may release therapeutic agents upon in vivo implantation after tumor resection. The terms "sustained" and "extended" may mean that any of the therapeutic agents are released on a timescale ranging from 1 minute to 1 month. In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of any of the therapeutic agents is released in vivo within 4 weeks, 3 weeks, 2 weeks, 10 days, 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, 10 minutes, or 1 minute after implantation of the composition or device. In certain embodiments, greater than or equal to 99%, greater than or equal to 95%, greater than or equal to 90%, greater than or equal to 80%, greater than or equal to 70%, greater than or equal to 60%, greater than or equal to 50%, greater than or equal to 40%, greater than or equal to 30%, greater than or equal to 20%, greater than or equal to 10%, greater than or equal to 5%, or greater than or equal to 1% of any of the therapeutic agents is released in vivo within 1 day, 18 hours, 12 hours, 8 hours, 6 hours, 4 hours, 3 hours, 2 hours, 1 hours, 45 minutes, 30 minutes, 20 minutes, 15 minutes, 10 minutes, or 1 minute after implantation of the composition or device.

BRIEF DESCRIPTION OF THE DRAWINGS

FIG. 30 also shows images of individual mice after a solution containing IL-15 superagonist, anti-PD-1, and small molecule therapeutics (celecoxib or EW7197 dissolved in DMSO) was administered via local administration following inoculation and resection of tumors originating from 4T1-Luc2 syngeneic breast cancer cells. The images show appearance/disappearance of tumor over a 3-week period.

FIG. 37A shows a picture of a representative scaffold loaded with R848. FIG. 37B shows fluorescence IVIS imaging depicting the in vivo release profile of a model small molecule payload (Cy7 carboxylic acid). FIG. 37C shows quantification of the in vivo release profile of Cy7 carboxylic acid. The experiment was performed once with n=5 biological replicates. Fold difference is indicated for each time point. Statistics were calculated using a two-sided unpaired t-test. Data are presented as mean±SD * $p \leq 0.05$, * $p \leq 0.001$, ** $p \leq 0.0001$.

FIGS. 57A-57C show increased numbers of leukocytes with activated and effector phenotypes were observed. Quantitation of flow cytometry gating of subsets of NK cells (day 3) (FIG. 57A), dendritic cells (day 3) (FIG. 57B), and CD4$^+$ T cells and CD8$^+$ T cells (day 14) is shown (FIG. 57C). FIGS. 57D-57E show increased numbers of T cells producing pro-inflammatory cytokines and cytologic molecules were observed. Quantitation of flow cytometry gating of CD4$^+$ T cells and CD9$^+$ T cells (day 14) are shown. Splenocytes were cultured for 5 hours in the presence of phorbol ester, ionomycin, and brefeldin A (FIG. 57D) or a specific immunodominant peptide expressed by 4T1 cells (survivin$_{66-74}$) and brefeldin A before flow cytometry was performed (FIG. 57E). FIG. 57F shows elevated concentrations of cytokines were observed in plasma collected on day 14 after surgery. Levels of type I interferons are shown (see FIG. 57F). Data were generated by multiplexing laser bead technology. Statistics were calculated using a two-tailed unpaired t-test. Data are presented as mean±SEM. * p≤0.05,  p≤0.01, * p≤0.001, **** p≤0.0001.

FIG. 62 also shows a series of graphs showing the total flux of bioluminescent 4T1-Luc2 cells after administration of exemplary drug delivery device 1 from the experiments described in FIG. 61. Data for individual mice are shown for tumors that recurred locally or metastasized to the lung following the treatments shown.

FIG. 63 also shows a series of graphs showing the total flux of bioluminescent 4T1-Luc2 cells after administration of exemplary drug delivery device 21.

FIGS. 82A-83B are a series of graphs showing that sustained local release of STING-RR was well tolerated after implantation of device 23 or local administration after tumor resection. None of the routes of administration or devices listed impacted the levels of liver enzymes measured 15 days post-surgery (FIG. 82A) or the weight of mice longitudinally (FIG. 82B). The weight loss observed in the first week was related to the stress of the surgery itself, as it was observed in all groups, including the no treatment negative control. "Hydrogel (RR)" refers to loading of STING-RR into a hydrogel prepared from hyaluronic acid (device 23); "Hydrogel (Alginate)" refers to loading of STING-RR (100 μg) into a hydrogel prepared from alginate. Data in FIG. 82A are presented as mean±SEM. Dashed lines indicate established normal ranges.

FIGS. 83A-83D show extended local release of agonists of innate immunity prevents tumor recurrence and distal metastasis, curing a majority of mice following perioperative treatment. Tumors were resected from mice 10 days after orthotopic inoculation of 4T1-Luc2 cells, and hydrogels loaded with the following payloads were evaluated: anti-PD-1, anti-CTLA-4, IL-15sa, celecoxib, STING-RR, or R848. No hydrogel was examined as a negative control. FIG. 83A shows IVIS imaging of 4T1-Luc2 cells is shown for all groups and illustrates tumor burden. FIG. 83B shows a Kaplan-Meier curve comparing antibodies that induce immune checkpoint blockade (device 19 or 31 (300 μg anti-CTLA-4) to no hydrogel. FIG. 83C shows a Kaplan-Meier curve comparing the potent cytokine IL-15sa (device 18) to no hydrogel. FIG. 83D shows a Kaplan-Meier curve comparing various immunomodulatory small molecules (device 3 (1500 μg celecoxib), 22, 23, or 30) to no hydrogel. The number of mice per group (n) and median survival (ms) are listed. The experiment was performed with biological replicates at least three times. Statistics were calculated relative to the group treated with no hydrogel using the Log-rank (Mantel-Cox) test.  $p \leq 0.01$, * $p \leq 0.001$.

FIG. 84A shows a Kaplan-Meier curve for all groups described: no hydrogel, weekly intraperitoneal (IP) injection of R848, weekly intravenous (IV) injection of R848, an empty hydrogel plus local administration of R848 in solution, or a hydrogel loaded with R848 (device 22). FIG. 84B shows a Kaplan-Meier curve for all groups described: no hydrogel, an empty hydrogel plus local administration of STING-RR in solution, or a hydrogel loaded with STING-RR (device 23). Tumors were injected intratumorally (IT) with a single dose of R848 or STING-RR 10 days after orthotopic inoculation of 4T1-Luc2 cells (see FIGS. 84C-84D). Tumor volume (FIG. 84C) and mouse survival (FIG. 84D) were measured. Tumors were resected from mice 10 days after orthotopic inoculation of 4T1-Luc2 cells (see FIGS. 84E-84F. FIG. 84E shows a Kaplan-Meier curve for all groups described: no hydrogel, Cc14 (device 32), Cc15 (device 33), or Cxc110 (device 34). FIG. 84F shows a Kaplan-Meier curve for all groups described: no hydrogel, paclitaxel (device 35), or doxorubicin (device 36). The number of mice per group (n) and median survival (ms) are listed. The experiment was performed with biological replicates at least three times. Statistics were calculated relative to the group treated with hydrogel containing the indicated agonist of innate immunity using the Log-rank (Mantel-Cox) test. * $p=0.05$,  $p \leq 0.05$, * $p \leq 0.001$.

FIG. 85A shows a Kaplan-Meier curve for no hydrogel and three consecutive daily IP injections of R848 (200 μg). FIG. 85B depicts the weights of the mice for the treatment groups. The number of mice per group (n) and median survival (ms) are listed. The experiment was performed with biological replicates at least three times.

As shown in FIGS. 91A-91C, increased numbers of leukocytes with activated and effector phenotypes are observed. Quantitation of flow cytometry gating of subsets of NK cells (day 3) (FIG. 91A), dendritic cells (day 3) (FIG. 91B), and $CD4^+$ T cells and $CD8^+$ T cells (day 14) (FIG. 91C) is shown. FIG. 91D shows that increased numbers of central memory-like $CD8^+$ T cells are observed. FIG. 91E shows that increased numbers of T cells producing pro-inflammatory cytokines and cytolytic molecules are observed. Quantitation of flow cytometry gating of $CD4^+$ cells and $CD8^+$ T cells (day 14) are shown. Splenocytes were cultured for 6 hours in the presence of a specific immunodominant peptide expressed by 4T1 cells ($gp70_{423-431}$) and brefeldin A before flow cytometry was performed. Elevated concentrations of cytokines are observed in plasma collected at various time points after surgery (see FIGS. 91F-91G). In FIG. 91F, levels of type I interferons are shown. In FIG. 91G, levels of a panel of cytokines are shown. Data were generated by multiplexing laser bead technology. The experiment was performed once with n=5 biological replicates. Statistics were calculated using a two-sided unpaired t-test. Data are presented as mean±SEM. * $p \leq 0.05$,  $p \leq 0.01$, * $p \leq 0.001$, **** $p \leq 0.0001$.

FIGS. 99A-99C show Kaplan-Meier curves for no hydrogel or R848 (device 22) (FIGS. 99A-99B) or STING-RR (device 23) (FIG. 99C).

FIG. 99D shows a Kaplan-Meier curve for mice following resection of orthotopic 4T1-Luc2 tumors and treatment with no hydrogel, an alginate hydrogel loaded with DMSO vehicle ("empty"), or an alginate hydrogel loaded with R848. The number of mice per group (n) and median survival (ms) are listed. The experiment was performed with biological replicates at least three times. Statistics were calculated relative to the group treated with hydrogel containing the indicated agonist of innate immunity using the Log-rank (Mantel-Cox) test. * p≤0.05.

FIGS. 102A-102C show Kaplan-Meier curves for no hydrogel or the triple combination of 2'3'-cGAMP, IL-15sa, and anti-PD-1 (device 1). The number of mice per group (n) and median survival (ms) are listed. The experiment was performed with biological replicates at least three times. Statistics were calculated relative to the group treated with hydrogel containing triple combination using the Log-rank (Mantel-Cox) test. * p≤0.05.

FIG. 103A shows a picture of PLGA scaffolds when dry (top) or wet (bottom). PLGA scaffolds were prepared by weighing out 100 mg of PLGA (50:50, ester endcap, Mn ~50,000 Da; Akina AP121) per scaffold, mixing overnight with 200 μg of solid R848 (per 100 mg of PLGA), pressing with 1500 psi (5000 lbs) of pressure for one minute, and foaming overnight with 850 psi of carbon dioxide. FIG. 103B shows cumulative drug release after scaffolds were placed in PBS (pH 7.4) and drug release was measured by HPLC. Release of R848 from the PLGA scaffolds requires weeks rather than hours. FIG. 103C shows that this delayed release attenuates the efficacy of the localized release of the agonist of innate immunity. A Kaplan-Meier curve is shown for the control and treatment groups. The number of mice per group (n) and median survival (ms) are listed.

DETAILED DESCRIPTION OF CERTAIN EMBODIMENTS OF THE INVENTION

Figure 1:
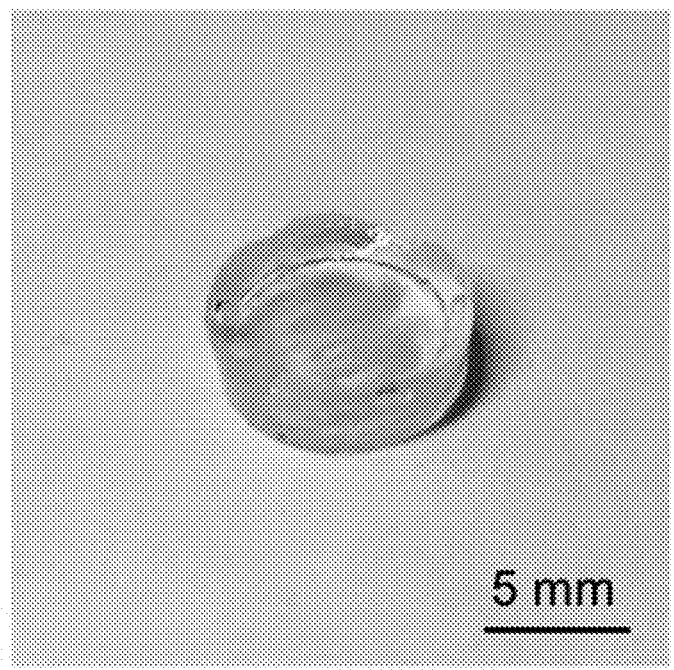
FIG. 1 is an image of exemplary drug delivery device F conjugated with ALEXA FLUOR® 750 dye.

Provided herein are drug delivery compositions and devices. The drug delivery compositions and devices may comprise a biomaterial and an activator of innate immune response. The drug delivery compositions and devices may comprise a biomaterial, an activator of innate immune response, and a cytokine. The drug delivery compositions and devices may comprise a biomaterial, an activator of innate immune response, and a chemokine. The drug delivery compositions and devices may comprise a biomaterial and a cytokine. The drug delivery compositions and devices may comprise a biomaterial and a chemokine. The drug delivery compositions and devices may further comprise one or more activators of adaptive immune response.

The drug delivery compositions and devices may comprise a biomaterial and an activator of adaptive immune response. The drug delivery compositions and devices may further comprise an additional activator of adaptive immune response. The drug delivery compositions and devices may further comprise additional therapeutic agents (e.g., a modulator of macrophage effector function or chemotherapeutic agents).

The therapeutic agents provided within the drug delivery compositions and devices may activate the innate immune response system and/or the adaptive immune response system, thus providing unique tools for the treatment of cancer, particularly solid tumors. The compositions, devices, methods, systems, and kits provided herein are also advantageous over existing methods in that they do not require administration of cells (e.g., adoptive cell transfer) or the incorporation of additional components such as microparticles, peptides, or tumor antigens.

The drug delivery compositions and devices are useful for treating cancer in the perioperative setting. In particular, the compositions and devices may deliver immunotherapies by implantation of the device or devices at the site of therapeutic need in a subject in need thereof. The drug delivery compositions and devices are particularly advantageous over existing immunotherapies because they can be delivered directly to a site of tumor resection, avoiding systemic administration. Accordingly, the drug delivery compositions and devices provide a vehicle for drug delivery at the site of tumor resection that avoids potential toxicities that can be associated with traditional systemic administration of immunotherapies. Concentrating the immunotherapy at the site of tumor resection can similarly improve efficacy. In certain embodiments, the drug delivery compositions and devices are useful for slowing and/or impeding tumor growth, preventing cancer recurrence, preventing tumor metastasis, and/or preventing primary tumor regrowth.

Drug Delivery Compositions and Devices
Biomaterial/Hydrogel

The drug delivery compositions and devices include a biomaterial. In certain embodiments, the biomaterial is a scaffold or depot. The scaffold or depot comprises any synthetic or naturally occurring material that is suitable for containing and promoting the sustained or extended release of any therapeutic agents in the drug delivery compositions and devices as described herein. Accordingly, the biomaterial possesses properties that provide the advantageous properties of the compositions and devices described herein (e.g., storage modulus, biodegradation, release profile of therapeutic agents). In certain embodiments, the biomaterial extends the release of a therapeutic agent in the tumor resection site relative to administration of the same therapeutic agent in solution. In certain embodiments, the biomaterial extends the release of a therapeutic agent in the tumor resection site relative to administration of the same therapeutic agent in solution by at least 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 18 hours, 24 hours, 2 days, 3 days, 4 days, 5 days, 6 days, 7 days, 2 weeks, 3 weeks, or 4 weeks.

In certain embodiments, the biomaterial comprises hyaluronic acid, alginate, chitosan, chitin, chondroitin sulfate, dextran, gelatin, collagen, starch, cellulose, polysaccharide, fibrin, ethylene-vinyl acetate (EVA), poly(lactic-co-glycolic) acid (PLGA), polylactic acid (PLA), polyglycolic acid (PGA), polyethylene glycol (PEG), PEG diacrylate (PEGDA), disulfide-containing PEGDA (PEGSSDA), PEG dimethacrylate (PEGDMA), polydioxanone (PDO), polyhydroxybutyrate (PHB), poly(2-hydroxyethyl methacrylate) (pHEMA), polycaprolactone (PCL), poly(beta-amino ester) (PBAE), polyester amide), poly(propylene glycol) (PPG), poly(aspartic acid), poly(glutamic acid), poly(propylene fumarate) (PPF), poly(sebacic anhydride) (PSA), poly(trimethylene carbonate) (PTMC), poly(desaminotyrosyltyrosine alkyl ester carbonate) (PDTE), poly[bis(trifluoroethoxy) phosphazene], polyoxymethylene, single-wall carbon nanotubes, polyphosphazene, polyanhydride, poly(N-vinyl-2-pyrrolidone) (PVP), poly(vinyl alcohol) (PVA), poly(acrylic acid) (PAA), poly(methacrylic acid) (PMA), polyacetal, poly(alpha ester), poly(ortho ester), polyphosphoester, polyurethane, polycarbonate, polyamide, polyhydroxyalkanoate, polyglycerol, polyglucuronic acid, derivatives thereof, and/or combinations thereof.

In certain embodiments, the biomaterial is a hydrogel, in certain embodiments, the hydrogel comprises hyaluronic acid, alginate, chitosan, chondroitin sulfate, dextran, gelatin, collagen, starch, cellulose, polysaccharide, fibrin, polyethylene glycol (PEG), PEG diacrylate (PEGDA), disulfide-containing PEGDA (PEGSSDA), PEG dimethacrylate (PEGDMA), poly(2-hydroxyethyl methacrylate) (pHEMA), poly(beta-amino ester) (PBAE), poly(aspartic acid), poly(glutamic acid), poly(propylene glycol) (PPG), poly(vinyl alcohol) (PVA), polyacetal, polyglycerol, or polyglucuronic acid. In certain embodiments, when the biomaterial is a hydrogel, then the therapeutic agent(s) of the composition or device are hydrophilic molecules. In certain embodiments, when the biomaterial is a hydrogel, then the therapeutic agent(s) of the composition or device are hydrophobic molecules. In certain embodiments, when the biomaterial is a hydrogel, then the therapeutic agent(s) of the composition or device are hydrophobic or hydrophilic molecules. In certain embodiments, when the biomaterial is a hydrogel, then the therapeutic agent(s) of the composition or device are hydrophobic and hydrophilic molecules.

In certain embodiments, the biomaterial is hyaluronic acid or alginate. In certain embodiments, the biomaterial is cross-linked hyaluronic acid or cross-linked alginate. In certain embodiments, the biomaterial comprises hyaluronic acid or alginate. In certain embodiments, the biomaterial comprises cross-linked hyaluronic acid or cross-linked alginate. In certain embodiments, the hydrogel is hyaluronic acid or alginate. In certain embodiments, the hydrogel is cross-linked hyaluronic acid or cross-linked alginate. In certain embodiments, the hydrogel comprises hyaluronic acid or alginate. In certain embodiments, the hydrogel comprises cross-linked hyaluronic acid or cross-linked alginate.

In certain embodiments, the biomaterial comprises hyaluronic acid. In certain embodiments, the biomaterial comprises cross-linked hyaluronic acid. In certain embodiments, the biomaterial is hyaluronic acid. In certain embodiments, the biomaterial is cross-linked hyaluronic acid. In certain embodiments, the hydrogel comprises hyaluronic acid. In certain embodiments, the hydrogel comprises cross-linked hyaluronic acid. In certain embodiments, the hydrogel is hyaluronic acid. In certain embodiments, the hydrogel is cross-linked hyaluronic acid.

Hyaluronic acid, also known as hyaluronan, is an anionic, non-sulfated glycosaminoglycan distributed widely throughout connective, epithelial, and neural tissues. It is unique among glycosaminoglycans in that it is non-sulfated, forms in the plasma membrane instead of the Golgi, and can be very large, with its molecular weight often reaching the millions.

One of the chief components of the extracellular matrix, hyaluronic acid plays a significant role in cancer metastasis as it contributes significantly to cell proliferation and migration. In some cancers, hyaluronic acid levels correlate with malignancy and poor prognosis. Hyaluronic acid is often used as a tumor marker for certain cancers (e.g., prostate and breast cancer) and may also be used to monitor the progression of the disease in individuals. Therefore, use of hyaluronic acid as a biomaterial in the disclosed drug delivery compositions and devices provides an unexpectedly useful and efficacious cancer therapy.

In certain embodiments, hyaluronic acid can be cross-linked by attaching thiols (EXTRACEL®, HYSTEM®), methacrylates, hexadecylamides (HYMOVIS®), and tyramines (CORGEL®). Hyaluronic acid can also be cross-linked directly with formaldehyde (HYLAN-A®) or with divinylsulfone (HYLAN-B®).

In certain embodiments, hyaluronic acid comprises thiol-modified hyaluronic acid and a cross-linking agent. In certain embodiments, the hydrogel comprises thiol-modified hyaluronic acid (e.g., GLYCOSIL®), and a thiol-reactive PEGDA cross-linker (e.g., EXTRALINK®). In certain embodiments, the thiol-modified hyaluronic acid and the thiol-reactive PEGDA cross-linker are combined to form a cross-linked hydrogel useful in the drug delivery compositions and devices described herein.

In certain embodiments, the amount and concentration of thiol-modified hyaluronic acid, thiol-reactive hyaluronic acid, and cross-linking agent can be adjusted to provide drug delivery compositions and devices with desired physical properties, such as having a storage modulus of about 500 Pa to about 3000 Pa.

In certain embodiments, the biomaterial comprises alginate. In certain embodiments, the biomaterial comprises cross-linked alginate. In certain embodiments, the biomaterial is alginate. In certain embodiments, the biomaterial is cross-linked alginate. In certain embodiments, the hydrogel comprises alginate. In certain embodiments, the hydrogel comprises cross-linked alginate. In certain embodiments, the hydrogel is alginate. In certain embodiments, the hydrogel is cross-linked alginate. In certain embodiments, the biomaterial does not comprise alginate. In certain embodiments, the biomaterial is not alginate. In certain embodiments, the hydrogel is not alginate. In certain embodiments, the hydrogel does not comprise alginate.

In certain embodiments, alginate can be cross-linked ionically by adding a salt that promotes cross-linking (e.g., calcium chloride).

In certain embodiments, alginate comprises alginate and a cross-linking agent (e.g., calcium chloride). In certain embodiments, the hydrogel comprises alginate and a cross-linking agent (e.g., calcium chloride). In certain embodiments, the alginate and the calcium chloride (e.g., ionic cross-linker) are combined to form a cross-linked hydrogel useful in the drug delivery compositions and devices described herein.

In certain embodiments, the amount and concentration of alginate and calcium chloride can be adjusted to provide drug delivery compositions and devices with desired physical properties, such as having a storage modulus of about 500 Pa to about 3000 Pa.

In certain embodiments, the biomaterial is a hydrophobic polymer. In certain embodiments, the hydrophobic polymer is ethylene-vinyl acetate (EVA), polylactic-co-glycolic) acid (PLGA), polylactic acid (PLA), polyglycolic acid (PGA), polydioxanone (PDO), polyhydroxybutyrate (PHB), polycaprolactone (PCL), poly(ester amide), poly(propylene fumarate) (PPF), poly(sebacic anhydride) (PSA), poly(trimethylene carbonate) (PTMC), poly(desaminotyrosyltyrosine alkyl ester carbonate) (PDTE), poly[bis(trifluoroethoxy) phosphazene], polyoxymethylene, single-wall carbon nanotubes, polyphosphazene, polyanhydride, poly(N-vinyl-2-pyrrolidone) (PVP), poly(acrylic acid) (PAA), poly(methacrylic acid) (PMA), poly(alpha ester), poly(ortho ester), polyphosphoester, polyurethane, polycarbonate, polyamide, or polyhydroxyalkanoate. Use of a hydrophobic polymer as the biomaterial may be particularly useful when the therapeutic agent(s) in the composition or device is hydrophilic. Hydrophobic therapeutic agents would be expected to be released over longer periods of time (e.g., days/weeks) rather than a release timescale more conducive to imparting a therapeutic effect (e.g., hours). Accordingly, in certain embodiments, when the biomaterial is a hydrophobic polymer, then the therapeutic agent(s) of the composition or device are hydrophilic molecules.

In certain embodiments, the biomaterial comprises a cross-linked biologic. In certain embodiments, the biologic is cross-linked by the self-immolating cross-linker dithiobis(ethyl 1H-imidazole-1-carboxylate) (DIC). In certain embodiments, the resultant hydrogel is loaded with a small molecule.

Activator of Innate Immune Response

The drug delivery compositions and devices may comprise an activator of innate immune response. The drug delivery compositions and devices may comprise more than one activator of innate immune response. The major functions of the innate immune response include recruiting immune cells to sites of infection through the production of chemical factors, including specialized chemical mediators (e.g., cytokines); activation of the complement cascade to identify bacteria, activate cells, and promote clearance of antibody complexes or dead cells; identification and removal of foreign substances present in organs, tissues, blood, and lymph by specialized white blood cells; activation of the adaptive immune system through a process known as antigen presentation; and acting as a physical and chemical barrier to infectious agents (e.g., epithelial surfaces, gastrointestinal tract). Typically, leukocytes are the white blood cells that carry out the actions of the innate immune system. These cells include natural killer cells, mast cells, eosinophils, basophils, macrophages, neutrophils, and dendritic cells. These cells function within the immune system by identifying and eliminating pathogens that might cause infection.

In certain embodiments, the the activator of innate immune response is a of a pattern recognition receptor (PRR).

In certain embodiments, the the activator of innate immune response is an agonist of a pattern recognition receptor (PRR).

In certain embodiments, the activator of innate immune response is an inducer of type I interferon. In certain embodiments, the activator of innate immune response is a recombinant interferon.

In certain embodiments, the activator of innate immune response is an effective inducer of activation and/or proliferation of NK cells. In certain embodiments, "effective inducer" refers to an activator of innate immune response that directly induces activation and/or proliferation of NK cells.

In certain embodiments, the activator of innate immune response is an effective inducer of activation and/or maturation of dendritic cells. In certain embodiments, "effective inducer" refers to an activator of innate immune response that directly induces activation and/or maturation of dendritic cells.

In certain embodiments, the activator of innate immune response is an effective inducer of type I interferon by dendritic cells. In certain embodiments, "effective inducer"

refers to an activator of innate immune response that directly induces type I interferon by dendritic cells.

In certain embodiments, the activator of innate immune response is a small molecule or a biologic. In certain embodiments, the activator of innate immune response is a small molecule. In certain embodiments, the activator of innate immune response is a biologic.

In certain embodiments, the activator of innate immune response is a stimulator of interferon genes (STING) agonist, a cytosolic DNA sensor (CDS) agonist, a Toll-like receptor (TLR) agonist, a C-type lectin receptor (CLR) agonist, a NOD-like receptor (NLR) agonist, a RIG-I-like receptor (RLR) agonist, or an inflammasome inducer.

In certain embodiments, the activator of innate immune response is a stimulator of interferon genes (STING) agonist, a Toll-like receptor (TLR) agonist, or a NOD-like receptor (NLR) agonist. In certain embodiments, the activator of innate immune response is a stimulator of interferon genes (STING) agonist or a Toll-like receptor (TLR) agonist. In certain embodiments, the activator of innate immune response is a stimulator of interferon genes (STING) agonist, a TLR7 agonist, or a TLR8 agonist.

In certain embodiments, the activator of innate immune response is 2′-3′-cGAMP, 2′-3′-cGAMP, 2′-3′-cGAM(PS)2 (Rp/Rp), 2′-3′-cGAM(PS)2 (Rp/Sp), 2′-2′-cGAMP, c-di-AMP, 2′-3′-c-di-AMP, 2′-3′-c-di-AMP(PS)2 (Rp/Rp), 2′-3′-c-di-AMP(PS)2 (Rp/Sp), c-di-GMP, c-di-IMP, HSV-60, ISD, VACV-70, poly(dA:dT), poly(dG:dC), heat-killed bacteria, lipoglycans, lipopolysaccharides (LPS), lipoteichoic acids, peptidoglycans (PGNs), synthetic lipoproteins, poly(A:U), poly(I:C), Monophosphoryl Lipid A (MPLA), GSK1795091, G100, SD-101, MGN1703, CMP-001, flagellin (FLA), polyU, poly(dT), gardiquimod, imiquimod (R837), base analogs, adenine analogs, guanosin analogs, purine derivatives, benoazepine analogs, imidazoquinolines, thiazoquinolines, loxoribine, resiquimod (R848), dactolisib, sumanirole, N1-glycinyl[4-((6-amino-2-(butylamino)-8-hydroxy-9H-purin-9-yl)methyl) benzoyl] spermine (CL307), CL264, CL097, CL075, MEDI9197, MEDI5083, hypoxanthine, TL8-506, PF-4878691, isatoribine, SM-324405, SM-324406, AZ12441970, AZ12443988, CpG oligonucleotides, bacterial DNA, beta glucans, beta glucans from fungal and bacterial cell walls, γ-D-Glu-mDAP (iE-DAP), iE-DAP derivatives, muramyl dipeptide (MDP), MDP derivatives, 5′-triphosphate double stranded RNA, poly(dA:dT), ATP, chitosan, aluminum potassium sulfate, calcium pyrophosphate dehydrate, silica dioxide, MurNAc-L-Ala-γ-D-Glu-mDAP (M-TriDAP), a xanthenone analog (e.g., DMXAA; vadimezan), a TREX1 inhibitor, a cyclic dinucleotide, derivatives thereof, or pharmaceutically acceptable salts thereof.

In certain embodiments, the activator of innate immune response is a fluorinated derivative of any of the above activators. In certain embodiments, the activator of innate immune response is an O-methylated derivative of any of the above activators.

In certain embodiments, the activator of innate immune response is 3′-3′-cGAMP, 2′-3′-cGAMP, 2′-3′-cGAM(PS)2 (Rp,Rp), 2′-3′-cGAM(PS)2 (Rp,Sp), 2′-2′-cGAMP, c-di-AMP, 2′-3′-c-di-AMP, 2′-3′-c-di-AM(PS)2 (Rp,Rp), 2′-3′-c-di-AM(PS)2 (Rp,Sp), c-di-GMP, 2′-3′-c-di-GMP, 2′-3′-c-di-GM(PS)2 (Rp,Rp), 2′-3′-c-di-GM(PS)2 (Rp,Sp), c-di-IMP, resiquimod. CpG oligonucleotides, polyinosinic:polycytidylic acid, or pharmaceutically acceptable salts thereof.

In certain embodiments, the activator of innate immune response is a fluorinated derivative of 3′-3′-cGAMP, 2′-3′-cGAMP, 2′-3′-cGAM(PS)2 (Rp,Rp), 2′-3′-cGAM(PS)2 (Rp,Sp), 2′-2′-cGAMP, c-di-AMP, 2′-3′-c-di-AMP, 2′-3′-c-di-AM(PS)2 (Rp,Rp), 2′-3′-c-di-AM(PS)2 (Rp,Sp), c-di-GMP, 2′-3′-c-di-GMP, 2′-3′-c-di-GM(PS)2 (Rp,Rp), 2′-3′-c-di-GM(PS)2 (Rp,Sp), c-di-IMP, or pharmaceutically acceptable salts thereof.

In certain embodiments, the activator of innate immune response is an O-methylated derivative of 3′-3′-cGAMP, 2′-3′-cGAMP, 2′-3′-cGAM(PS)2 (Rp,Rp), 2′-3′-cGAM(PS)2 (Rp,Sp), 2′-2′-cGAMP, c-di-AMP, 2′-3′-c-di-AMP, 2′-3′-c-di-AM(PS)2 (Rp,Rp), 2′-3′-c-di-AM(PS)2 (Rp,Sp), c-di-GMP, 2′-3′-c-di-GMP, 2′-3′-c-di-GM(PS)2 (Rp,Rp), 2′-3′-c-di-GM(PS)2 (Rp,Sp), c-di-IMP, or pharmaceutically acceptable salts thereof.

In certain embodiments, the activator of innate immune response is 2′-3′-cGAMP, 2′-3′-c-di-AM(PS)2 (Rp,Rp), MurNAc-L-Ala-γ-D-Glu-mDAP (M-TriDAP), c-di-GMP, or resiquimod. In certain embodiments, the activator of innate immune response is 2′-3′-cGAMP, 2′-3′-c-di-AM(PS)2 (Rp,Rp), MurNAc-L-Ala-γ-D-Glu-mDAP (M-TriDAP), or resiquimod. In certain embodiments, the activator of innate immune response is 2′-3′-cGAMP, 2′-3′-c-di-AM(PS)2 (Rp,Rp), or resiquimod. In certain embodiments, the activator of innate immune response is 2′-3′-c-di-AM(PS)2 (Rp,Rp) or resiquimod.

In certain embodiments, the activator of innate immune response is 2′-3′-cGAMP, or a pharmaceutically acceptable salt thereof. In particular, 2′-3′-cGAMP (cyclic [G(2′-5′)pA(3′-5′)p]) has been described to function as an endogenous second messenger, inducing STING-dependent type I interferon response. 2′-3′-cGAMP has also been shown to be an effective adjuvant that boosts the production of antigen-specific antibodies and T cell responses in mice. 2′-3′-cGAMP exercises antiviral functions in the cell where it is produced but can also cross cell membranes by passive diffusion to exert effects on neighboring cells.

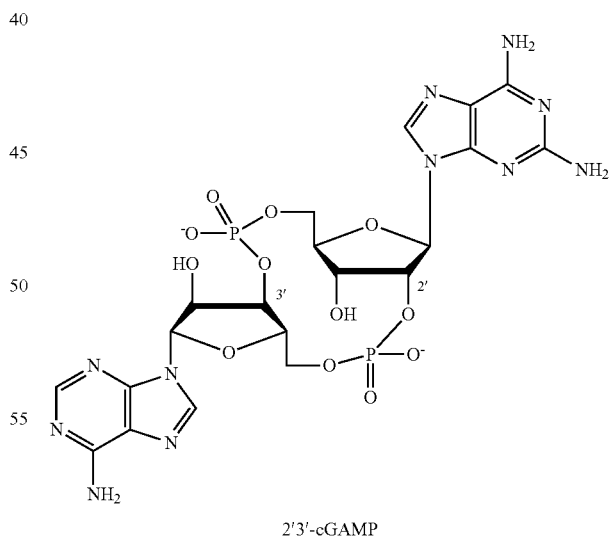

2′3′-cGAMP

In certain embodiments, the activator of innate immune response is 2′-3′-c-di-AM(PS)2 (Rp,Rp), or a pharmaceutically acceptable salt thereof. 2′-3′-c-di-AM(PS)2 (Rp,Rp) is the Rp,Rp-isomer of the 2′3′ bisphosphorothioate analog of 3′3′-cyclic adenosine monophosphate (c-di-AMP). It is also a STING agonist.

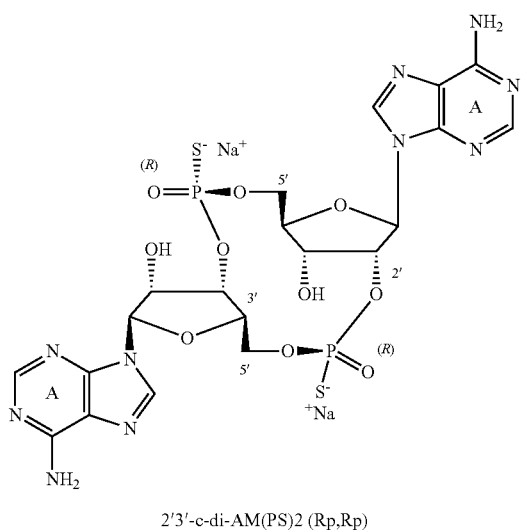

2'3'-c-di-AM(PS)2 (Rp,Rp)

In certain embodiments, the activator of innate immune response is a STING agonist, wherein the STING agonist is a cyclic dinucleotide. In certain embodiments, the cyclic dinucleotide is any cyclic dinucleotide disclosed in U.S. patent application Ser. No. 15/234,182, filed Aug. 11, 2016, the entire contents of which are incorporated herein by reference.

In certain embodiments, the activator of innate immune response is a cytosolic DNA sensor (CDS) agonist. In certain embodiments, the CDS agonist is a cyclic GMP-AMP synthase (cGAS) agonist.

In certain embodiments, the activator of innate immune response is any STING agonist or cGAS agonist disclosed in U.S. application Ser. No. 14/653,586, filed Dec. 16, 2013, the entire contents of which are incorporated herein by reference. In certain embodiments, the activator of innate immune response is any STING agonist or cGAS agonist disclosed in U.S. patent application Ser. No. 14/268,967, filed May 2, 2014, the entire contents of which are incorporated herein by reference. In certain embodiments, the activator of innate immune response is any STING agonist car cGAS agonist disclosed in U.S. patent application Ser. No. 14/787,611, filed Apr. 29, 2014, the entire contents of which are incorporated herein by reference. In certain embodiments, the activator of innate immune response is any STING agonist or cGAS agonist disclosed in U.S. patent application Ser. No. 14/908,019, filed Jul. 31, 2014, the entire contents of which are incorporated herein by reference.

In certain embodiments, the activator of innate immune response is any STING agonist disclosed in U.S. patent application Ser. No. 13/057,662, filed Jun. 14, 2011, the entire contents of which are incorporated herein by reference. In certain embodiments, the activator of innate immune response is any STING agonist disclosed in U.S. patent application Ser. No. 14/106,687, filed Dec. 13, 2013, the entire contents of which are incorporated herein by reference. In certain embodiments, the activator of innate immune response is any STING agonist disclosed in U.S. patent application Ser. No. 15/035,432, filed May 19, 2016, the entire contents of which are incorporated herein by reference. In certain embodiments, the activator of innate immune response is any STING agonist disclosed in International Patent Application PCT/US2017/013049, filed Jan. 11, 2017, the entire contents of which are incorporated herein by reference. In certain embodiments, the activator of innate immune response is any STING agonist disclosed in International Patent Application PCT/US2017/013066, filed Jan. 11, 2017, the entire contents of which are incorporated herein by reference. In certain embodiments, the activator of innate immune response is any STING agonist disclosed in International Patent Application PCT/US2014/038525, filed May 18, 2014, the entire contents of which are incorporated herein by reference. In certain embodiments, the activator of innate immune response is any STING agonist disclosed in U.S. patent application Ser. No. 13/912,960, filed Jun. 7, 2013, the entire contents of which are incorporated herein by reference. In certain embodiments, the activator of innate immune response is any STING agonist disclosed in International Patent Application PCT/II32016/057265, filed Jan. 12, 2016, the entire contents of which are incorporated herein by reference.

In certain embodiments, the activator of innate immune response is MurNAc-L-Ala-γ-D-Glu-mDAP (M-TriDAP), or a pharmaceutically acceptable salt thereof. M-TriDAP is a peptidoglycan (PGN) degradation product found mostly in Gram-negative bacteria. M-TriDAP is recognized by the intracellular sensor NOD1 (CARD4) and to a lesser extend NOD2 (CARD15). Recognition of M-TriDAP by NOD1/NOD2 induces a signaling cascade involving the serine/threonine RIP2 (RICK, CARDIAK) kinase, which interacts with IKK leading to the activation of NE-κB and the production of inflammatory cytokines such as TNF-α and IL-6. M-TriDAP induces the activation of NF-κB at similar levels to Tri-DAP.

In certain embodiments, the activator of innate immune response is a TLR7 agonist. In certain embodiments, the activator of innate immune response is a TLR8 agonist. In certain embodiments, the activator of innate it inane response is a TLR7 agonist and a TLR8 agonist.

In certain embodiments, the activator of innate immune response is an immune response modifier (IRM).

In certain embodiments, the activator of innate immune response is any IRM disclosed in U.S. patent application Ser. No. 08/620,779, filed Mar. 22, 1996, the entire contents of which are incorporated herein by reference. In certain embodiments, the activator of innate immune response is any IRM disclosed in U.S. patent application Ser. No. 08/957,192, filed Oct. 24, 1997, the entire contents of which are incorporated herein by reference. In certain embodiments, the activator of innate immune response is any IRM disclosed in U.S. patent application Ser. No. 09/528,620, filed Mar. 20, 2000, the entire contents of which are incorporated herein by reference. In certain embodiments, the activator of innate immune response is any IRM disclosed in U.S. patent application Ser. No. 06/798,385, filed Nov. 15, 1985, the entire contents of which are incorporated herein by reference. In certain embodiments, the activator of innate immune response is any IRM disclosed in U.S. patent application Ser. No. 08/303,216, filed Sep. 8, 1994, the entire contents of which are incorporated herein by reference. In certain embodiments, the activator of innate immune response is any IRM disclosed in U.S. patent application Ser. No. 09/210,114, filed Dec. 11, 1998, the entire contents of which are incorporated herein by reference. In certain embodiments, the activator of innate immune response is any IRM disclosed in U.S. patent application Ser. No. 09/361,544, filed Jul. 27, 1999, the entire contents of which are incorporated herein by reference. In certain embodiments, the activator of innate immune response is any IRM disclosed in International Patent Application PCT/US2004/032480, filed Oct. 1, 2004, the entire contents of which are incorporated herein by reference.

In certain embodiments, the activator of innate immune response is CL307 (N1-glycinyl[4-((6-amino-2-(butylamino)-8-hydroxy-9H-purin-9-yl)methyl) benzoyl]spermine), or a pharmaceutically acceptable salt thereof. CL307 is a very potent TLR7 agonist. Titration experiments have showed that CL307 induces robust NF-κB activation even at concentrations as low as 20 nM (10 ng/ml).

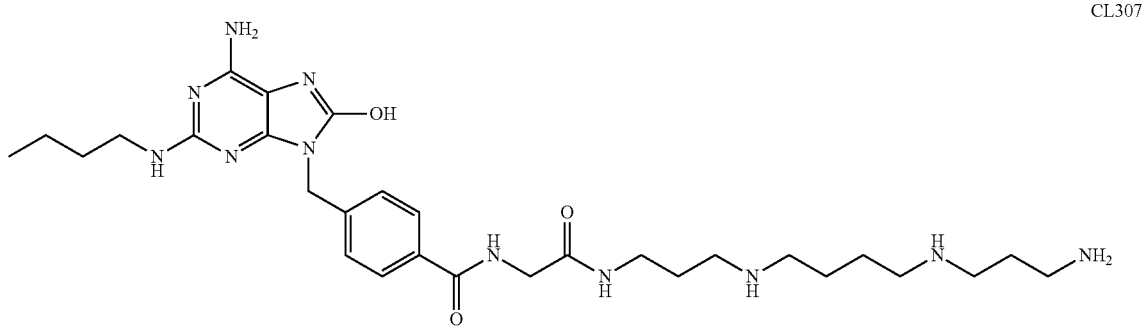 [SMILES: CCCCNc1nc(N)c2nc(O)n(Cc3ccc(C(=O)NCC(=O)NCCCNCCCCNCCCN)cc3)c2n1]

CL307

In certain embodiments, the activator of innate immune response is CL264, or a pharmaceutically acceptable salt thereof. CL264 induces the activation of NF-κB and the secretion of IFN-α, in TLR7-expressing cells. CL264 is a TLR7-specific ligand, it does not stimulate TLR8 even at high concentrations (>10 μg/ml). In TLR7-transfected HEK293 cells, CL264 triggers NF-κB activation at a concentration of 0.1 μM which is 5-10 times less than imiquimod.

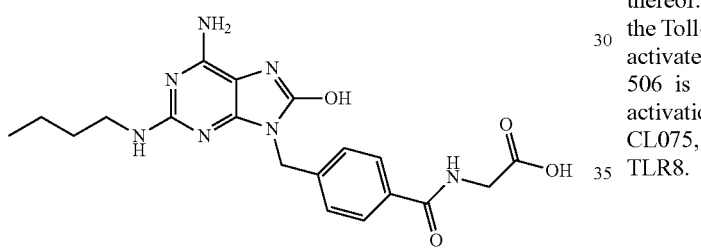

CL264

In certain embodiments, the activator of innate immune response is loxoribine, or a pharmaceutically acceptable salt thereof. Loxoribine is a guanosine analog derivatized at positions $N^7$ and $C^8$. This nucleoside is a very powerful stimulator of the immune system. Loxoribine activates the innate immune system through TLR7 and this activation requires endosomal maturation. Loxoribine recognition is restricted to TLR7.

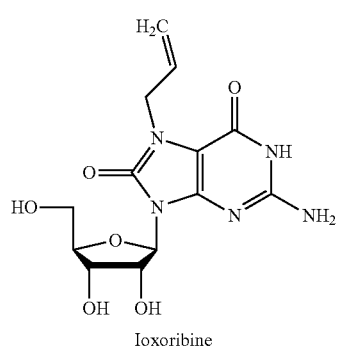

Loxoribine

In certain embodiments, the activator of innate immune response is hypoxanthine, or a pharmaceutically acceptable salt thereof. Hypoxanthine is a naturally occurring purine derivative.

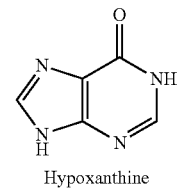

Hypoxanthine

In certain embodiments, the activator of innate immune response is TL8-506, or a pharmaceutically acceptable salt thereof. TL8-506 is a benzoazepine compound, an analog of the Toll-like receptor 8 (TLR8) agonist VTX-2337. TL8-506 activates TLR8 more potently than R848 and CL075. TL8-506 is ~50× and ~25× more potent in inducing NF-κB activation in TLR8-transfected HEK293 cells than R848 and CL075, respectively. TL8-506 is a selective agonist of TLR8.

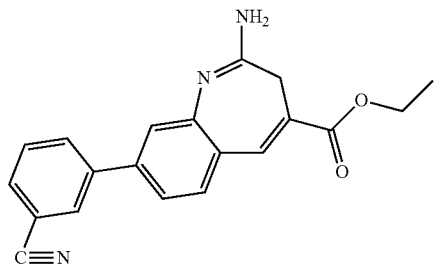

TL8-506

In certain embodiments, the activator of innate immune response is PF-4878691, isatoribine, SM-324405, SM-324406, AZ12441970, AZ12443988, or pharmaceutically acceptable salts thereof. PF-4878691, isatoribine, SM-324405, SM-324406, AZ12441970, and AZ12443988 are T L R7 agonists.

In certain embodiments, the activator of innate immune response is an imidazoquinoline derivative, including dactolisib, imiquimod, gardiquimod, resiquimod, sumanirole, and pharmaceutically acceptable salts thereof.

In certain embodiments, the activator of innate immune response is CL097, or a pharmaceutically acceptable salt thereof. CL097 is a highly water-soluble derivative resiquimod (≥ 20 mg/ml). CL097 is a TLR7 and TLR8 ligand. It induces the activation of NF-κB at 0.4 μM (0.1 μg/ml) in TLR7-transfected HEK293 cells and at 4 μM (1 μg/ml) in TLR8-transfected HEK293 cells.

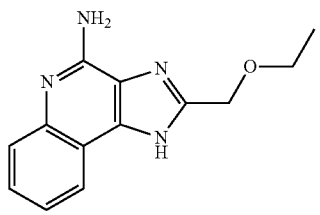

CL097

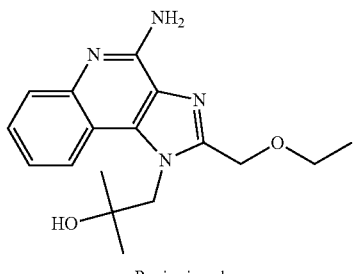

Resiquimod

In certain embodiments, the activator of innate immune response is CL075, or a pharmaceutically acceptable salt thereof. CL075 (3M002) is a thiazoloquinolone derivative that stimulates TLR8 in human peripheral blood mononuclear cells. It activates NF-κB and triggers preferentially the production of TNF-α and IL-12. CL075 also induces the secretion of IFN-α, through TLR7, but to a lesser extent. It induces the activation of NF-κB at 0.4 μM (0.1 μg/ml) in TLR8-transfected HEK293 cells, and ~10 times more CL075 is required to activate NF-κB in TLR7-transfected HEK293 cells.

In certain embodiments, the activator of innate immune response is a TLR7-selective antedrug. In certain embodiments, the activator of innate immune response is SM-324405, AZ12441970, or pharmaceutically acceptable salts thereof.

In certain embodiments, the activator of innate immune response is an inflammasome inducer. Inflammasomes are multimeric protein complexes that are crucial for host defense to infection and endogenous danger signals. They promote the secretion of the pro-inflammatory cytokines interleukin (IL)-1β and IL-18 and cause a rapid and pro-inflammatory form of cell death called pyroptosis.

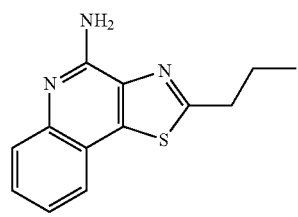

CL075

In certain embodiments, the activator of innate immune response is MEDI9197, or a pharmaceutically acceptable salt thereof. MEDI9197 (3M052) is an injectable TLR7 and TLR8 agonist. It is an imidazoquinoline immune response modifier (IRM) bearing a C18 lipid moiety and designed for slow dissemination from the site of application.

In certain embodiments, the activator of innate immune response is an inducer of NLRP3, AIM2, NLRC4, or NLRP1 inflammasomes.

In certain embodiments, the activator of innate immune response is

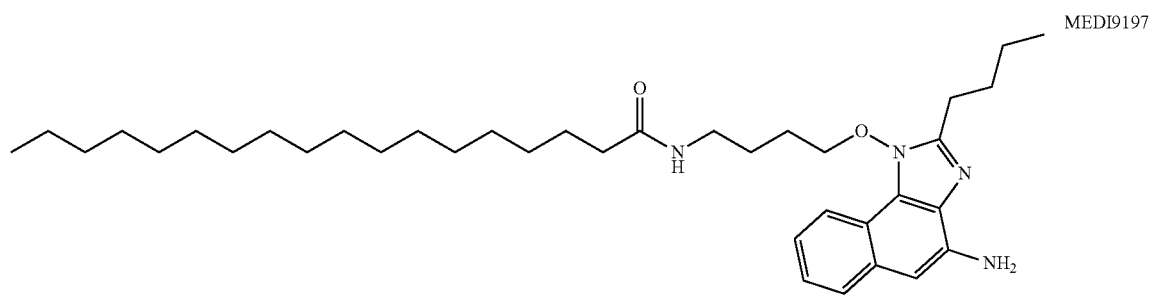 [SMILES: CCCCCCCCCCCCCCCCCC(=O)NCCCCOn1c(CCCC)nc2c(N)cc3ccccc3c21]

MEDI9197

In certain embodiments, the activator of innate immune response is resiquimod (R848), or a pharmaceutically acceptable salt thereof. In particular, resiquimod is an agent that acts as an immune response modifier and has antiviral and antitumor activity. It is used as a topical gel in the treatment of skin lesions such as those caused by the herpes simplex virus and cutaneous T cell lymphoma. It is also used as an adjuvant to increase the effectiveness of vaccines. It has several mechanisms of action, being both an agonist for toll-like receptor 7 (TLR7) and 8 (TLR8), and an upregulator of the opioid growth factor receptor.

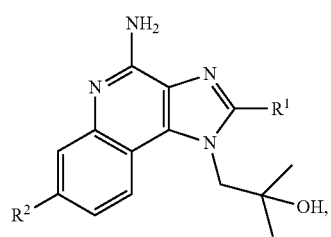

or a pharmaceutically acceptable salt thereof, wherein: $R^1$ is H, and $R^2$ is H; $R^1$ is a butyl group and $R^2$ is H; $R^1$ is H and $R^2$ is —$CO_2CH_3$; or $R^1$ is a butyl group and $R^2$ is —$CO_2CH_3$.

In certain embodiments, the activator of innate immune response is an imadazoquinoline; an imidazonaphthyridine; a pyrazolopyridine; an aryl-substituted imidazoquinoline; a compound having a 1-alkoxy 1H-imidazo ring system; an oxazolo [4,5-c]-quinolin-4-amine; a thiazolo [4,5-c]-quinolin-4-amine; a selenazolo [4,5-c]-quinolin-4-amine; an imidazonaphthyridine; an imidazoquinolinamine; a 1-substituted, 2-substituted 1H-imidazo[4,5-C]quinolin-4-amine, a fused cycloalkylimidazopyridine; a 1H-imidazo[4,5-c]quinolin-4-amine; a 1-substituted 1H-imidazo-[4,5-c]quinolin-4-amine; an imidazo-[4,5-C]quinolin-4-amine; a 2-ethyl 1H-imidazo[4,5-ciquinolin-4-amine; an olfenic 1H-imidazo[4,5-c]quinolin-4-amine; a 6,7-dihydro-8-(imidazol-1-yl)-5-methyl-1-oxo-1H,5H-benzo[i]quinolizine-2-carboxylic acid; a pyridoquinoxaline-6-carboxylic acid; a 6,7-dihydro-8-(imidazol-1-yl)-5-methyl-1-oxo-1H,5H-benzo[ij]quinolizine-2-carboxylic acid; a substituted naphtho[ij]quinolizine; a substituted pyridoquinoxaline-6-carboxylic acid; a 7-hydroxy-benzo[ij]quinolizine-2-carboxylic acid derivative; a substituted benzo[ij]quinolizine-2-carboxylic acid; a 7-hydroxy-benzo[ij]quinolizine-2-carboxylic acid; a substituted pyrido[1,2,3,-de]-1,4-benzoxazine; a N-methylene malonate of tetrahydroquinoline, or pharmaceutically acceptable salts thereof.

In certain embodiments, the activator of innate immune response is any NLRP3 agonist disclosed in U.S. patent application Ser. No. 15/253,215, filed Aug. 31, 2016, the entire contents of which are incorporated herein by reference.

In certain embodiments, the activator of innate immune response is a RORγ agonist. A RORγ agonist is an agent that promotes RORγ activity, such as by binding to and activating RORγ or by increasing expression of RORγ in a patient or population of cells. The RORγ agonist may be, for example, a small organic molecule, polypeptide, or nucleic acid. Various RORγ agonists are reported in the literature, such as in U.S. patent application Ser. No. 14/398,774; Zhang et al. in *Mol. Pharmacol.* (2012) vol. 82, pages 583-590; and Wang et al. in *ACS Chem. Biol.* (2010), vol. 5, pages 1029-1034; each of which is hereby incorporated by reference.

In certain embodiments, the activator of innate immune response is a RORγ agonist such as

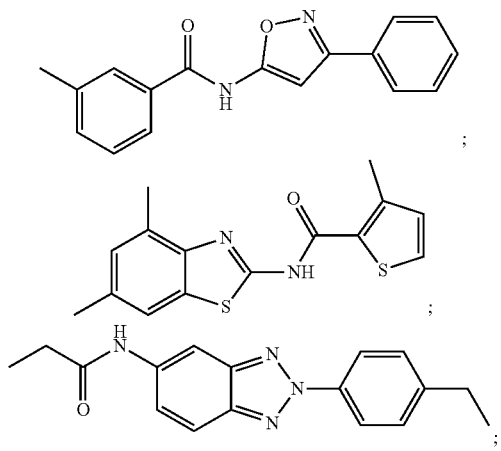

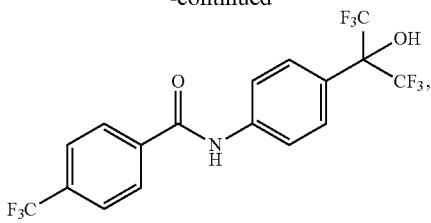

and pharmaceutically acceptable salts thereof.

In certain embodiments, the activator of innate immune response is a generic or specific compound described in U.S. patent application Ser. No. 14/398,774, such as a compound of Formula (I):

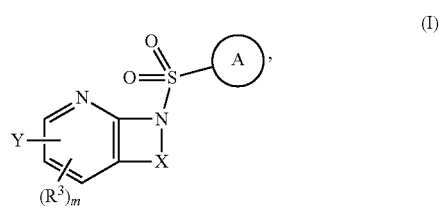

or a pharmaceutically acceptable salt thereof; wherein:

A is aryl, aralkyl, heteroaryl, cycloalkyl, or heterocycloalkyl; each of which is optionally substituted with 1, 2, or 3 substituents independently selected from the group consisting of halogen, hydroxyl, $C_1$-$C_6$alkyl, $C_1$-$C_6$haloalkyl, $C_1$-$C_6$hydroxyalkyl, $C_1$-$C_6$alkoxy, $C_1$-$C_6$haloalkoxy, —$N(R^4)(R^5)$, —$CO_2R^6$, —$C(O)R^6$, —CN, —$C_1$-$C_4$alkylene-$C_1$-$C_4$alkoxy, —$C_1$-$C_4$alkylene-$N(R^4)(R^5)$, —$C_1$-$C_4$alkylene $CO_2R^6$, —O—$C_1$-$C_6$alkylene $N(R^4)(R^5)$, —$N(R^4)C(O)$—$C_1$-$C_6$alkylene-$N(R^4)(R^5)$, —$S(O)_pC_1$-$C_6$alkyl, —$SO_2N(R^4)(R^5)$, —$N(R^4)(R^5)$, —$N(R^4)SO_2$ ($C_1$-$C_6$alkyl), —$C(O)N(R^4)(R^5)$, and —$N(R^4)C(O)N(R^4)(R^5)$;

X is —O—[$C(R^6)(R^7)$]—[$C(R^6)_2]_m$—Ψ, —O—C$(R^6)_2$—$C(R^6)(C(R^7)_2$—Ψ, —O—$C(R^6)_2$—$C(R^6)(R^7)$—Ψ, —$C(R^6)_2$—[$C(R^6)(R^7)$]—[$C(R^6)_2]_m$—Ψ, —C(O)—[$C(R^6)(R^7)$]—[$C(R^6)_2$]m, —$C(R^6)_2$—N$(R^8)$—[$C(R^6)(R^7)$]—[$C(R^6)_2$]m-Ψ, —$C(R^6)$=N—Ψ, —$C(R^6)_2C(R^6)$=N—Ψ, N=$C(R^6)$—Ψ, or N=$C(R^6)$ $C(R^6)_2$—Ψ; wherein Ψ is a bond to the sulfonamide ring nitrogen atom in Formula I;

Y is —$N(R^2)(R^3)$ or —O-aralkyl, wherein said aralkyl is optionally substituted with 1, 2, or 3 substituents independently selected from the group consisting of halogen, hydroxyl, $C_{1-6}$alkoxy, $C_{1-6}$haloalkoxy, —$N(R^4)(R^5)$, —CN, —$CO_2$—$C_{1-6}$alkyl, —$C(O)$—$C_{1-6}$alkyl, —$C(O)N(R^4)(R^5)$, —$SO_2N(R^4)(R^5)$, and —$N(R^4)SO_2$ ($C_{1-6}$alkyl);

$R^1$ represents independently for each occurrence hydrogen, halogen, or $C_{1-6}$alkyl;

$R^2$ is —C(O)-aryl, —C(O)-aralkyl, —C(O)—[$C(R^6)_2]_m$-cycloalkyl, —C(O)—[$C(R^6)_2]_m$-heterocyclyl, —C(O)—$C_{1-6}$alkyl, —C(O)—$C_{1-6}$alkylene-$C_{1-6}$alkoxyl, —C(O)—$C_{1-6}$alkylene-cycloalkyl, or —C(O)—$C_{1-6}$alkylene-heterocycloalkyl; each of which is optionally substituted with 1, 2, or 3 substituents independently selected from the group consisting of halogen, hydroxyl, $C_{1-6}$alkoxy, $C_{1-6}$haloalkoxy, $C_{1-6}$haloalkyl, —$N(R^4)(R^5)$, —CN, —$CO_2$—$C_1$-

$_6$alkyl, —C(O)—C$_{1-6}$alkyl, —C(O)N(R$^4$)(R$^5$), —S(O)$_p$C$_{1-6}$alkyl, —SO$_2$N(R$^4$)(R$^5$), and —N(R$^4$)SO$_2$(C$_{1-6}$alkyl);

R$^3$ is hydrogen or C$_{1-6}$alkyl;

R$^4$ and R$^5$ each represent independently for each occurrence hydrogen or C$_{1-6}$alkyl; or R$^4$ and R$^5$ taken together with the nitrogen atom to which they are attached form a 3-7 membered heterocyclic ring;

R$^6$ represents independently for each occurrence hydrogen or C$_{1-6}$alkyl;

R$^7$ is hydrogen, hydroxyl, C$_{1-6}$hydroxyalkyl, —CO$_2$R$^6$, C$_{1-6}$alkylene-CO$_2$R$^6$, C$_{1-4}$hydroxyalkylene-CO$_2$R$^6$, —N(R$^4$)(R$^5$), C$_{1-6}$alkylene-N(R$^4$)(R$^5$), C$_{1-6}$hydroxyalkylene-N(R$^4$)(R$^5$), —N(R$^4$)C(O)R$^9$, C$_{1-6}$alkylene-N(R$^4$)C(O)R$^9$, C$_{1-6}$alkylene-C(O)N(R$^4$)(R$^5$), —N(R$^4$)CO$_2$—C$_{1-6}$alkyl, or C$_{1-6}$alkylene-N(R$^4$)(C(O)N(R$^4$)(R$^5$); or R$^7$ is heterocycloalkyl or C$_{1-4}$alkylene-heterocycloalkyl, wherein the heterocycloalkyl is optionally substituted with 1, 2, or 3 substituents independently selected from the group consisting of oxo, halogen, hydroxyl, C$_{1-6}$alkyl, C$_{1-6}$hydroxyalkyl, C$_{1-6}$alkoxy, and C$_{1-6}$haloalkoxy;

R$^8$ is hydrogen, C$_{1-6}$alkyl, or —C(O)—C$_{1-6}$alkyl;

R$^9$ is hydrogen, C$_{1-6}$alkyl, C$_{1-6}$hydroxyalkyl, C$_{1-6}$alkylene-N(R$^4$) or C$_{1-6}$alkylene-N(R$^4$C(O)—C$_{1-6}$alkyl;

n is 1 or 2; and m and p each represent independently for each occurrence 0, 1, or 2.

In certain embodiments, the activator of innate immune response is any RORγ agonist disclosed in U.S. patent application Ser. No. 14/398,774, filed Nov. 4, 2014, the entire contents of which are incorporated herein by reference. In certain embodiments, the activator of innate immune response is any RORγ agonist disclosed in U.S. patent application Ser. No. 15/120,798, filed Aug. 23, 2016, the entire contents of which are incorporated herein by reference.

Cytokine

The drug delivery compositions and devices may comprise a cytokine. Cytokines are a broad category of small proteins (~5-20 kDa) that are important in cell signaling. Their release has an effect on the behavior of cells around them. Cytokines are involved in autocrine signalling, paracrine signaling, and endocrine signaling as immunomodulating agents. Cytokines include chemokines, interferons, interleukins, lymphokines, and tumour necrosis factors. Cytokines are produced by a broad range of cells, including immune cells, such as macrophages, B lymphocytes, T lymphocytes, and mast cells, as well as endothelial cells, fibroblasts, and various stromal cells. They act through receptors and play an important role in the immune system. Cytokines modulate the balance between humoral and cell-based immune responses, and they regulate the maturation, growth, and responsiveness of particular cell populations. Some cytokines enhance or inhibit the action of other cytokines in complex ways. Cytokines are important in host responses to infection, immune responses, inflammation, trauma, sepsis, cancer, and reproduction.

Furthermore, it is currently known in the art that the method of delivery, dosing and scheduling, and toxicity-related issues must be addressed to enable the immune-stimulating function of many cytokines and chemokines to be fully exploited.

In certain embodiments, the cytokine is IL-1, IL-1α, IL-1β, IL-2, an IL-2 superkine, IL-6, IL-7, IL-9, AM0010, IL-12, IL-15, an IL-15 superagonist, ALT-803, NIZ985, IL-16, IL-18, IL-21, an IL-21 superagonist, denenicokin, an IL-21 superagonist antibody, IFN-α, IFN-β, IFN-γ, TNF-α, GM-CSF, a cytokine fusion, RG7461, RG7813, or M9241.

In certain embodiments, the cytokine is ALT-803, NIZ985, denenicokin, RG7461, RG7813, M9241, IFN-α, IFN-β, or IFN-γ.

In certain embodiments, the cytokine is an IL-15 superagonist or IL-21. In certain embodiments, the cytokine is an IL-15 superagonist.

In certain embodiments, the cytokine is an IL-15 superagonist, IL-21, IFN-α, IFN-β, IFN-γ, CCL4, CCL5, or CXCL10. In certain embodiments, the cytokine is an IL-15 superagonist, IFN-α, or IFN-γ. In certain embodiments, the cytokine is an IL-15 superagonist or IFN-α.

IL-15 (Interleukin 15) is a cytokine with structural similarity to IL-2 and is secreted by mononuclear phagocytes following infection by virus(es). IL-15 induces cell proliferation of natural killer cells, cells whose, principal role is to kill virally infected cells. The combination of IL-15 with soluble IL-15Rα generates a complex termed IL-15 superagonist (IL-15sa) that possesses greater biological activity than IL-15 alone. IL-15sa is an antitumor and antiviral agent because of its ability to selectively expand NK and memory CD8+ T (mCD8+ T) lymphocytes.

In certain embodiments, the cytokine is an IL-15 superagonist known as ALT-803, an IL-15 superagonist. ALT-803 is thought to induce memory CD8+ T cells to proliferate, upregulate receptors involved in innate immunity, secrete interferon-γ, and acquire the ability to kill malignant cells in the absence of antigenic stimulation. Thus, ALT-803 can promote the expansion and activation of memory CD8+ T cells while converting them into innate immune effector cells that exhibit robust antineoplastic activity. ALT-803 is a fusion protein of an IL-15 mutant and the IL-15Rα/Fc complex that has recently entered clinical trials as a direct immunomodulatory agent. ALT-803 exhibits >25-fold enhancement in biological activity as compared to IL-15.

In certain embodiments, the cytokine is NIZ985 (hetIL-15). Studies have demonstrated that hetIL-15 administration can promote an increase of tumor infiltration and persistence of CD8+ T cells, including tumor-specific T cells, and result in an increased CD8+/Treg ratio. Tumor-resident CD8+ T cells show features of effector cells and are characterized by increased proliferation (Ki67+) and high cytotoxic potential (Granzyme B+). In the absence of hetIL-15, the smaller population of tumor-infiltrating T cells exhibit high levels of the exhaustion marker PD-1, potentially limiting their anti-cancer effectiveness. Provision of hetIL-15 can result in a significant decrease in lymphocyte expression of PD-1, alleviating one potential mechanism for the exhaustion phenotype. Preclinical cancer studies support the use of hetIL-15 in tumor immunotherapy approaches to promote the development of anti-tumor responses by favoring effector over regulatory cells.

In certain embodiments, the cytokine is interferon α (IFN-α). The IFN-α proteins are produced by leukocytes. They are mainly involved in innate immune response against viral infection.

In certain embodiments, the cytokine is interferon β (IFN-β). IFN-β comprises proteins produced by fibroblasts and is involved in innate immune response. IFN-β stimulates both macrophages and NK cells to elicit an anti-viral response, and are also active against tumors. In mice, IFN-β inhibits immune cells to produce growth factors, thereby slowing tumor growth, and inhibits other cells from producing vessel producing growth factors, thereby blocking tumor angiogenesis and hindering the tumor from connecting into the blood vessel system.

In certain embodiments, the cytokine is interferon γ (IFN-γ). IFN-γ, or type II interferon, is a cytokine that is useful for innate and adaptive immunity. IFN-γ is an important activator of macrophages and inducer of Class II major histocompatibility complex (MHC) molecule expression. The in vitro study of IFN-γ in cancer cells is extensive and results indicate anti-proliferative activity of IFN-γ leading to growth inhibition or cell death, generally induced by apoptosis but sometimes by autophagy. Clinical administration of IFN-γ has resulted in improved survival for patients with ovarian, bladder, and melanoma cancers.

In certain embodiments, the cytokine is IL-1β. IL-1β is produced as a proprotein, which is proteolytically processed to its active form by caspase 1. This cytokine is an important mediator of the inflammatory response and is involved in a variety of cellular activities.

In certain embodiments, the cytokine is a chemokine. Chemokines are a family of small cytokines. The major role of chemokines is to act as a chemoattractant to guide the migration of cells. Some chemokines control cells of the immune system during processes of immune surveillance, such as directing lymphocytes to the lymph nodes so they can screen for invasion of pathogens by interacting with antigen-presenting cells residing in these tissues. These are known as homeostatic chemokines and are produced and secreted without any need to stimulate their source cell(s). Some chemokines play a role in development, promote angiogenesis (the growth of new blood vessels), or guide cells to tissues that provide specific signals critical for cellular maturation. Other chemokines are inflammatory and are released from a wide variety of cells in response to bacteria, viruses, and agents that cause physical damage, such as silica or the urate crystals that occur in gout. Their release is often stimulated by pro-inflammatory cytokines, such as interleukin 1. Inflammatory chemokines function mainly as chemoattractants for leukocytes, recruiting monocytes, neutrophils, and other effector cells from the blood to sites of infection or tissue damage. Certain inflammatory chemokines activate cells to initiate an immune response or promote wound healing. They are released by many different cell types and serve to guide cells of both the innate immune system and adaptive immune system.

Furthermore, it is currently known in the art that the method of delivery, dosing and scheduling, and toxicity-related issues must be addressed to enable the immune-stimulating function of many chemokines to be fully exploited.

In certain embodiments, the chemokine is CCL1, CCL2, CCL3, CCL4, CCL5, CCL17, CCL19, CCL21, CCL22, CXCL9, CXCL10, CXCL11, CXCL13, CXCL16, or CX3CL1.

Activator of Adaptive Immune Response

The drug delivery compositions and devices may comprise one or more activators of adaptive immune response.

The adaptive immune response system, also known as the acquired immune system, is a subsystem of the overall immune system that includes highly specialized systemic cells and processes that eliminate or prevent pathogen growth. The adaptive immune system is one of the two main immunity strategies found in vertebrates (the other being the innate immune system). Adaptive immunity creates immunological memory after an initial response to a specific pathogen and leads to an enhanced response to subsequent encounters with that pathogen. This process of acquired immunity is the basis of vaccination. Like the innate system, the adaptive system includes both humoral immunity components and cell-mediated immunity components. Unlike the innate immune system, the adaptive immune system is highly specific to a particular pathogen.

The adaptive immune response system is triggered in vertebrates when a pathogen evades the innate immune response system, generates a threshold level of antigen, and generates "stranger" or "danger" signals activating dendritic cells. The major functions of the acquired immune system include recognition of specific "non-self" antigens in the presence of "self" during the process of antigen presentation; generation of responses that are tailored to eliminate specific pathogens or pathogen-infected cells; and development of immunological memory, in which pathogens are "remembered" through memory B cells and memory T cells.

Useful approaches to activating the adaptive immune response system (e.g., activating therapeutic antitumor immunity) include the blockade of immune checkpoints. Immune checkpoints refer to a plethora of inhibitory pathways hardwired into the immune system that are crucial for maintaining self-tolerance and modulating the duration and amplitude of physiological immune responses in peripheral tissues in order to minimize collateral tissue damage. Tumors co-opt certain immune-checkpoint pathways as a major mechanism of immune resistance, particularly against T cells that are specific for tumor antigens. Because many of the immune checkpoints are initiated by ligand-receptor interactions, they can be readily blocked by antibodies or modulated by recombinant forms of ligands or receptors. Cytotoxic T-lymphocyte-associated antigen 4 (CTLA-4) antibodies were the first of this class of immunotherapeutics to receive FDA approval (ipilimumab). Preliminary clinical findings with blockers of additional immune-checkpoint proteins, such as programmed cell death protein 1 (PD-1), indicate broad and diverse opportunities to enhance antitumor immunity with the potential to produce durable clinical responses.

PD-1, functioning as an immune checkpoint, plays an important role in down-regulating the immune system by preventing the activation of T cells, which in turn reduces autoimmunity and promotes self-tolerance. The inhibitory effect of PD-1 is accomplished through a dual mechanism of promoting apoptosis (programmed cell death) in antigen-specific T cells in lymph nodes while simultaneously reducing apoptosis in regulatory T cells (suppressor T cells). A new class of therapeutics that block PD-1, the PD-1 inhibitors (e.g., anti-PD-1 antibodies), activate the immune system to attack tumors and are therefore used to treat some types of cancer. In addition, antibodies of Programmed death-ligand 1 (PD-L1) provide a similar impact on activating the adaptive immune response as antibodies targeting PD-1. Accordingly, compositions and devices comprising anti-PD-L1 antibodies are expected to provide a similar therapeutic effect as those comprising anti-PD-1 antibodies.

In certain embodiments, the activator of adaptive immune response is a small molecule. In certain embodiments, the activator of adaptive immune response is a biologic. In certain embodiments, the biologic is a protein. In certain embodiments, the biologic is an antibody or fragment thereof. In certain embodiments, the biologic is a nucleic acid that encodes a protein.

In certain embodiments, the activator of adaptive immune response is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD3 antibody, an anti-CD27 antibody, an anti-CD28 antibody, an anti-CD28H antibody, an anti-CD30 antibody, an anti-CD39 antibody, an anti-CD40 antibody, an anti-CD43 antibody, an anti-CD47 antibody, an anti-CD48 antibody, an anti-CD70 antibody, an anti-CD73 antibody, an anti-CD96 antibody, an anti-CD123 antibody, an anti-CD155 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-CEACAM1 antibody, an anti-CEACAM5 antibody, an anti-CEACAM6 antibody, an anti-MICA antibody, an anti-MICB antibody, an anti-NKG2D antibody, an anti-NKG2A antibody, an anti-A2AR antibody, an anti-C5aR antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, an anti-Tie2 antibody, an anti-CCR4 antibody, or an anti-TRAIL-DR5 antibody.

In certain embodiments, the activator of adaptive immune response is a fragment of any of the antibodies listed above. In certain embodiments, the activator of adaptive immune response is a humanized form of any of the antibodies listed above. In certain embodiments, the activator of adaptive immune response is a single chain of any of the antibodies listed above. In certain embodiments, the activator of immune response is a multimeric form of any of the antibodies listed above (e.g., dimeric IgA molecules, pentavalent IgM molecules).

In certain embodiments, the activator of adaptive immune response is an anti-PD-1 antibody, an agonist anti-CD137 antibody, an agonist anti-CD40 antibody, an anti-CTLA-4 antibody, an anti-LAG-3 antibody, an anti-TIM3, or a combination thereof, in certain embodiments, the activator of adaptive immune response is an anti-PD-1 antibody or an anti-CTLA-4 antibody. In certain embodiments, the activator of adaptive immune response is an anti-PD-1 antibody. In certain embodiments, the activator of adaptive immune response is an anti-CTLA-4 antibody. In certain embodiments, the activator of adaptive immune response is an agonist anti-CD137 antibody. In certain embodiments, the activator of adaptive immune response is an anti-LAG-3 antibody. In certain embodiments, the activator of adaptive immune response is an anti-T1M3 antibody.

In certain embodiments, the activator of adaptive immune response is pembrolizumab, nivolumab, pidilizumab, ipilimumab, tremelimumab, durvalumab, atezolizumab, avelumab, PF-06801591, utomilumab, PDR001, PBE-509, MGB453, LAG-525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, IPH5401, IPH4102, IPH4301, IPH52, IPH53, varlilumab, ulocuplumab, monalizumab, MEDI0562, MEDI0680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, IMC-CS4, emactuzumab, trastuzumab, pertuzumab, obinutuzumab, cabiralizumab, margetuximab, enoblituzumab, mogamulizumab, panitumumab, carlumab, ramucirumab, bevacizumab, rituximab, cetuximab, fresolimumab, denosumab, MGA012, AGEN1884, AGEN2034, LY3300054, JTX-4014, teplizumab, FPA150, PE-04136309, PF-06747143, AZD5069, GSK3359609, FAZ053, TSR022, MBG453, REGN2810, REGN3767, MOXR0916PF-04518600, RO7009789, BMS986156, GWN323, JTX-2011, NKTR-214, GSK3174998, DS-8273a, NIS793, or BGB-A317.

In certain embodiments, the activator of adaptive immune response is pembrolizumab, nivolumab, pidilizumab, ipilimumab, tremelimumab, durvalumab, atezolizumab, REGN2810, MGA012, AGEN1884, AGEN2034, LY3300054, ITX-4014, or avelumab.

In certain embodiments, the activator of adaptive immune response is an antibody mimetic or antibody fusion.

In certain embodiments, the activator of adaptive immune response is a bispecific antibody. In certain embodiments, the bispecific antibody is RG7802 (antibody targeting carcinoembryonic antigen (CEA) and the CD3 receptor), RG7828 (a bispecific monoclonal antibody that targets CD20 on B cells and CD3 on T cells), RG7221 (a bispecific monoclonal antibody that targets VEGE and angiopoietin 2), RG7386 (a bispecific monoclonal antibody that targets FAP and DR5), ERY974 (a bispecific monoclonal antibody that targets CD3 and glypican-3), MGD012 (a bispecific monoclonal antibody that targets PD-1 and LAG-3), AMG211 (a bispecific T cell engager that targets CD3 and CEA), MED1573 (a bispecific monoclonal antibody that targets IGF1 and IGF2), MED1565 (a bispecific monoclonal antibody that targets CD3 and CEA), FS17 (undisclosed targets), FS18 (a bispecific monoclonal antibody that targets LAG3 and an undisclosed target), FS20 (undisclosed targets), FS22 (undisclosed targets), FS101 (a bispecific monoclonal antibody that targets EGFR and HGF), FS117 (undisclosed targets), FS118 (a bispecific monoclonal antibody that targets LAG3 and PD-L1), RO6958688 (a bispecific monoclonal antibody that targets CD3 and CEA), MCLA-128 (a bispecific monoclonal antibody that targets HER2 and HER3), M7824 (bi-functional fusion-protein targeting PD-L1 and TGFβ), MGD009 (a humanized antibody that recognizes both B7-H3 and CD3), or MGD013 (a bispecific PD-1 and LAG-3 antibody).

In certain embodiments, the activator of adaptive immune response is an antibody-drug conjugate. In certain embodiments, the antibody-drug conjugate is trastuzumab emtansine, inotuzumab ozogamicin, PF-06647020, PF-06647263, PF-06650808, RG7596, RG7841, RG7882, RG7986, DS-8201, ABBV-399, glembatumumab vedotin, inotuzumab ozogamicin, MED14276, or pharmaceutically acceptable salts thereof.

In certain embodiments, the activator of adaptive immune response is a small molecule. In certain embodiments, the small molecule is an IDO inhibitor, a TGFβR inhibitor, a BRAF inhibitor, a KIT inhibitor, an A2aR inhibitor, a Tie2 inhibitor, an arginase inhibitor, an iNOS inhibitor, an HIF1α inhibitor, a STAT3 inhibitor, a PGE2 inhibitor, a PDE5 inhibitor, a RON inhibitor, an mTOR inhibitor, a JAK2 inhibitor, a HSP90 inhibitor, a PI3K-AKT inhibitor, a β-catenin inhibitor, a GSK3β inhibitor, an IAP inhibitor, an HDAC inhibitor, a DNMT inhibitor, a BET inhibitor, a COX2 inhibitor, a PDGFR inhibitor, a VEGFR inhibitor, a BCR-ABL inhibitor, a proteasome inhibitor, an angiogenesis inhibitor, a MEK inhibitor, a BRAF+MEK inhibitor, a pan-RAF inhibitor, an EGFR inhibitor, a PARP inhibitor, a glutaminase inhibitor, a WNT inhibitor, a FAK inhibitor, an ALK inhibitor, a CDK4/6 inhibitor, or an FGFR3 inhibitor.

In certain embodiments, the small molecule is celecoxib, sunitinib, imatinib, vemurafenib, dabrafenib, bortezomib, vorinostat, pomalidomide, thalidomide, lenalidomide, epacadostat, indoximid, GDC0919, BMS986205, AZD8055, AZD4635, CPI-444, PBF509, LCL161, CB-839, CB-1158, FPA008, BLZ945, IPI-549, pexidartinib, galunisertib, birinapant, trametinib, cobimetinib, binimetinib, ensartib, gefitinib, pazopanib, sorafenib, nintedanib, SYM004, veliparib, olaparib, BGB-290, everolimus, LXH254, azacitidine, decitabine, guadecitabine, RRX001, CC486, romidepsin, entinostat, panobinostat, tamoxifen, ibrutinib, idelalisib, capmatinib, selumetinib, abemaciclib, palbocielib, glasdegib, enzalutamide, AZD9150, PF-06840003, SRF231, Hu5F9-G4, CC-900002, TTI-621, WNT974, BGJ398, LY2874455, or pharmaceutically acceptable salts thereof.

Additional Therapeutic Agents

The drug delivery compositions and devices may comprise additional therapeutic agents.

In certain embodiments, the drug delivery compositions and devices may comprise a modulator of macrophage effector function. Macrophages are immune cells that are derived from circulating monocytes, reside in all tissues, and participate in many states of pathology. Macrophages play a dichotomous role in cancer, where they can promote tumor growth but also can serve as critical immune effectors of therapeutic antibodies. Macrophages express all classes of Fcγ receptors, and they have potential to destroy tumors via the process of antibody-dependent cellular phagocytosis. A number of studies have demonstrated that macrophage phagocytosis is a major mechanism of action of many antibodies approved to treat cancer. Consequently, a number of approaches to augment macrophage responses to therapeutic antibodies are under investigation, including the exploration of new targets and development of antibodies with enhanced functions. The response of macrophages to antibody therapies can also be enhanced with engineered Fc variants, bispecific antibodies, or antibody-drug conjugates. Macrophages have demonstrated success as effectors of cancer immunotherapy.

In certain embodiments, the modulator of macrophage effector function is a modulator of suppressive myeloid cells, including myeloid-derived suppressor cells (MDSCs). In certain embodiments, the modulator of macrophage effector function may kill, deplete, or potentiate macrophages and/or MDSCs. In certain embodiments, the modulator of macrophage effector function is an anti-CD40 antibody, an anti-CD47 antibody, an anti-CSF1 antibody, or an anti-CSF1R antibody. In certain embodiments, the modulator of macrophage effector function is SRF231, Hu5F9-G4, CC-900002, or TTI-621 (anti-CD47 antibodies). In certain embodiments, the modulator of macrophage effector function is MCS-110 (an anti-CSF1 antibody). In certain embodiments, the modulator of macrophage effector function is FPA008, RG7155, IMC-CS4, AMG820, or UCB6352 (anti-CSF1R antibodies). In certain embodiments, the modulator of macrophage effector function is a small molecule inhibitor of CSF1R. In certain embodiments, the modulator of macrophage effector function is BLZ945, GW2580, or PLX3397 (small molecule inhibitors of CSF1R). In certain embodiments, the modulator of macrophage effector function is a BTK inhibitor, an ITK inhibitor, a PI3Kγ inhibitor, or a PI3Kδ inhibitor. In certain embodiments, the modulator of macrophage effector function may replace one or more activators of adaptive immune response in the composition or device.

In certain embodiments, the drug delivery compositions and devices may further comprise an oncolytic virus. In certain embodiments, the oncolytic virus includes, but is not limited to, herpes simplex viruses (e.g., HSV1716, OncoVex GM-CSF); adenoviruses (e.g., H101, Onyx-15); polioviruses (e.g., PV1(RIPO)); reoviruses (e.g., reolysin); senecaviruses (e.g., NTX-010, SVV-001); Rigvir virus; maraba virus; measles; Newcastle disease virus; vaccinia; or ECHO virus.

In certain embodiments, the drug delivery compositions and devices may further comprise a radioactive isotope (e.g., as part of a molecule or on a bead). In certain embodiments the radioactive isotope is Yttrium-90, Palladium-103, Iodine-125, Cesium 131, or Iridium 192.

In certain embodiments, the drug delivery compositions and devices may further comprise a chemotherapeutic agent. In certain embodiments, the chemotherapeutic agent includes, but is not limited to, anti-estrogens (e.g., tamoxifen, raloxifene, and megestrol), LHRH agonists (e.g., goscrelin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine and temozolomide), platinum-containing compounds (e.g., cisplatin, carboplatin, and oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, and mytomycin C), anti-metabolites, DHFR inhibitors (e.g., methotrexate, dichloromethotrexate, trimetrexate, and edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, and capecitabine), cytosine analogs (e.g., cytarabine (ara C), cytosine arabinoside, and fludarabine), purine analogs (e.g., mercaptopurine and thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, and peplomycin), anthracycline (e.g., daunorubicin, doxorubicin, pegylated liposomal doxorubicin, idarubicin, epirubicin, pirarubicin, zorubicin, and mitoxantrone). MDR inhibitors (e.g., verapamil), $Ca^{2+}$ ATPase inhibitors (e.g., thapsigargin), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, hexamethyl melamine, and pharmaceutically acceptable salts thereof.

In certain embodiments, the chemotherapeutic agent is an immunomodulatory chemotherapeutic agent. In certain embodiments, the chemotherapeutic agent has known immunomodulatory function (e.g., induction of immunogenic cell death or depletion of immunosuppressive regulatory immune cells). In certain embodiments, the chemotherapeutic agent is included in the drug delivery compositions and devices due to its immunotherapeutic properties rather than its use as a conventional cancer-cell intrinsic cytotoxic chemotherapy. In certain embodiments, the drug delivery compositions and devices do not comprise a chemotherapeutic agent. In certain embodiments, the drug delivery compositions and devices do not comprise a cytotoxic agent.

In certain embodiments, the drug delivery compositions and devices may further comprise a targeted agent. In certain embodiments, the targeted agent includes, but is not limited to, an IDO inhibitor, a TGFβ inhibitor, an arginase inhibitor, an iNOS inhibitor, a HIF1α inhibitor, a STAT3 inhibitor, a CSF1R inhibitor, a PGE2 inhibitor, a PDE5 inhibitor, a RON inhibitor, an mTOR inhibitor, a JAK2 inhibitor, an HSP90 inhibitor, a PI3K-AKT inhibitor, a β-catenin inhibitor, a GSK3β inhibitor, an IAP inhibitor, an HDAC inhibitor, a DNMT inhibitor, a BET inhibitor, an A2AR inhibitor, a BRAF+MEK inhibitor, a pan-RAF inhibitor, a PI3Kγ inhibitor, a PI3Kδ inhibitor, an EGFR inhibitor, a VEGF inhibitor, a PARP inhibitor, a glutaminase inhibitor, a BTK inhibitor, an inhibitor, a WNT inhibitor, a FAK inhibitor, an ALK inhibitor, a CDK4/6 inhibitor, a or an FGFR3 inhibitor.

In certain embodiments, the targeted agent includes, but is not limited to, imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG 10), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), epacadostat, indoximid, GDC0919, BMS986205, AZD4635, CPI-444, PBF509, LCL161, CB-839, CB-1158, FPA008, BLZ945, IPI-549, pexidartinib, galunisertib, birinapant, trametinib, dabrafenib, vemurafenib, cobimetinib, binimetinib, ensartib, pazopanib, nintedanib, SYM004, veliparib, olaparib, BGB-290. LXH254, azacitidine, decitabine, guadecitabine, RRX001, CC486, romidepsin, entinostat, vorinostat, panobinostat, tamoxifen, ibrutinib, idelalisib, capmatinib, selumetinib, abemaciclib, palbociclib, glasdegib, enzalutamide, AZD9150, PF-06840003, SRF231, Hu5F9-G4, CC-900002, TTI-621, WNT974, BGJ398, LY2874455, an anti-Tie2 antibody, or pharmaceutically acceptable salts thereof.

Embodiments of the Drug Delivery Compositions and Devices

In certain embodiments, the drug delivery compositions and devices comprise a hydrogel and an activator of innate immune response.

In certain embodiments, the drug delivery compositions and devices comprise a hydrogel, an activator of innate immune response, and an additional activator of innate immune response.

In certain embodiments, the drug delivery compositions and devices comprise a hydrogel, an activator of innate immune response, and a cytokine.

In certain embodiments, the drug delivery compositions and devices comprise a hydrogel, an activator of innate immune response, an additional activator of innate immune response, and a cytokine.

In certain embodiments, the drug delivery compositions and devices comprise a hydrogel, an activator of innate immune response, and a chemokine.

In certain embodiments, the drug delivery compositions and devices comprise a hydrogel, an activator of innate immune response, an additional activator of innate immune response, and a chemokine.

In certain embodiments, the drug delivery compositions and devices comprise a hydrogel and a cytokine.

In certain embodiments, the drug delivery compositions and devices comprise a hydrogel and a chemokine.

In certain embodiments, the drug delivery compositions and devices comprise a hydrogel and an activator of adaptive immune response.

In certain embodiments, the drug delivery compositions and devices comprise a hydrogel, an activator of innate immune response, and an activator of adaptive immune response.

In certain embodiments, the drug delivery compositions and devices comprise a hydrogel, an activator of innate immune response, an additional activator of innate immune response, and an activator of adaptive immune response.

In certain embodiments, the drug delivery compositions and devices comprise a hydrogel, an activator of adaptive immune response, and an additional activator of adaptive immune response.

In certain embodiments, the drug delivery compositions and devices comprise a hydrogel, an activator of adaptive immune response, and two additional activators of the adaptive immune response.

In certain embodiments, the drug delivery compositions and devices comprise a hydrogel, an activator of innate immune response, a cytokine, and an activator of adaptive immune response.

In certain embodiments, the drug delivery compositions and devices comprise a hydrogel, an activator of innate immune response, an additional activator of innate immune response, a cytokine, and an activator of adaptive immune response.

In certain embodiments, the drug delivery compositions and devices comprise a hydrogel, an activator of innate immune response, a cytokine, an activator of adaptive immune response, and an additional activator of adaptive immune response.

In certain embodiments, the drug delivery compositions and devices comprise a hydrogel, an activator of innate immune response, an additional activator of innate immune response, a cytokine, an activator of adaptive immune response, and an additional activator of adaptive immune response.

In certain embodiments, the drug delivery compositions and devices comprise a hydrogel, an activator of innate immune response, a chemokine, and an activator of adaptive immune response.

In certain embodiments, the drug delivery compositions and devices comprise a hydrogel, an activator of innate immune response, an additional activator of innate immune response, a chemokine, and an activator of adaptive immune response.

In certain embodiments, the drug delivery compositions and devices comprise a hydrogel, an activator of innate immune response, a chemokine, an activator of adaptive immune response, and an additional activator of adaptive immune response.

In certain embodiments, the drug delivery compositions and devices comprise a hydrogel, an activator of innate immune response, an additional activator of innate immune response, a chemokine, an activator of adaptive immune response, and an additional activator of adaptive immune response.

In certain embodiments, the drug delivery compositions and devices comprise a hydrogel, a cytokine, and an activator of adaptive immune response.

In certain embodiments, the drug delivery compositions and devices comprise a hydrogel, a cytokine, an activator of adaptive immune response, and an additional activator of adaptive immune response.

In certain embodiments, the drug delivery compositions and devices comprise a hydrogel, a chemokine, and an activator of adaptive immune response.

In certain embodiments, the drug delivery compositions and devices comprise a hydrogel, a chemokine, an activator of adaptive immune response, and an additional activator of adaptive immune response.

In certain embodiments, the drug delivery compositions and devices comprise a hydrogel and an NLR agonist.

In certain embodiments, the drug delivery compositions and devices comprise a hydrogel and M-TriDAP.

In certain embodiments, the drug delivery compositions and devices comprise a hydrogel, M-TriDAP, and an IL-15 superagonist.

In certain embodiments, the drug delivery compositions and devices comprise a hydrogel, M-TriDAP, and an anti-PD-1 antibody.

In certain embodiments, the drug delivery compositions and devices comprise a hydrogel, M-TriDAP, and an anti-CTLA-4 antibody.

In certain embodiments, the drug delivery compositions and devices comprise hydrogel, a stimulator of interferon genes (STING) agonist, and M-TriDAP.

In certain embodiments, the drug delivery compositions and devices comprise a hydrogel, a stimulator of interferon genes (STING) agonist, M-TriDAP, and an IL-15 superagonist.

In certain embodiments, the drug delivery compositions and devices comprise a hydrogel, a TLR7 and/or TLR8 agonist, and M-TriDAP.

In certain embodiments, the drug delivery compositions and devices comprise a hydrogel, a TLR7 and/or TLR8 agonist, M-TriDAP, and an anti-PD-1 antibody.

In certain embodiments, the drug delivery compositions and devices comprise a hydrogel and IL-1β.

In certain embodiments, the drug delivery compositions and devices comprise a hydrogel and a stimulator of interferon genes (STING) agonist.

In certain embodiments, the drug delivery compositions and devices comprise a hydrogel and 2′-3′-cGAMP.

In certain embodiments, the drug delivery compositions and devices comprise a hydrogel and 2′-3′-c-di-AM(PS)2 (Rp,Rp).

In certain embodiments, the drug delivery compositions and devices comprise a hydrogel and an IL-15 superagonist.

In certain embodiments, the drug delivery compositions and devices comprise a hydrogel and interferon α (IFN-α).

In certain embodiments, the drug delivery compositions and devices comprise a hydrogel and interferon β (IFN-β).

In certain embodiments, the drug delivery compositions and devices comprise a hydrogel and interferon γ (IFN-γ).

In certain embodiments, the drug delivery compositions and devices comprise a hydrogel, a stimulator of interferon genes (STING) agonist, and an IL-15 superagonist.

In certain embodiments, the drug delivery compositions and devices comprise a hydrogel, 2′-3′-cGAMP, and an IL-15 superagonist.

In certain embodiments, the drug delivery compositions and devices comprise a hydrogel, 2′-3′-c-di-AM(PS)2 (Rp, Rp), and an IL-15 superagonist.

In certain embodiments, the drug delivery compositions and devices comprise a hydrogel, a stimulator of interferon genes (STING) agonist, and interferon α (IFN-α).

In certain embodiments, the drug delivery compositions and devices comprise a hydrogel, a stimulator of interferon genes (STING) agonist, and interferon β (IFN-β).

In certain embodiments, the drug delivery compositions and devices comprise a hydrogel, a stimulator of interferon genes (STING) agonist, and interferon γ (IFN-γ).

In certain embodiments, the drug delivery compositions and devices comprise a hydrogel, a TLR7 and/or TLR8 agonist and interferon α (IFN-α).

In certain embodiments, the drug delivery compositions and devices comprise a hydrogel, a TLR7 and/or TLR8 agonist and interferon β (IFN-β).

In certain embodiments, the drug delivery compositions and devices comprise a hydrogel, a TLR7 and/or TLR8 agonist and interferon γ (IFN-γ).

In certain embodiments, the drug delivery compositions and devices comprise a hydrogel, a stimulator of interferon genes (STING) agonist and an anti-PD-1 antibody.

In certain embodiments, the drug delivery compositions and devices comprise a hydrogel, a stimulator of interferon genes (STING) agonist, an IL-15 superagonist, and an anti-PD-1 antibody.

In certain embodiments, the drug delivery compositions and devices comprise a hydrogel, a stimulator of interferon genes (STING) agonist, interferon α (IFN-α), and an anti-PD-1 antibody.

In certain embodiments, the drug delivery compositions and devices comprise a hydrogel, a stimulator of interferon genes (STING) agonist, interferon α (IFN-α), an IL-15 superagonist, and an anti-PD-1 antibody.

In certain embodiments, the drug delivery compositions and devices comprise a hydrogel, interferon α (IFN-α), and an anti-PD-1 antibody.

In certain embodiments, the drug delivery compositions and devices comprise a hydrogel, a stimulator of interferon genes (STING) agonist, interferon β (IFN-β), and an anti-PD-1 antibody.

In certain embodiments, the drug delivery compositions and devices comprise a hydrogel, a stimulator of interferon genes (STING) agonist, interferon β(IFN-β), an IL-15 superagonist, and an anti-PD-1 antibody.

In certain embodiments, the drug delivery compositions and devices comprise a hydrogel, interferon β (IFN-β), and an anti-PD-1 antibody.

In certain embodiments, the drug delivery compositions and devices comprise a hydrogel, a stimulator of interferon genes (STING) agonist, interferon γ (IFN-γ), and an anti-PD-1 antibody.

In certain embodiments, the drug delivery compositions and devices comprise a hydrogel, a stimulator of interferon genes (STING) agonist, interferon γ (IFN-γ), an IL-15 superagonist, and an anti-PD-1 antibody.

In certain embodiments, the drug delivery compositions and devices comprise a hydrogel, interferon γ (IFN-γ), and an anti-PD-1 antibody.

In certain embodiments, the drug delivery compositions and devices comprise a hydrogel, 2ʹ3ʹ-cGAMP, an IL-15 superagonist, and an anti-PD-1 antibody.

In certain embodiments, the drug delivery compositions and devices comprise a hydrogel, 2ʹ3ʹ-c-di-AM(PS)2 (Rp, Rp), an IL-15 superagonist, and an anti-PD-1 antibody.

In certain embodiments, the drug delivery compositions and devices comprise a hydrogel, c-di-GMP, an IL-15 superagonist, and an anti-PD-1 antibody.

In certain embodiments, the drug delivery compositions and devices comprise a hydrogel, a stimulator of interferon genes (STING) agonist, an IL-15 superagonist, and an agonist anti-CD137 antibody.

In certain embodiments, the drug delivery compositions and devices comprise a hydrogel, 2ʹ3ʹ-cGAMP, an IL-15 superagonist, and an anti-CD137 antibody.

In certain embodiments, the drug delivery compositions and devices comprise a hydrogel, 2ʹ3ʹ-c-di-AM(PS)2 (Rp, Rp), an IL-15 superagonist, and an anti-CD137 antibody.

In certain embodiments, the drug delivery compositions and devices comprise a hydrogel, a stimulator of interferon genes (STING) agonist, an IL-15 superagonist, and an agonist anti-CD40 antibody.

In certain embodiments, the drug delivery compositions and devices comprise a hydrogel, a TLR7 and/or TLR8 agonist, an IL-15 superagonist, and an anti-PD-1 antibody.

In certain embodiments, the drug delivery compositions and devices comprise a hydrogel, resiquimod, an IL-15 superagonist, and an anti-PD-1 antibody.

In certain embodiments, the drug delivery compositions and devices comprise a hydrogel, a TLR3 agonist, an IL-15 superagonist, and an anti-PD-1 antibody.

In certain embodiments, the drug delivery compositions and devices comprise a hydrogel, poly(I:C), an IL-15 superagonist, and an anti-PD-1 antibody.

In certain embodiments, the drug delivery compositions and devices comprise a hydrogel, a TLR9 agonist, an IL-15 superagonist, and an anti-PD-1 antibody.

In certain embodiments, the drug delivery compositions and devices comprise a hydrogel, a CpG oligonucleotide, an IL-15 superagonist, and an anti-PD-1 antibody.

In certain embodiments, the drug delivery compositions and devices comprise a hydrogel, a stimulator of interferon genes (STING) agonist, an anti-CTLA-4 antibody, and an anti-PD-1 antibody.

In certain embodiments, the drug delivery compositions and devices comprise a hydrogel, a stimulator of interferon genes (STING) agonist and an anti-CTLA-4 antibody.

In certain embodiments, the drug delivery compositions and devices comprise a hydrogel, a stimulator of interferon genes (STING) agonist, an anti-LAG-3 antibody, and an anti-PD-1 antibody.

In certain embodiments, the drug delivery compositions and devices comprise a hydrogel, a stimulator of interferon genes (STING) agonist, an IL-15 superagonist, and an anti-LAG-3 antibody.

In certain embodiments, the drug delivery compositions and devices comprise a hydrogel, a stimulator of interferon genes (STING) agonist, IL-15, and an agonist anti-CD40 antibody.

In certain embodiments, the drug delivery compositions and devices comprise a hydrogel and a TLR7 and/or TLR8 agonist.

In certain embodiments, the drug delivery compositions and devices comprise a hydrogel and a TLR7 agonist.

In certain embodiments, the drug delivery compositions and devices comprise a hydrogel and a TLR8 agonist.

In certain embodiments, the drug delivery compositions and devices comprise a hydrogel and resiquimod.

In certain embodiments, the drug delivery compositions and devices comprise hydrogel, a TLR7 and/or TLR8 agonist, and an IL-15 superagonist.

In certain embodiments, the drug delivery compositions and devices comprise a hydrogel, resiquimod, and an IL-15 superagonist.

In certain embodiments, the drug delivery compositions and devices comprise a hydrogel, a TLR7 and/or TLR8 agonist, and an anti-PD-1 antibody.

In certain embodiments, the drug delivery compositions and devices comprise a hydrogel, a TLR7 and/or TLR8 agonist, an IL-15 superagonist, and an agonist anti-CD137 antibody.

In certain embodiments, the drug delivery compositions and devices comprise a hydrogel, a TLR7 and/or TLR8 agonist, an IL-15 superagonist, and an agonist anti-CD40 antibody.

In certain embodiments, the drug delivery compositions and devices comprise a hydrogel, a TLR7 and/or TLR8 agonist, an anti-CTLA-4 antibody, and an anti-PD-1 antibody.

In certain embodiments, the drug delivery compositions and devices comprise a hydrogel, resiquimod, an anti-CTLA-4 antibody, and an anti-PD-1 antibody.

In certain embodiments, the drug delivery compositions and devices comprise a hydrogel, a TLR7 and/or TLR8 agonist and an anti-CTLA-4 antibody.

In certain embodiments, the drug delivery compositions and devices comprise a hydrogel, a TLR7 and/or TLR8 agonist, an anti-LAG-3 antibody, and an anti-PD-1 antibody.

In certain embodiments, the drug delivery compositions and devices comprise a hydrogel, a TLR7 and/or TLR8 agonist, an IL-15 superagonist, and an anti-LAG-3 antibody.

In certain embodiments, the drug delivery compositions and devices comprise a hydrogel, a TLR7 and/or TLR8 agonist, an IL-15, and an agonist anti-CD40 antibody.

In certain embodiments, the drug delivery compositions and devices comprise a hydrogel, a stimulator of interferon genes (STING) agonist, an agonist anti-CD137 antibody, and an anti-CTLA-4 antibody.

In certain embodiments, the drug delivery compositions and devices comprise a hydrogel, a TLR7 and/or TLR8 agonist, an agonist anti-CD137 antibody, and an anti-CTLA-4 antibody.

In certain embodiments, the drug delivery compositions and devices comprise a hydrogel, a stimulator of interferon genes (STING) agonist, an agonist anti-CD137 antibody, and an anti-PD-1 antibody.

In certain embodiments, the drug delivery compositions and devices comprise a hydrogel, a TLR7 and/or TLR8 agonist, an agonist anti-CD137 antibody, and an anti-PD-1 antibody.

In certain embodiments, the drug delivery compositions and devices comprise a hydrogel and an agonist anti-CD137 antibody.

In certain embodiments, the drug delivery compositions and devices comprise a hydrogel and an anti-CTLA-4 antibody.

In certain embodiments, the drug delivery compositions and devices comprise a hydrogel and an anti-PD-1 antibody.

In certain embodiments, the drug delivery compositions and devices comprise a hydrogel, an agonist anti-CD137 antibody, and an anti-PD-1 antibody.

In certain embodiments, the drug delivery compositions and devices comprise a hydrogel, an agonist anti-CD137 antibody, and an anti-CTLA-4 antibody.

In certain embodiments, the drug delivery compositions and devices comprise a hydrogel, an anti-PD-1 antibody, and an anti-CTLA-4 antibody.

In certain embodiments, the drug delivery compositions and devices comprise a hydrogel, an agonist anti-CD137 antibody, an anti-PD-1 antibody, and an anti-CTLA-4 antibody.

In certain embodiments, the drug delivery compositions and devices comprise a hydrogel and an activator of innate immune response, wherein the activator of innate immune response is 2′-3′-cGAMP, 2′-3′-c-di-AM(PS)2 (Rp,Rp), MurNAc-L-Ala-γ-D-Glu-mDAP (M-TriDAP), or resiquimod.

In certain embodiments, the drug delivery compositions and devices comprise a hydrogel and a chemokine, wherein the chemokine is an IL-15 superagonist, IFN-α, IFN-β, or IFN-γ.

In certain embodiments, the drug delivery compositions and devices comprise a hydrogel, an activator of innate immune response, and a chemokine; wherein the activator of innate immune response is 2′-3′-cGAMP, 2′-3′-c-di-AM (PS)2 (Rp,Rp), MurNAc-L-Ala-γ-D-Glu-mDAP (M-TriDAP), or resiquimod; and the chemokine is an IL-15 superagonist, IFN-α, IFN-β, or IFN-γ.

In certain embodiments, the drug delivery compositions and devices comprise a hydrogel, an activator of innate immune response, a chemokine, and an activator of adaptive immune response; wherein the activator of innate immune response is 2′-3′-cGAMP, 2′-3′-c-di-AM(PS)2 (Rp,Rp), MurNAc-L-Ala-γ-D-Glu-mDAP (M-TriDAP), or resiquimod; the chemokine is an IL-15 superagonist, IFN-α, IFN-β, or IFN-γ; and the activator of adaptive immune response is an anti-PD-1 antibody, an anti-CTLA4 antibody, an anti-CD40 antibody, or an anti-CD137 antibody.

In certain embodiments, the drug delivery composition is selected from the group consisting of:
 a composition comprising a hydrogel and 2′-3′-cGAMP;
 a composition comprising a hydrogel and 2′-3′-c-di-AM(PS)2 (Rp,Rp);
 a composition comprising a hydrogel and resiquimod;
 a composition comprising a hydrogel and M-TriDAP;
 a composition comprising a hydrogel and an IL-15 superagonist;
 a composition comprising a hydrogel and interferon α (IFN-α);
 a composition comprising a hydrogel and interferon β (IFN-β);
 a composition comprising a hydrogel and interferon γ (IFN-γ);
 a composition comprising a hydrogel, 2′-3′-cGAMP, and an IL-15 superagonist;
 a composition comprising a hydrogel, 2′-3′-c-di-AM (PS)2 (Rp,Rp), and an IL-15 superagonist;
 a composition comprising a hydrogel, resiquimod, and an IL-15 superagonist;
 a composition comprising a hydrogel, 2′-3′-cGAMP, an IL-15 superagonist, and an anti-PD-1 antibody;
 a composition comprising a hydrogel, 2′-3′-c-di-AM (PS)2 (Rp,Rp), an IL-15 superagonist, and an anti-PD-1 antibody; and
 a composition comprising a hydrogel, resiquimod, an IL-15 superagonist, and an anti-PD-1 antibody.

In certain embodiments, the drug delivery device is selected from the group consisting of:
 a device comprising a hydrogel and 2′-3′-cGAMP;
 a device comprising a hydrogel and 2′-3′-c-di-AM(PS)2 (Rp,Rp);
 a device comprising a hydrogel and resiquimod;
 a device comprising a hydrogel and M-TriDAP;
 a device comprising a hydrogel and an IL-15 superagonist;
 a device comprising a hydrogel and interferon α (IFN-α);
 a device comprising a hydrogel and interferon β (IFN-β)
 a device comprising a hydrogel and interferon γ (IFN-γ);
 a device comprising a hydrogel, 2′-3′-cGAMP, and an IL-15 superagonist;
 a device comprising a hydrogel, 2′-3′-c-di-AM(PS)2 (Rp,Rp), and an IL-15 superagonist;
 a device comprising a hydrogel, resiquimod, and an IL-15 superagonist;
 a device comprising a hydrogel, 2′-3′-cGAMP, an IL-15 superagonist, and an anti-PD-1 antibody;
 a device comprising a hydrogel, 2′-3′-c-di-AM(PS)2 (Rp,Rp), an IL-15 superagonist, and an anti-PD-1 antibody; and
 a device comprising a hydrogel, resiquimod, an IL-15 superagonist, and an anti-PD-1 antibody.

In certain embodiments, the drug delivery compositions and devices comprise hyaluronic acid and an NLR agonist.

In certain embodiments, the drug delivery compositions and devices comprise hyaluronic acid and M-TriDAP.

In certain embodiments, the drug delivery compositions and devices comprise hyaluronic acid, M-TriDAP, and an IL-15 superagonist.

In certain embodiments, the drug delivery compositions and devices comprise hyaluronic acid, M-TriDAP, and an anti-PD-1 antibody.

In certain embodiments, the drug delivery compositions and devices comprise hyaluronic acid, M-TriDAP, and an anti-CTLA-4 antibody.

In certain embodiments, the drug delivery compositions and devices comprise hyaluronic acid, a stimulator of interferon genes (STING) agonist, and M-TriDAP.

In certain embodiments, the drug delivery compositions and devices comprise hyaluronic acid, a stimulator of interferon genes (STING) agonist, M-TriDAP, and an IL-15 superagonist.

In certain embodiments, the drug delivery compositions and devices comprise hyaluronic acid, a TLR7 and/or TLR8 agonist, and M-TriDAP.

In certain embodiments, the drug delivery compositions and devices comprise hyaluronic acid, a TLR7 and/or TLR8 agonist, M-TriDAP, and an anti-PD-1 antibody.

In certain embodiments, the drug delivery compositions and devices comprise hyaluronic acid and IL-1β.

In certain embodiments, the drug delivery compositions and devices comprise hyaluronic acid, a stimulator of interferon genes (STING) agonist, and IL-1β.

In certain embodiments, the drug delivery compositions and devices comprise hyaluronic acid, a TLR7 and/or TLR8 agonist, and IL-1β.

In certain embodiments, the drug delivery compositions and devices comprise hyaluronic acid and a stimulator of interferon genes (STING) agonist.

In certain embodiments, the drug delivery compositions and devices comprise hyaluronic acid and 2′,3′-cGAMP.

In certain embodiments, the drug delivery compositions and devices comprise hyaluronic acid and 22′,3′-c-di-AM(PS)2 (Rp,Rp).

In certain embodiments, the drug delivery compositions and devices comprise hyaluronic acid and an IL-15 superagonist.

In certain embodiments, the drug delivery compositions and devices comprise hyaluronic acid and interferon α (IFN-α).

In certain embodiments, the drug delivery compositions and devices comprise hyaluronic acid and interferon β (IFN-β).

In certain embodiments, the drug delivery compositions and devices comprise hyaluronic acid and interferon γ (IFN-γ).

In certain embodiments, the drug delivery compositions and devices comprise hyaluronic acid, a stimulator of interferon genes (STING) agonist, and an IL-15 superagonist.

In certain embodiments, the drug delivery compositions and devices comprise a hyaluronic acid, 22′,3′-cGAMP, and an IL-15 superagonist.

In certain embodiments, the drug delivery compositions and devices comprise a hyaluronic acid, 22′,3′-c-di-AM(PS)2 (Rp,Rp), and an IL-15 superagonist.

In certain embodiments, the drug delivery compositions and devices comprise hyaluronic acid, a stimulator of interferon genes (STING) agonist, and interferon α (IFN-α).

In certain embodiments, the drug delivery compositions and devices comprise hyaluronic acid, a stimulator of interferon genes (STING) agonist, and interferon β (IFN-β).

In certain embodiments, the drug delivery compositions and devices comprise hyaluronic acid, a stimulator of interferon genes (STING) agonist, and interferon γ (IFN-γ).

In certain embodiments, the drug delivery compositions and devices comprise a hyaluronic acid, a TLR7 and/or TLR8 agonist and interferon α (IFN-α).

In certain embodiments, the drug delivery compositions and devices comprise a hyaluronic acid, a TLR7 and/or TLR8 agonist and interferon β (IFN-β).

In certain embodiments, the drug delivery compositions and devices comprise a hyaluronic acid, a TLR7 and/or TLR8 agonist and interferon γ (IFN-γ).

In certain embodiments, the drug delivery compositions and devices comprise a hyaluronic acid, a stimulator of interferon genes (STING) agonist and an anti-PD-1 antibody.

In certain embodiments, the drug delivery compositions and devices comprise a hyaluronic acid, a stimulator of interferon genes (STING) agonist, an IL-15 superagonist, and an anti-PD-1 antibody.

In certain embodiments, the drug delivery compositions and devices comprise a hyaluronic acid, a stimulator of interferon genes (STING) agonist, interferon α (IFN-α), and an anti-PD-1 antibody.

In certain embodiments, the drug delivery compositions and devices comprise a hyaluronic acid, a stimulator of interferon genes (STING) agonist, interferon α (IFN-α), an IL-15 superagonist, and an anti-PD-1 antibody.

In certain embodiments, the drug delivery compositions and devices comprise a hyaluronic acid, interferon α (IFN-α), and an anti-PD-1 antibody.

In certain embodiments, the drug delivery compositions and devices comprise hyaluronic acid, a stimulator of interferon genes (STING) agonist, interferon β (IFN-β), and an anti-PD-1 antibody.

In certain embodiments, the drug delivery compositions and devices comprise hyaluronic acid, a stimulator of interferon genes (STING) agonist, interferon β(IFN-β), an IL-15 superagonist, and an anti-PD-1 antibody.

In certain embodiments, the drug delivery compositions and devices comprise hyaluronic acid, interferon β (IFN-β), and an anti-PD-1 antibody.

In certain embodiments, the drug delivery compositions and devices comprise hyaluronic acid, a stimulator of interferon genes (STING) agonist, interferon γ (IFN-γ), and an anti-PD-1 antibody.

In certain embodiments, the drug delivery compositions and devices comprise hyaluronic acid, a stimulator of interferon genes (STING) agonist, interferon γ (IFN-γ), an IL-15 superagonist, and an anti-PD-1 antibody.

In certain embodiments, the drug delivery compositions and devices comprise hyaluronic acid, interferon γ (IFN-γ), and an anti-PD-1 antibody.

In certain embodiments, the drug delivery compositions and devices comprise hyaluronic acid, 2′3′-cGAMP, an IL-15 superagonist, and an anti-PD-1 antibody.

In certain embodiments, the drug delivery compositions and devices comprise hyaluronic acid, 2′3′-c-di-AM(PS)2 (Rp,Rp), an IL-15 superagonist, and an anti-PD-1 antibody.

In certain embodiments, the drug delivery compositions and devices comprise hyaluronic acid, c-di-GMP, an IL-15 superagonist, and an anti-PD-1 antibody.

In certain embodiments, the drug delivery compositions and devices comprise hyaluronic acid, a stimulator of interferon genes (STING) agonist, an IL-15 superagonist, and an agonist anti-CD137 antibody.

In certain embodiments, the drug delivery compositions and devices comprise hyaluronic acid, 2′3′-cGAMP, an IL-15 superagonist, and an anti-CD137 antibody.

In certain embodiments, the drug delivery compositions and devices comprise hyaluronic acid, 2′3′-c-di-AM(PS)2 (Rp,Rp), an IL-15 superagonist, and an anti-CD137 antibody.

In certain embodiments, the drug delivery compositions and devices comprise hyaluronic acid, a stimulator of interferon genes (STING) agonist, an IL-15 superagonist, and an agonist anti-CD40 antibody.

In certain embodiments, the drug delivery compositions and devices comprise hyaluronic acid, a TLR7 and/or TLR8 agonist, an IL-15 superagonist, and an anti-PD-1 antibody.

In certain embodiments, the drug delivery compositions and devices comprise hyaluronic acid, resiquimod, an IL-15 superagonist, and an anti-PD-1 antibody.

In certain embodiments, the drug delivery compositions and devices comprise hyaluronic acid, a TLR3 agonist, an IL-15 superagonist, and an anti-PD-1 antibody.

In certain embodiments, the drug delivery compositions and devices comprise hyaluronic acid, poly(I:C), an IL-15 superagonist, and an anti-PD-1 antibody.

In certain embodiments, the drug delivery compositions and devices comprise hyaluronic acid, a TLR9 agonist, an IL-15 superagonist, and an anti-PD-1 antibody.

In certain embodiments, the drug delivery compositions and devices comprise hyaluronic acid, a CpG oligonucleotide, an IL-15 superagonist, and an anti-PD-1 antibody.

In certain embodiments, the drug delivery compositions and devices comprise hyaluronic acid, a stimulator of interferon genes (STING) agonist, an anti-CTLA-4 antibody, and an anti-PD-1 antibody.

In certain embodiments, the drug delivery compositions and devices comprise hyaluronic acid, a stimulator of interferon genes (STING) agonist and an anti-CTLA-4 antibody.

In certain embodiments, the drug delivery compositions and devices comprise hyaluronic acid, a stimulator of interferon genes (STING) agonist, an anti-LAG-3 antibody, and an anti-PD-1 antibody.

In certain embodiments, the drug delivery compositions and devices comprise hyaluronic acid, a stimulator of interferon genes (STING) agonist, an IL-15 superagonist, and an anti-LAG-3 antibody.

In certain embodiments, the drug delivery compositions and devices comprise hyaluronic acid, a stimulator of interferon genes (STING) agonist, IL-15, and an agonist anti-CD40 antibody.

In certain embodiments, the drug delivery compositions and devices comprise hyaluronic acid and a TLR7 and/or TLR8 agonist.

In certain embodiments, the drug delivery compositions and devices comprise hyaluronic acid and a TLR7 agonist.

In certain embodiments, the drug delivery compositions and devices comprise hyaluronic acid and a TLR8 agonist.

In certain embodiments, the drug delivery compositions and devices comprise hyaluronic acid and resiquimod.

In certain embodiments, the drug delivery compositions and devices comprise hyaluronic acid, a TLR7 and/or TLR8 agonist and an IL-15 superagonist.

In certain embodiments, the drug delivery compositions and devices comprise hyaluronic acid, resiquimod, and an IL-15 superagonist.

In certain embodiments, the drug delivery compositions and devices comprise hyaluronic acid, a TLR7 and/or TLR8 agonist, and an anti-PD-1 antibody.

In certain embodiments, the drug delivery compositions and devices comprise hyaluronic acid, a TLR7 and/or TLR8 agonist, an IL-15 superagonist, and an agonist anti-CD137 antibody.

In certain embodiments, the drug delivery compositions and devices comprise hyaluronic acid, a TLR7 and/or TLR8 agonist, an IL-15 superagonist, and an agonist anti-CD40 antibody.

In certain embodiments, the drug delivery compositions and devices comprise hyaluronic acid, a TLR7 and/or TLR8 agonist, an anti-CTLA-4 antibody, and an anti-PD-1 antibody.

In certain embodiments, the drug delivery compositions and devices comprise hyaluronic acid, resiquimod, an anti-CTLA-4 antibody, and an anti-PD-1 antibody.

In certain embodiments, the drug delivery compositions and devices comprise hyaluronic acid, a TLR7 and/or TLR8 agonist and an anti-CTLA-4 antibody.

In certain embodiments, the drug delivery compositions and devices comprise hyaluronic acid, a TLR7 and/or TLR8 agonist, an anti-LAG-3 antibody, and an anti-PD-1 antibody.

In certain embodiments, the drug delivery compositions and devices comprise hyaluronic acid, a TLR7 and/or TLR8 agonist, an IL-15 superagonist, and an anti-LAG-3 antibody.

In certain embodiments, the drug delivery compositions and devices comprise hyaluronic acid, a TLR7 and/or TLR8 agonist, IL-15, and an agonist anti-CD40 antibody.

In certain embodiments, the drug delivery compositions and devices comprise hyaluronic acid, a stimulator of interferon genes (STING) agonist, an agonist anti-CD137 antibody, and an anti-CTLA-4 antibody.

In certain embodiments, the drug delivery compositions and devices comprise hyaluronic acid, a TLR7 and/or TLR8 agonist, an agonist anti-CD137 antibody, and an anti-CTLA-4 antibody.

In certain embodiments, the drug delivery compositions and devices comprise hyaluronic acid, a stimulator of interferon genes (STING) agonist, an agonist anti-CD137 antibody, and an anti-PD-1 antibody.

In certain embodiments, the drug delivery compositions and devices comprise hyaluronic acid, a TLR7 and/or TLR8 agonist, an agonist anti-CD137 antibody, and an anti-PD-1 antibody.

In certain embodiments, the drug delivery compositions and devices comprise hyaluronic acid and an agonist anti-CD137 antibody.

In certain embodiments, the drug delivery compositions and devices comprise hyaluronic acid and an anti-CTLA-4 antibody.

In certain embodiments, the drug delivery compositions and devices comprise hyaluronic acid and an anti-PD-1 antibody.

In certain embodiments, the drug delivery compositions and devices comprise hyaluronic acid, an agonist anti-CD137 antibody, and an anti-PD-1 antibody.

In certain embodiments, the drug delivery compositions and devices comprise hyaluronic acid, an agonist anti-CD137 antibody, and an anti-CTLA-4 antibody.

In certain embodiments, the drug delivery compositions and devices comprise hyaluronic acid, an anti-PD-1 antibody, and an anti-CTLA-4 antibody.

In certain embodiments, the drug delivery compositions and devices comprise hyaluronic acid, an agonist anti-CD137 antibody, an anti-PD-1 antibody, and an anti-CTLA-4 antibody.

In certain embodiments the drug delivery composition is selected from the group consisting of:
- a device comprising a hyaluronic acid and 2′-3′-cGAMP;
- a device comprising a hyaluronic acid and 2′-3′-c-di-AM(PS)2 (Rp,Rp);
- a device comprising a hyaluronic acid and resiquimod;
- a device comprising a hyaluronic acid and M-TriDAP;
- a device comprising a hyaluronic acid and an IL-15 superagonist;
- a device comprising a hyaluronic acid and interferon α (IFN-α);
- a device comprising a hyaluronic acid and interferon β (IFN-β);
- a device comprising a hyaluronic acid and interferon γ (IFN-γ);
- a composition comprising hyaluronic acid, 2′,3′-cGAMP, and an IL-15 superagonist;
- a composition comprising hyaluronic acid, 2′,3′-c-di-AM(PS)2 (Rp,Rp), and an IL-15 superagonist;

a composition comprising hyaluronic acid, resiquimod, and an IL-15 superagonist;

a composition comprising hyaluronic acid, 2′,3′-cGAMP, an IL-15 superagonist, and an anti-PD-1 antibody;

a composition comprising hyaluronic acid, 2′,3′-c-di-AM(PS)2 (Rp,Rp), an IL-15 superagonist, and an anti-PD-1 antibody; and a composition comprising hyaluronic acid, resiquimod, an IL-15 superagonist, and an anti-PD-1 antibody.

In certain embodiments, the drug delivery device is selected from the group consisting of:

a device comprising a hyaluronic acid and 2′,3′-cGAMP;

a device comprising a hyaluronic acid and 2′,3′-c-di-AM(PS)2 (Rp,Rp);

a device comprising a hyaluronic acid and resiquimod;

a device comprising a hyaluronic acid and M-TriDAP;

a device comprising a hyaluronic acid and an IL-15 superagonist;

a device comprising a hyaluronic acid and interferon α (IFN-α);

a device comprising a hyaluronic acid and interferon β (IFN-β);

a device comprising a hyaluronic acid and interferon γ (IFN-γ);

a device comprising hyaluronic acid, 2′,3′-cGAMP, and an IL-15 superagonist;

a device comprising hyaluronic acid, 2′,3′-c-di-AM (PS)2 (Rp,Rp), and an IL-15 superagonist;

a device comprising hyaluronic acid, resiquimod, and an IL-15 superagonist;

a device comprising hyaluronic acid, 2′,3′-cGAMP, an IL-15 superagonist, and an anti-PD-1 antibody;

a device comprising hyaluronic acid, 2′,3′-c-di-AM (PS)2 (Rp,Rp), an IL-15 superagonist, and an anti-PD-1 antibody; and a device comprising hyaluronic acid, resiquimod, an IL-15 superagonist, and an anti-PD-1 antibody.

In certain embodiments, the drug delivery compositions and devices comprise alginate and an NLR agonist.

In certain embodiments, the drug delivery compositions and devices comprise alginate and M-TriDAP.

In certain embodiments, the drug delivery compositions and devices comprise alginate, M-TriDAP, and an IL-15 superagonist.

In certain embodiments, the drug delivery compositions and devices comprise alginate, M-TriDAP, and an anti-PD-1 antibody.

In certain embodiments, the drug delivery compositions and devices comprise alginate, M-TriDAP, and an anti-CTLA-4 antibody.

In certain embodiments, the drug delivery compositions and devices comprise alginate, a stimulator of interferon genes (STING) agonist, and M-TriDAP.

In certain embodiments, the drug delivery compositions and devices comprise alginate, a stimulator of interferon genes (STING) agonist, M-TriDAP, and an IL-15 superagonist.

In certain embodiments, the drug delivery compositions and devices comprise alginate, a TLR7 and/or TLR8 agonist, and M-TriDAP.

In certain embodiments, the drug delivery compositions and devices comprise alginate, a TLR7 and/or TLR8 agonist, M-TriDAP, and an anti-PD-1 antibody.

In certain embodiments, the drug delivery compositions and devices comprise alginate and IL-1β.

In certain embodiments, the drug delivery compositions and devices comprise alginate, a stimulator of interferon genes (STING) agonist, and IL-1β.

In certain embodiments, the drug delivery compositions and devices comprise alginate, a TLR7 and/or TLR8 agonist, and IL-1β.

In certain embodiments, the drug delivery compositions and devices comprise alginate and a stimulator of interferon genes (STING) agonist.

In certain embodiments, the drug delivery compositions and devices comprise alginate and 2′,3′-cGAMP.

In certain embodiments, the drug delivery compositions and devices comprise alginate and 2′3′-c-di-AM(PS)2 (Rp,Rp).

In certain embodiments, the drug delivery compositions and devices comprise alginate and an IL-15 superagonist.

In certain embodiments, the drug delivery compositions and devices comprise alginate and interferon α (IFN-α).

In certain embodiments, the drug delivery compositions and devices comprise alginate and interferon β (IFN-β).

In certain embodiments, the drug delivery compositions and devices comprise alginate and interferon γ (IFN-γ).

In certain embodiments, the drug delivery compositions and devices comprise alginate, a stimulator of interferon genes (STING) agonist, and an IL-15 superagonist.

In certain embodiments, the drug delivery compositions and devices comprise a alginate, 2′,3′-cGAMP, and an IL-15 superagonist.

In certain embodiments, the drug delivery compositions and devices comprise a alginate, 2′3′-c-di-AM(PS)2 (Rp,Rp), and an IL-15 superagonist.

In certain embodiments, the drug delivery compositions and devices comprise alginate, a stimulator of interferon genes (STING) agonist, and interferon α (IFN-α).

In certain embodiments, the drug delivery compositions and devices comprise alginate, a stimulator of interferon genes (STING) agonist, and interferon β (IFN-β).

In certain embodiments, the drug delivery compositions and devices comprise alginate, a stimulator of interferon genes (STING) agonist, and interferon γ (IFN-γ).

In certain embodiments, the drug delivery compositions and devices comprise alginate, a TLR7 and/or TLR8 agonist, and interferon α (IFN-α).

In certain embodiments, the drug delivery compositions and devices comprise alginate, a TLR7 and/or TLR8 agonist, and interferon β (IFN-β).

In certain embodiments, the drug delivery compositions and devices comprise alginate, a TLR7 and/or TLR8 agonist, and interferon γ(IFN-γ).

In certain embodiments, the drug delivery compositions and devices comprise alginate, a stimulator of interferon genes (STING) agonist, and an anti-PD-1 antibody.

In certain embodiments, the drug delivery compositions and devices comprise alginate, a stimulator of interferon genes (STING) agonist, an IL-15 superagonist, and an anti-PD-1 antibody.

In certain embodiments, the drug delivery compositions and devices comprise alginate, a stimulator of interferon genes (STING) agonist, interferon α (IFN-α), and an anti-PD-1 antibody.

In certain embodiments, the drug delivery compositions and devices comprise alginate, a stimulator of interferon genes (STING) agonist, interferon α (IFN-α), an IL-15 superagonist, and an anti-PD-1 antibody.

In certain embodiments, the drug delivery compositions and devices comprise alginate, interferon α (IFN-α), and an anti-PD-1 antibody.

In certain embodiments, the drug delivery compositions and devices comprise alginate, a stimulator of interferon genes (STING) agonist, interferon β (IFN-β), and an anti-PD-1 antibody.

In certain embodiments, the drug delivery compositions and devices comprise alginate, a stimulator of interferon genes (STING) agonist, interferon β (IFN-β), an IL-15 superagonist, and an anti-PD-1 antibody.

In certain embodiments, the drug delivery compositions and devices comprise alginate, interferon β (IFN-β), and an anti-PD-1 antibody.

In certain embodiments, the drug delivery compositions and devices comprise alginate, a stimulator of interferon genes (STING) agonist, interferon γ (IFN-γ), and an anti-PD-1 antibody.

In certain embodiments, the drug delivery compositions and devices comprise alginate, a stimulator of interferon genes (STING) agonist, interferon γ (IFN-γ), an IL-15 superagonist, and an anti-PD-1 antibody.

In certain embodiments, the drug delivery compositions and devices comprise alginate, interferon γ(IFN-γ), and an anti-PD-1 antibody.

In certain embodiments, the drug delivery compositions and devices comprise alginate, 2′,3′-cGAMP, an IL-15 superagonist, and an anti-PD-1 antibody.

In certain embodiments, the drug delivery compositions and devices comprise alginate, 2′,3′-c-di-AM(PS)2 (Rp, Rp), an IL-15 superagonist, and an anti-PD-1 antibody.

In certain embodiments, the drug delivery compositions and devices comprise alginate, c-di-GMP, an IL-15 superagonist, and an anti-PD-1 antibody.

In certain embodiments, the drug delivery compositions and devices comprise alginate, a stimulator of interferon genes (STING) agonist, an IL-15 superagonist, and an agonist anti-CD137 antibody.

In certain embodiments, the drug delivery compositions and devices comprise alginate, 2′,3′-cGAMP, an IL-15 superagonist, and an anti-CD137 antibody.

In certain embodiments, the drug delivery compositions and devices comprise alginate, 2′,3′-c-di-AM(PS)2 (Rp, Rp), an IL-15 superagonist, and an anti-CD137 antibody.

In certain embodiments, the drug delivery compositions and devices comprise alginate, a stimulator of interferon genes (STING) agonist, an IL-15 superagonist, and an agonist anti-CD40 antibody.

In certain embodiments, the drug delivery compositions and devices comprise alginate, a TLR7 and/or TLR8 agonist, an IL-15 superagonist, and an anti-PD-1 antibody.

In certain embodiments, the drug delivery compositions and devices comprise alginate, resiquimod, an IL-15 superagonist, and an anti-PD-1 antibody.

In certain embodiments, the drug delivery compositions and devices comprise alginate, a TLR3 agonist, an IL-15 superagonist, and an anti-PD-1 antibody.

In certain embodiments, the drug delivery compositions and devices comprise alginate, poly(I:C), an IL-15 superagonist, and an anti-PD-1 antibody.

In certain embodiments, the drug delivery compositions and devices comprise alginate, a TLR9 agonist, an IL-15 superagonist, and an anti-PD-1 antibody.

In certain embodiments, the drug delivery compositions and devices comprise alginate, a CpG oligonucleotide, an IL-15 superagonist, and an anti-PD-1 antibody.

In certain embodiments, the drug delivery compositions and devices comprise alginate, a stimulator of interferon genes (STING) agonist, an anti-CTLA-4 antibody, and an anti-PD-1 antibody.

In certain embodiments, the drug delivery compositions and devices comprise alginate, a stimulator of interferon genes (STING) agonist and an anti-CTLA-4 antibody.

In certain embodiments, the drug delivery compositions and devices comprise alginate, a stimulator of interferon genes (STING) agonist, an anti-LAG-3 antibody, and an anti-PD-1 antibody.

In certain embodiments, the drug delivery compositions and devices comprise alginate, a stimulator of interferon genes (STING) agonist, an IL-15 superagonist, and an anti-LAG-3 antibody.

In certain embodiments, the drug delivery compositions and devices comprise alginate, a stimulator of interferon genes (STING) agonist, IL-15, and an agonist anti-CD40 antibody.

In certain embodiments, the drug delivery compositions and devices comprise alginate and a TLR7 and/or TLR8 agonist.

In certain embodiments, the drug delivery compositions and devices comprise alginate and a TLR7 agonist.

In certain embodiments, the drug delivery compositions and devices comprise alginate and a TLR8 agonist.

In certain embodiments, the drug delivery compositions and devices comprise alginate and resiquimod.

In certain embodiments, the drug delivery compositions and devices comprise alginate, a TLR7 and/or TLR8 agonist, and an IL-15 superagonist.

In certain embodiments, the drug delivery compositions and devices comprise alginate, resiquimod, and an IL-15 superagonist.

In certain embodiments, the drug delivery compositions and devices comprise alginate, a TLR7 and/or TLR8 agonist, and an anti-PD-1 antibody.

In certain embodiments, the drug delivery compositions and devices comprise alginate, a TLR7 and/or TLR8 agonist, an IL-15 superagonist, and an agonist anti-CD137 antibody.

In certain embodiments, the drug delivery compositions and devices comprise alginate, a TLR7 and/or TLR8 agonist, an IL-15 superagonist, and an agonist anti-CD40 antibody.

In certain embodiments, the drug delivery compositions and devices comprise alginate, a TLR7 and/or TLR8 agonist, an anti-CTLA-4 antibody, and an anti-PD-1 antibody.

In certain embodiments, the drug delivery compositions and devices comprise alginate, resiquimod, an anti-CTLA-4 antibody, and an anti-PD-1 antibody.

In certain embodiments, the drug delivery compositions and devices comprise alginate, a TLR7 and/or TLR8 agonist, and an anti-CTLA-4 antibody.

In certain embodiments, the drug delivery compositions and devices comprise alginate, a TLR7 and/or TLR8 agonist, an anti-LAG-3 antibody, and an anti-PD-1 antibody.

In certain embodiments, the drug delivery compositions and devices comprise alginate, a TLR7 and/or TLR8 agonist, an IL-15 superagonist, and an anti-LAG-3 antibody.

In certain embodiments, the drug delivery compositions and devices comprise alginate, a TLR7 and/or TLR8 agonist, IL-15, and an agonist anti-CD40 antibody.

In certain embodiments, the drug delivery compositions and devices comprise alginate, a stimulator of interferon genes (STING) agonist, an agonist anti-CD137 antibody, and an anti-CTLA-4 antibody.

In certain embodiments, the drug delivery compositions and devices comprise alginate, a TLR7 and/or TLR8 agonist, an agonist anti-CD137 antibody, and an anti-CTLA-4 antibody.

In certain embodiments, the drug delivery compositions and devices comprise alginate, a stimulator of interferon genes (STING) agonist, an agonist anti-CD137 antibody, and an anti-PD-1 antibody.

In certain embodiments, the drug delivery compositions and devices comprise alginate, a TLR7 and/or TLR8 agonist, an agonist anti-CD137 antibody, and an anti-PD-1 antibody.

In certain embodiments, the drug delivery compositions and devices comprise alginate and an agonist anti-CD137 antibody.

In certain embodiments, the drug delivery compositions and devices comprise alginate and an anti-CTLA-4 antibody.

In certain embodiments, the drug delivery compositions and devices comprise alginate and an anti-PD-1 antibody.

In certain embodiments, the drug delivery compositions and devices comprise alginate, an agonist anti-CD137 antibody, and an anti-PD-1 antibody.

In certain embodiments, the drug delivery compositions and devices comprise alginate, an agonist anti-CD137 antibody, and an anti-CTLA-4 antibody.

In certain embodiments, the drug delivery compositions and devices comprise alginate, an anti-PD-1 antibody, and an anti-CTLA-4 antibody.

In certain embodiments, the drug delivery compositions and devices comprise alginate, an agonist anti-CD137 antibody, an anti-PD-1 antibody, and an anti-CTLA-4 antibody.

In certain embodiments, the drug delivery composition is selected from the group consisting of:
a composition comprising alginate and 2′-3′-cGAMP;
a composition comprising alginate and 2′-3′-c-di-AM(PS)2 (Rp,Rp);
a composition comprising alginate and resiquimod;
a composition comprising alginate and M-TriDAP;
a composition comprising alginate and an IL-15 superagonist;
a composition comprising alginate and interferon α (IFN-α);
a composition comprising alginate and interferon β (IFN-β);
a composition comprising alginate and interferon γ (IFN-γ);
a composition comprising alginate, 2′-3′-cGAMP, and an IL-15 superagonist;
a composition comprising alginate, 2′-3′-c-di-AM(PS)2 (Rp,Rp), and an IL-15 superagonist;
a composition comprising alginate, resiquimod, an IL-15 superagonist,
a composition comprising alginate, 2′-3′-cGAMP, an IL-15 superagonist, and an anti-PD-1 antibody;
a composition comprising alginate, 2′-3′-c-di-AM(PS)2 (Rp,Rp), and an IL-15 superagonist, and an anti-PD-1 antibody; and
a composition comprising alginate, resiquimod, an IL-15 superagonist, and an anti-PD-1 antibody.

In certain embodiments the drug delivery device is selected from the group consisting of:
a device comprising alginate and 2′-3′-cGAMP;
a device comprising alginate and 2′-3′-c-di-AM(PS)2 (Rp,Rp);
a device comprising alginate and resiquimod;
a device comprising alginate and M-TriDAP;
a device comprising alginate and an IL-15 superagonist;
a device comprising alginate and interferon α (IFN-α);
a device comprising alginate and interferon β (IFN-β);
a device comprising alginate and interferon γ (IFN-γ);
a device comprising alginate, 2′-3′-cGAMP, and an IL-15 superagonist,
a device comprising alginate, 2′-3′-c-di-AM(PS)2 (Rp, Rp), and an IL-15 superagonist;
a device comprising alginate, resiquimod, and an IL-15 superagonist;
a device comprising alginate, 2′-3′-cGAMP, an IL-15 superagonist, and an anti-PD-1 antibody;
a device comprising alginate, 2′-3′-c-di-AM(PS)2 (Rp, Rp), an IL-15 superagonist, and an anti-PD-1 antibody; and
a device comprising alginate, resiquimod, an IL-15 superagonist, and an anti-PD-1 antibody.

In certain embodiments, the drug delivery compositions and devices do not comprise alginate, a COX-2 inhibitor (e.g., celecoxib), and an anti-PD-1 antibody.

In certain embodiments, the drug delivery compositions and devices do not comprise 1,3-bis(2-chloroethyl)-1-nitrosourea (BCNU) and ethylene-vinyl acetate copolymer.

Properties of the Drug Delivery Compositions and Devices

The biomaterials useful for the drug delivery compositions and devices described herein are biocompatible. The biomaterials (e.g., hydrogel) are biodegradable. The drug delivery compositions and devices are able to be degraded, chemically and/or biologically, within a physiological environment, such as within the body. Degradation of the compositions and devices may occur at varying rates, depending on the components and hydrogel used. For example, the half-life of the compositions and devices (the time at which 50% of the composition is degraded into monomers and/or other non-polymeric moieties) may be on the order of days, weeks, months, or years. The compositions and devices may be biologically degraded, e.g., by enzymatic activity or cellular machinery, in some cases, for example, through exposure to a lysozyme (e.g., having relatively low pH), or by simple hydrolysis. In some cases, the compositions and devices may be broken down into monomers and/or other non-polymeric moieties that cells can either reuse or dispose of without significant toxic effect on the cells. The drug delivery compositions and devices are stable in vivo such that they deliver drug to the intended target in a suitable amount of time.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the device remains in vivo 12 months after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 6 months after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 5 months after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 4 months after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 3 months after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 2 months after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 1 month after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 1 week after implantation of the drug delivery composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 4%, less than or equal to 3%, less than or equal to 2%, less than or equal to 1%, less than or equal to 0.5%, or less than or equal to 0.1%, of the composition remains in vivo 1 day after implantation of the drug delivery composition or device.

The storage modulus in a viscoelastic material measures the stored energy of the elastic portion of the material. Storage modulus may be measured with a rheometer. Measurements provided herein were made at room temperature with TA Instruments AR-G2 Magnetic Bearing Rheometer. The storage modulus of the drug delivery compositions and devices will vary based on the components of the composition.

Generally, the relationship between storage modulus and concentration of thiol-modified hyaluronic acid (e.g., GLYCOSIL®) and the thiol-reactive PEGDA cross-linker (e.g., EXTRALINK®) is linear (excluding the limits of sensitivity). For example, a formulation of 0.8% GLYCOSIL® and 0.2% EXTRALINK® will have a storage modulus of about 100 Pa, and a formulation of 1.3% GLYCOSIL® and 2% EXTRALINK® will have a storage modulus of about 1600 Pa.

In certain embodiments, the drug delivery composition or device has a storage modulus of at least 50 Pa, at least 100 Pa, at least 200 Pa, at least 300 Pa, at least 400 Pa, at least 500 Pa, at least 600 Pa, at least 700 Pa, at least 800 Pa, at least 900 Pa, at least 1000 Pa, at least 1100 Pa, at least 1200 Pa, at least 1300 Pa, at least 1400 Pa, at least 1500 Pa, at least 1600 Pa, at least 1700 Pa, at least 1800 Pa, at least 1900 Pa, at least 2000 Pa, at least 2100 Pa, at least 2200 Pa, at least 2300 Pa, at least 2400 Pa, at least 2500 Pa, at least 2600 Pa, at least 2700 Pa, at least 2800 Pa, at least 2900 Pa, or at least 3000 Pa.

In certain embodiments, the drug delivery composition or device has a storage modulus of about 50 Pa to about 100,000,000 Pa, about 50 Pa to about 100,000 Pa, about 50 Pa to about 10,000 Pa, about 50 Pa to about 3,000 Pa, about 100 Pa to about 3,000 Pa, about 100 Pa to about 2,000 Pa, about 500 Pa to about 3,000 Pa, about 500 Pa to about 2,000 Pa, about 1,000 Pa to about 2,000 Pa, about 1,200 Pa to about 1,800 Pa, about 1,300 Pa to about 1,700 Pa, or about 1,400 Pa to about 1,600 Pa.

In certain embodiments, the drug delivery composition or device has a storage modulus of up to about 600 Pa, up to about 700 Pa, up to about 800 Pa, up to about 900 Pa, up to about 1,000 Pa, up to about 1,100 Pa, up to about 1,200 Pa, up to about 1,300 Pa, up to about 1,400 Pa, up to about 1,500 Pa, up to about 1,600 Pa, up to about 1,700 Pa, up to about 1,800 Pa, up to about 1,900 Pa, up to about 2,000 Pa, up to about 2,500 Pa, up to about 3,000 Pa, up to about 5,000 Pa, up to about 10,000 Pa, up to about 100,000 Pa, up to about 1,000,000 Pa, up to about 10,000,000 Pa, or up to about 100,000,000 Pa.

The drug delivery compositions and devices release the therapeutic agents under physiological conditions, such as within the body. Release of the therapeutic agents may occur at varying rates, depending on the components of the composition or device (e.g., identity and concentration of the hydrogel). For example, the release rate of the therapeutic agents (the time at which the therapeutic agents are no longer a part of the composition or device) may be on the order of minutes, hours, days, weeks, months, or years. The therapeutic agents may be released by various mechanisms, e.g., by diffusion, chemical activity, enzymatic activity, or cellular machinery. The drug delivery compositions and devices are stable in vivo such that they deliver drug to the intended target in a suitable amount of time.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of the activator of the innate immune system is released in vivo within 4 weeks, 3 weeks, 2 weeks, 10 days, 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, greater than or equal to 99%, greater than or equal to 95%, greater than or equal to 90%, greater than or equal to 80%, greater than or equal to 70%, greater than or equal to 60%, greater than or equal to 50%, greater than or equal to 40%, greater than or equal to 30%, greater than or equal to 20%, greater than or equal to 10%, greater than or equal to 5%, or greater than or equal to 1% of the activator of the innate immune system is released in vivo within 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of any additional activator of the innate immune system is released in vivo within 4 weeks, 3 weeks, 2 weeks, 10 days, 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, greater than or equal to 99%, greater than or equal to 95%, greater than or equal to 90%, greater than or equal to 80%, greater than or equal to 70%, greater than or equal to 60%, greater than or equal to 50%, greater than or equal to 40%, greater than or equal to 30%, greater than or equal to 20%, greater than or equal to 10%, greater than or equal to 5%, or greater than or equal to 1% of any additional activator of the innate immune system is released in vivo within 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of the activator of the the adaptive immune system is released in vivo within 4 weeks, 3 weeks, 2 weeks, 10 days, 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, greater than or equal to 99%, greater than or equal to 95%, greater than or equal to 90%, greater than or equal to 80%, greater than or equal to 70%, greater than or equal to 60%, greater than or equal to 50%, greater than or equal to 40%, greater than or equal to 30%, greater than or equal to 20%, greater than or equal to 10%, greater than or equal to 5%, or greater than or equal to 1% of the activator of the adaptive immune system is released in vivo within 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of any additional activator of the the adaptive immune system is released in vivo within 4 weeks, 3 weeks, 2 weeks, 10 days, 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, greater than or equal to 99%, greater than or equal to 95%, greater than or equal to 90%, greater than or equal to 80%, greater than or equal to 70%, greater than or equal to 60%, greater than or equal to 50%, greater than or equal to 40%, greater than or equal to 30%, greater than or equal to 20%, greater than or equal to 10%, greater than or equal to 5%, or greater than or equal to 1% of any additional activator of the adaptive immune system is released in vivo within 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, or less than or equal to 1% of the cytokine is released in vivo within 4 weeks, 3 weeks, 2 weeks, 10 days, 7 days, 6 days, 5 days, 4 days, 3 days, 2 days, 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

In certain embodiments, greater than or equal to 99%, greater than or equal to 95%, greater than or equal to 90%, greater than or equal to 80%, greater than or equal to 70%, greater than or equal to 60%, greater than or equal to 50%, greater than or equal to 40%, greater than or equal to 30%, greater than or equal to 20%, greater than or equal to 10%, greater than or equal to 5%, or greater than or equal to 1% of the cytokine is released in vivo within 1 day, 18 hours, 12 hours, 8 hours, 6 hours, 4 hours, 3 hours, 2 hours, 1 hours, 45 minutes, 30 minutes, 20 minutes, 15 minutes, or 10 minutes after implantation of the composition or device.

Preparation and Administration of the Drug Delivery Compositions and Devices

The present disclosure provides drug delivery compositions and devices comprising therapeutic agents, as described herein. In certain embodiments, the therapeutic agents are provided in an effective amount in the drug delivery compositions and devices to treat and/or prevent a disease (e.g., a proliferative disease, such as cancer). In certain embodiments, the effective amount is a therapeutically effective amount of a particular therapeutic agent. In certain embodiments, the effective amount is a prophylactically effective amount of a particular therapeutic agent.

The drug delivery compositions and devices described herein can be prepared by any method known in the art of pharmacology. In certain embodiments, such preparatory methods include the steps of adding a thiol-modified hyaluronic acid into a mold; optionally adding an activator of adaptive immune response to the mold; optionally adding a chemokine or cytokine to the mold; optionally adding an activator of innate immune response to the mold; adding a cross-linking agent to the mold (e.g., a thiol-reactive PEGDA cross-linker); and allowing the mixture to stand for at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 1 hour, at least 90 minutes, at least 2 hours, at least 3 hours, at least 4 hours, at least 5 hours, or at least 6 hours for solidification.

In certain embodiments, the concentration of thiol-modified hyaluronic acid (e.g., GLYCOSIL®) used for the preparation of the hydrogel is, by weight/volume, about 1% to about 10%, about 1% to about 5%, about 1% to about 3%, or about 1.5% to about 2.5%; and the amount of thiol-reactive PEGDA cross-linker (e.g., EXTRALINK®) used for the preparation of the hydrogel is, by weight/volume, about 1% to about 20%, about 10% to about 20%, about 5% to about 15%, or about 10% to about 15%. In certain preferred embodiments, the concentration of thiol-modified hyaluronic acid is about 2% w/v and the concentration of thiol-reactive PEGDA cross-linker is about 12.5% w/v. In certain embodiments, the formulation of 2% thiol-modified hyaluronic acid and 12.5% provides a hydrogel with a storage modulus of about 1000 Pa to about 2000 Pa.

For the preparation of standard tissue engineering applications known in the art, the typical concentration of thiol-modified hyaluronic acid (e.g., GLYCOSIL®) is about 1% w/v and the typical concentration of thiol-reactive PEGDA cross-linker (e.g., EXTRALINK®) is about 1% w/v. Thus, the use of 2% w/v thiol-modified hyaluronic acid (e.g., GLYCOSIL®) and 12.5% thiol-reactive PEGDA cross-linker (e.g., EXTRALINK®) provides an unexpectedly useful and advantageous biomaterial in the disclosed drug delivery compositions and devices.

In certain embodiments, the concentration of the alginate used for the preparation of the hydrogel is, by weight/volume, about 0.5% to about 2.5%, about 0.75% to about 2.0%, or about 1.0% to about 1.5% alginate. In certain embodiments, the amount of 1 M calcium chloride cross-linker solution used for the preparation of the hydrogel is about 5 µL, to 25 µL, about 10 µL to 20 µL, or about 15 µL. In certain embodiments, the payload of interest can be loaded in about 10 µL to 70 µL solvent (PBS or DMSO). 20 µL to 60 µL solvent (PBS or DMSO), about 30 µL to 50 µL solvent (PBS or DMSO), or about 40 µL solvent (PBS or DMSO).

The drug delivery compositions and devices may further comprise at least one excipient. In certain embodiments, the excipient is phosphate-buffered saline, tris(hydroxymethyl) aminomethane, sodium chloride, potassium chloride, calcium chloride, magnesium sulfate, sodium bicarbonate, sodium phosphate, potassium phosphate, calcium nitrate, glucose, lactose, trehalose, sucrose, or a combination thereof. In certain embodiments, the excipient is phosphate-buffered saline, tris(hydroxymethyl)aminomethane, sodium chloride, or a combination thereof. In certain embodiments, the excipient is phosphate-buffered saline.

In certain embodiments, the drug delivery compositions and devices do not include nanoparticles or microparticles. Nanoparticles include particles between 1 and 100 nm in size. Microparticles include particles between 0.1 and 100 µm in size. In certain embodiments, the drug delivery compositions and devices do not include silica microparticles, polyethylene microparticles, polystyrene microparticles, polyester microparticles, polyanhydride microparticles, polycaprolactone microparticles, polycarbonate microparticles, or polyhydroxybutyrate microparticles. In certain embodiments, the drug delivery compositions and devices do not include porous silica microparticles.

In certain embodiments, the drug delivery compositions and devices include one or more organic solvents. In certain embodiments, the drug delivery compositions and devices include dimethylsulfoxide (DMSO).

In certain embodiments, the drug delivery compositions and devices do not include organic; solvent. In certain embodiments, organic solvents are not used in the preparation of the compositions or devices. In certain embodiments, the drug delivery compositions and devices are free of organic solvent. In certain embodiments, the drug delivery compositions and devices are substantially free of organic solvent. In certain embodiments, the drug delivery compositions and devices comprise, by weight, less than 10%, less than 5%, less than 4%, less than 3%, less than 2%, less than 1%, less than 0.5%, less than 0.1%, less than 0.01%, less than 0.001%, or less than 0.0001% of organic solvent. In certain embodiments, the drug delivery compositions and devices comprise, by weight, less than 1000 ppm, less than 500 ppm, less than 400 ppm, less than 300 ppm, less than 200 ppm, less than 100 ppm, less than 50 ppm, less than 40 ppm, less than 30 ppm, less than 20 ppm, less than 10 ppm, less than 1 ppm, less than 10 ppb, or less than 1 ppb of organic solvent. In certain embodiments, the drug delivery composition does not include dimethylsulfoxide (DMSO).

In certain embodiments, the drug delivery compositions comprise organic solvent certain embodiments, the organic solvent is cyclodextrin, methanol, ethanol, isopropanol, ethylene glycol, propylene glycol, or a combination thereof.

The drug delivery compositions and devices can be prepared, packaged, and/or sold in bulk, as a single unit dose, and/or as a plurality of single unit doses. A "unit dose" is a discrete amount of the composition or device comprising a predetermined amount of the therapeutic agents. The amount of the therapeutic agents is generally equal to the dosage of the therapeutic agents which would be administered to a subject and/or a convenient fraction of such a dosage, such as, for example, one-half, one-third, or one-quarter of such a dosage.

Relative amounts of the therapeutic agents, the excipient, and/or any additional ingredients in a composition or device of the disclosure will vary, depending upon the identity, size, and/or condition of the subject treated. By way of example, the composition or device may comprise between 0.1% and 99% (w/w), between 0.1% and 90% (w/w), between 0.1% and 80% (w/w), between 0.1% and 70% (w/w), between 1% and 50% (w/w), between 10% and 80% (w/w), between 10% and 90% (w/w), between 10% and 80% (w/w), between 20% and 80% (w/w), between 30% and 80% (w/w), between 30% and 70% (w/w), or between 40% and 60% (w/w), of the therapeutic agents.

Additional pharmaceutically acceptable excipients may be used in the manufacture of the provided drug delivery compositions and devices. These include inert diluents, dispersing and/or granulating agents, surface-active agents and/or emulsifiers, disintegrating agents, binding agents, preservatives, buffering agents, lubricating agents, and/or oils. Excipients such as cocoa butter and suppository waxes, coloring agents, and coating agents may also be present in the composition or device.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked polyvinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80)), polyoxyethylene esters (e.g., polyoxyethylene monostearate (MYRJ 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (BRIJ 30)), polyvinyl-pyrrolidone), diethylene glycol monolaurate, triethanolamine oleate, sodium oleate, potassium oleate, ethyl oleate, oleic acid, ethyl laurate, sodium lauryl sulfate, PLURONIC F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS, PHENONIP, methylparaben, GERMALL 115, GERMABEN II, NEOLONE, KATHON, and EUXYL.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borne, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Although the descriptions of drug delivery compositions provided herein are principally directed to compositions which are suitable for administration to humans, it will be understood by the skilled artisan that such compositions are generally suitable for administration to animals of all sorts. Modification of drug delivery compositions suitable for administration to humans in order to render the compositions suitable for administration to various animals is well understood, and the ordinarily skilled veterinary pharmacologist can design and/or perform such modification with ordinary experimentation.

The drug delivery compositions and devices provided herein are typically formulated in a size (e.g., volume) and weight appropriate for the intended use (e.g., surgical implantation) for ease of administration. It will be understood, however, that the total amount of the composition or device of the present disclosure (e.g., number of devices implanted) will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; the drugs used in combination or coincidental with the specific active ingredient employed; and like factors well known in the medical arts.

The drug delivery compositions and devices provided herein can be administered by surgical implantation. For example, the drug delivery composition or device may be administered by surgical implantation in the void volume of a resected tumor.

The exact amount of the therapeutic agents required to achieve effective amounts will vary from subject to subject, depending, for example, on species, age, and general condition of a subject, severity of the side effects or disorder, identity of the particular agent(s), and the like.

In certain embodiments, an effective amount of the composition or device for administration to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg.

In certain embodiments, the composition or device may be at dosage levels sufficient to deliver about 0.001 rag/kg to about 100 mg/kg, about 0.01 mg/kg to about 50 mg/kg, about 0.1 mg/kg to about 40 mg/kg, about 0.5 mg/kg to about 30 mg/kg, about 0.01 mg/kg to about 10 mg/kg, about 0.1 mg/kg to about 10 mg/kg, or about 1 mg/kg to about 25 mg/kg, of subject body weight per day, of any of the therapeutic agents present in the composition, to obtain the desired therapeutic effect.

It will be appreciated that dose ranges as described herein provide guidance for the administration of the provided drug delivery compositions and devices to an adult. The amount to be administered to, for example, a child or an adolescent can be determined by a medical practitioner or person skilled in the art and can be lower or the same as that administered to an adult.

It will be also appreciated that compositions and devices, as described herein, can be administered in combination with one or more additional pharmaceutical agents. For example, the compositions and devices can be administered in combination with additional pharmaceutical agents that reduce and/or modify their metabolism, inhibit their excretion, and/or modify their distribution within the body. It will also be appreciated that the additional therapy employed may achieve a desired effect for the same disorder, and/or it may achieve different effects.

The compositions and devices can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents will be administered separately in different doses and/or different routes of administration. The particular combination to employ in a regimen will take into account compatibility of the drug delivery composition with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-inflammatory agents, immunosuppressant agents, and pain-relieving agents. Pharmaceutical agents include small molecule therapeutics such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the drug delivery compositions and devices do not include cells. In certain embodiments, the drug delivery compositions and devices do not include adoptively transferred cells. In certain embodiments, the drug delivery compositions and devices do not include T cells. In certain embodiments, the additional pharmaceutical agent is not adoptively transferred cells. In certain embodiments, the additional pharmaceutical agent is not T cells. In certain embodiments, the drug delivery compositions and devices do not include tumor antigens. In certain embodiments, the drug delivery compositions and devices do not include tumor antigens loaded ex vivo.

In certain embodiments, "drug delivery composition" refers to the composition in a liquid form. In certain embodiments, the term "drug delivery device" refers to the composition in a solid form. In certain embodiments, the transition from composition to device may occur upon sufficient cross-linking such that the resulting material has a storage modulus consistent with a solid form that allows it to be physically manipulated and implanted in a surgical procedure. Accordingly, the drug delivery device, in its solid form, may be particularly amenable for carrying out an intended use of the present disclosure (e.g., surgical implantation).

In certain embodiments, the drug delivery composition and/or drug delivery device is prepared just prior to in vivo implantation (e.g., in an operating room or close proximity). In certain embodiments, the drug delivery composition and/or drug delivery device is prepared within 24 hours, 18 hours, 12 hours, 11 hours, 10 hours, 9 hours, 8 hours, 7 hours, 6 hours, 5 hours, 4 hours, 3 hours, 2 hours, 1 hour, 30 minutes, 20 minutes, 10 minutes, 5 minutes, or 1 minute of in vivo implantation.

In certain embodiments, the drug delivery composition and/or drug delivery device is prepared in advance of in vivo implantation. In certain embodiments, the drug delivery composition and/or drug delivery device is prepared within 31 days, 28 days, 21 days, 14 days, 7 days, 6 days, 5 days, 4 days, 3 days, 2 days, or 1 day of in vivo implantation.

In certain embodiments, the drug delivery composition is prepared within 1 year, 10 months, 8 months, 6 months, 4 months, 3 months, 2 months, 31 days, 28 days, 21 days, 14 days, 7 days, 6 days, 5 days, 4 days, 3 days, 2 days, or 1 day of its use in a therapeutic setting. In certain embodiments, the prepared drug delivery composition is then used to prepare the corresponding drug delivery device by addition of a cross-linking agent, as described herein, within 31 days, 28 days, 21 days, 14 days, 7 days, 6 days, 5 days, 4 days, 3 days, 2 days, 1 day, 18 hours, 12 hours, 11 hours, 10 hours, 9 hours, 8 hours, 7 hours, 6 hours, 5 hours, 4 hours, 3 hours, 2 hours, 1 hour, 30 minutes, 20 minutes, 10 minutes, 5 minutes, or 1 minute of in vivo implantation.

Also encompassed by the disclosure are kits. The kits provided may comprise compositions and/or devices described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the kit comprises precursor components (e.g., hyaluronic acid and a cross-linker; or alginate and a cross-linker) to the drug delivery composition and/or drug delivery device.

In certain embodiments, the kit comprises a hydrogel and an activator of innate immune response. In certain embodiments, the kit comprises a hydrogel and a cytokine. In certain embodiments, the kit comprises a hydrogel and an activator of adaptive immune response. In certain embodiments, the kit further comprises an activator of innate immune function. In certain embodiments, the kit further comprises a cytokine. In certain embodiments, the kit further comprises an activator of adaptive immune response. In certain embodiments, the kit further comprises a modulator of macrophage effector function. In certain embodiments, the kit further comprises an additional activator of adaptive immune response. In certain embodiments, the kit further comprises an oncolytic virus, a radioactive isotope, an immunomodulatory chemotherapeutic agent, a targeted agent, or a combination thereof. In certain embodiments, the kit comprises any drug delivery composition described herein. In certain embodiments, the kit comprises any drug delivery device described herein.

In certain embodiments, the kit does not comprise a chemotherapeutic agent. In certain embodiments, the kit does not comprise a cytotoxic agent.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating cancer. A kit described herein may include one or more additional pharmaceutical agents described herein as a separate composition.

Methods of Treatment and Uses

The present disclosure provides methods of using the drug delivery compositions and devices described herein, for the treatment and/or prevention of a proliferative disease, such as cancer (e.g. a sarcoma, a carcinoma, a lymphoma, a germ cell tumor, or a blastoma) in a subject.

In some embodiments, the drug delivery compositions and devices described herein are useful in treating cancer. In some embodiments, the drug delivery compositions and devices described herein are useful to delay the onset of, slow the progression of, or ameliorate the symptoms of cancer. In some embodiments, the drug delivery compositions and devices described herein are useful to prevent cancer. In some embodiments, the drug delivery compositions and devices described herein are useful to prevent primary tumor regrowth. In some embodiments, the drug delivery compositions and devices described herein are useful to prevent tumor metastasis. In some embodiments, the drug delivery compositions and devices described herein are administered in combination with other compounds, drugs, or therapeutic agents to treat cancer.

In certain embodiments, the cancer is a solid tumor. In certain embodiments, the cancer is a sarcoma, a carcinoma, a lymphoma, a germ cell tumor, a blastoma, or a combination thereof. In certain embodiments, the tumor is a sarcoma, a carcinoma, a lymphoma, a germ cell tumor, a blastoma, or a combination thereof.

In some embodiments, the drug delivery compositions and devices described herein are useful for treating a cancer including, but not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bile duct cancer; bladder cancer; bone cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cardiac tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ductal carcinoma in situ; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; multiple myeloma; heavy chain disease (e.g., alpha chain disease, gamma chain disease, mu chain disease); hemangioblastoma; histiocytosis; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); melanoma; midline tract carcinoma; multiple endocrine neoplasia syndrome; muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); nasopharynx cancer; neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN). Islet cell tumors); parathyroid cancer; papillary adenocarcinoma; penile cancer (e.g., Paget's disease of the penis and scrotum); pharyngeal cancer; pinealoma; pituitary cancer; pleuropulmonary blastoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; retinoblastoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; stomach cancer; small intestine cancer; sweat gland carcinoma; synovioma; testicular cancer (e.g., seminoma, testicular embryonal carcinoma); thymic cancer; thyroid cancer (e.g., papillary carcinoma of the thyroid, papillary thyroid carcinoma (PTC), medullary thyroid cancer); urethral cancer; uterine cancer; vaginal cancer; vulvar cancer (e.g., Paget's disease of the vulva), or any combination thereof.

In certain embodiments, the cancer is breast cancer. In certain embodiments, the cancer is skin cancer. In certain embodiments, the cancer is melanoma. In certain embodiments, the cancer is lung cancer. In certain embodiments, the cancer is kidney cancer. In certain embodiments, the cancer is liver cancer. In certain embodiments, the cancer is pancreatic cancer. In certain embodiments, the cancer is colorectal cancer. In certain embodiments, the cancer is bladder cancer. In certain embodiments, the cancer is lymphoma. In certain embodiments, the cancer is prostate cancer, in certain embodiments, the cancer is thyroid cancer.

In some embodiments, the drug delivery compositions and devices described herein are useful in treating adenocarcinoma, adrenal gland cancer, anal cancer, angiosarcoma, appendix cancer, bile duct cancer, bladder cancer, bone cancer, brain cancer, breast cancer, bronchus cancer, carcinoid tumor, cardiac tumor, cervical cancer, choriocarcinoma, chordoma, colorectal cancer, connective tissue cancer, craniopharyngioma, ductal carcinoma in situ, endotheliosarcoma, endometrial cancer, ependymoma, epithelial carcinoma, esophageal cancer, Ewing's sarcoma, eye cancer, familiar hypereosinophilia, gall bladder cancer, gastric cancer, gastrointestinal carcinoid tumor, gastrointestinal stromal tumor (GIST), germ cell cancer, head and neck cancer, hemangioblastoma, histiocytosis, Hodgkin lymphoma, hypopharynx cancer, inflammatory myofibroblastic tumors, intraepithelial neoplasms, immunocytic amyloidosis, Kaposi sarcoma, kidney cancer, liver cancer, lung cancer, leiomyosarcoma (LMS), mastocytosis, melanoma, midline tract carcinoma, multiple endocrine neoplasia syndrome, multiple myeloma, muscle cancer, myelodysplastic syndrome (MDS), mesothelioma, myeloproliferative disorder (MPD), nasopharynx cancer, neuroblastoma, neurofibroma, neuroendocrine cancer, non-Hodgkin lymphoma, osteosarcoma, ovarian cancer, pancreatic cancer, paraneoplastic syndromes, parathyroid cancer, papillary adenocarcinoma, penile cancer, pharyngeal cancer, pheochromocytoma, pinealoma, pituitary cancer, pleuropulmonary blastoma, primitive neuroectodermal tumor (PNT), plasma cell neoplasia, prostate cancer, rectal cancer, retinoblastoma, rhabdomyosarcoma, salivary gland cancer, sebaceous gland carcinoma, skin cancer, small bowel cancer, small intestine cancer, soft tissue sarcoma, stomach cancer, sweat gland carcinoma, synovioma, testicular cancer, thymic cancer, thyroid cancer, urethral cancer, uterine cancer, vaginal cancer, vascular cancer, vulvar cancer, or a combination thereof.

In some embodiments, the drug delivery compositions and devices described herein are useful in treating and/or preventing solid tumors and metastases.

In certain embodiments, the methods described herein include implanting in a subject an effective amount of the drug delivery composition or device described herein. In certain embodiments, the methods described herein include surgically implanting in a subject an effective amount of the drug delivery composition or device described herein. In certain embodiments, the methods described herein further comprise implanting the drug delivery composition or device after surgical resection of a tumor. In certain embodiments, the methods described herein further comprise implanting the drug delivery composition or device at the site of tumor resection. In certain embodiments, the methods described herein further comprise implanting the drug delivery composition or device in the void volume of the resected tumor. In certain embodiments, the methods described herein further comprise implanting the drug delivery composition or device in the tumor resection site during tumor resection surgery.

In certain embodiments, the methods described herein comprise implanting the drug delivery composition or device after removal of, by weight, greater than or equal to 50%, greater than or equal to 55%, greater than or equal to 60%, greater than or equal to 65%, greater than or equal to 70%, greater than or equal to 75%, greater than or equal to 80%, greater than or equal to 85%, greater than or equal to 90%, greater than or equal to 95%, greater than or equal to 96%, greater than or equal to 97%, greater than or equal to 98%, or greater than or equal to 99% of the resected tumor. In certain embodiments, the methods described herein comprise implanting the drug delivery composition or device after removal of, by volume, greater than or equal to 50%, greater than or equal to 55%, greater than or equal to 60%, greater than or equal to 65%, greater than or equal to 70%, greater than or equal to 75%, greater than or equal to 80%, greater than or equal to 85%, greater than or equal to 90%, greater than or equal to 95%, greater than or equal to 96%, greater than or equal to 97%, greater than or equal to 98%, or greater than or equal to 99% of the resected tumor.

In certain embodiments, the methods described herein do not comprise implanting the drug delivery composition or device adjacent to a tumor. In certain embodiments, the methods described herein do not comprise implanting the drug delivery composition or device adjacent to a tumor without resection of the tumor.

In certain embodiments, the drug delivery compositions and devices described herein are administered in combination with one or more additional therapeutic agents described herein. In certain embodiments, the additional therapeutic agent is an anti-cancer agent.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal, such as a rodent, pig, dog, or non-human primate. In certain embodiments, the subject is a non-human transgenic animal such as a transgenic mouse or transgenic pig.

EXAMPLES

In order that the invention described herein may be more fully understood, the following examples are set forth. It should be understood that these examples are for illustrative purposes only and are not to be construed as limiting this invention in any manner.

Figure 68:
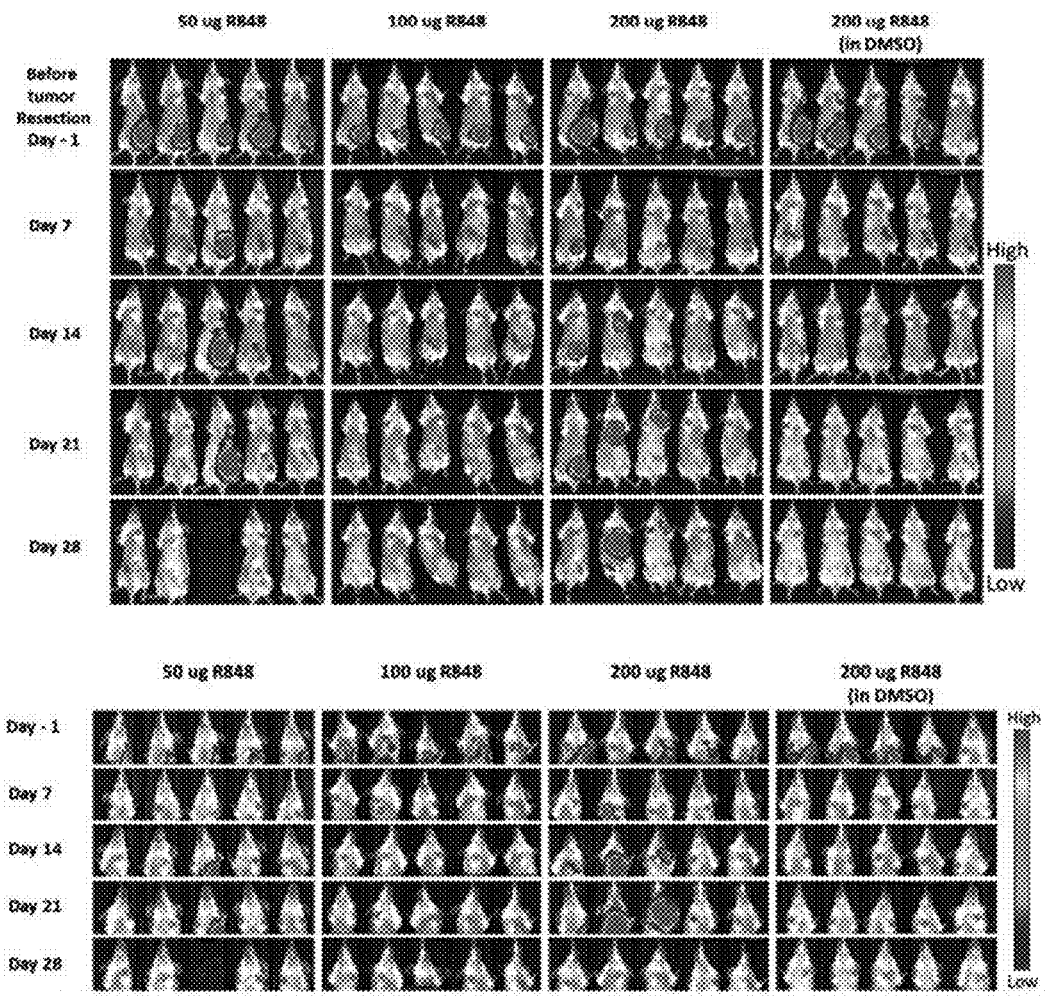
FIG. 68 shows images of individual mice after implantation of exemplary drug delivery device 22 wherein resiquimod (R848, Invivogen) (50 µg, 100 µg, or 200 µg) was dissolved in water for formation of the device; and exemplary drug delivery device 22 wherein resiquimod (R848, Sigma) (200 µg) was dissolved in DMSO for formation of the device. The devices were implanted following inoculation of tumors originating from 4T1-Luc2 syngeneic breast cancer cells. The images show the appearance/disappearance of tumor over a 4-week period. The upper images monitor the site of resection (local tumor recurrence) while the low images show lung metastasis.
Figure 69:
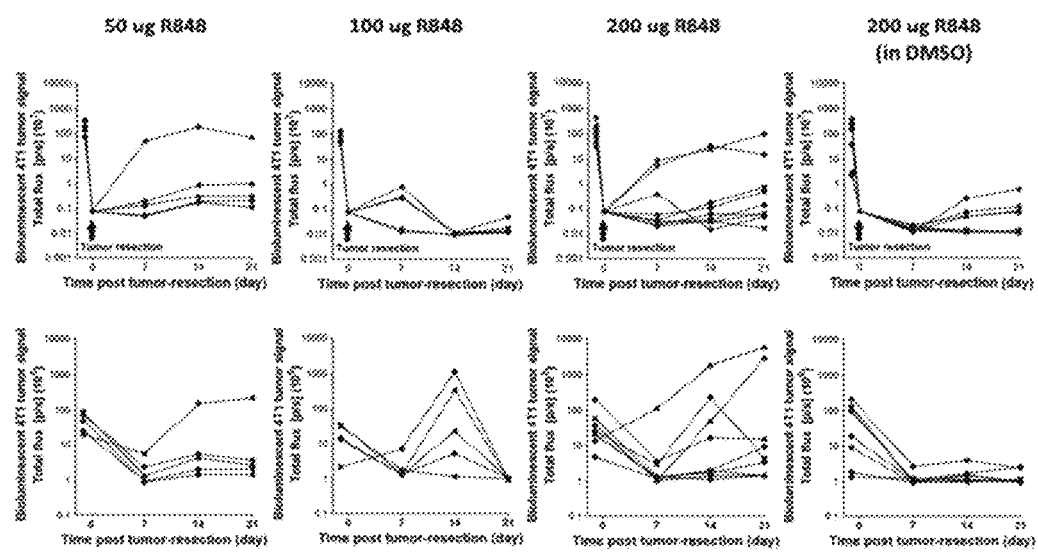
FIG. 69 is a series of graphs showing the total flux of bioluminescent 4T1-Luc2 cells after administration of the exemplary drug delivery devices described in FIG. 68. The upper images show the site of resection (local tumor recurrence) while the lower images show lung metastasis.
Figure 70:
FIG. 70 shows images of individual mice after implantation of exemplary drug delivery devices 5 (3 µg IL-15sa), 4 (300 µg anti-PD-1 antibody), 24 (15 µg IFN-α), 25 (3 µg IFN-β), and 26 (30 µg IFN-γ) following inoculation of tumors originating from 4T1-Luc2 syngeneic breast cancer cells. The images show the appearance/disappearance of tumor over a 4-week period. The upper images monitor the site of resection (local tumor recurrence) while the lower images show lung metastasis.
Figure 71:
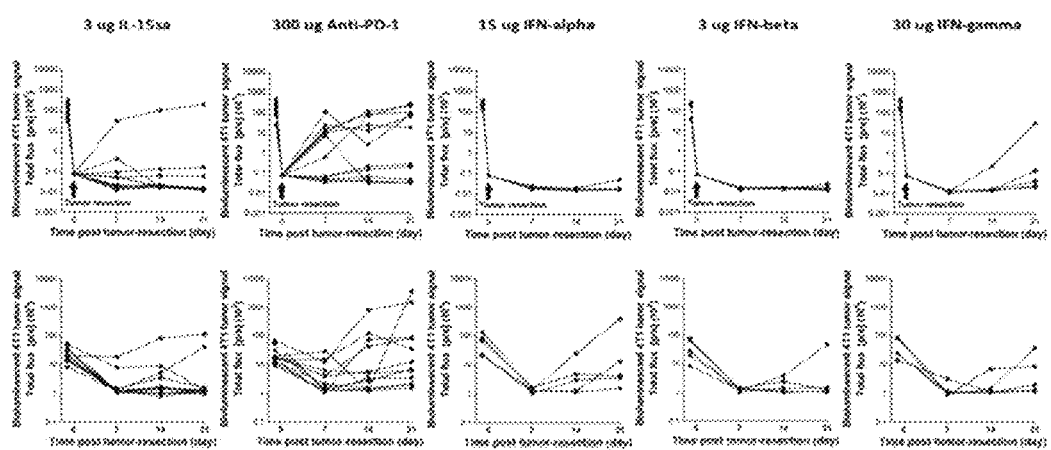
FIG. 71 is a series of graphs showing the total flux of bioluminescent 4T1-Luc2 cells after administration of the exemplary drug delivery devices described in FIG. 70. The upper images show the site of resection (local tumor recurrence) while the lower images show lung metastasis.

Materials and Methods for Preparation of Hydrogels:

GLYCOSIL® hyaluronic acid (a thiol-modified hyaluronic acid and a constituent of native extracellular matrix) and EXTRALINK® polyethylene glycol diacrylate (a thiol-reactive cross-linker) were purchased from ESI BIO. Hystem hydrogel kits (ESI Bio) were used to prepare the hydrogels. A Teflon mold (9 mm diameter) was first filled with 1.20 µl Glycosil, and then 200 µg of R848 (Sigma, SML0196) or 100 µg of c-di-AM(PS)2 (Rp,Rp) (Invivogen, tlrl-nacda2r) was added. For comparative studies, 300 µs rat anti-mouse PD-1 (anti-PD-1) (BioXCell, clone 29F.1A12), 300 µg hamster anti-mouse CTLA-4 (anti-CTLA-4) (BioXCell, clone 9H10), 3 µg mouse IL-15/IL-15R complex recombinant protein carrier-free (IL-15sa) (eBioscience, 34-8152-82), 100 µg of 2'3'-cGAMP (Invivogen, tlrl-nacga23), 200 µg of lenalidomide (Sigma, CDS022536), 1500 µg of celecoxib (Selleckchem, S1261), 10 µg of Ccl4 (R&D Systems, 451-MB/CF), 10 µg of Ccl5 (R&D Systems, 478-MR/CF), 10 µg of Cxcl10 (R&D Systems, 466-CR/CF), 100 µg of paclitaxel (Selleckchem, S1150), or 100 µg of doxorubicin (Selleckchem, S1208) was added. Next, 30 µl of Extralink was added into the mold, and the hydrogel was allowed to cross-link for at least one hour. For in vitro release studies and confocal imaging, anti-PD-1 and IL-15sa were fluorescently tagged with Alexa Fluor 405 NHS Ester (Thermo Fisher Scientific, A30000) and VivoTag 680XL Protein Labeling Kit (Perkin Elmer, NEV11118), respectively, according to the manufacturer's guidelines, and fluorescein-tagged 2'3'-cGAMP (BIOLOG Life Science Institute, C195) was used as a model compound for 2'3'-c-di-PS (2) (Rp, Rp). For in viva imaging, both anti-PD-1 and IL-15sa were fluorescently labeled with VivoTag 800 (Perkin Elmer, NEV11107), and sulfo-Cy7-labeled 2'3'-cGAMP (BIOLOG Life Science Institute, custom order) was used. For evaluation of in vivo degradation of the hydrogel, 1.2 µl Alexa Fluor 750 C5-maleimide (Molecular Probes, 30459) was conjugated directly to the hydrogel. Alginate hydrogels were prepared by filling a Teflon mold with 200 µl of sodium alginate solution (amsbio, AMS.CSR-ABC-AL) and then adding 200 µg of R848 followed by 15 µl of 1 M calcium chloride (bioWORLD, 40320005). The hydrogel was allowed to set for at least 30 minutes. Protein conjugation and hydrogel preparation were done under sterile conditions. Anti-CD40 (clone, FGK45) and anti-CD137 (clone 3H3) antibodies were also purchased from BioxCell. c-di-GMP, resiquimod (TLR7/8 agonist) (for FIG. 68 and FIG. 69, wherein resiquimod was dissolved in water rather than DMSO), poly(I:C) (TLR3 agonist), and CpG (TLR9 agonist) were purchased from Invivogen. ALEXA FLUOR® 750 dye was purchased from Thermo Fisher Scientific.

Confocal Microscopy:

Fluorescently tagged 2"3"-cGAMP, IL-15sa, and anti-PD-1 as described herein were imaged under a confocal laser scanning microscope (Leica TCS SP8 STED CW; Leica Microsystems). The obtained images were processed using Leica LAS AF software (Leica Microsystems).

Cell Lines:

The metastatic murine 4T1 breast cancer cells, which express Luc2 (Perkin Elmer), were cultured in complete RPMI 1640 medium with 10% FBS, 1% penicillin-streptomycin, and 1% L-glutamine. The metastatic murine 4T1 breast cancer (ATCC, CRL2539) and B16-BL6 melanoma (kindly provided by Dr. Glenn Merlino, NIH) cell lines were cultured in complete RPMI 1640 medium with 10% FBS, 1% penicillin-streptomycin, and 1% L-glutamine. The murine LLC lung cancer cell line (kindly provided by Dr. Harvey Cantor, DFCI) were cultured in complete DMEM with 10% FBS, 1% penicillin-streptomycin, and 1% sodium pyruvate. Cells were tested for mycoplasma contamination and found to be negative.

Mice:

All animal experiments were carried out in accordance with protocols approved by the Dana-Farber Cancer Institute (DFCI) Institutional Animal Care and Use Committee (IACUC). For the metastic breast cancer model, female BALB/cJ mice (6-8 weeks old) were purchased from Jackson Laboratories (Stock #000651). For the metastatic melanoma model, B6(Cg)-Tyrc-2J/J mice (7 weeks old) were purchased from Jackson Laboratories (Stock #000058). For the lung cancer model, female C57BL/6J mice (6-8 weeks old) were purchased from Jackson Laboratories (Stock #000664). Mice were housed in the animal facility of DFCI.

General Surgical Procedures:

Seven-week-old female Balb/c mice were inoculated orthotopically with 100,000 4T1-Luc2 syngeneic breast cancer cells (into the fourth mammary fat pad). After 10 days, the mice were anesthetized, tumors were surgically resected, and compositions were placed in the resection site. For in vivo degradation studies, compositions were placed by the mammary fat pad; for most mice, no tumors were inoculated or removed for these studies, as the majority of mice succumb to relapse if immunotherapy is not included in the compositions, though one mouse survived through surgery alone. The order of surgeries avoided systematic error by dividing up the groups. Standard follow-up care (wound clips, analgesic) was provided.

In Vitro Release Study:

To determine the release kinetics of each payload from the hydrogel, a hydrogel loaded with fluorescently tagged anti-PD-1, fluorescently tagged IL-15sa, lenalidomide, celecoxib, fluorescently tagged 2'3'-cGAMP, or R848 was immersed in 3 mL pH 7.4 phosphate buffered saline (PBS). At each time point, 1 mL of media was taken out and the same amount of fresh buffer was added back. The amount of payload that had been released was then measured using a fluorescence plate reader or via HPLC.

In Vivo Evaluation of Hydrogel Degradation:

In vivo degradation of fluorophore-labeled hydrogels was monitored using an IVIS Spectrum In Vivo Imaging System (Perkin Elmer) after the hydrogels were surgically implanted into mice. Fluorescent imaging was obtained weekly and analyzed with Living Imaging software (Perkin Elmer). Both tumor-bearing mice and non-tumor-bearing mice were tested for in vivo hydrogel degradation evaluation, though only one tumor-bearing mouse survived for more than a few weeks in the absence of therapy, as tumors recurred in nearly all animals receiving surgery alone.

In Vivo Release Study:

To evaluate the in vivo release profiles of Cy7 carboxylic acid (a model compound for R848), anti-PD-1, IL-15sa, and 2'3'-cGAMP, hydrogels containing the fluorophore or one of the fluorescently labeled payloads were surgically implanted into non-tumor-bearing mice. Fluorescent imaging was monitored using an IVIS Spectrum In Vivo Imaging System (Perkin Elmer).

In Vivo Tumor Models and Treatment:

For the metastatic breast cancer model, $10^5$ 4T1-Luc2 or 4T1 cells (in 30 µl DPBS) were inoculated orthotopically into the fourth mammary pad of mice to generate a local tumor mass. Cells were injected without any incision to expose the fat pad. Mice were randomly assigned to treatment groups, and surgery was performed 10 days after tumor inoculation. For the metastatic melanoma and lung cancer models, $10^6$ B16-BL6 or $5 \times 10^5$ LLC cells (in 100 µl DPBS) were inoculated subcutaneously in mice to generate a local tumor mass. Mice were randomly assigned to treatment groups, and surgery was performed when tumor volumes reached ~600 mm$^3$. While mice were kept under anesthesia at 2% isoflurane, the tumor was resected, and the hydrogel was placed in the site of the resultant cavity at the time of surgery. The wound was closed with medical clips. Control experiments were performed in which therapy was administered in solution at the site of surgery, intraperitoneally, or intravenously. For tumor re-challenge experiments, $10^4$ 4T1-Luc2 cells were inoculated in the contralateral fourth mammary fat pad. The surgeries were performed independently at least three times, and the surgeon was often blinded.

In Vivo Bioluminescence and Imaging:

After surgery, mice were inspected weekly for tumor recurrence and distal metastasis by bioluminescence imaging (BLI). To this end, 10 min after intraperitoneal injection of D-luciferin (150 mg/kg), a substrate of Luc2, the mice were anesthetized with 2% isoflurane and imaged using an IVIS Spectrum In Vivo Imaging System (Perkin Elmer).

Depletion of NK cells, CD8$^+$ T cells, or CD4$^+$ T Cells and Neutralization of IFNAR-1:

Specific cell subsets (NK cells, CD8$^+$ T cells, or CD4$^+$ T cells) were depleted by administering depleting antibody intraperitoneally every three days, beginning one day prior to therapy. The antibodies used for depletion were anti-Asialo GM1 (polyclonal, Wako Chemical, 30 µl), anti-mouse CD8a (clone 2.43), and anti-mouse CD4 (clone GK1), respectively. To test the role of type I IFN signaling, mice were administered a blocking anti-IFN alpha/beta receptor subunit 1 (anti-IFNAR-1, clone. MARL-5A3). All antibodies were purchased from BioXCell, and 200 µg of antibody was used unless otherwise specified. Cellular depletion of NK cells, CD8$^+$ T cells, and CD4$^+$ T cells was confirmed by flow cytometry of leukocytes isolated from the blood of mice to which antibodies or PBS had been administered.

In Vivo Cytokine Analysis:

Blood was collected from mice 14 days after resection of tumor and placement of scaffold (empty or containing the triple combination). Blood was collected from mice 1.5 hours, 6 hours, 3 days, and 14 days after resection of tumor and treatment with an R848-loaded hydrogel or no hydrogel. In other experiments, STING-RR-loaded hydrogels were used. Plasma was sent to Eve Technologies in order to measure the levels of circulating cytokines that were produced in response to the therapy. The MD-31 panel was complemented by assessment of IFN-α and IFN-β.

Flow Cytometry:

Flow cytometry was performed on a BD LSRFortessa X-20 (BD Biosciences), and all antibodies were purchased from BioLegend, eBioscience, or BD Biosciences (Table 6). Leukocyte Activation Cocktail with BD GolgiPlug (BD Biosciences) was used to stimulate splenocytes. GWEPDDNPI (purity >95%), an immunodominant peptide of survivin (amino acids 66-74), was purchased from New England Peptide. SPSYVYFIQF (purity>95%), an immunodominant peptide of Murine leukemia virus envelope glycoprotein gp70 (amino acids 423-431), was purchased from New England Peptide. GolgiPlug (BD Biosciences) was used for inspection of intracellular cytokines and cytolytic molecules.

Evaluation of Blood Counts and Liver Enzymes:

Blood was collected from mice 15 days after resection of tumor and administration of therapy or 3 and 14 days after resection of tumor and administration of therapy. Blood counts (hemoglobin, hematocrit, white blood cells, platelets, differentials, and red blood cell indices) were quantified by a HEMAVET 950FS in the DFCI Animal Research Facility.

Serum was isolated from the blood and liver enzymes (AST, ALT, and BUN) were quantified by IDEXX BioResearch.

Statistical Methods:

Statistical methods were not used to predetermine necessary sample size. The sample sizes were selected based on the results of pilot experiments so that relevant statistical tests could reveal significant differences between experimental groups. Statistical analysis was performed using GraphPad Prism software version 7.01. Data are presented as mean±SEM as indicated in the Figure legends. For statistical significance comparing two groups, the two-tailed unpaired t-test was used. For survival analysis, the Log-rank (Mantel-Cox) test was employed. * p≤0.05,  p≤0.01, * p≤0.001, **** p≤0.0001

Example 1. Preparation of the Drug Delivery Compositions

A series of hydrogels were prepared to determine useful preparation methods and amounts of reagents required to construct the hydrogel system. Generally, the GLYCOSIL® hyaluronic acid and EXTRALINK® polyethylene glycol diacrylate cross-linker were combined in a TEFLON® mold. The hydrogel was formed upon allowing the combined reagents to stand for at least 1 hour. The storage modulus of the hydrogel was measured with a rheometer. These are summarized in Table 1.

TABLE 1

| Hydrogel | GLYCOSIL® (w/v.) | EXTRALINK® (w/v) | total volume | mold size | storage modulus |
|---|---|---|---|---|---|
| 1 | 2.5%; 200 µL | 10%; 50 µL | 250 µL | Diameter: 8 mm Height: 5 mm | |
| 2 | 2.5%; 160 µL | 10%; 40 µL | 200 µL | Diameter: 9 mm Height: 3.2 mm | |
| 3 | 2.0%; 160 µL | 10%; 40 µL | 200 µL | Diameter: 9 mm Height: 3.2 mm | |
| 4 | 2.0%; 120 µL | 12.5%; 30 µL | 150 µL | Diameter: 9 mm Height: 3.2 mm | ~1500 Pa |

Hydrogels were also prepared from alginate. To prepare hydrogel 5, 200 µL of sodium alginate solution (ca. 0.5-2.5% solution purchased from amsbio; product code: AMS.CSR-ABC-AL) was mixed with 15 µL of 1 M calcium chloride solution as well as the compound of interest (e.g., 100 µg of STING-RR dissolved in 40 µL PBS). An alginate hydrogel with resiquimod was prepared in analogous fashion. A Teflon mold was filled with 200 µL of the sodium alginate solution (ca. 0.5-2.5% solution purchased from amsbio, AMS.CSR-ABC-AL) and then 200 µg of resiquimod (dissolved in 20 µL of DMSO) was added, followed by 15 µL of 1 M calcium chloride (bioWORLD, 40320005). The hydrogel was allowed to set for at least 30 minutes before use.

General Procedure of Preparation of the Drug Delivery Composition:

120 µL GLYCOSIL® hyaluronic acid (2.0%) was poured into a TEFLON® mold (diameter: 9 mm; height: 3.2 mm). Optionally, an activator of adaptive immune response was dissolved in PBS (30 µL) and added to the mold. Optionally, a cytokine was dissolved in PBS (10 µL) and added to the mold. Optionally, an activator of innate immune response was dissolved in water (10 µL) and added to the mold. 30 µL EXTRALINK®) polyethylene glycol diacrylate (12.5%) was added to the mold. The mixture was allowed to stand for at least one hour for solidification.

Compositions were prepared according to the general procedure above and are summarized in Table 2. In Table 2. S=STING agonist (2′-3′-cGAMP); STING-RR=2′3′-c-di-AM(PS)2 (Rp,Rp); I=IL-15 superagonist; P=anti-PD-1 antibody; R848=resiquimod. Respective doses were 25 µg for S, 1.5 µg for I, and 150 µg for P, unless otherwise indicated. A fluorescent dye (e.g., ALEXA FLUOR® 750 dye) could be added to the compositions to allow for imaging of the device (e.g., device F is device 8+1.2 µL ALEXA FLUOR® 750 C5-maleimide, which was conjugated directly to the hydrogel; FIG. 1). Devices in this Table (as well as device F) were prepared according to the methods described for hydrogel 4 in Table 1.

TABLE 2

| Device | Activator of innate immune response | Cytokine/ chemokine | Activator of adaptive immune response | Storage modulus |
|---|---|---|---|---|
| 1 | S (25 µg) | I (1.5 µg) | P (150 µg) | 1380 Pa |
| 2 | — | I | P | |
| 3 | celecoxib (1 mg) | — | — | |
| 4 | — | — | P | |
| 5 | — | I | — | |
| 6 | c-di-GMP (25 µg) | I | P | |

TABLE 2-continued

| Device | Activator of innate immune response | Cytokine/ chemokine | Activator of adaptive immune response | Storage modulus |
|---|---|---|---|---|
| 7 | S | — | — | |
| 8 | — | — | — | |
| 9 | S | — | P | |
| 10 | S | I | — | |
| 11 | S | I | anti-CD137 (150 µg) | |
| 12 | S | I | anti-CD40 (150 µg) | |
| 13 | S | IL-21 (20 µg) | P | |
| 14 | R848 (50 µg) | I | P | |
| 15 | poly(I:C) (50 µg) | I | P | |
| 16 | CpG (50 µg) | I | P | |
| 17 | S (50 µg) | — | — | |
| 18 | — | I (3 µg) | — | |
| 19 | — | — | P (300 µg) | |
| 20 | S | I | Isotype control | |
| 21 | STING-RR | I | P | |
| 22 | R848 (200 µg) | — | — | |
| 23 | STING-RR (100 µg) | — | — | |
| 24 | — | IFN-α (15 µg) | — | |
| 25 | — | IFN-β (3 µg) | — | |

TABLE 2-continued

| Device | Activator of innate immune response | Cytokine/ chemokine | Activator of adaptive immune response | Storage modulus |
|---|---|---|---|---|
| 26 | — | IFN-γ (30 µg) | — | |
| 27 | — | — | anti-CTLA4 + P (150 µg each) | |
| 28 | R848 (50 µg) | — | anti-CTLA4 + P (150 µg each) | |
| 29 | M-TriDAP (300 µg) | — | — | |
| 30 | — | — | Lenalidomide (200 µg) | |
| 31 | — | — | anti-CTLA4 (300 µg) | |
| 32 | — | CCL4 (10 µg) | — | |
| 33 | — | CCL5 (10 µg) | — | |
| 34 | — | CXCL10 (10 µg) | — | |
| 35 | Paclitaxel (100 µg) | — | — | |
| 36 | Doxorubicin (100 µg) | — | — | |

Example 2. Biodegradation Studies

Figure 2:
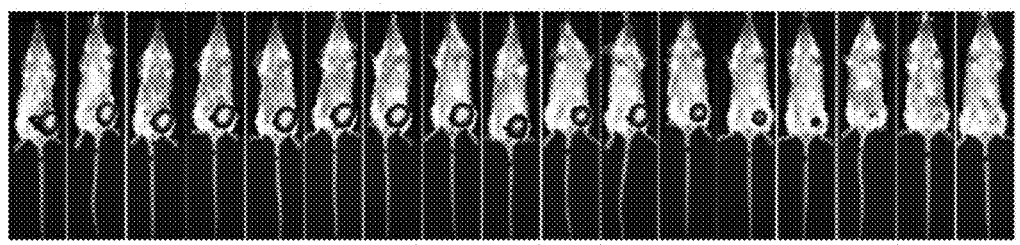
FIG. 2 shows images of an individual mouse after implantation of exemplary drug delivery device following tumor inoculation and resection. The images show degradation of the hydrogel, which was loaded with a fluorescent dye, over a 13-week period.
Figure 3:
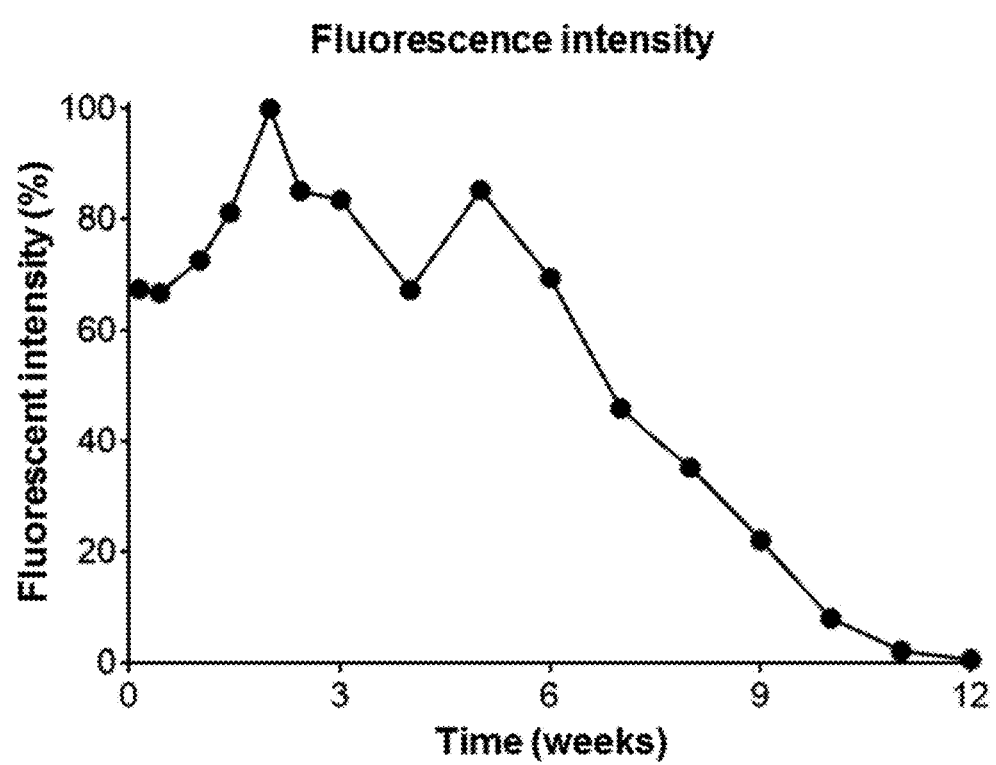
FIG. 3 is a graph showing biodegradation, over time, of exemplary drug delivery device F implanted in FIG. 2.

Seven-week-old female Balb/c mice were inoculated orthotopically with 100,000 4T1-Luc2 syngeneic breast cancer cells (into the fourth mammary fat pad). After 10 days, mice were anesthetized, tumors were surgically resected, and device F was placed in the resection site. The majority of the mice were sacrificed due to relapse of the tumors. The presence of the composition in the surviving mouse was monitored via imaging over the course of 13 weeks (FIG. 2). This composition was stable and completely biodegraded after 13 weeks (FIG. 3).

Figure 4:
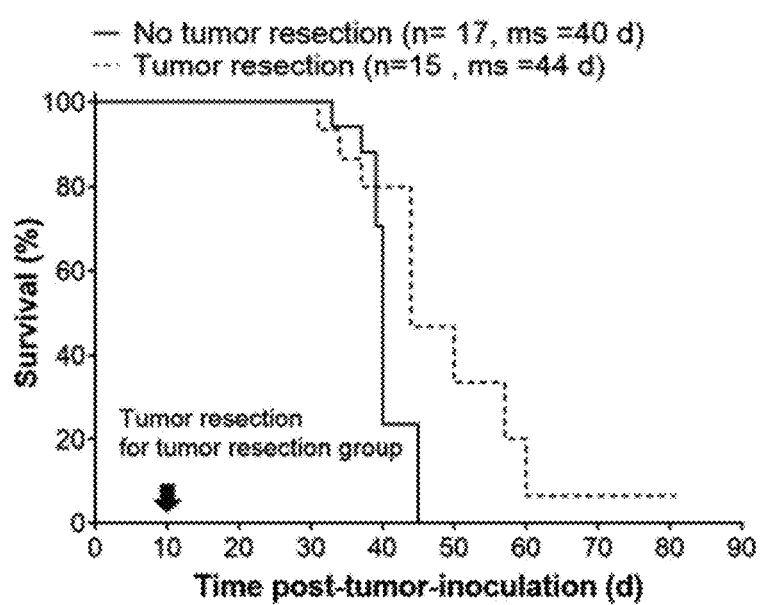
FIG. 4 is a Kaplan-Meier curve of female BALB/cJ mice inoculated orthotopically with 4T1-Luc2 cells whose tumors were either untreated or surgically resected.

Untreated mice harboring 4T1 tumors died from their primary tumors within seven weeks (median survival 40 d) of tumor inoculation, and surgical removal of the tumors provided little survival benefit (median survival 44 d), as mice succumbed to tumor recurrence and metastasis in this model (FIG. 4).

Figure 5:
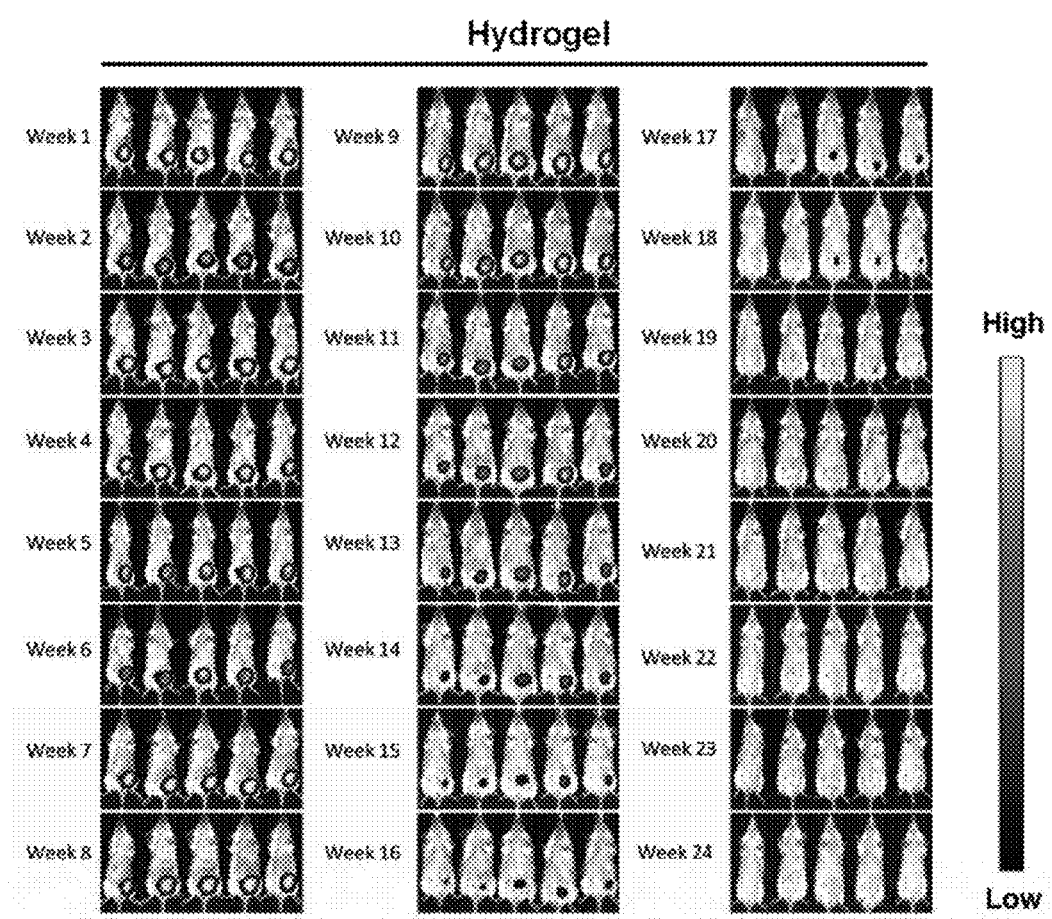
FIG. 5 shows images of individual mice after implantation of exemplary drug delivery device F by the mammary fat pad without tumor inoculation and resection. The images show degradation of the hydrogel, which was loaded with a fluorescent dye, over a 24-week period.
Figure 6:
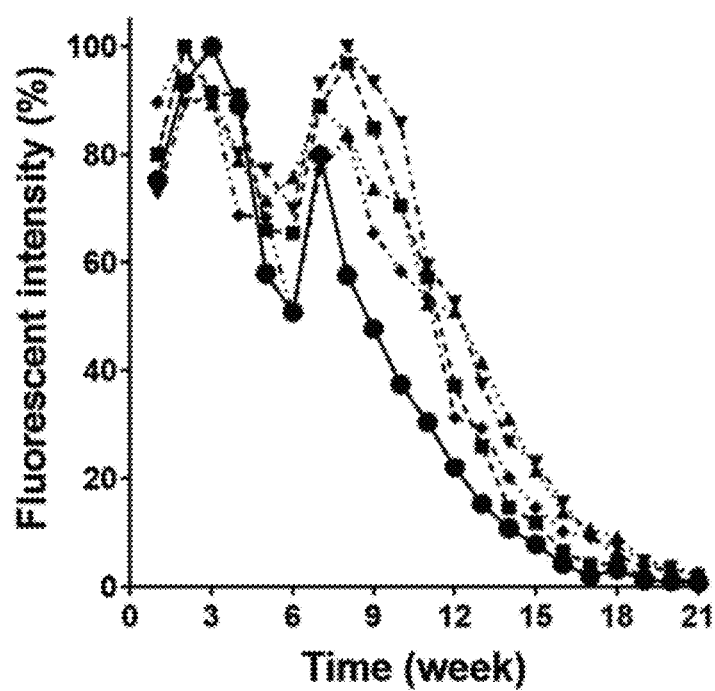
FIG. 6 is a graph showing biodegradation, over time, of the exemplary drug delivery device F implanted in FIG. 5.
Figure 7:
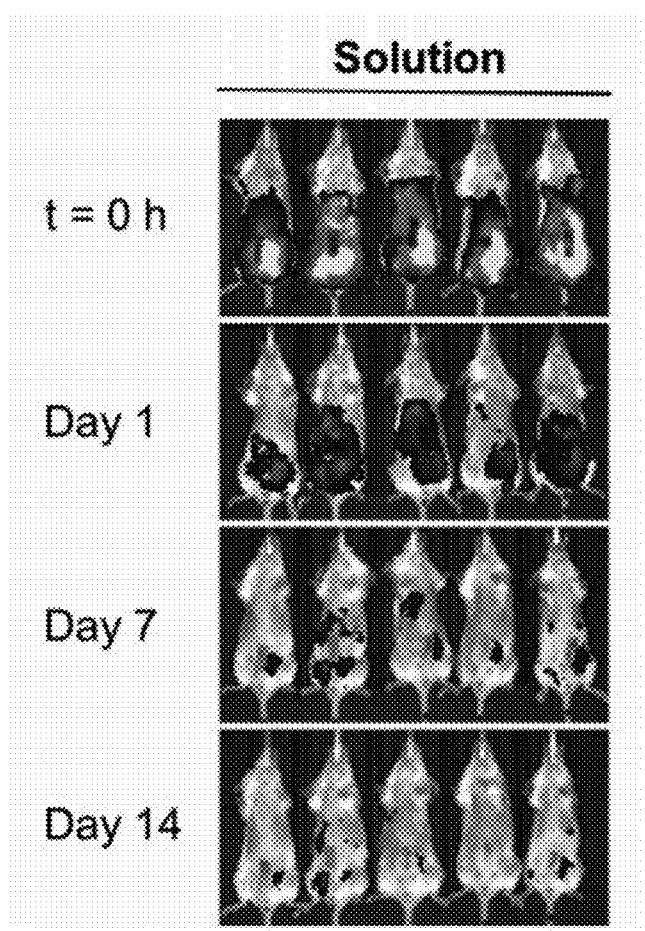
FIG. 7 shows images of individual mice after ALEXA FLUOR® 750 dye was administered in solution locally, and fluorescence IVIS imaging was performed at the indicated time points.
Figure 8:
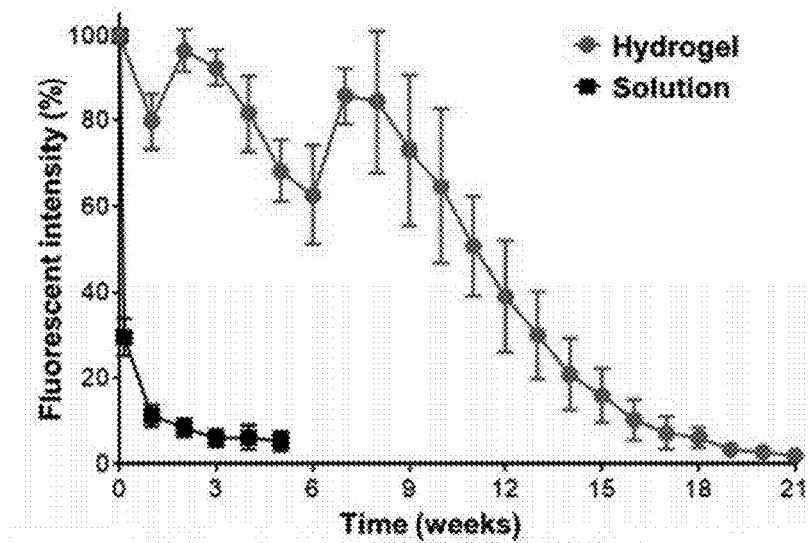
FIG. 8 is a graph comparing the biodegradation of exemplary drug delivery device F from FIG. 6 in comparison to in vivo diffusion of the free dye in FIG. 7.

In an additional study, device F was placed by the mammary fat pad of five mice in which no tumors were inoculated or removed. The presence of the hydrogel in the mice was monitored via imaging over the course of 20 weeks (FIG. 5). The hydrogels in the mice were stable, and less than 5% remained after 20 weeks (FIG. 6). The site of implantation was also subjected to histopathological analysis. No abnormalities were detected by a certified pathologist, confirming that the hydrogel is highly biocompatible. For comparison, a fluorescent dye solution was administered locally, revealing that the free dye diffuses away very rapidly if it is not conjugated to a scaffold (FIGS. 7 and 8). These data confirm that cross-linked hyaluronic acid can serve as a stable, biodegradable depot.

Example 3. Imaging of Hydrogel Compositions Comprising Therapeutic Agents

Figure 9:
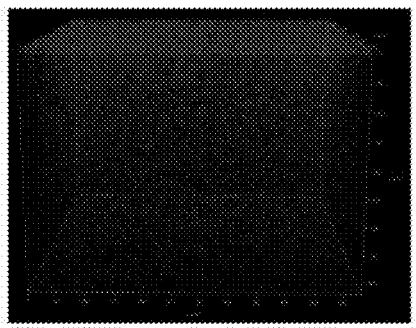
FIG. 9 shows fluorescent confocal images of exemplary drug delivery device 1 (fluorescently labeled 2′-3′-cGAMP+anti-PD-1 antibody+IL-15 superagonist).
Figure 9:
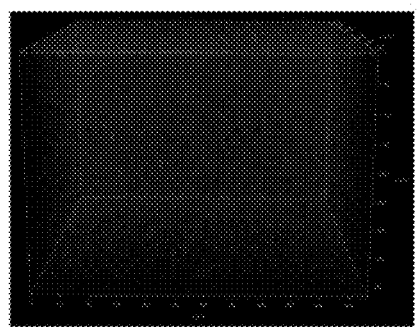
Figure 9:
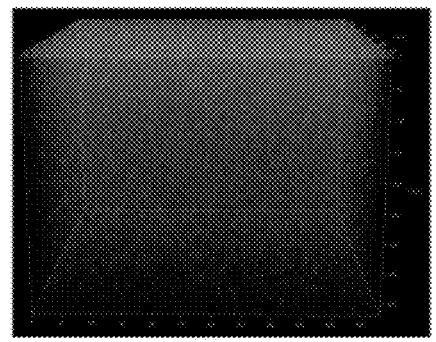

Device 1 was prepared with FITC conjugated to 2′-3′-cGAMP, ALEXA FLUOR® 405 dye conjugated to the anti-PD-1 antibody, and VIVOTAG® 680 dye conjugated to the IL-15sa. Confocal images were obtained, demonstrating that all three are distributed throughout the device (FIG. 9).

Figure 10:
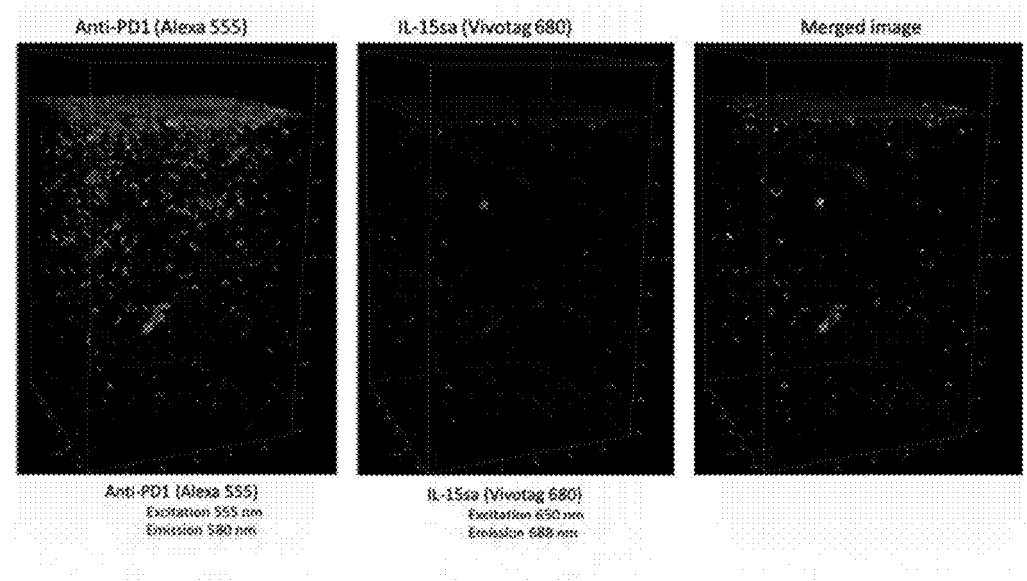
FIG. 10 shows fluorescent confocal images of exemplary drug delivery device 2 (fluorescently labeled anti-PD-1 antibody+IL-15 superagonist).

Device 2 was prepared with ALEXA FLUOR® 555 dye conjugated to the anti-PD-1 antibody and VIVOTAG® 680 dye conjugated to the IL-15sa, Confocal images were obtained, demonstrating that the anti-PD-1 antibody and IL-15sa are distributed throughout the device (FIG. 10).

Example 4. In Vitro Release of Therapeutic Agents from a Hydrogel Composition

Hydrogels were prepared according to the general procedure in Example 1. They contained either one or all of the payloads indicated. Fluorescent dyes were conjugated to the proteins to facilitate the measurement of protein release kinetics. The hydrogels were immersed in 3 mL of buffer (either PBS only, PBS with Tween80 (0.2% v/v), or RPMI with 10% FBS) and incubated at 37° C. with stirring.

At the indicated sampling time points, 1 mL of buffer was recovered for measurement and was replaced by an equivalent volume of fresh buffer. The aliquots were measured using a fluorescence plate reader to determine protein concentration. Aliquots were also assessed by HPLC to determine small molecule concentration.

Figure 11:
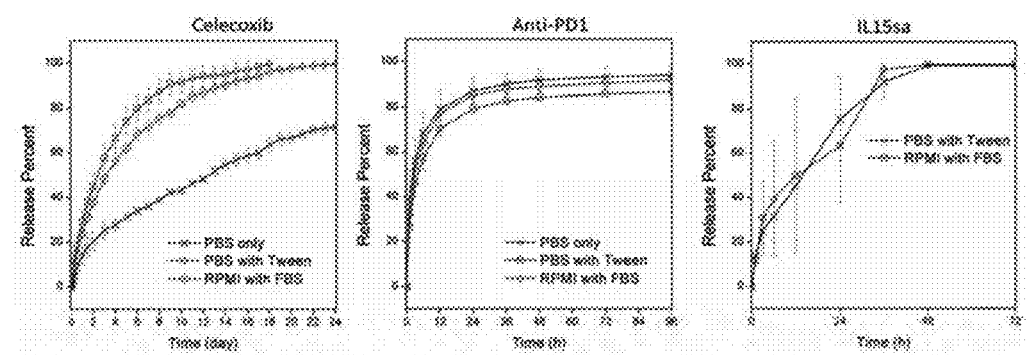
FIG. 11 is a series of graphs showing release rates of therapeutic agents (celecoxib, anti-PD-1 antibody, IL-15 superagonist) from drug delivery devices 3, 4, and 5 with varying excipients (Tween, PBS, RPMI+10% FBS).

Several compositions were prepared by varying therapeutic agents and excipients incorporated into the compositions. Device 3 was prepared according to the general procedure in Example 1. Drug release from this device was studied in PBS, PBS+Tween80 (0.2% v/v), or RPMI+10% FBS. The release of celecoxib was delayed the longest in PBS buffer (FIG. 11).

Device 4 was prepared according to the general procedure in Example 1. Drug release from this device was studied in PBS, PBS+Tween80 (0.2% v/v), car RPMI+10% FBS, The release rate of anti-PD-1 was similar in all three buffers (FIG. 11).

Device 5 was prepared according to the general procedure in Example 1. Drug release from this device was studied in PBS+Tween80 (0.2% v/v) or RPMI+1.0% FBS. The release rate of IL-15sa was similar in both of these buffers (FIG. 11).

Figure 12:
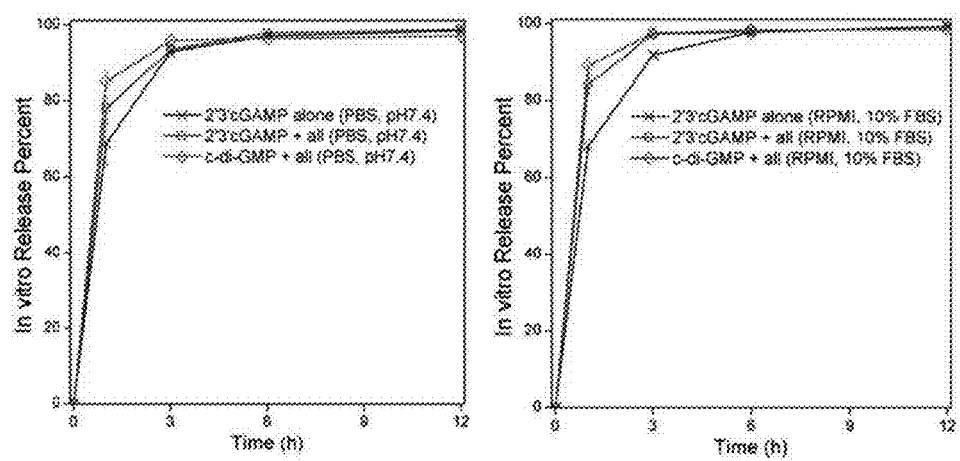
FIG. 12 is a graph showing release rates of c-di-GMP from drug delivery device 6 and of 2′-3′-cGAMP from drug delivery devices 1 and 7 with varying excipients (PBS, RPMI+10% FBS).

Device 6 [c-di-GMP+I+P] was prepared according to the general procedure in Example 1. Device 1 [2′-3′-cGAMP+I+P] and device 7 [only 2′-3′-cGAMP] were prepared according to the general procedure in Example 1. Drug release from these devices was studied in PBS or RPMI+10% PBS. The release rate of c-di-GMP and 2′-3′-cGAMP is similar in both of these buffers. The release rate of 2′-3′-cGAMP is similar whether the small molecule is formulated alone or with proteins (FIG. 12).

Figure 13:
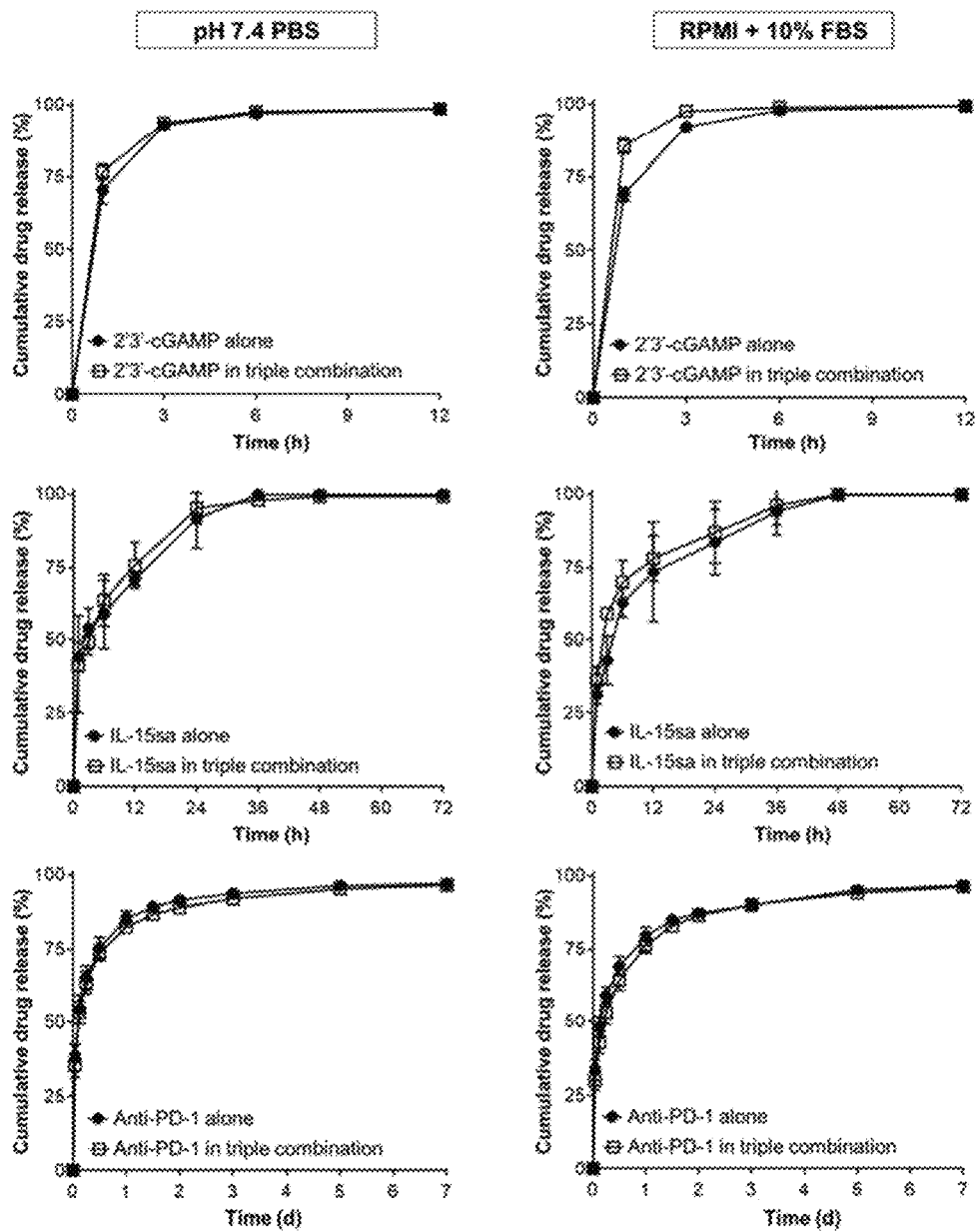
FIG. 13 is a series of graphs showing release rates of: 2′-3′-cGAMP from drug delivery devices 1 and 7 in different media (PBS, RPMI+10% FBS); IL-15 superagonist from drug delivery devices 1 and 5 in different media (PBS, RPMI+10% FBS); and anti-PD-1 antibody from drug delivery devices 1 and 4 in different media (PBS, RPMI+10% FBS).

Additional comparisons of the release rates of 2′-3′-cGAMP, IL-15sa, and anti-PD-1 antibody from devices 1, 4, 5, and 7 are shown in FIG. 13. The release kinetics were nearly identical in PBS and media, ranging from hours for the small molecule to days for the biologics, under sink conditions in vitro. The inclusion of multiple payloads did not affect the release kinetics of any individual molecule, as the results were indistinguishable whether a compound was loaded alone or in combination with the two other compounds.

Figure 65:
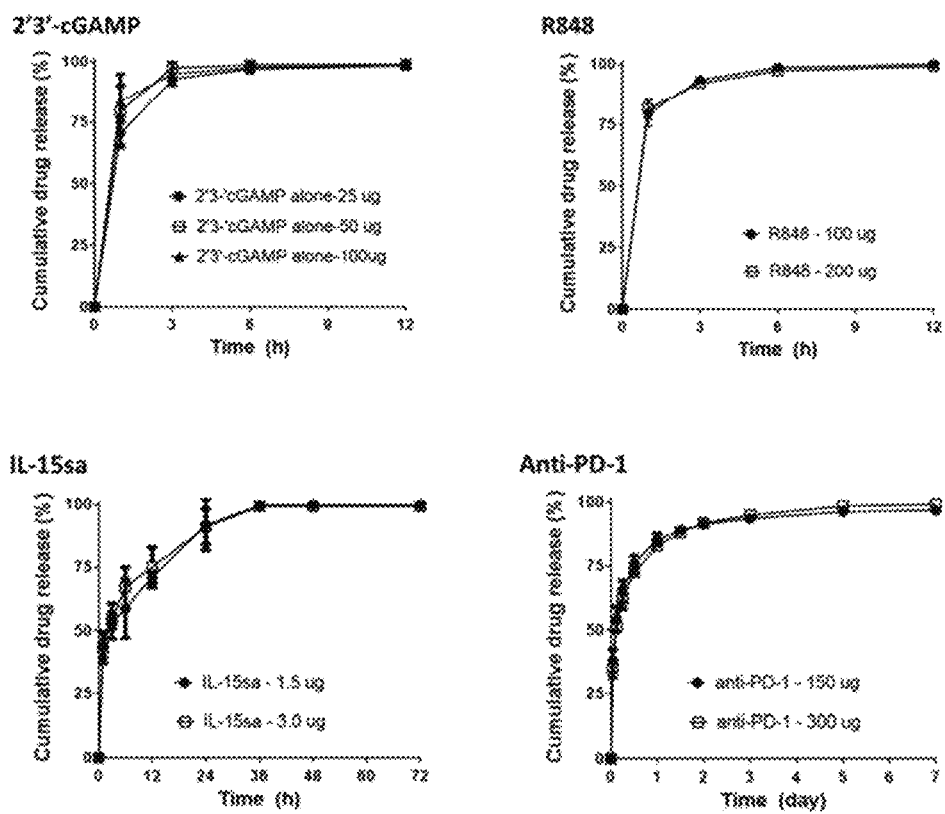
FIG. 65 is a series of graphs showing in vitro release rates of: 2′-3′-cGAMP (25 µg, 50 µg, 100 µg) from drug delivery device 7 in PBS (pH 7.4); resiquimod (R848; 100 µg, 200 µg) from drug delivery devices 22 in PBS (pH 7.4); anti-PD-1 antibody (150 µg, 300 µg) from drug delivery device 4 in PBS (pH 7.4); and IL-15sa (1.5 µg, 3.0 µg) from drug delivery device 5 in PBS (pH 7.4).
Figure 66:
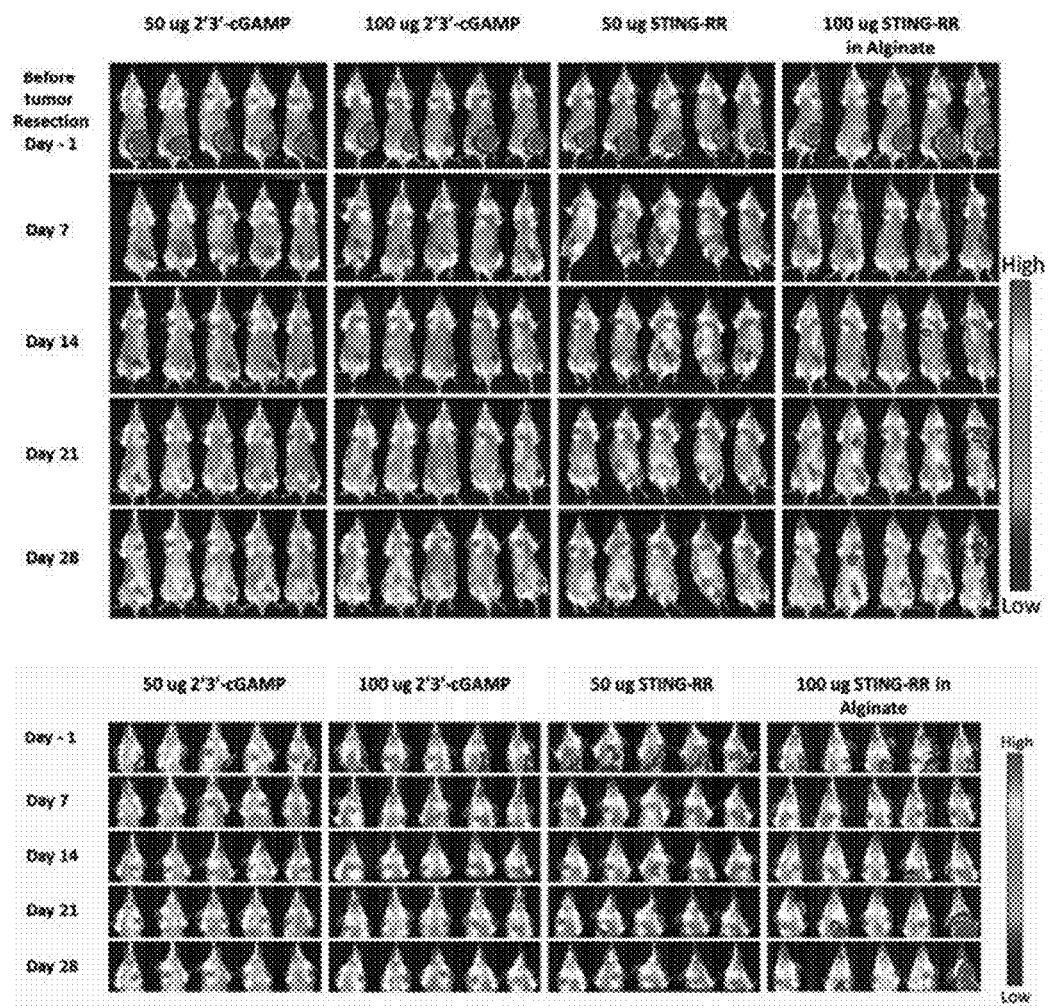
FIG. 66 shows images of individual mice after implantation of exemplary drug delivery devices 7 (50 µg or 100 µg S), 23 (50 µg STING-RR), or alginate loaded with STING-RR (100 µg) following inoculation of tumors originating from 4T1-Luc2 syngeneic breast cancer cells. The images show the appearance/disappearance of tumor over a 4-week period. The upper images monitor the site of resection (local tumor recurrence) while the lower images show lung metastasis.
Figure 67:
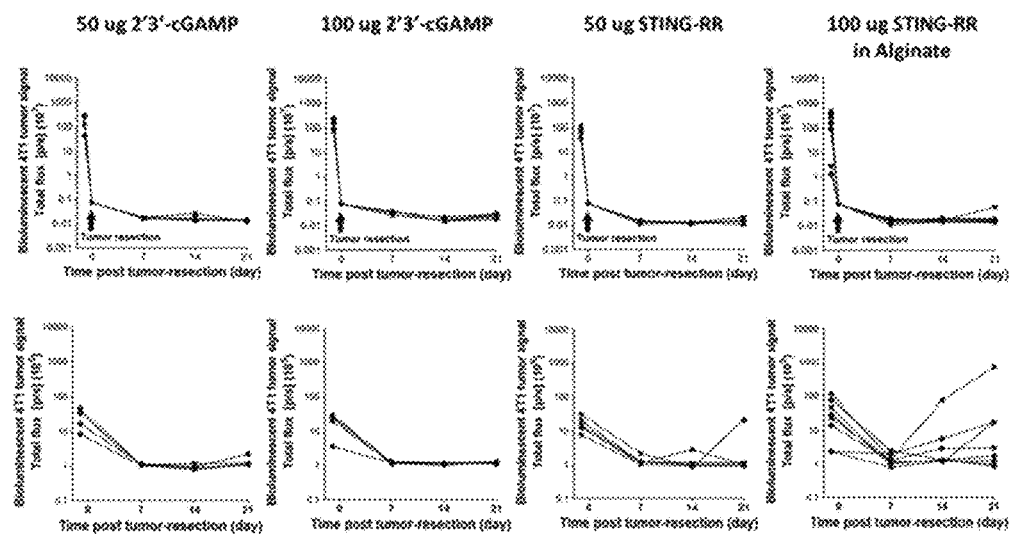
FIG. 67 is a series of graphs showing the total flux of bioluminescent 4T1-Luc2 cells after administration of the exemplary drug delivery devices described in FIG. 66. The upper images show the site of resection (local tumor recurrence) while the lower images show lung metastasis.

In addition, devices 4, 5, 7, and 22 were prepared by varying the amount of drug loaded into each device. Release rates of 2′-3′-cGAMP (25 µg, 50 µg, 100 µg) from drug delivery device 7 in PBS (pH 7.4); resiquimod (R848; 100 µg, 200 µg) from drug delivery device 22 in PBS (pH 7.4); anti-PD-1 antibody (150 µg, 300 µg) from drug delivery device 4 in PBS (pH 7.4); and IL-15sa from drug delivery device 5 in PBS (pH 7.4) were determined. There was little dependence on the concentration of drug for the release rate in each experiment (FIG. 65).

Figure 37A:
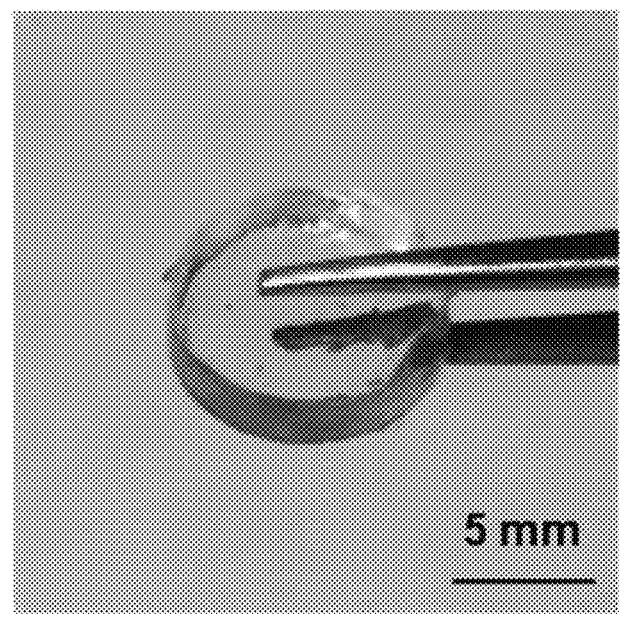
FIGS. 37A-37C show a biodegradable hydrogel scaffold extends local release of payloads in situ, enabling focused perioperative cancer immunotherapy.
Figure 37B:
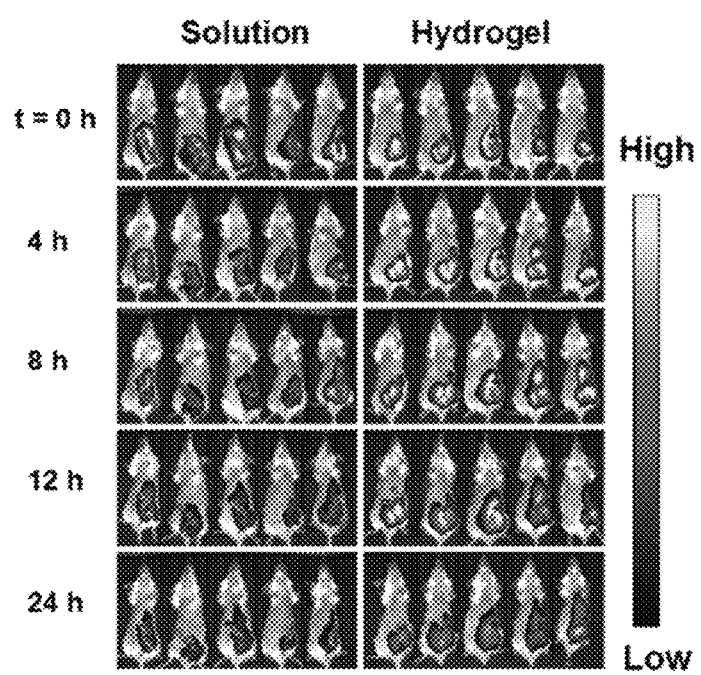
Figure 37C:
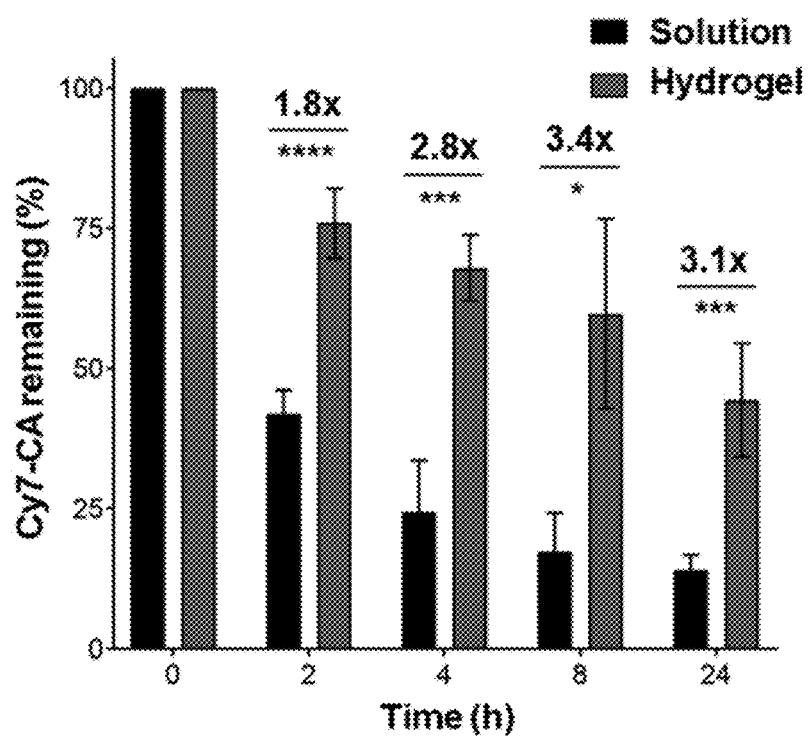
Figure 38A:
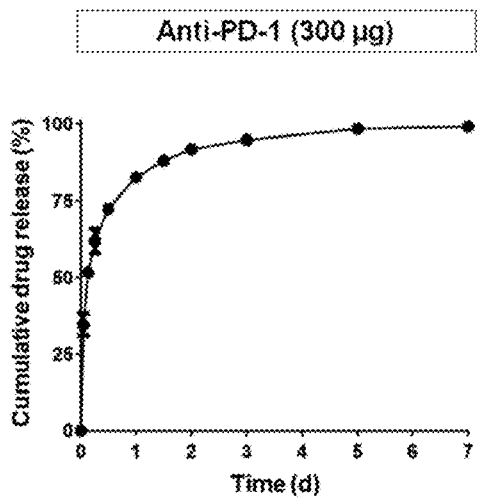
FIGS. 38A-38F show that the hydrogel scaffold extends the release of biologics and small molecules in vitro. Scaffolds were placed in PBS (pH 7.4), and drug release was measured using a fluorescence plate reader or HPLC. The following payloads were evaluated: anti-PD-1 (FIG. 38A), IL-15sa (FIG. 38B), lenalidomide (FIG. 38C), celecoxib (FIG. 38D), 2'3'-cGAMP (model compound for 2'3'-c-di-AM(PS)2 (Rp,Rp). "STING-RR") (FIG. 38E), and R848 (FIG. 38F). The experiment was performed with biological replicates (n=4+) three times. Data are presented as mean±SD.
Figure 38B:
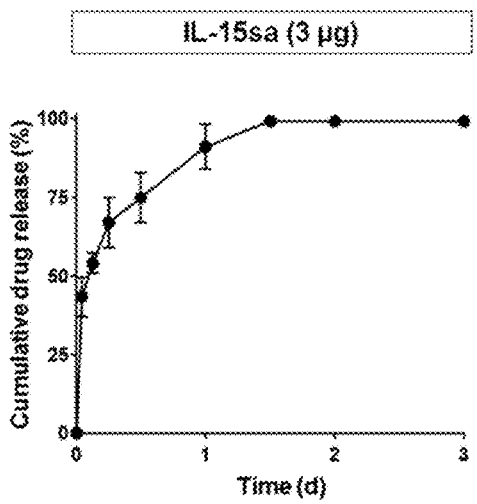
Figure 38C:
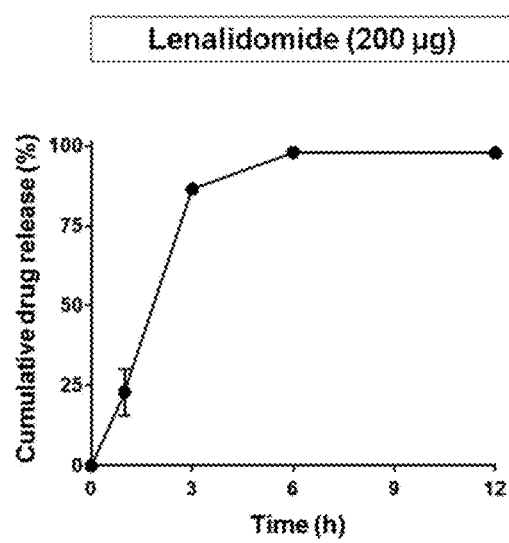
Figure 38D:
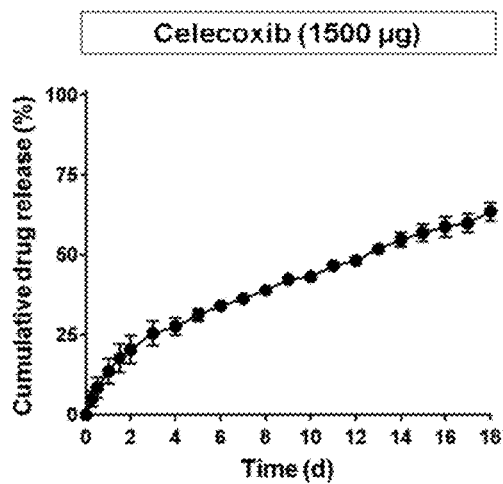
Figure 38E:
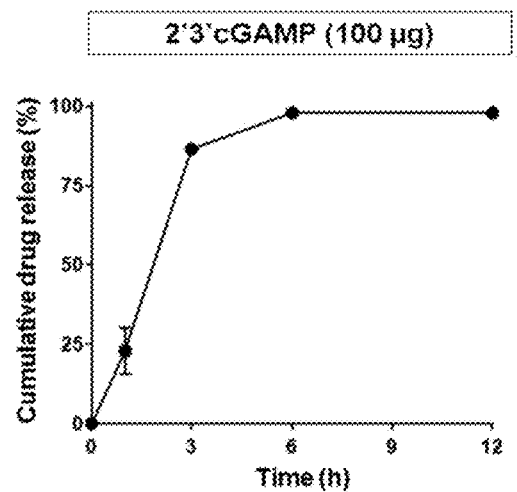
Figure 38F:
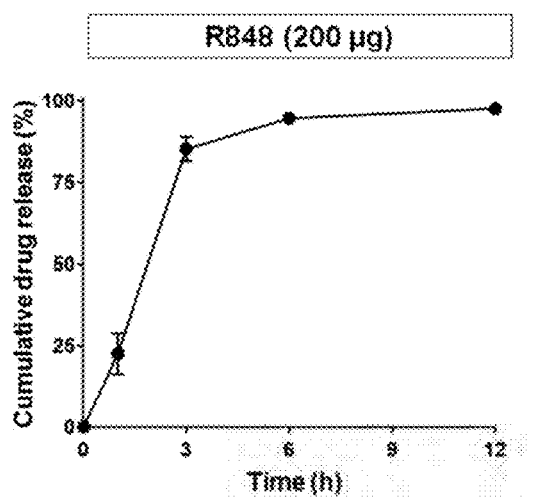

The loading and release properties of the hydrogel were examined in additional experiments. Under sink conditions in phosphate buffered saline (PBS), the release kinetics of devices 3 (1500 µg celecoxib), 7 (100 µg S), 18, 19, 22, and 30 ranged from hours for the small molecules to days for the biologics (FIGS. 38A-38F). It was then confirmed that the hydrogel extends the release of the small molecules and biologics in vivo. Cy7 carboxylic acid (Cy7-CA) was used as a model small molecule payload, as its physical properties are very similar to those of resiquimod (R848). Cy7-CA was administered to non-tumor-bearing mice, either in solution or loaded in a scaffold placed by the fourth mammary fat pad. The mice were assessed by fluorescence IVIS imaging (FIG. 37B), and the data were quantified (FIG. 37C). Whereas a loss of ~60% of the signal was detected within two hours of administration of the fluorophore in solution, this amount of signal decay required 24 hours for the fluorophore loaded in the hydrogel. Over this time course, there was a roughly three-fold increase in signal for the latter group, on average.

Figure 14:
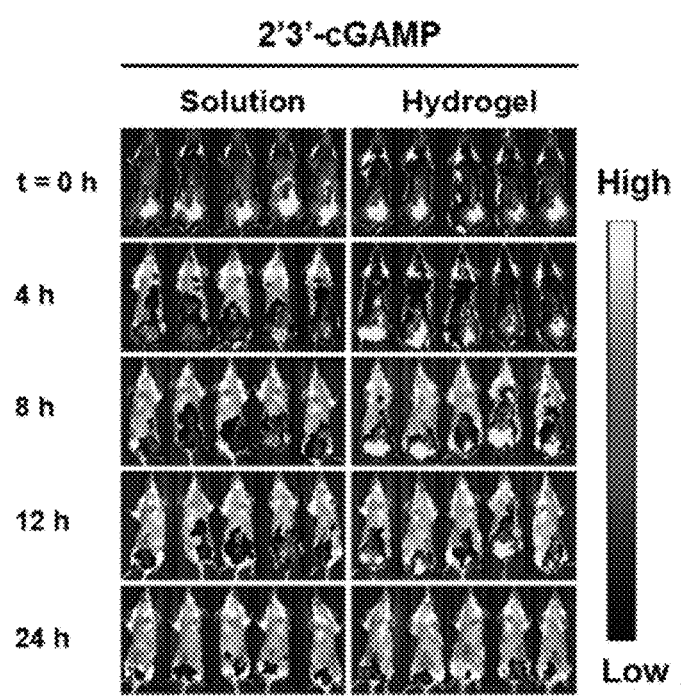
FIG. 14 shows images of individual mice after administration of fluorescently labeled 2′-3′-cGAMP in solution or exemplary drug delivery device 7 implanted next to the fourth mammary fat pad of non-tumor-bearing female BALB/cJ mice.
Figure 15:
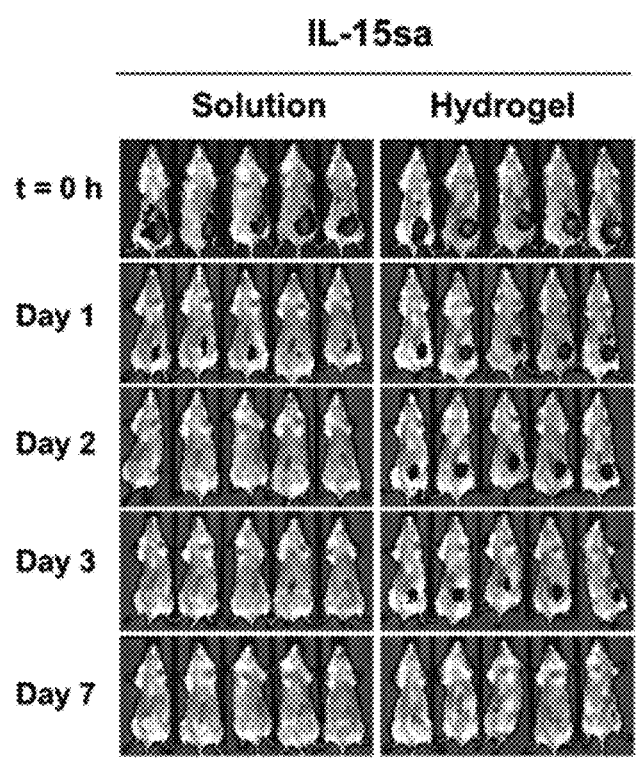
FIG. 15 shows images of individual mice after administration of fluorescently labeled IL-15 superagonist (IL-15sa) in solution or exemplary drug delivery device 5 implanted next to the fourth mammary fat pad of non-tumor-bearing female BALB/cJ mice.
Figure 16:
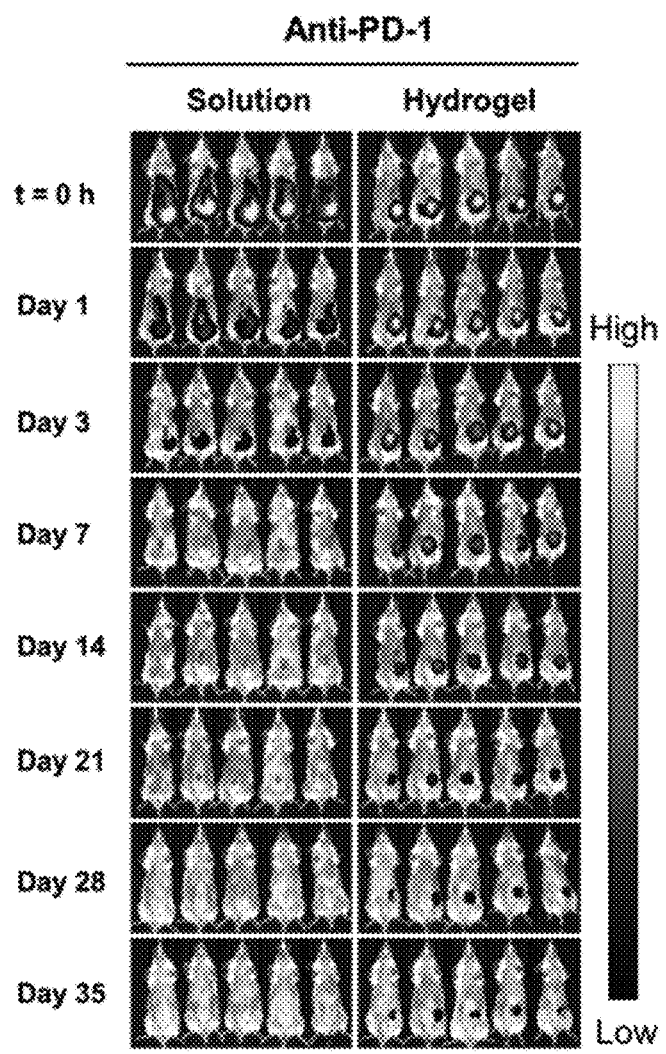
FIG. 16 shows images of individual mice after administration of fluorescently labeled anti-PD-1-antibody in solution or exemplary drug delivery device 4 implanted next to the fourth mammary fat pad of non-tumor-bearing female BALB/cJ mice.
Figure 17:
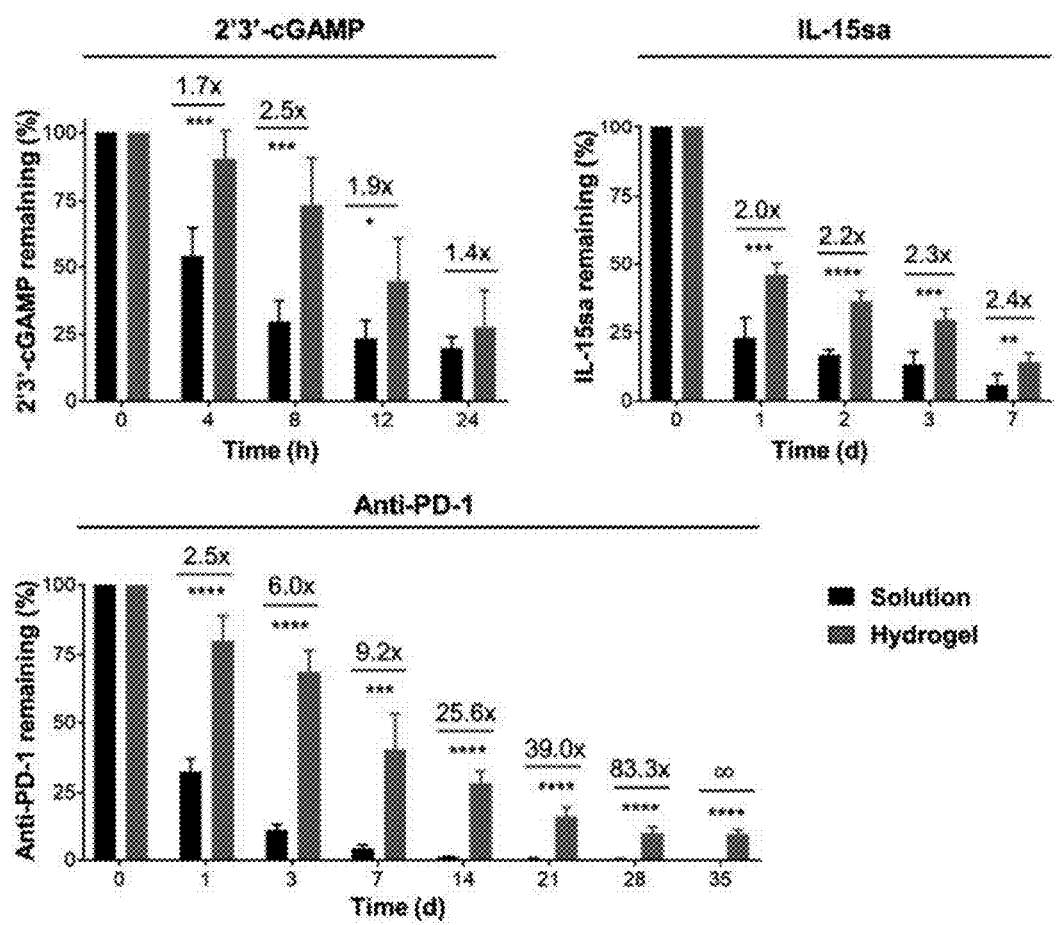
FIG. 17 is a series of graphs quantifying the release kinetics for 2′-3′-cGAMP, IL-15sa, and anti-PD-1 from the experiments in FIGS. 14-16. Fold difference is indicated for each time point. Data are presented as mean±SEM, * $p \leq 0.05$,  $p \leq 0.01$, * $p \leq 0.001$, **** $p \leq 0.0001$.

Example 5. In Vivo Implantation and Evaluation of Exemplary Drug Delivery Compositions To confirm that the hydrogel sustains the release of the small molecule and biologics in vivo, fluorescently labeled versions of 2′-3′-cGAMP, IL-15sa, or anti-PD-1 were administered to non-tumor-bearing mice, either in solution or in a device (fluorescently labeled devices 4, 5, and 7) following placement by the fourth mammary fat pad. The mice were assessed by fluorescence IVIS imaging using an IVIS Spectrum In Vivo Imaging System (Perkin Elmer) (FIGS. 14-16), and the data were analyzed and quantified with Living Imaging software (Perkin Elmer). (FIG. 17). The release rates in vivo exhibited prolonged kinetics relative to those in vitro, as expected for an environment that is more physiologically relevant than sink conditions. For 2′-3′-cGAMP, the percentage remaining locally following delivery via the hydrogel was, on average, nearly twice that of free compound at each time point examined over the first 24 hours. For IL-15sa, the percentage remaining locally following delivery via the hydrogel was slightly more than twice that of free compound at each time point examined over the first week. For anti-PD-1, the difference in the percentage remaining locally following delivery in solution versus via the hydrogel was by far the most pronounced, likely owing to the size of the molecule (150,000 g/mol versus 674 g/mol for 2′-3′-cGAMP and 29,400 g/mol for IL-15sa), For the monoclonal antibody, nearly all of the compound delivered in solution diffused away from the site of administration within one week. In contrast, more than two thirds of the antibody dose remained at the site of administration beyond one week if it was delivered in a hydrogel. The hydrogel extends the presence of the antibody for up to at least five weeks post-administration. These data confirm that the hydrogel scaffold can sustain the local release of immunomodulatory compounds substantively relative to local delivery of the same compounds in solution.

A series of compositions described above in Table 2 were evaluated in viva. In each group of evaluations, seven-week-old female Balb/c mice were inoculated orthotopically with 100,000 4T1-Luc2 syngeneic breast cancer cells (into the fourth mammary fat pad). After 10 days, mice were anesthetized, tumors were surgically resected, and the composition was placed in the resection site. Tumor relapse and metastasis were monitored via imaging over the course of 6 weeks. Table 3 summarizes the results of these studies.

Imaging of the mouse studies are shown in FIGS. 18-29, 32-33, and 39. Additional imaging studies are shown in FIGS. 30-31 and 34-36.

TABLE 3

Figure 18:
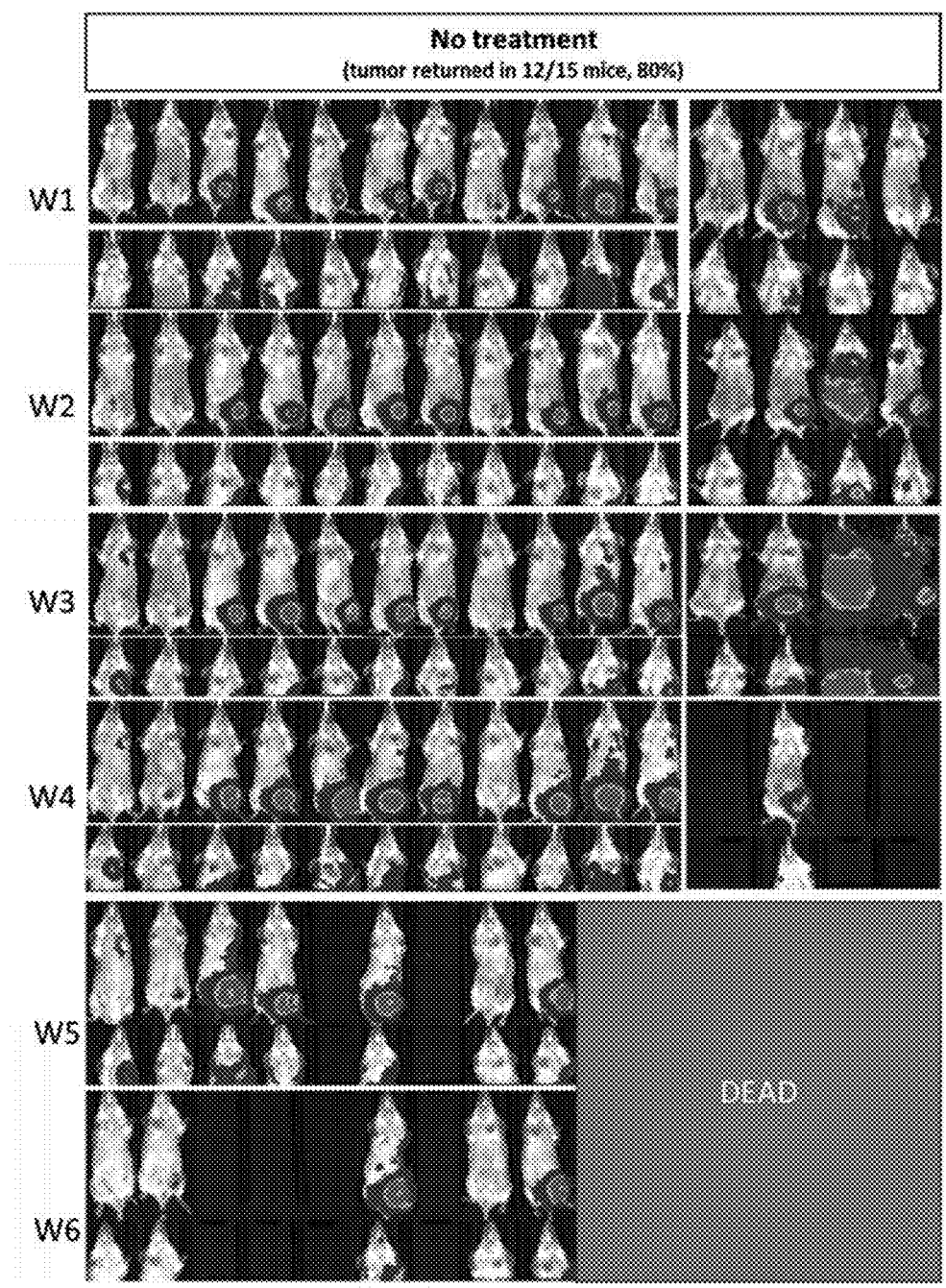
FIG. 18 shows images of individual mice after inoculation and resection of tumors originating from 4T1-Luc2 syngeneic breast cancer cells. The images show appearance/disappearance of tumor over a 6-week period.
Figure 19:
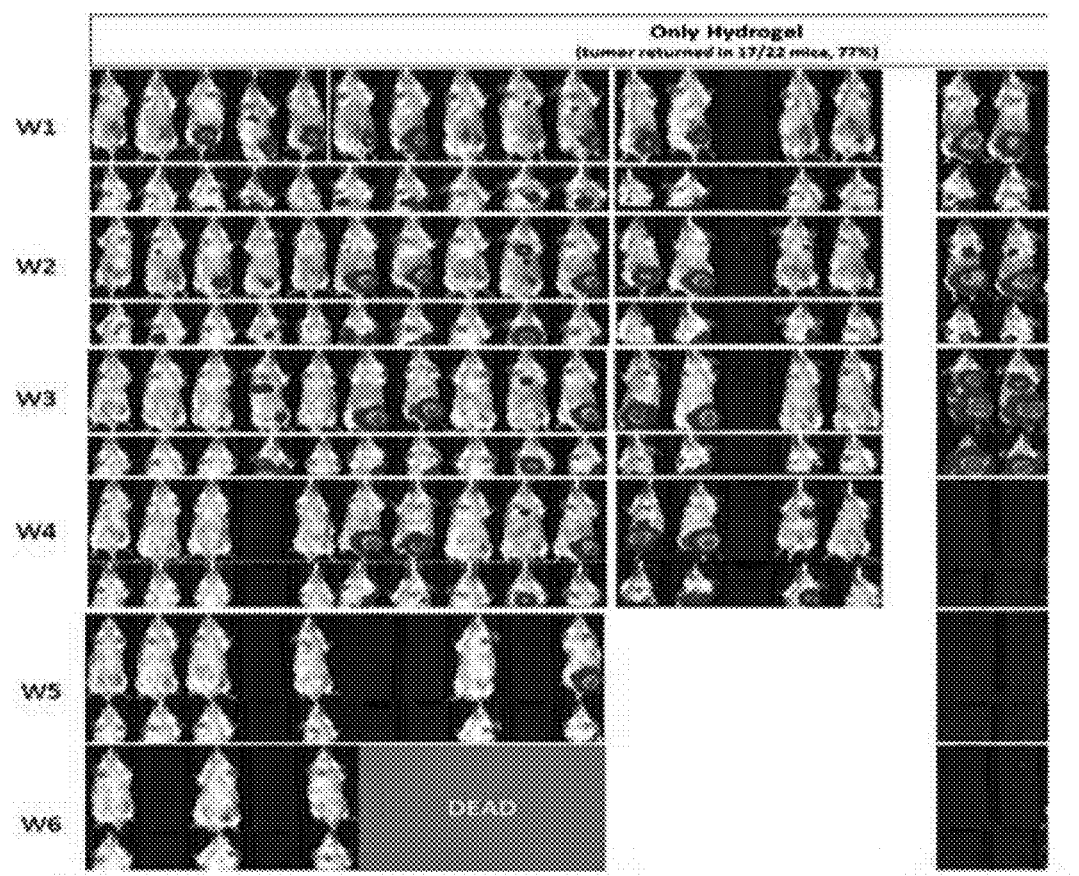
FIG. 19 shows images of individual mice after implantation of a non-drug-containing hydrogel, device 8, following inoculation and resection of tumors originating from 4T1-Luc2 syngeneic breast cancer cells. The images show appearance/disappearance of tumor over a 6-week period.
Figure 20:
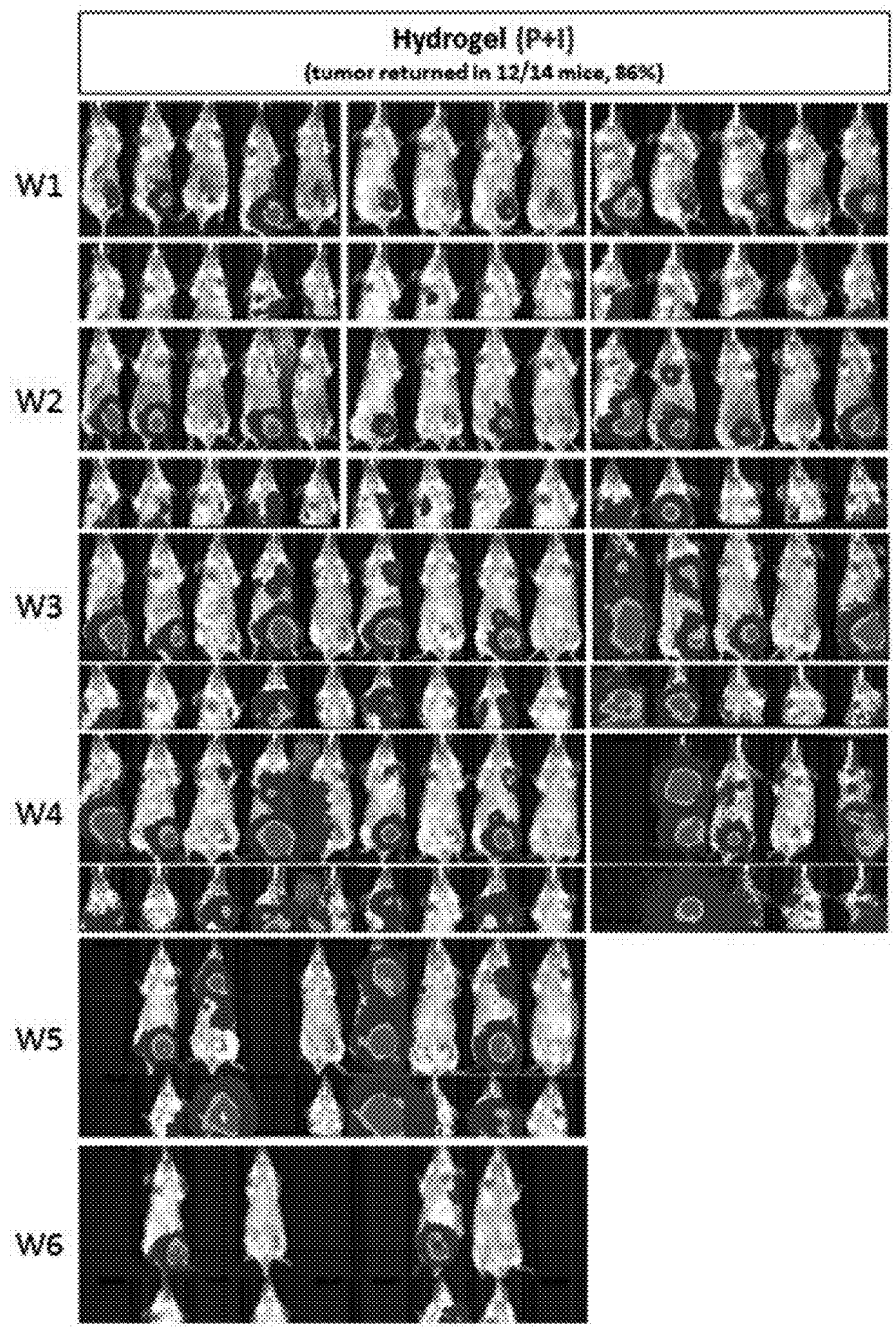
FIG. 20 shows images of individual mice after implantation of exemplary drug delivery device 2 (anti-PD-1 antibody+IL-15 superagonist) following inoculation and resection of tumors originating from 4T1-Luc2 syngeneic breast cancer cells. The images show appearance/disappearance of tumor over a 6-week period.
Figure 21:
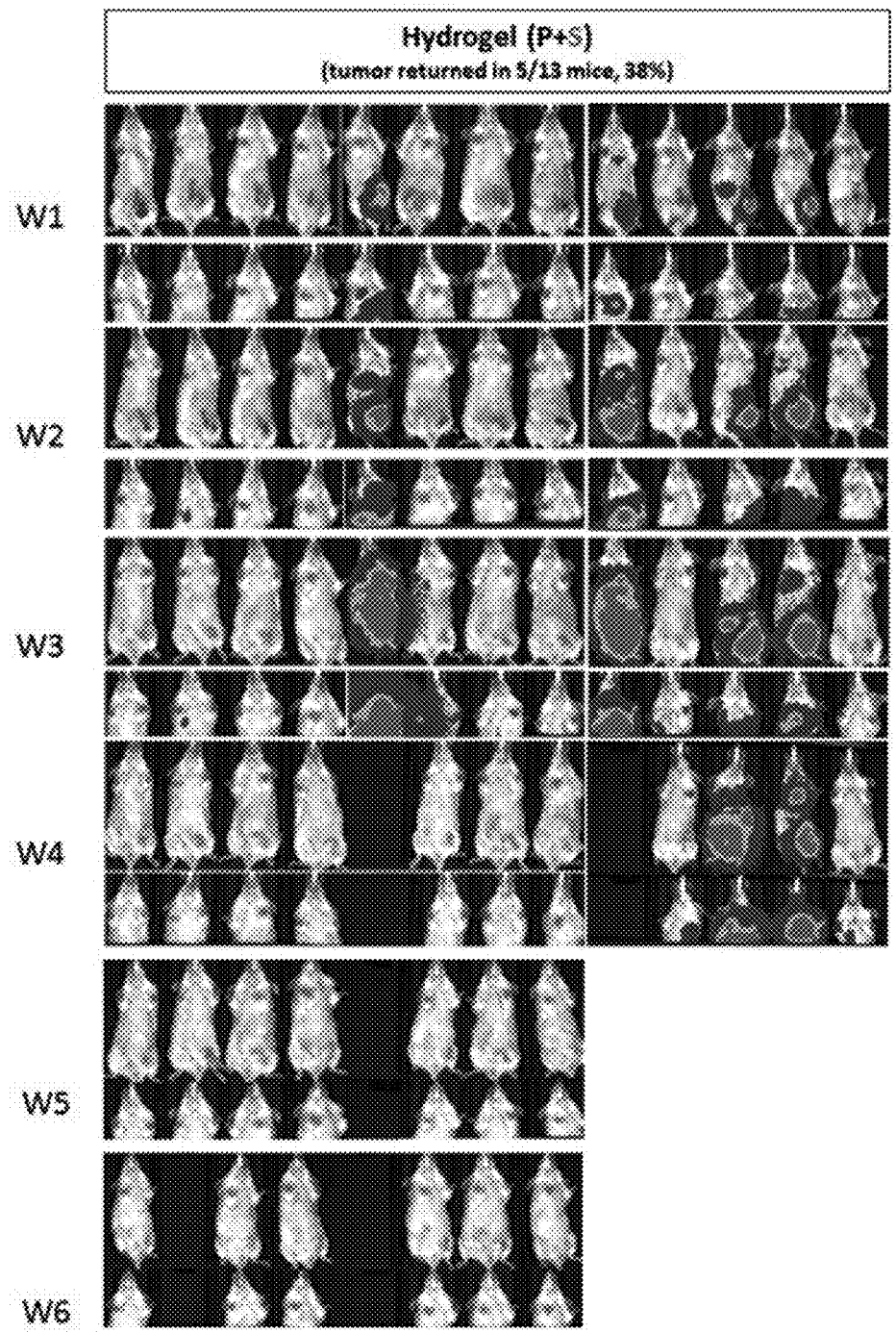
FIG. 21 shows images of individual mice after implantation of exemplary drug delivery device 9 (STING agonist+anti-PD-1 antibody) following inoculation and resection of tumors originating from 4T1-Luc2 syngeneic breast cancer cells. The images show appearance/disappearance of tumor over a 6-week period.
Figure 22:
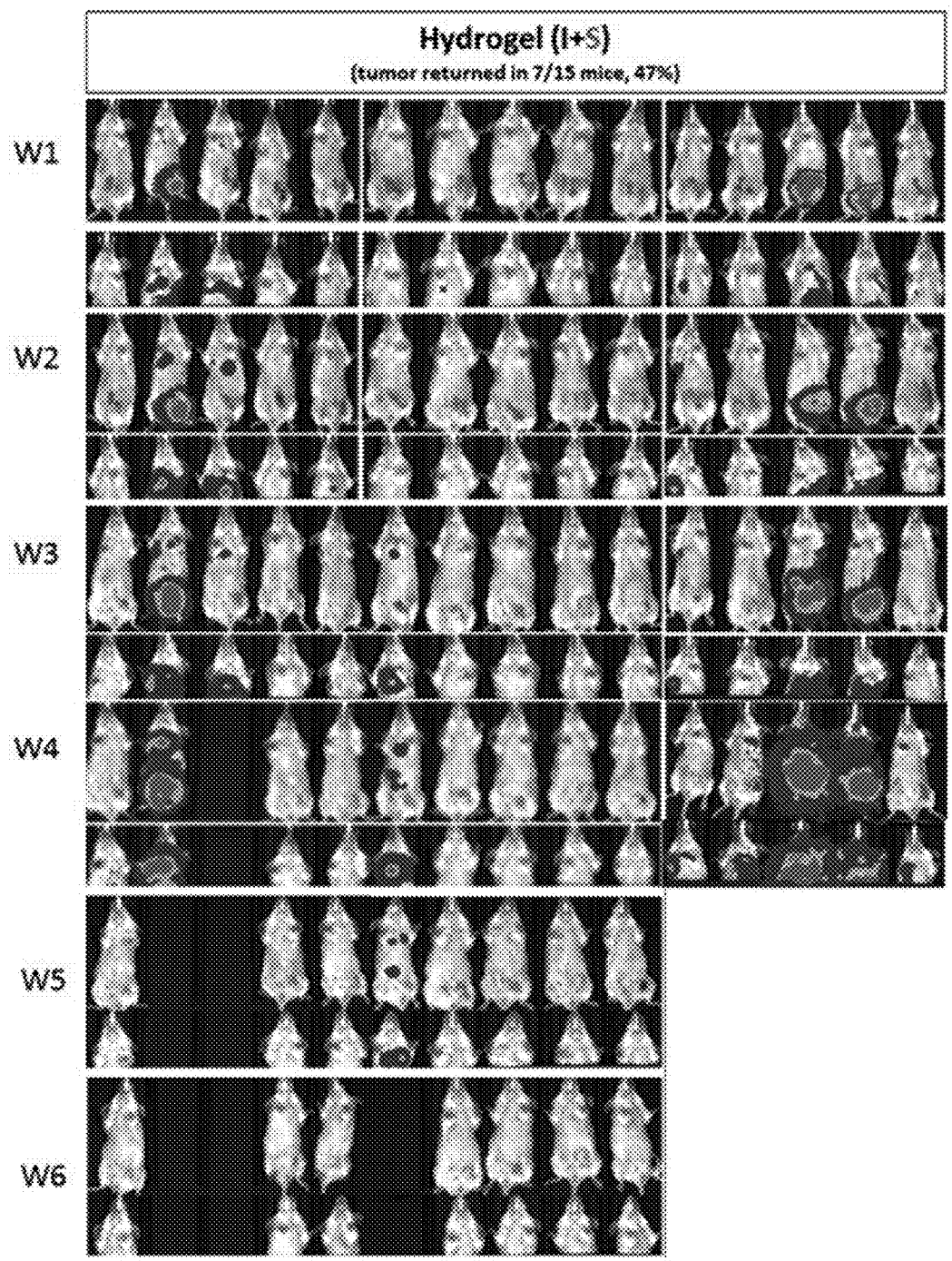
FIG. 22 shows images of individual mice after implantation of exemplary drug delivery device 10 (STING agonist+IL-15 superagonist) following inoculation and resection of tumors originating from 4T1-Luc2 syngeneic breast cancer cells. The images show appearance/disappearance of tumor over a 6-week period.
Figure 23:
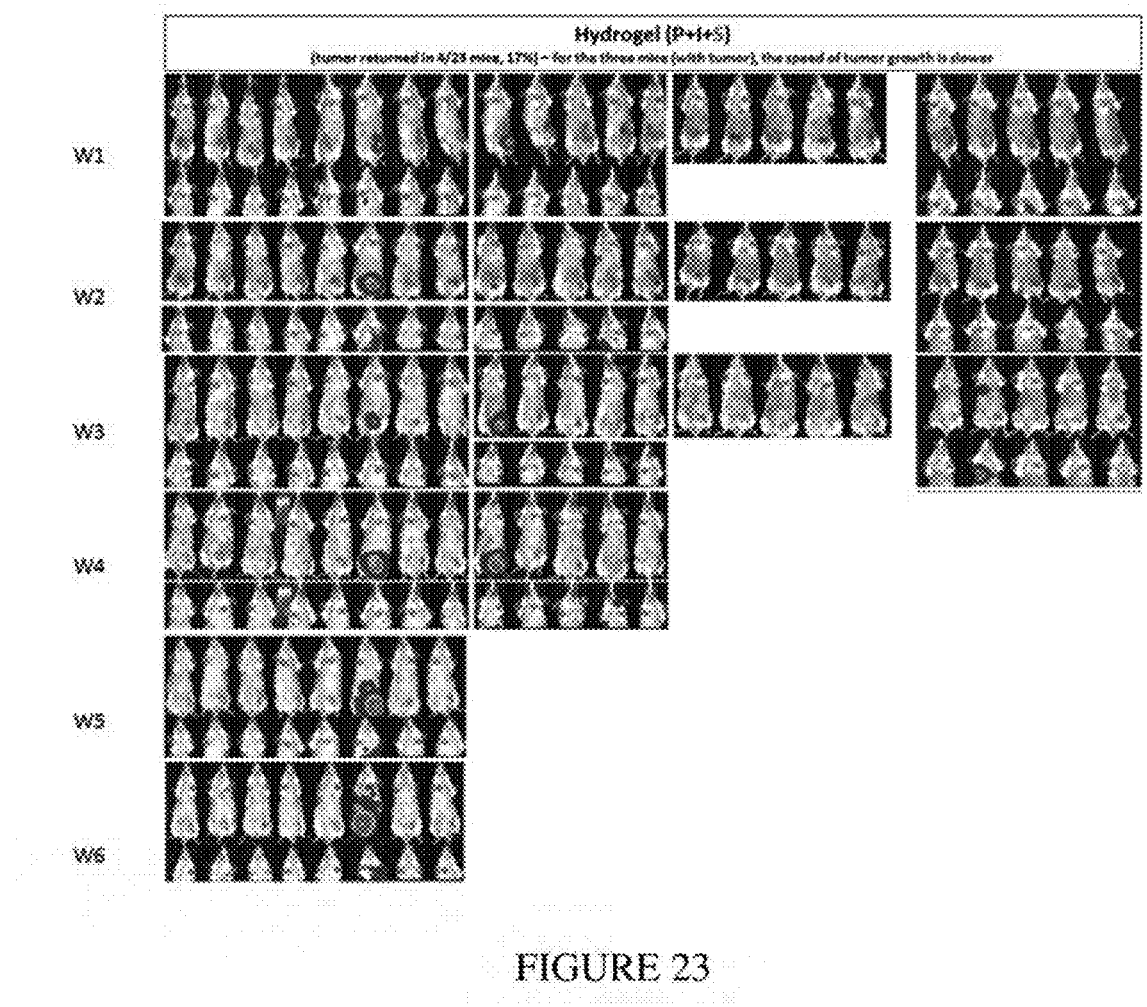
FIG. 23 shows images of individual mice after implantation of exemplary drug delivery device 1 (STING agonist+IL-15 superagonist+anti-PD-1 antibody) following inoculation and resection of tumors originating from 4T1-Luc2 syngeneic breast cancer cells. The images show appearance/disappearance of tumor over a 6-week period.
Figure 24:
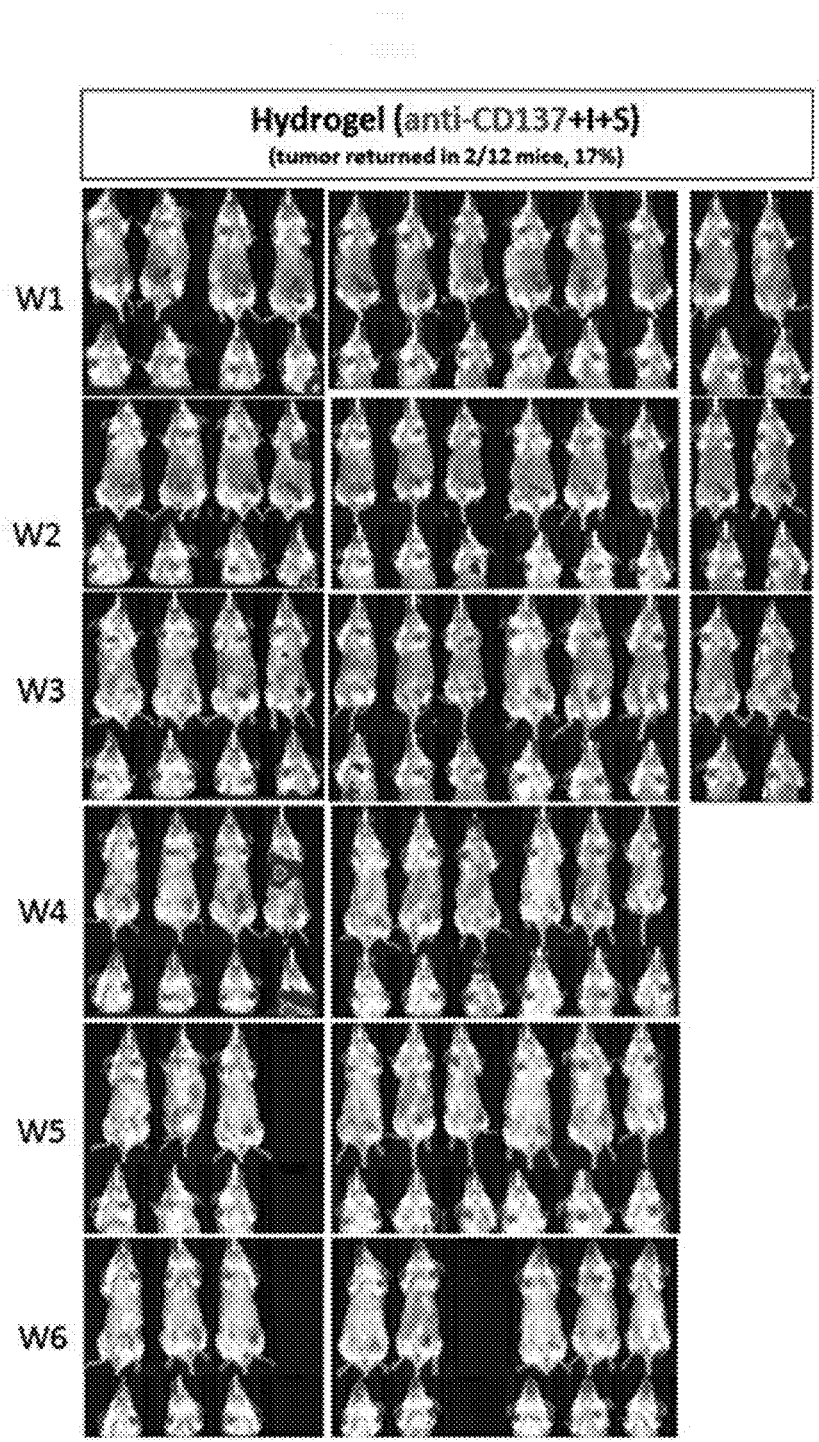
FIG. 24 shows images of individual mice after implantation of exemplary drug delivery device 11 (STING agonist+IL-15 superagonist+agonist anti-CD137 antibody) following inoculation and resection. The images show appearance/disappearance of tumor over a 6-week period.
Figure 25:
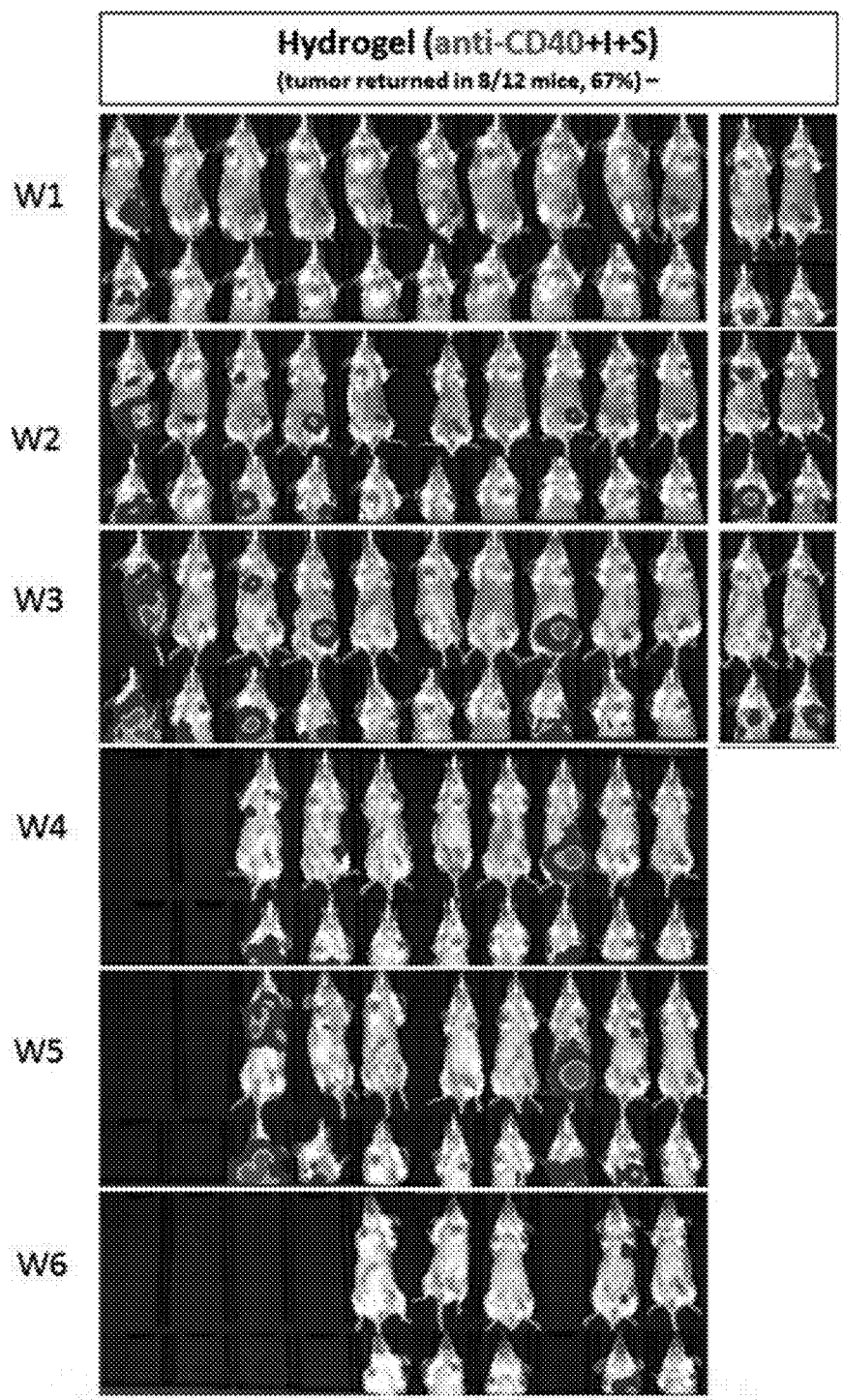
FIG. 25 shows images of individual mice after implantation of exemplary drug delivery device 12 (STING agonist+IL-15 superagonist+agonist anti-CD40 antibody) following inoculation and resection of tumors originating from 4T1-Luc2 syngeneic breast cancer cells. The images show appearance/disappearance of tumor over a 6-week period.
Figure 26:
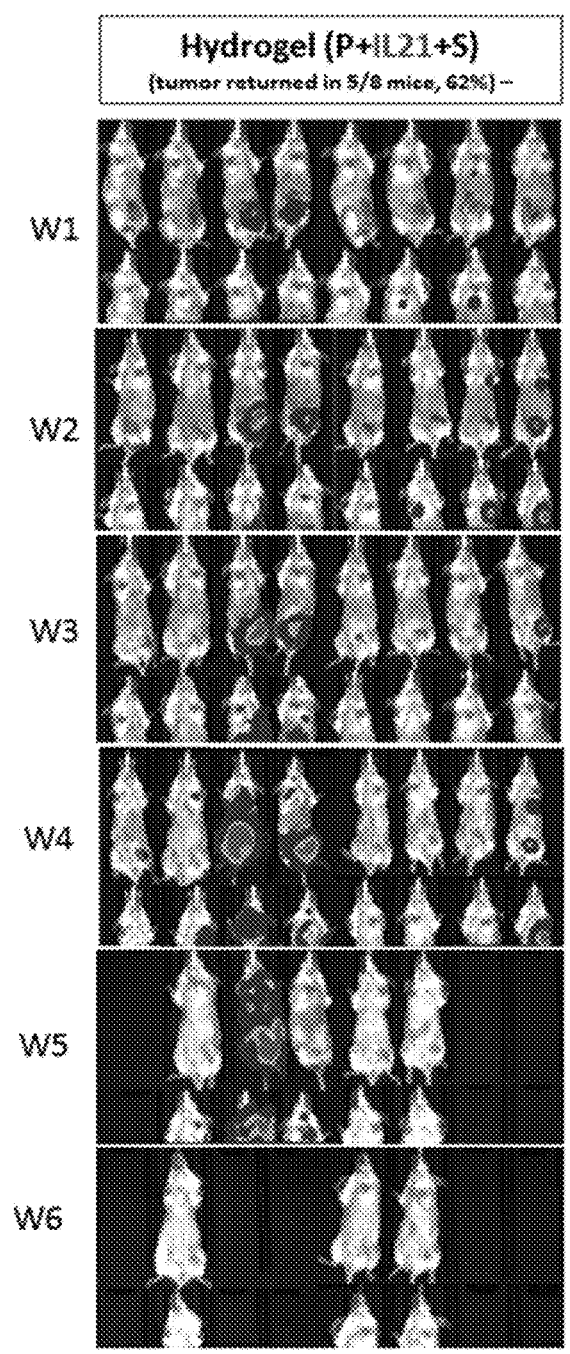
FIG. 26 shows images of individual mice after implantation of exemplary drug delivery device 13 (STING agonist+IL-21+anti-PD-1 antibody) following inoculation and resection of tumors originating from 4T1-Luc2 syngeneic breast cancer cells. The images show appearance/disappearance of tumor over a 6-week period.
Figure 27:
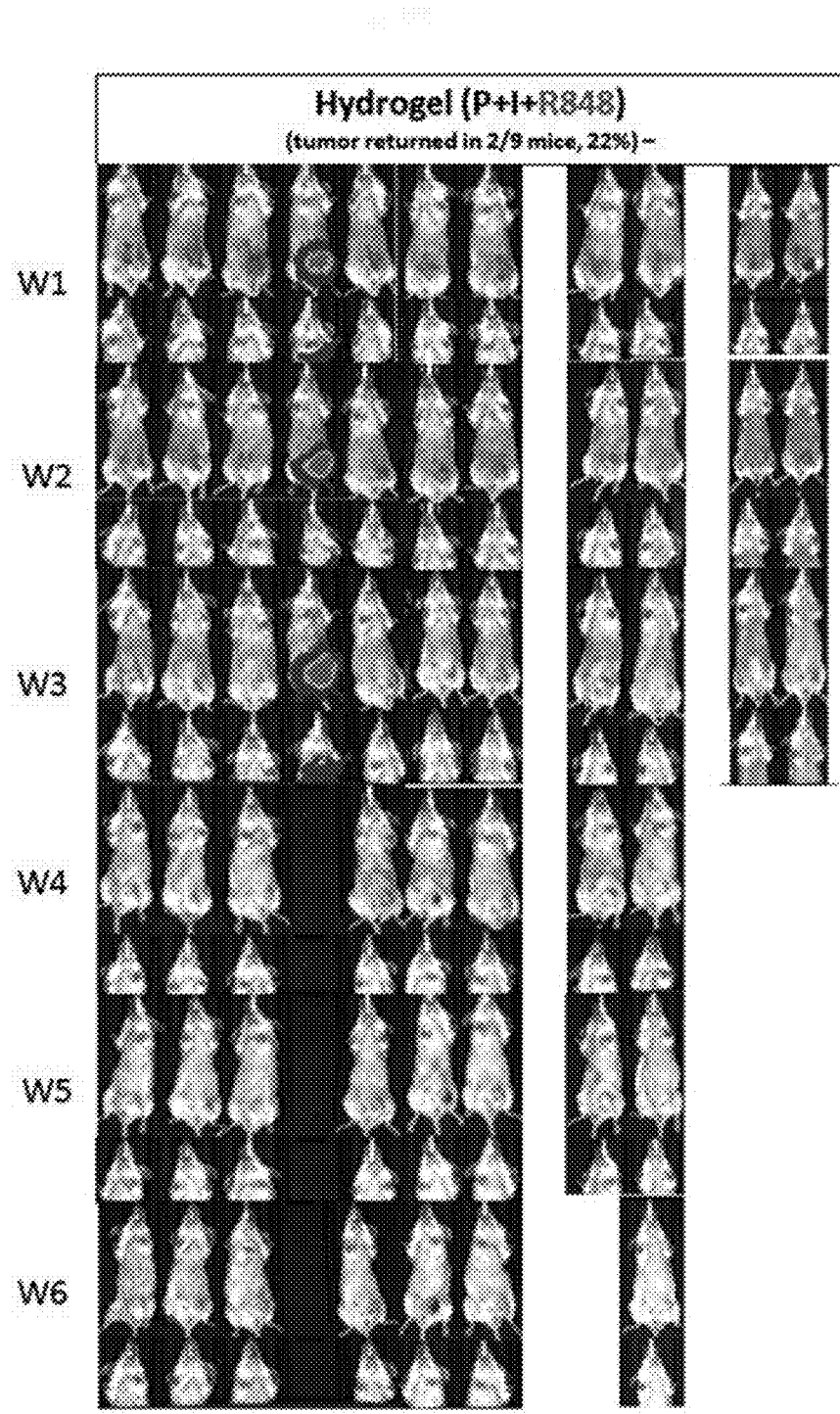
FIG. 27 shows images of individual mice after implantation of exemplary drug delivery device 14 (resiquimod+IL-15 superagonist+anti-PD-1 antibody) following inoculation and resection of tumors originating from 4T1-Luc2 syngeneic breast cancer cells. The images show appearance/ disappearance of tumor over a 6-week period.
Figure 28:
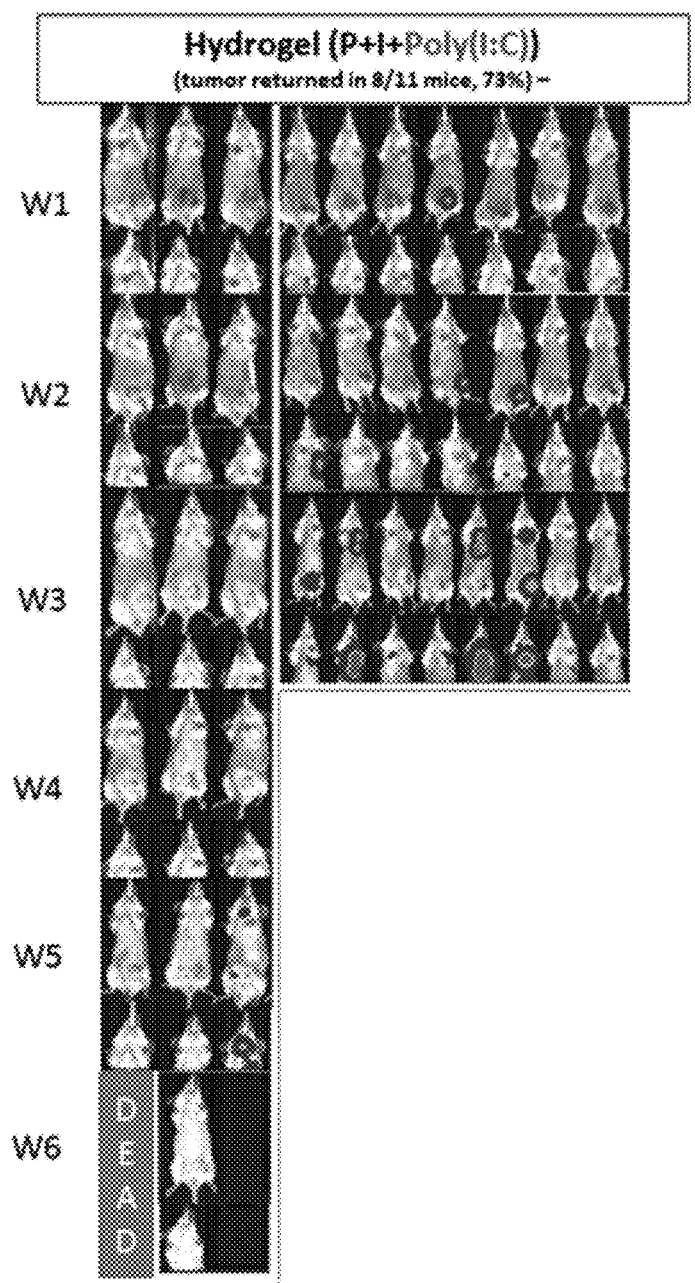
FIG. 28 shows images of individual mice after implantation of exemplary drug delivery device 15 (poly(I:C)+IL-15 superagonist+anti-PD-1 antibody) following inoculation and resection of tumors originating from 4T1-Luc2 syngeneic breast cancer cells. The images show appearance/ disappearance of tumor over a 6-week period.
Figure 29:
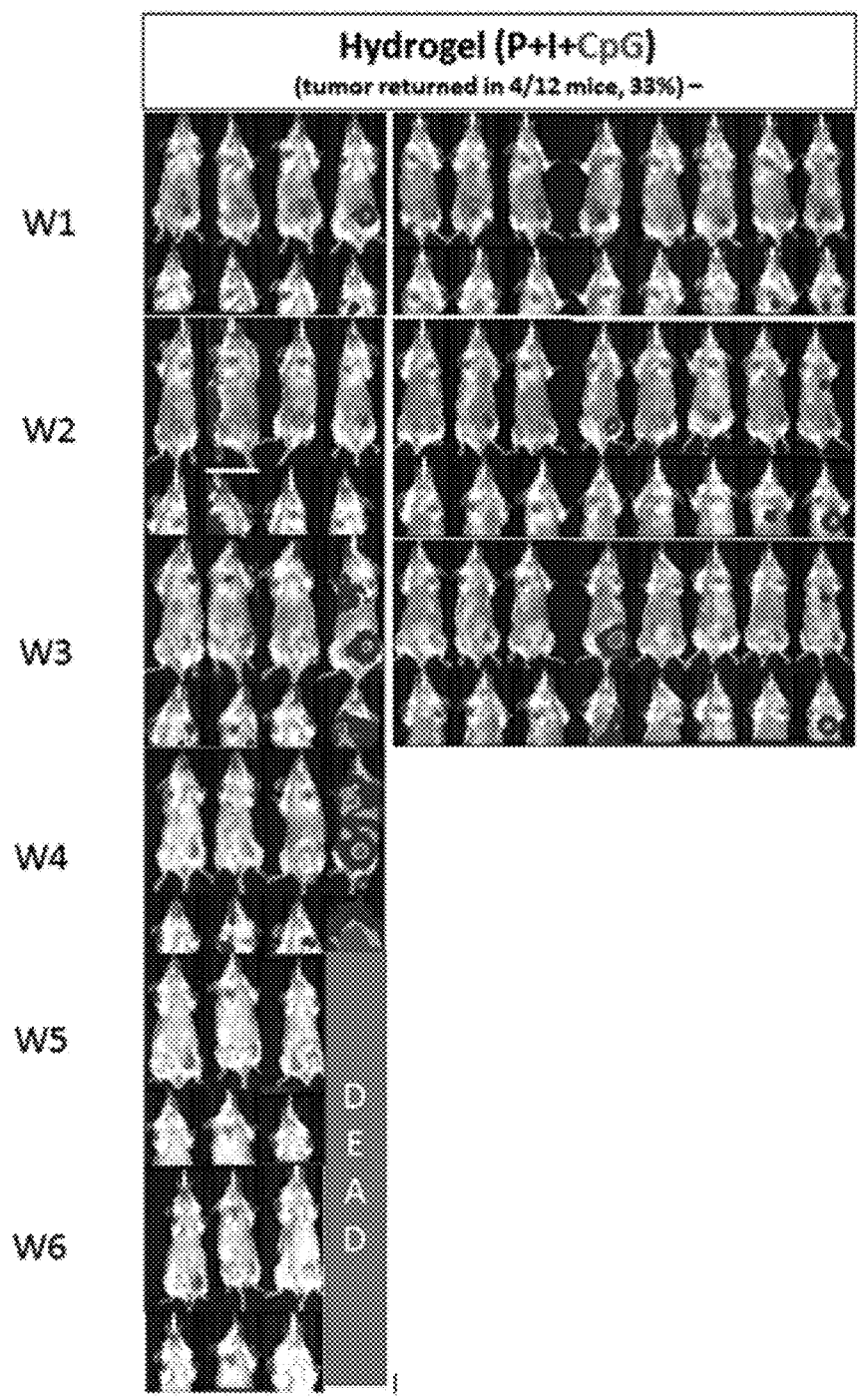
FIG. 29 shows images of individual mice after implantation of exemplary drug delivery device 16 (CpG oligonucleotide+IL-15 superagonist+anti-PD-1 antibody) following inoculation and resection of tumors originating from 4T1-Luc2 syngeneic breast cancer cells. The images show appearance/disappearance of tumor over a 6-week period.
Figure 32:
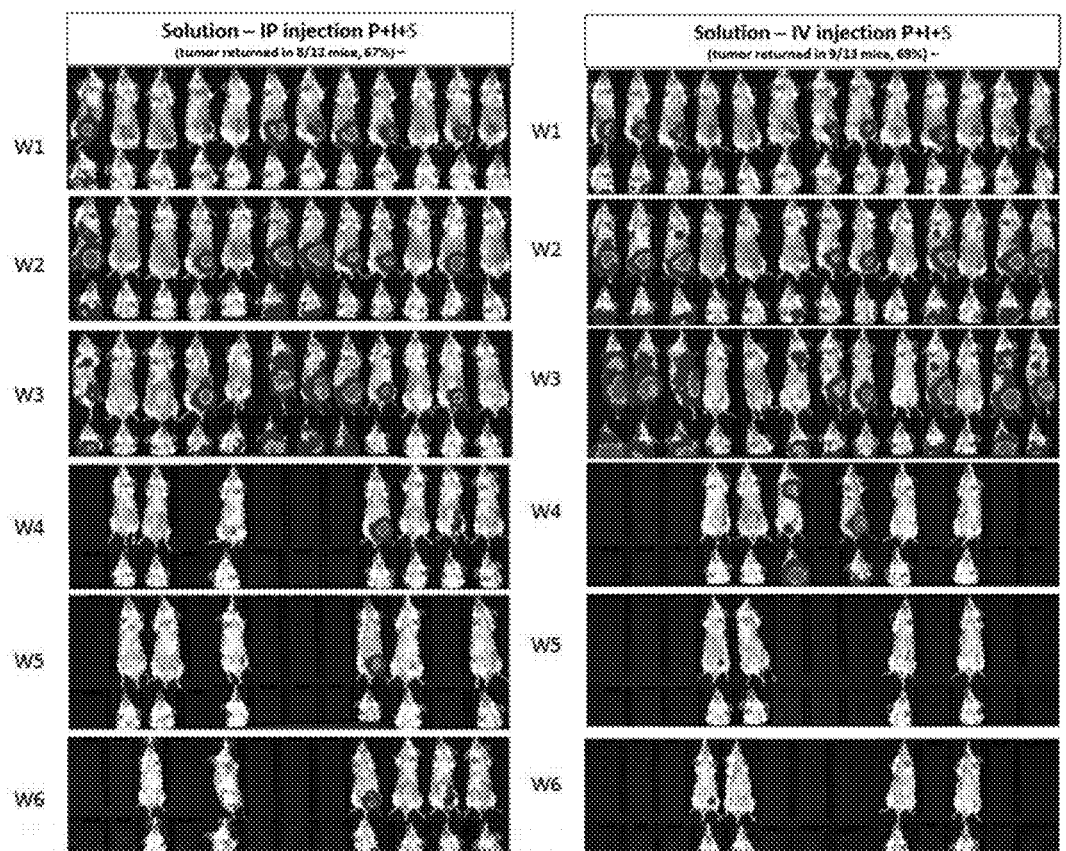
FIG. 32 shows images of individual mice after intraperitoneal (IP) or intravenous (IV) injection of a solution of an exemplary composition (STING agonist+IL-15 superagonist+anti-PD-1 antibody) following tumor inoculation and resection of tumors originating from 4T1-Luc2 syngeneic breast cancer cells. The images show the appearance/disappearance of tumor over a 6-week period.
Figure 33:
FIG. 33 shows images of individual mice after local administration of a solution of an exemplary composition (STING agonist+IL-15 superagonist+anti-PD-1 antibody) following tumor inoculation and resection of tumors originating from 4T1-Luc2 syngeneic breast cancer cells. The images show the appearance/disappearance of tumor over a 6-week period.
Figure 39:
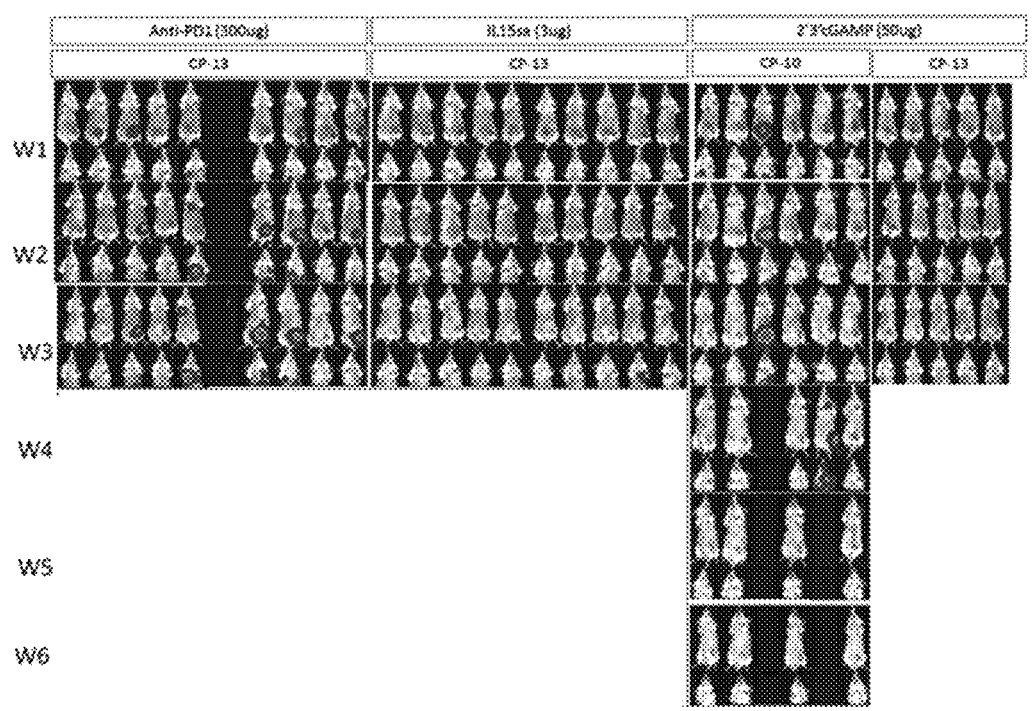
FIG. 39 shows images of individual mice after implantation of exemplary drug delivery devices 17 (STING agonist), 18 (IL-15 superagonist), or 19 (anti-PD-1 antibody) following inoculation and resection of tumors originating from 4T1-Luc2 syngeneic breast cancer cells. The images show the appearance/disappearance of tumor over a 6-week period. Doubling the close of STING agonist or IL-15 superagonist produces remarkable efficacy, demonstrating the use of these compounds as monotherapies, whereas doubling the dose of anti-PD-1 does not.
Figure 40:
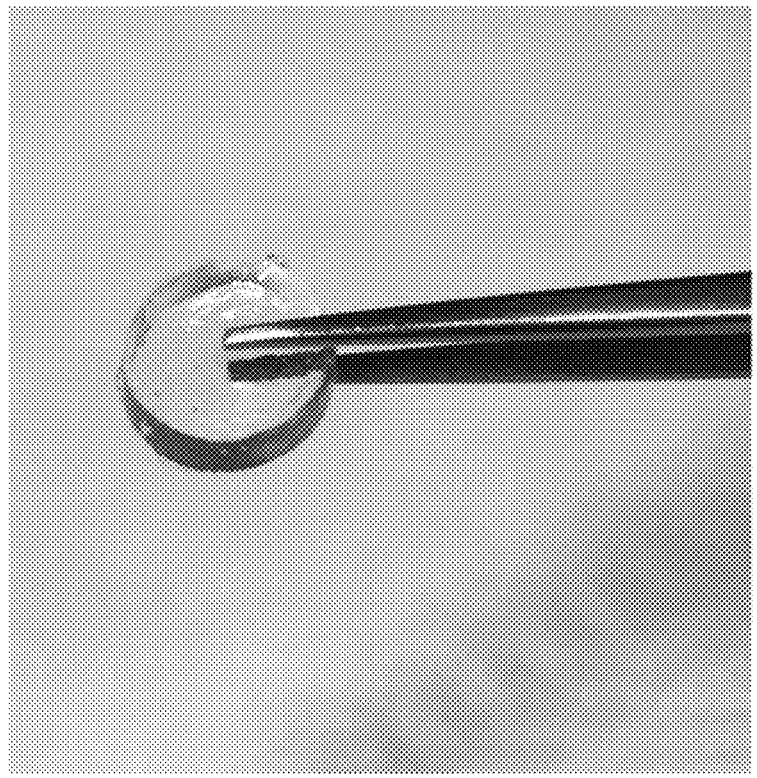
FIG. 40 is an image of device 1 that demonstrates the mechanical integrity of the hydrogel.
Figure 41:
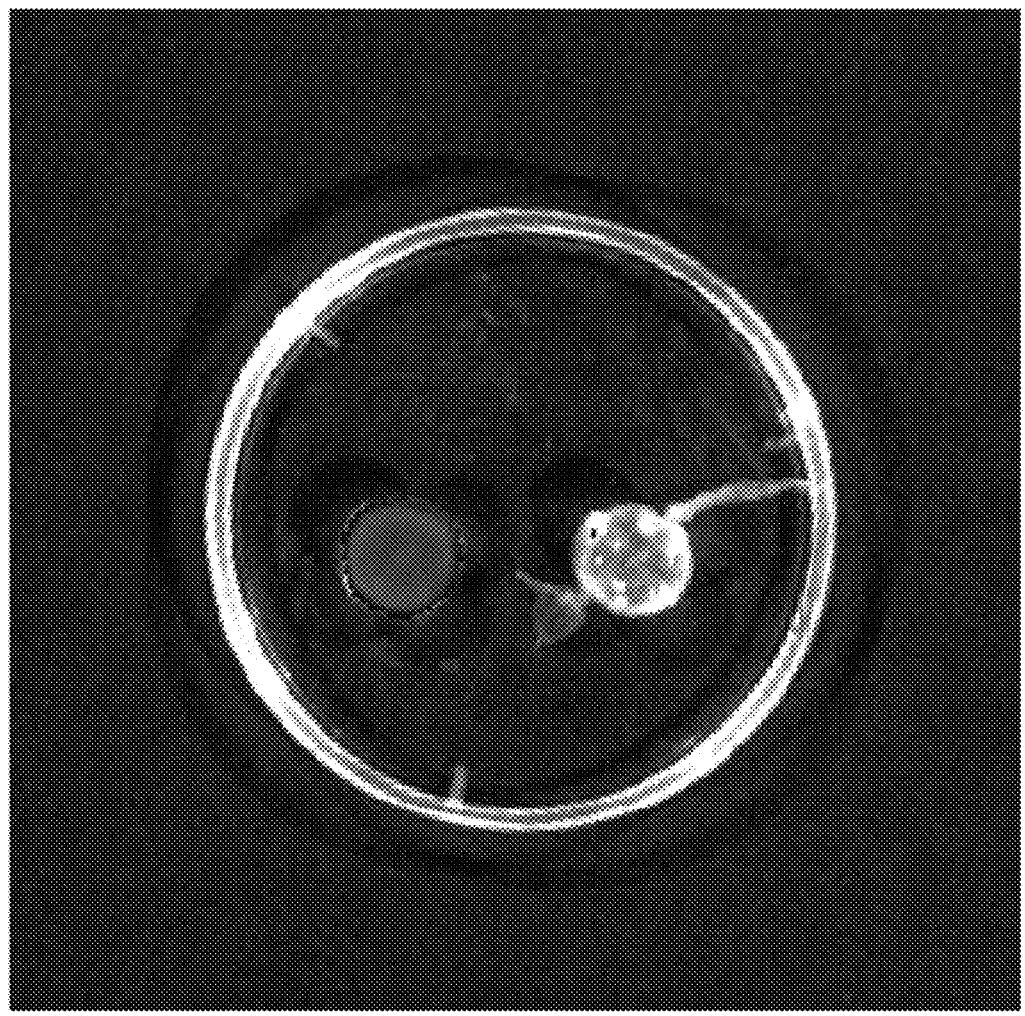
FIG. 41 is an image of a device loaded with ALEXA FLUOR® 750 dye (left) as well as a control device that was not loaded with fluorescent dye (right). The fluorescent image demonstrates that the loaded small molecule is distributed homogenously throughout the hydrogel.

| Device | mice evaluated | mice with relapsed tumor | FIG. |
| --- | --- | --- | --- |
| None (tumor resected only) | 15 | 12 (80%) | FIG. 18 |
| 8 | 22 | 17 (77%) | FIG. 19 |
| 2 | 14 | 12 (86%) | FIG. 20 |
| 9 | 13 | 5 (38%) | FIG. 21 |
| 10 | 15 | 7 (47%) | FIG. 22 |
| 1 | 23 | 4 (17%) | FIG. 23 |
| $1^a$ | 12 | 8 (67%) | FIG. 32 |
| $1^b$ | 13 | 9 (69%) | FIG. 32 |
| $1^c$ | 13 | 7 (54%) | FIG. 33 |
| 11 | 12 | 2 (17%) | FIG. 24 |
| 12 | 12 | 8 (67%) | FIG. 25 |
| 13 | 8 | 5 (62%) | FIG. 26 |
| 14 | 9 | 2 (22%) | FIG. 27 |
| 15 | 11 | 8 (73%) | FIG. 28 |
| 16 | 12 | 4 (33%) | FIG. 29 |
| 17 | 11 | 2 (18%) | FIG. 39 |
| 18 | 10 | 1 (10%) | FIG. 39 |
| 19 | 9 | 5 (56%) | FIG. 39 |

$^a$solution formulation—IP injection;
$^b$solution formulation—IV injection;
$^c$solution formulation—local administration Control experiments demonstrate that when no composition was implanted in the resection site, tumor relapse rate was high (80%). Implantation of device 8 (hydrogel 4 with no therapeutic agents) yielded similar results (77% relapse). Implantation of device 2 led to a high relapse rate (86%). The remaining compositions generally showed low to moderate tumor relapse. In particular, compositions that contained a STING agonist such as 2′-3′-cGAMP were particularly efficacious and resulted in surprisingly low tumor relapse. Administration of the hydrogel compositions by implantation at the tumor resection site provided greater efficacy than when the formulation was administered systemically or locally as a solution. For example, device 1, injected as a solution (IV or IP or local), resulted in much higher tumor relapse than implantation of the hydrogel (FIGS. 32 and 33; 67% or 69% or 54% vs. 17%).

Figure 30:
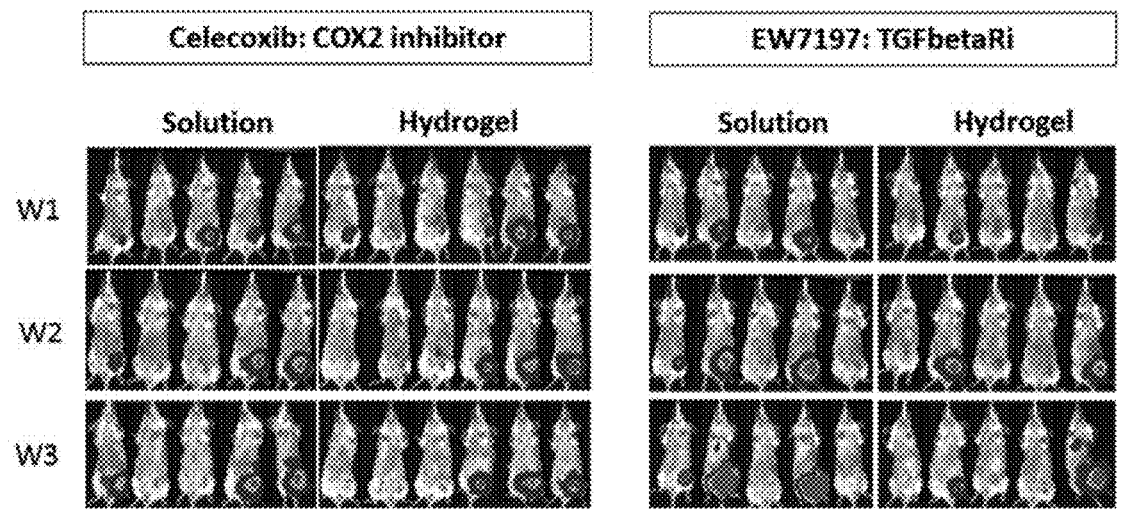
FIG. 30 shows images of individual mice after implantation of devices comprising the hydrogel containing IL-15 superagonist, anti-PD-1, and small molecule therapeutics (celecoxib or EW7197 dissolved in DMSO) following inoculation and resection of tumors originating from 4T1-Luc2 syngeneic breast cancer cells.

However, formulation of IL-15 superagonist, anti-PD-1, and a subset of small molecule therapeutic agents (that required dissolution in DMSO), which can facilitate immune responses, into hydrogel compositions provided less efficacious results (FIG. 30). These small molecule therapeutic agents include celecoxib (COX2 inhibitor) and EW7197 (TGFβR inhibitor).

Figure 31:
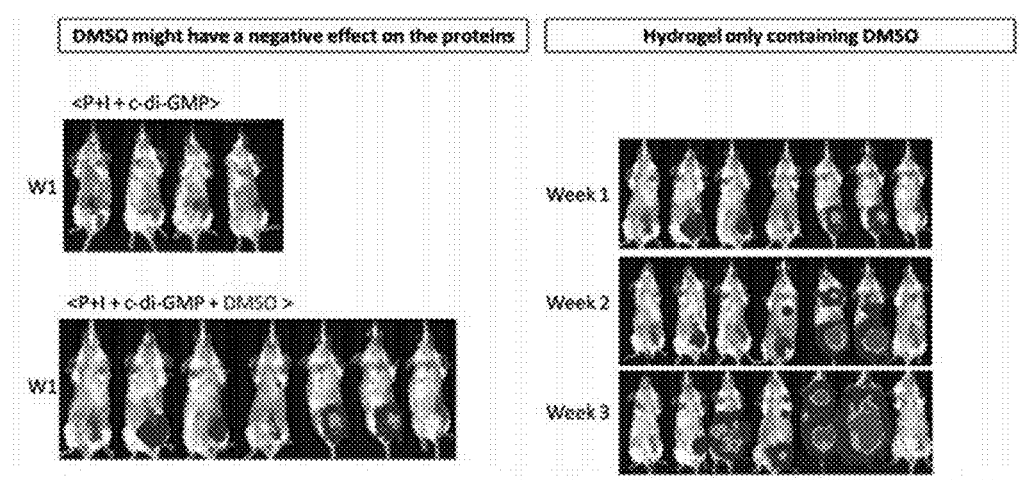
FIG. 31 shows images of different cohorts of mice after implantation of a series of devices: (c-di-GMP+IL-15 superagonist+anti-PD-1 antibody), (c-di-GMP+IL-15 superagonist+anti-PD-1 antibody+DMSO), or (DMSO) following inoculation and resection of tumors originating from 4T1-Luc2 syngeneic breast cancer cells. The images show appearance/disappearance of tumor over a 1-3 week period.

In addition, studies showed that incorporation of DMSO into the hydrogel composition decreased efficacy of otherwise effective compositions (FIG. 31), thus suggesting that organic solvents may have a deleterious effect on proteins in the composition. FIG. 31 shows that tumor relapse was much higher for a formulation comprising c-di-GMP, IL-15sa, anti-PD-1 antibody, and DMSO than the same composition without DMSO.

Figure 34:
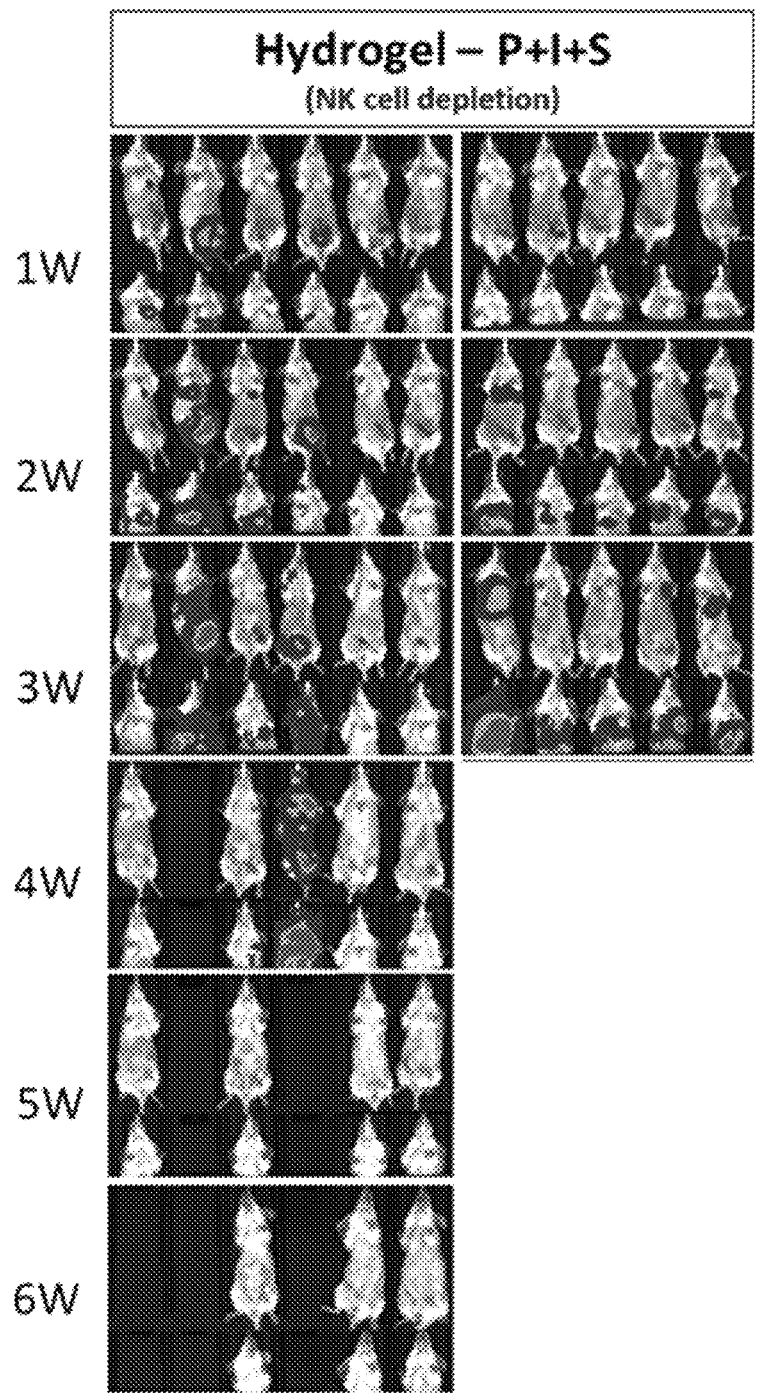
FIG. 34 shows images of individual mice after implantation of exemplary drug delivery device 1 (STING agonist+ IL-15 superagonist+anti-PD-1 antibody) following inoculation and resection of tumors originating from 4T1-Luc2 syngeneic breast cancer cells. The images show the appearance/disappearance of tumor over a 6-week period among mice depleted of NK cells.
Figure 35:
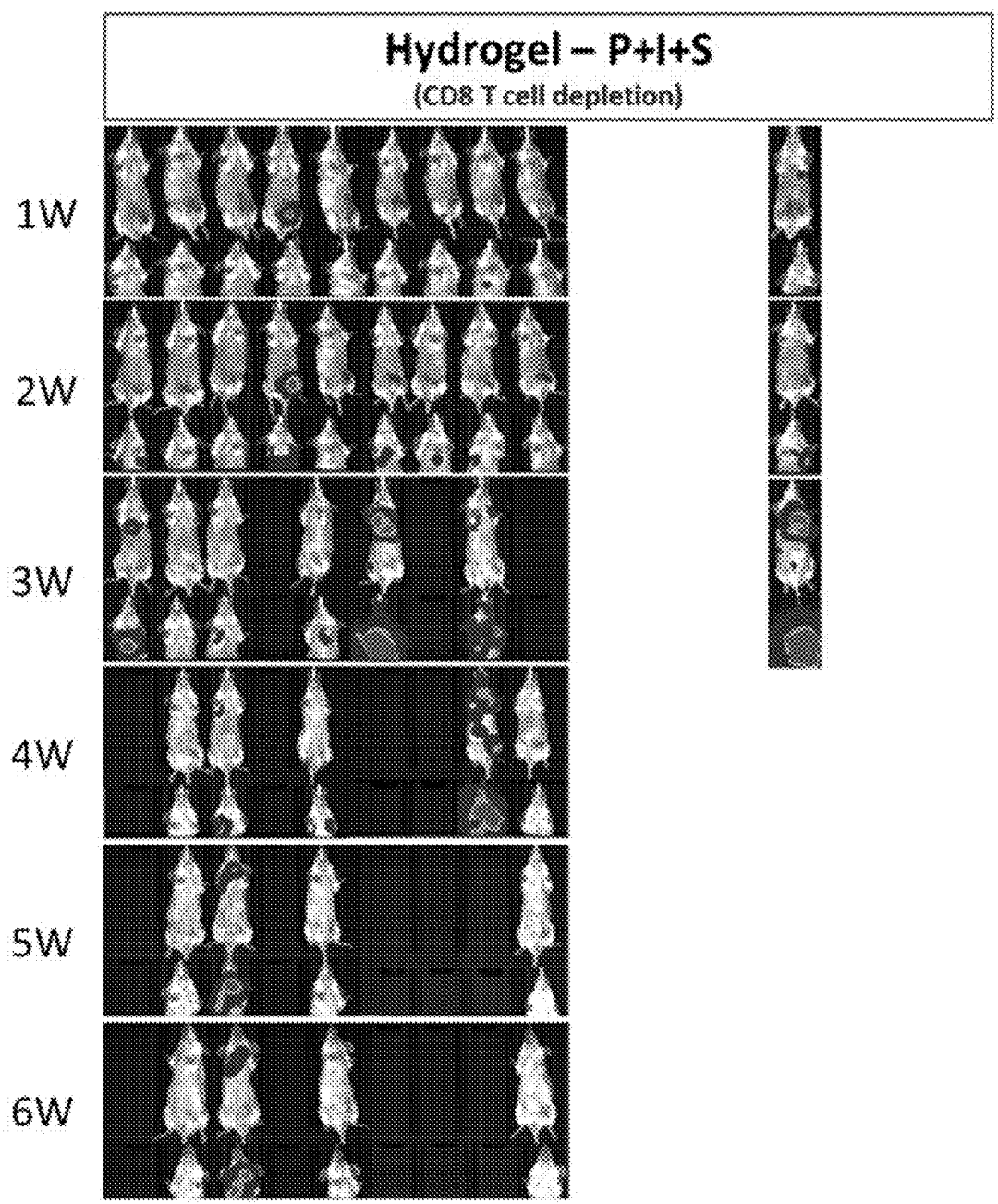
FIG. 35 shows images of individual mice after implantation of exemplary drug delivery device 1 (STING agonist+ IL-15 superagonist+anti-PD-1 antibody) following inoculation and resection of tumors originating from 4T1-Luc2 syngeneic breast cancer cells. The images show the appearance/disappearance of tumor over a 6-week period among mice depleted of CD8+ T cells.
Figure 36:
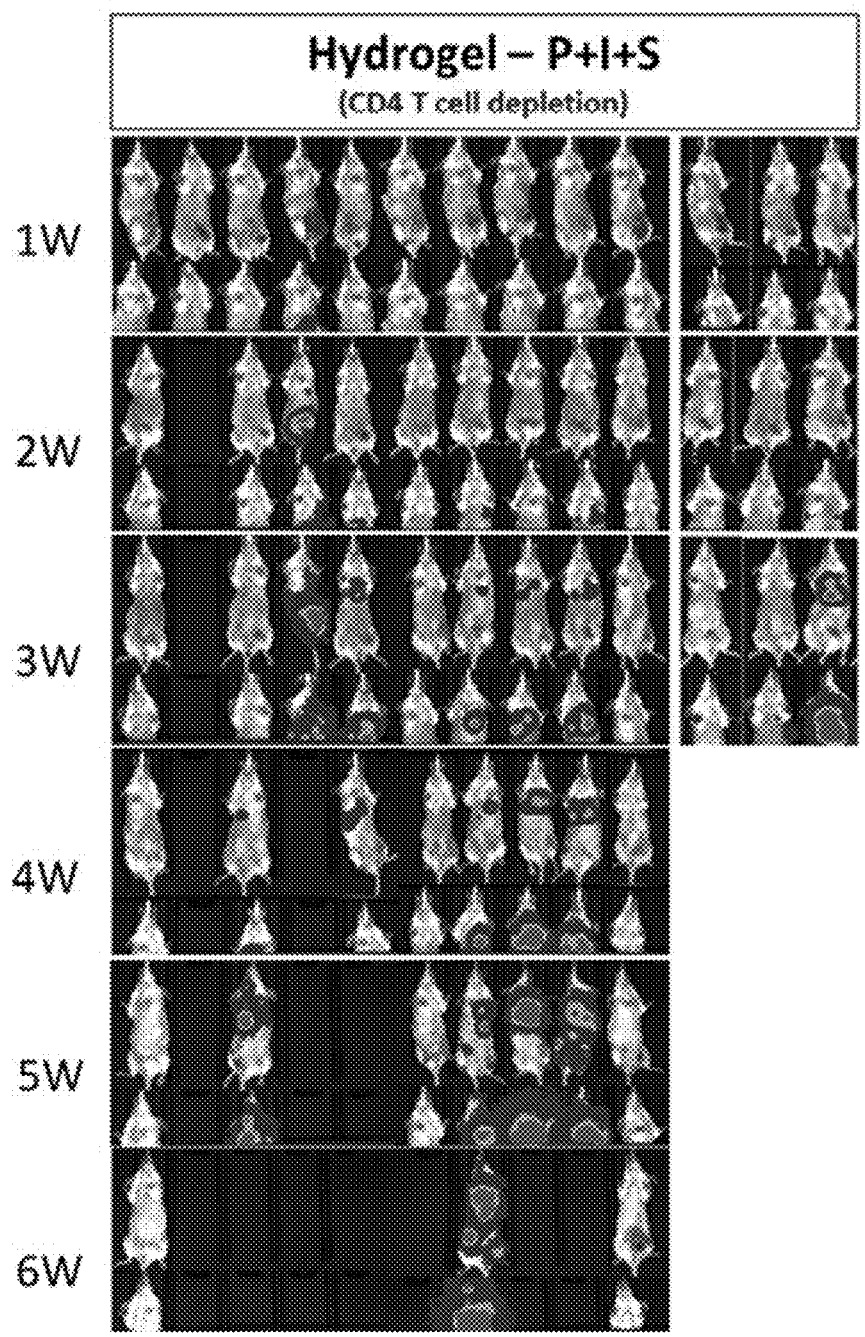
FIG. 36 shows images of individual mice after implantation of exemplary drug delivery device 1 (STING agonist+ IL-15 superagonist+anti-PD-1 antibody) following inoculation and resection of tumors originating from 4T1-Luc2 syngeneic breast cancer cells. The images show the appearance/disappearance of tumor over a 6-week period among mice depleted of CD4+ T cells.

From a mechanistic perspective, experiments suggest that NK cells, CD8+ T cells, and CD4+ T cells may all contribute to the antitumor effects mediated by the combination of 2′-3′-cGAMP, IL-15sa, and anti-PD-1 (FIGS. 34-36).

Figure 80A:
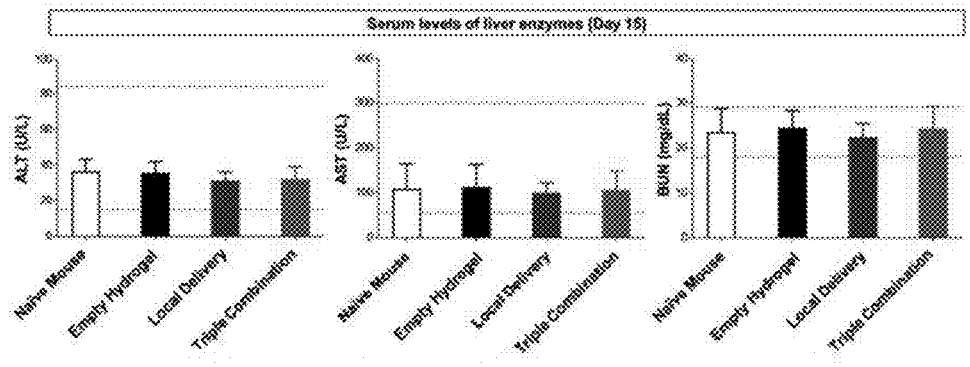
FIGS. 80A-80B are a series of graphs showing that sustained local release of 2′-3′-cGAMP, IL-15sa, and anti-PD-1 was well tolerated after implantation of a variety of different devices (1, 2, 9, 10) or administration via different routes (IP, IV, local) after tumor resection. None of the conditions listed impacted the levels of liver enzymes measured 15 days post-surgery (FIG. 80A) or the weight of mice longitudinally (FIG. 80B). The weight loss observed in the first week was related to the stress of the surgery itself, as it was observed in all groups, including the no treatment and empty hydrogel negative controls. Data in FIG. 80A is presented as mean±SEM. Dashed lines indicate established normal ranges.
Figure 80B:
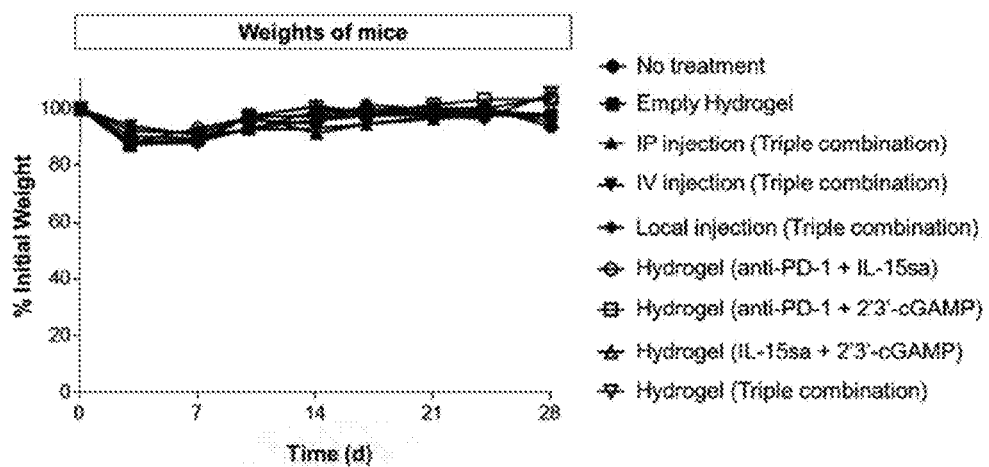

Overall, compositions that have a triple combination of an activator of innate immune response (e.g., STING agonist), a cytokine or chemokine (e.g., an IL-15 superagonist), and an activator of adaptive immune response (e.g., an anti-PD-1 antibody) demonstrate unexpectedly high survival rates of treated mice (FIG. 23). Compositions that contained a mu and/or TLR8 agonist such as R848 in place of the STING agonist were also particularly efficacious (FIG. 27), as were compositions that contained an agonist anti-CD137 antibody in place of anti-PD-1 (FIG. 24). Unexpectedly, doubling the dose of the STING agonist or IL-15sa demonstrated that either of these two molecules can be efficacious as a monotherapy, which was not observed for anti-PD-1 (FIG. 39). Compositions evaluated included: composition of STING agonist+IL-15 superagonist+anti-PD-1 antibody administered locally, IV, or IP. Devices evaluated included exemplary devices 1, 2, 8, 9, 10, 11, 12, 13, 14, 15, 16, 17, 18, and 19. Weight of the mice was also largely unaffected by implantation of the hydrogel compositions throughout these experiments, demonstrating the safety and non-toxicity of the hydrogel compositions (FIG. 80B). There are several instances wherein it seems that a tumor has relapsed or metastasized but the immune system subsequently clears these lesions.

Figure 42:
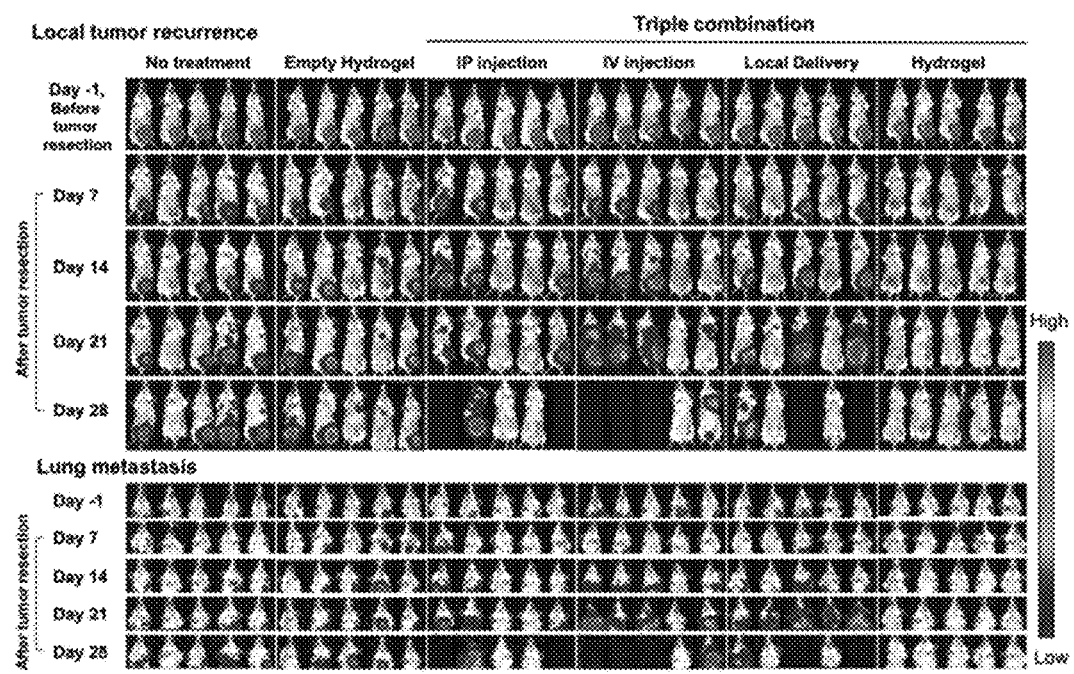
FIG. 42 shows images of individual mice after implantation of exemplary drug delivery device 1 following inoculation and resection of tumors originating from 4T1-Luc2 syngeneic breast cancer cells. The images show the appearance/disappearance of tumor over a 4-week period. The following groups were evaluated: no treatment (sham), empty hydrogel, intraperitoneal injection of the triple combination (2´3´-cGAMP, IL-15sa, and anti-PD-1), intravenous injection of the triple combination (2´3´-cGAMP, IL-15sa, and anti-PD-1), local administration of the triple combination (2´3´-cGAMP, IL-15sa, and anti-PD-1), or device 1. The hydrogels were placed in the tumor resection site, as was local administration of the triple combination in solution.
Figure 43:
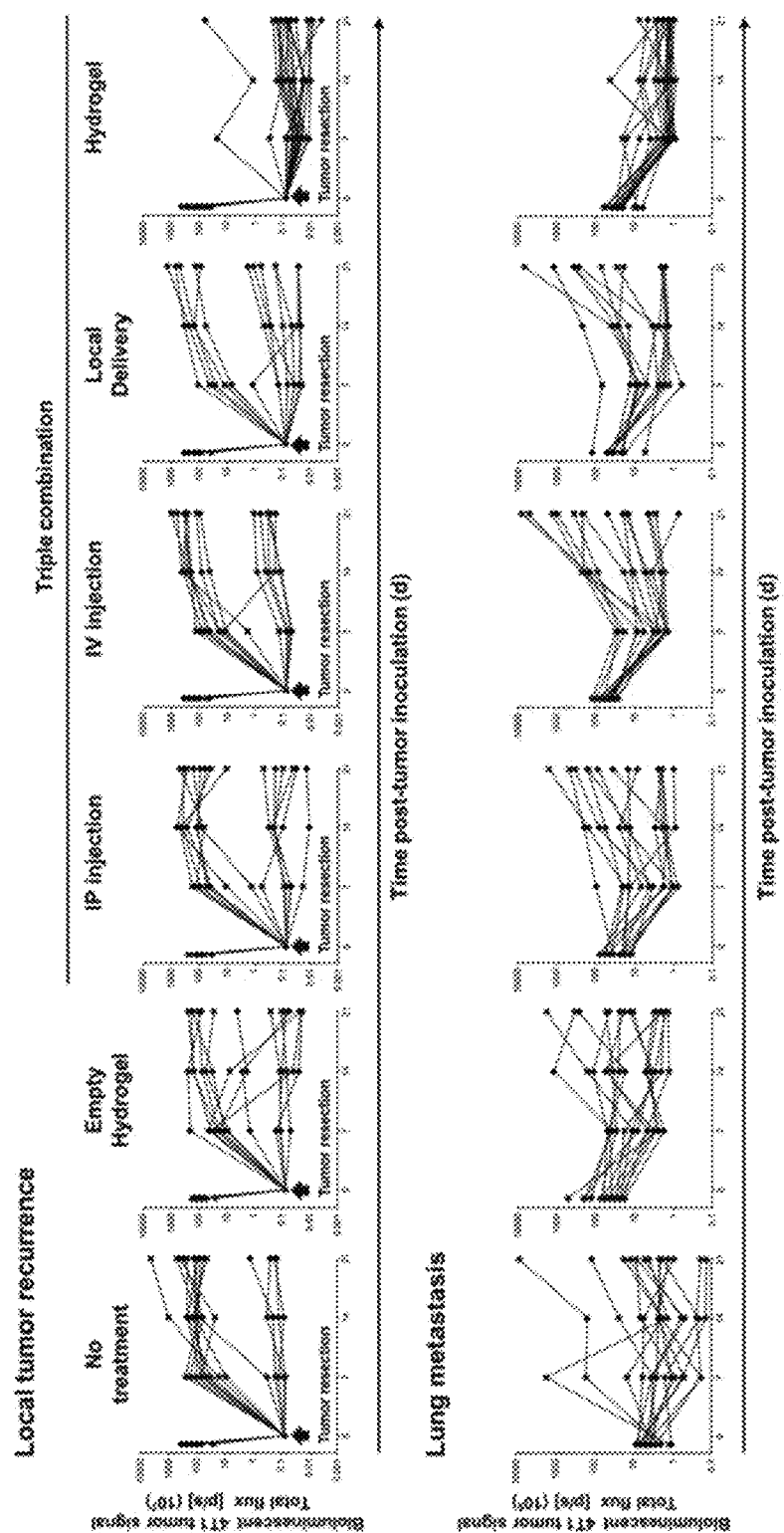
FIG. 43 shows a series of graphs wherein sustained local release of 2´3´-cGAMP, IL-15sa, and anti-PD-1 (device 1) prevents tumor recurrence and metastasis in a majority of mice, as illustrated by total flux of bioluminescent 4T1-Luc2 cells. Data for individual mice are shown for tumors that recurred locally or metastasized to the lung following the treatments shown.
Figure 44:
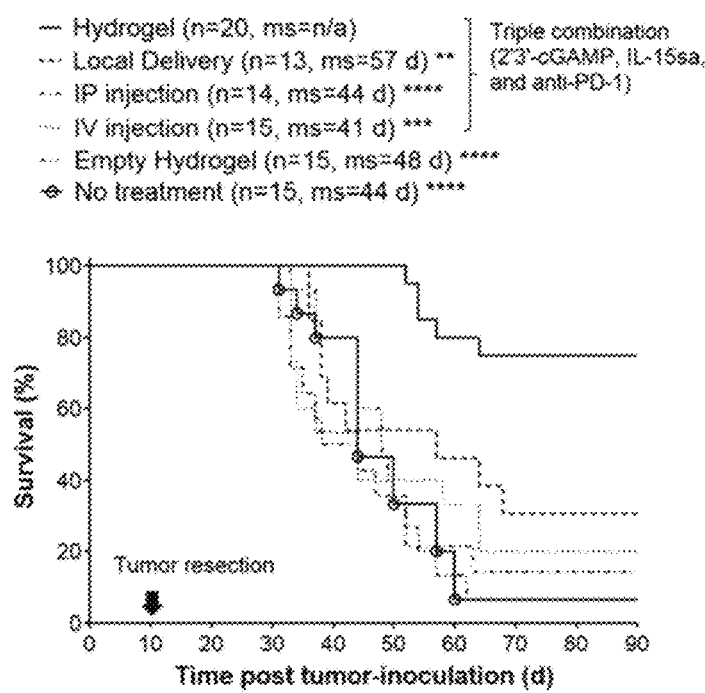
FIG. 44 is a Kaplan-Meier curve for all groups described in FIG. 42. The number of mice per group (n) and median survival (ms) are listed. Statistics were calculated relative to the group treated with hydrogel containing triple combination using the Log-rank (Mantel-Cox) test.  p≤0.01, * p≤0.001, **** p≤0.0001.
Figure 45:
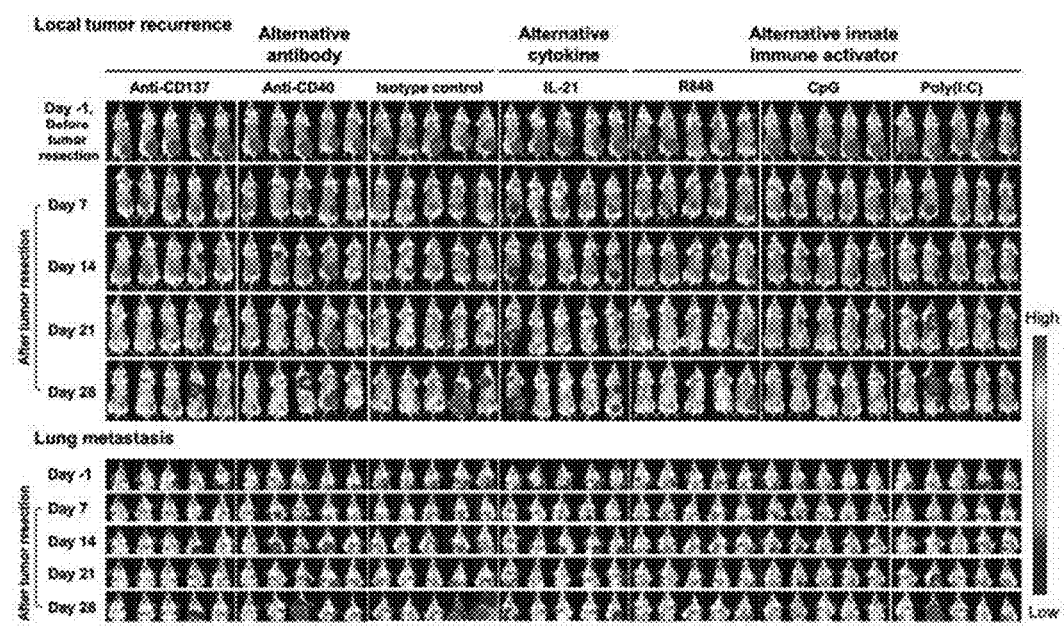
FIG. 45 shows images of individual mice after implantation of exemplary drug delivery devices 11-16 and 20 following inoculation and resection of tumors originating from 4T1-Luc2 syngeneic breast cancer cells. The images show the appearance/disappearance of tumor over a 4-week period. The devices were placed in the tumor resection site.
Figure 46:
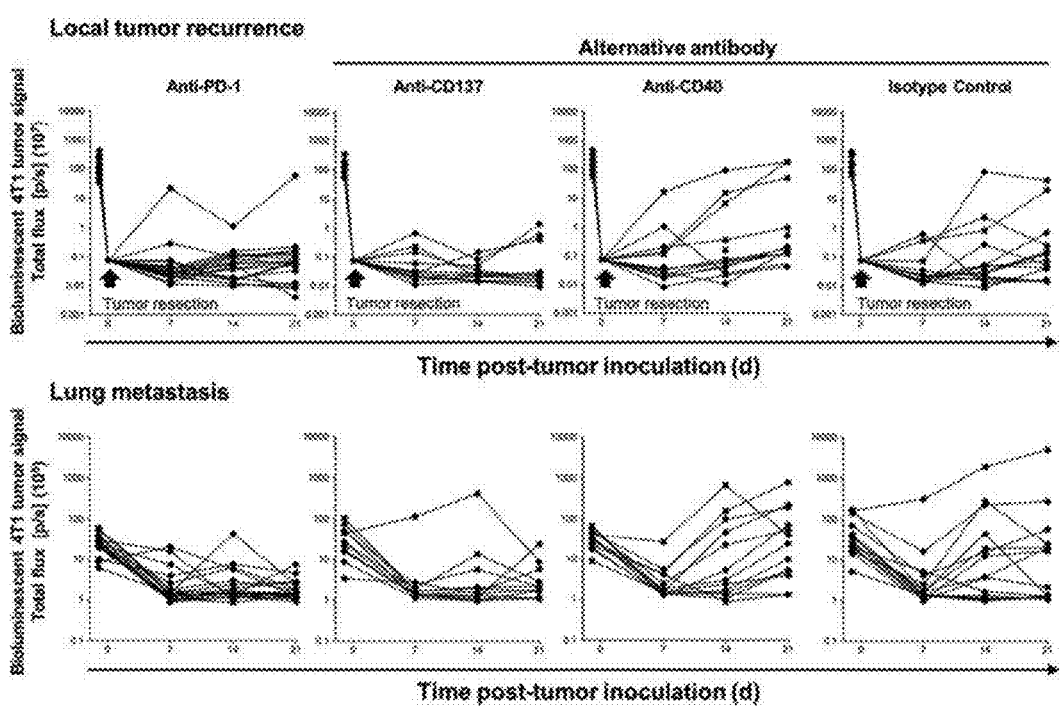
FIG. 46 is a series of graphs showing the total flux of bioluminescent 4T1-Luc2 cells after administration of devices 11, 12 and 20 from the experiment described in FIG. 45, in comparison to device 1 (containing anti-PD-1 as the antibody in combination with IL-15sa and 2'3'-cGAMP). Data, for individual mice are shown for tumors that recurred locally or metastasized to the lung following the treatments shown.
Figure 47:
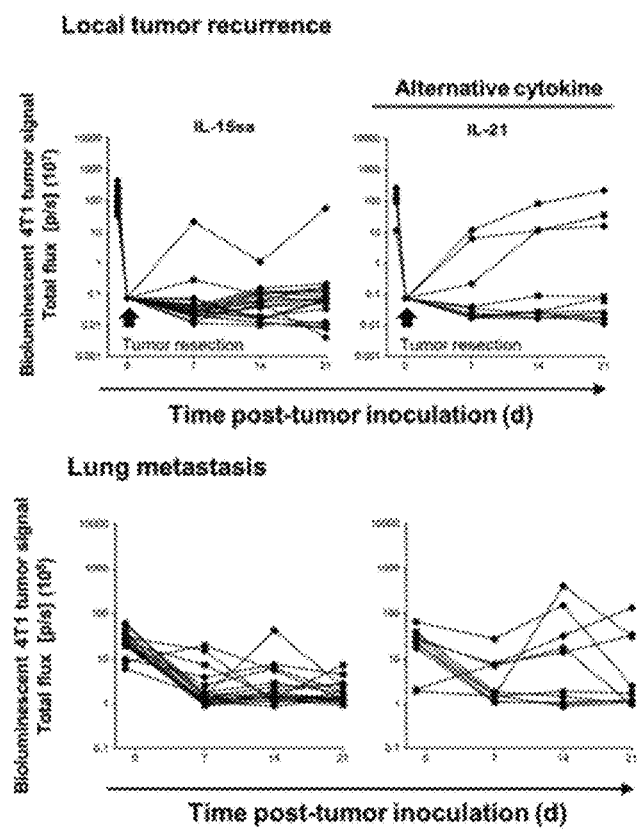
FIG. 47 is a series of graphs showing the total flux of bioluminescent 4T1-Luc2 cells after administration of device 13 from the experiment described in FIG. 45, in comparison to device 1 (containing IL-15sa as the cytokine in combination with 2'3'-cGAMP and anti-PD-1). Data for individual mice are shown for tumors that recurred locally or metastasized to the lung following the treatments shown.

Example 6. Sustained Local Release of Exemplary Drug Delivery Devices Prevents Tumor Relapse and Metastasis Female BALB/cJ mice were inoculated orthotopically with 4T1-Luc2 breast cancer cells in their fourth mammary fat pad. Nine days later, the mice were imaged by bioluminescent IVIS imaging to confirm that the size of the tumors was consistent across animals to enable randomization into groups. On day 10 post-tumor inoculation, tumors (~100 $mm^3$) were resected, and device 1 was placed in the tumor resection site. Controls included no treatment (sham), empty hydrogel (device 8/hydrogel 4), or delivery of the triple combination in solution (S+I+P)—via intraperitoneal injection, intravenous injection, or local administration. Tumor burden was monitored weekly by IVIS imaging, and it was confirmed that local tumor recurrence was prevented most effectively when the triple combination was administered via device 1 (FIGS. 42, 43). Notably, lung metastases had already been established by the time of surgery, and sustained local release of the triple combination was again the lone condition that eradicated the existing metastatic lesions (FIGS. 42, 43). The IVIS imaging provided a meaningful proxy for long-term survival, as the hydrogel loaded with the triple combination (device 1) conferred durable survival benefit to a majority of mice (FIG. 44). These data underscore the utility of having sustained local release of the immunomodulatory payloads relative to administration of the compounds in solution.

Figure 50:
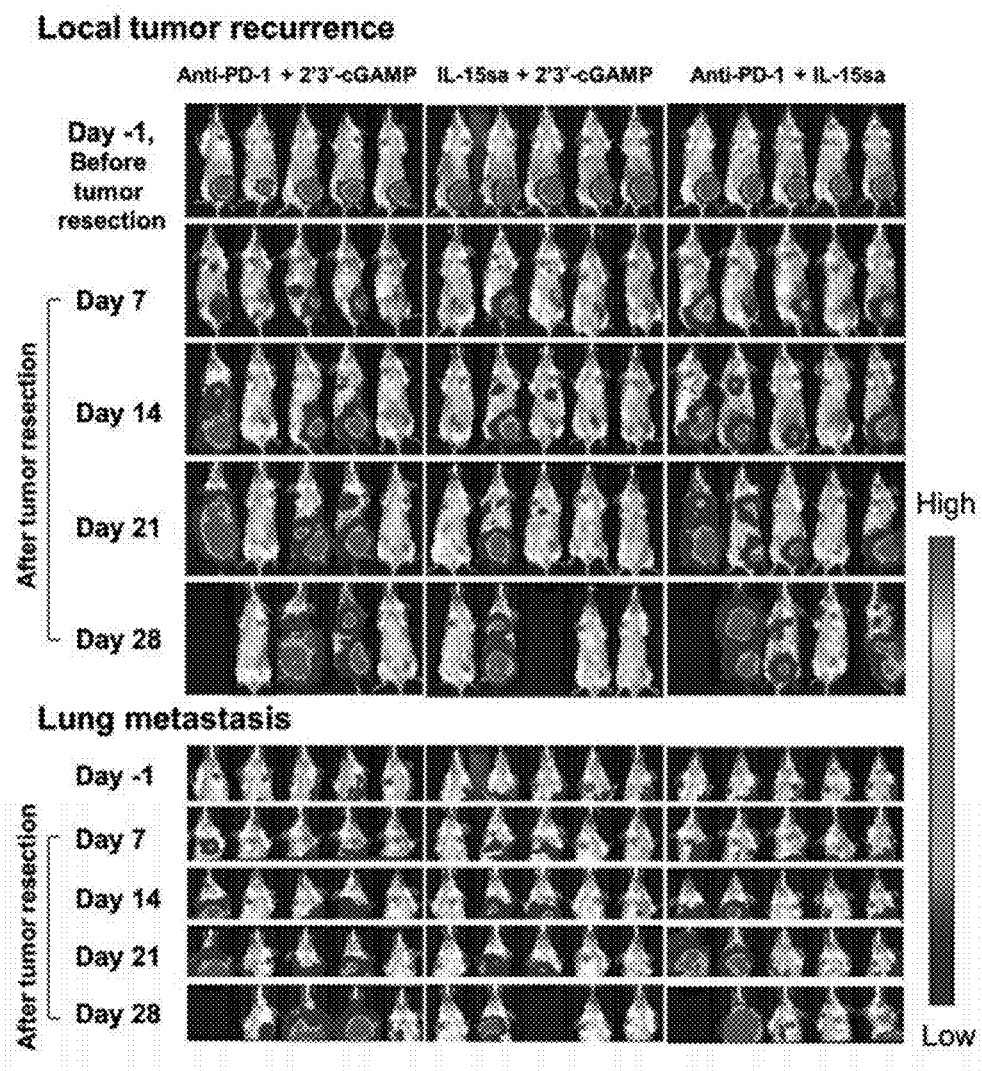
FIG. 50 shows images of individual mice after implantation of exemplary drug delivery devices 2, 9, and 10 following inoculation and resection of tumors originating from 4T1-Luc2 syngeneic breast cancer cells. The images show the appearance/disappearance of tumor over a 4-week period. The devices were placed in the tumor resection site.
Figure 51:
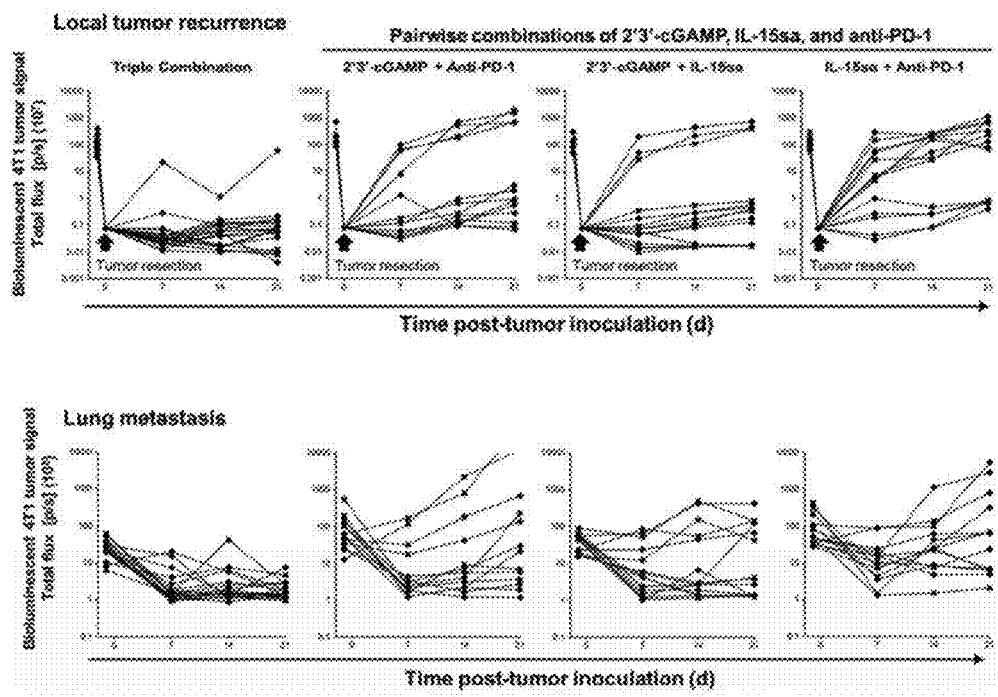
FIG. 51 is a series of graphs showing the total flux of bioluminescent 4T1-Luc2 cells after administration of exemplary drug delivery devices 2, 9, and 10 from the experiments described in FIG. 50, in comparison to device 1. Data for individual mice are shown for tumors that recurred locally or metastasized to the lung following the treatments shown.
Figure 52:
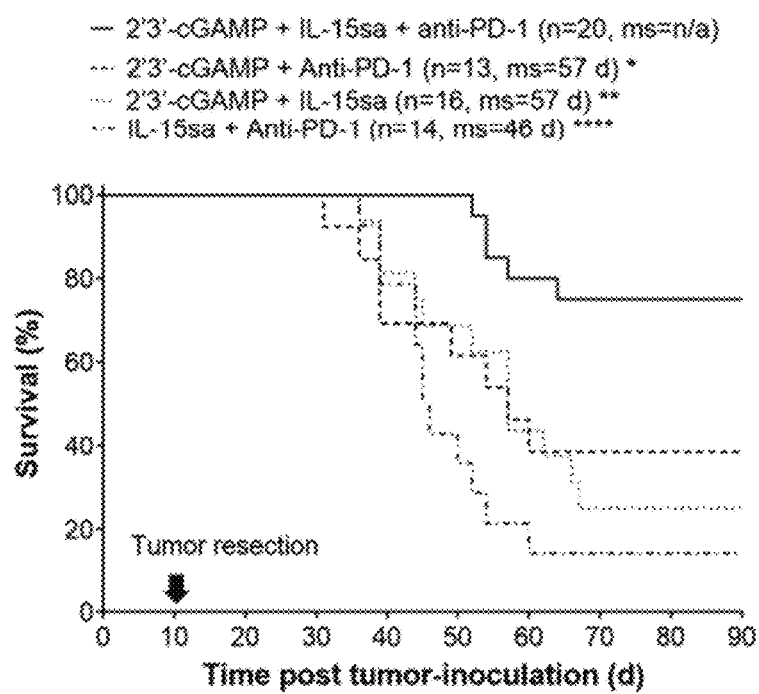
FIG. 52 shows a series of Kaplan-Meier curves for devices 1, 2, 9, and 10. The number of mice per group (n) and median survival (ms) are listed. Statistics were calculated relative to the group treated with device 1 using the Log-rank (Mantel-Cox) test. * p≤0.05,  p≤0.01, * p≤0.001.

The efficacies of devices 2, 9-16, and 20 were also evaluated under the same experimental conditions. 2´-3´-cGAMP and IL-15sa were combined with isotype control antibody to form exemplary drug delivery device 20. The results of these studies are shown in FIGS. 45-52. As a complement to 2´-3´-cGAMP and IL-15sa, anti-PD-1 conferred greater survival benefit than either agonist anti-CD137 or agonist anti-CD40) (FIG. 46 and FIGS. 49A-49C). Anti-CD137, which provides co-stimulatory signals to NK cells, CD8+ T cells, and CD4+ T cells, also provided benefit. In contrast, anti-CD40, which provides co-stimulatory signals to B cells, dendritic cells, and myeloid cells and is effective even in the absence of T cell-mediated immunity, had little impact relative to 2´-3´-cGAMP and IL-15sa alone (FIGS. 50-52). Consistent with the results observed in this study, it has been shown that the activity of anti-CD40, which is augmented by chemotherapy, is independent of the STING pathway.

Figure 48:
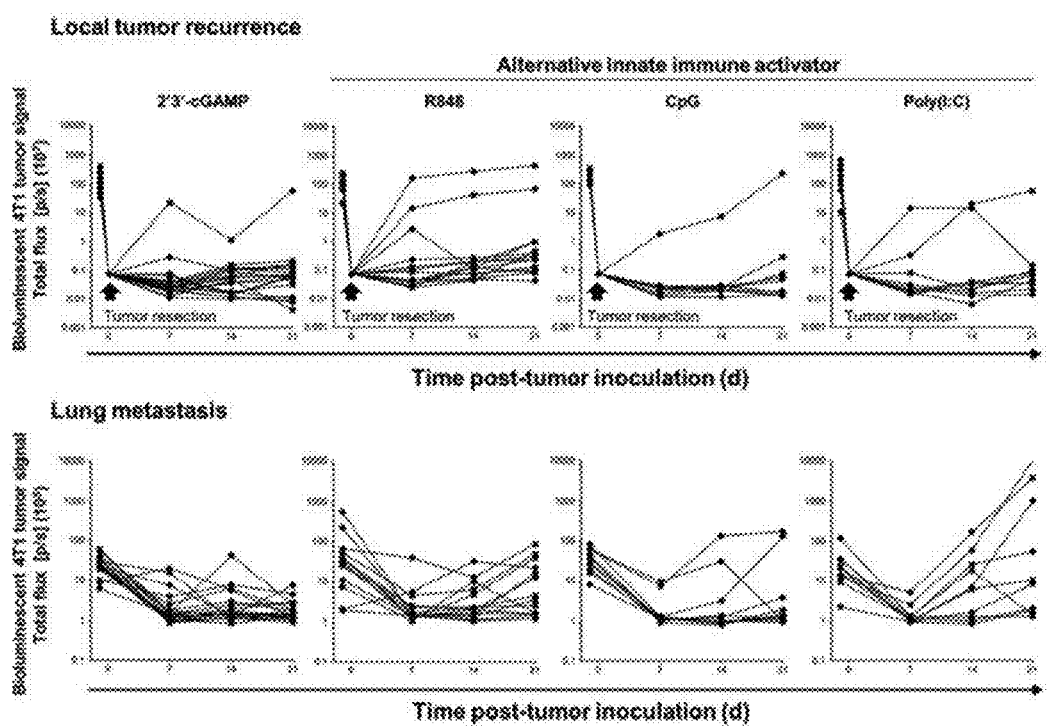
FIG. 48 is a series of graphs showing the total flux of bioluminescent 4T1-Luc2 cells after administration of devices 14-46 from FIG. 45, in comparison to device 1 (containing 2′-3′-cGAMP as the innate immune activator in combination with IL-15sa and anti-PD-1). Data for individual mice are shown for tumors that recurred locally or metastasized to the lung following the treatments shown.
Figure 49A:
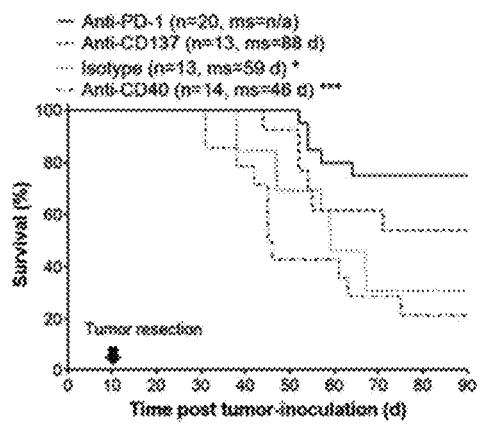
FIGS. 49A-49C show a series of Kaplan-Meier curves for devices 1, 11, 12, and 20 (FIG. 49A); devices 1 and 13 (FIG. 49B), and devices 1 and 14-16 (FIG. 49C). The number of mice per group (n) and median survival (ms) are listed. Statistics were calculated relative to the group treated with hydrogel containing anti-PD-1 (device 1) (FIG. 49A), IL-15sa (device 1) (FIG. 49B), or 2′-3′-cGAMP (device 1) (FIG. 49C) using the Log-rank (Mantel-Cox) test. * p≤0.05,  p≤0.01, * p≤0.001.
Figure 49B:
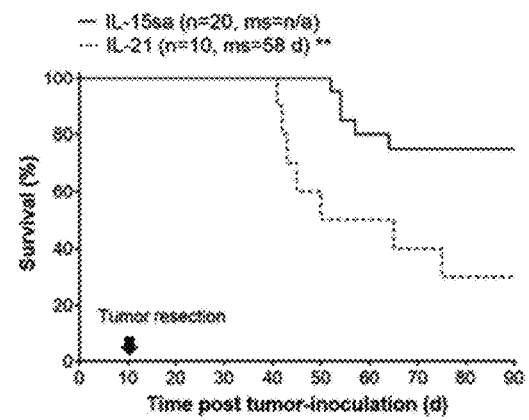
Figure 49C:
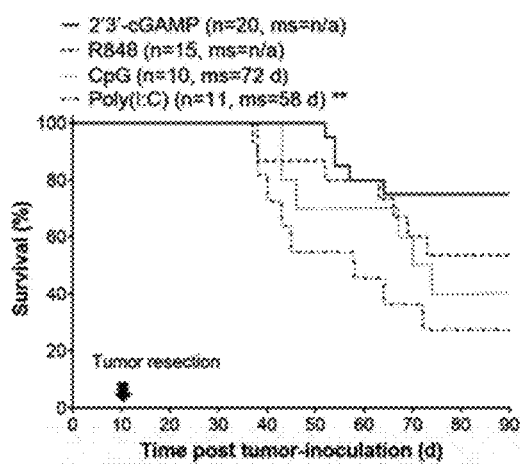

As a complement to 2´-3´-cGAMP and anti-PD-1, IL-15sa conferred greater survival benefit than IL-21 (FIGS. 47 and 49A-49C). IL-21 is a multifaceted regulator of immunity, as it promotes the proliferation of B cells, NK cells, and T cells, though it restricts the function and survival of dendritic cells. This pleiotropic cytokine, whose activity is context-dependent, had little impact relative to 2´-3´-cGAMP and anti-PD-1 alone (FIGS. 50-52). As a complement to IL-15sa and anti-PD-1, 2´-3´-cGAMP conferred greater survival benefit than the Toll-like receptor (TLR) 7/8 agonist R848, the TLR9 agonist CpG oligonucleotide, or the TLR3 agonist poly(I:C) (FIGS. 48 and 49). Activation of each of these TLRs can stimulate production of type I interferons, and these agonists are often used as adjuvants for cancer vaccines. The nucleic acid-based agonists CpG oligonucleotide and poly(I:C) had little impact relative to IL-15sa and anti-PD-1 alone (FIGS. 50-52). R848 conferred meaningful benefit as an innate immune activator, albeit less so than 2´-3´-cGAMP. While the former was similarly effective at preventing local tumor recurrence, it was less effective at combating lung metastases, so some mice treated with R848 succumbed to disease at later time points. These data suggest that these immunomodulatory agents have an effect on the antitumor immunity that is established. In particular, the inclusion of an effective inducer of type I interferon appears to be useful, as the least efficacious of the pairwise combinations was the one lacking 2´-3´-cGAMP (FIGS. 50-52).

Figure 53:
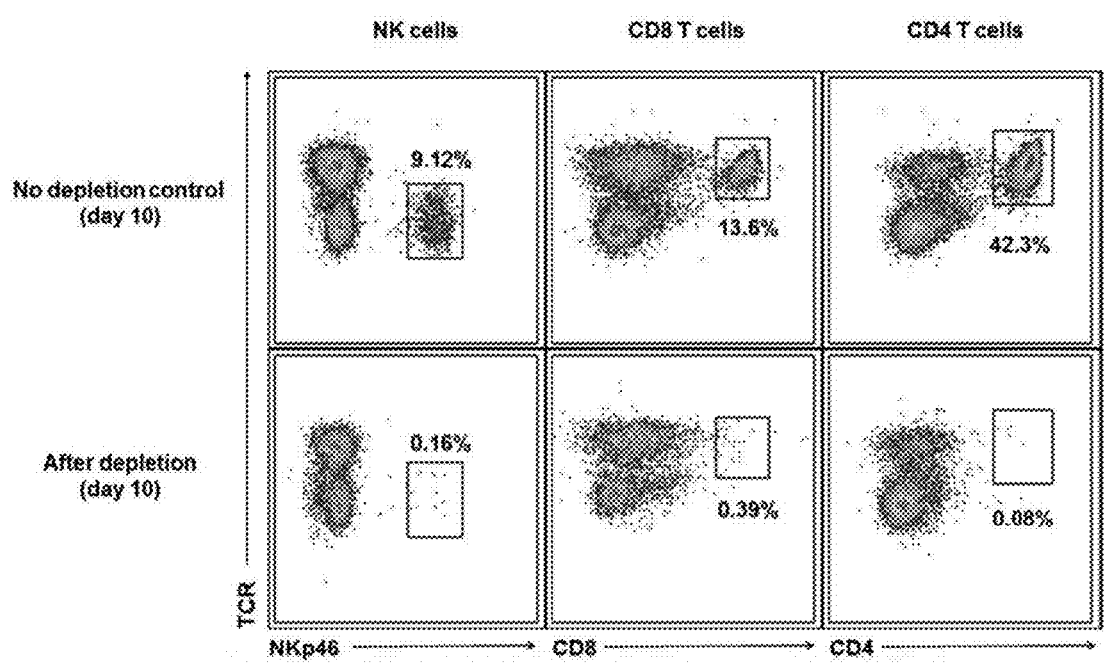
FIG. 53 is a series of plots showing flow cytometry analysis of leukocytes isolated from blood ten days after surgery. The plots confirm that NK cells, CD8+ T cells, and CD4+ T cells are depleted following administration of appropriate antibodies to mice.
Figure 54:
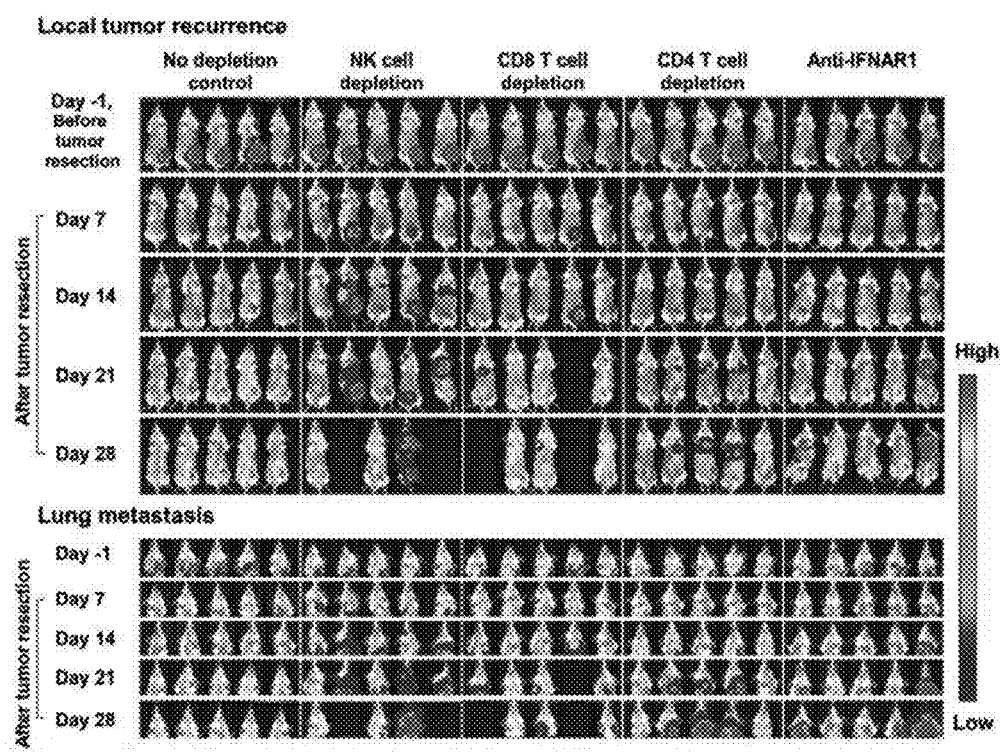
FIG. 54 shows images of individual mice after implantation of exemplary drug delivery device 1 following inoculation and resection of tumors originating from 4T1-Luc2 syngeneic breast cancer cells. The images show the appearance/disappearance of tumor over a 4-week period among mice depleted of NK cells, CD8+ T cells, or CD4+ T cells; or mice in which innate immune signaling (IFNARI) was inhibited.
Figure 55:
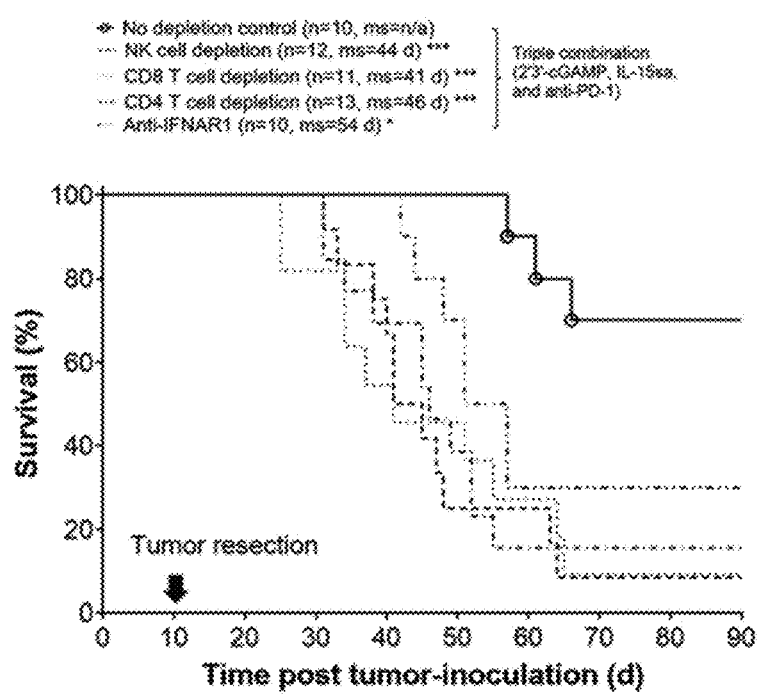
FIG. 55 is a Kaplan-Meier curve for all groups of the experiment described in FIG. 54. The number of mice per group (n) and median survival (ms) are listed. Statistics were calculated relative to the group treated with hydrogel containing triple combination (device 1) and treated with PBS (control) using the Log-rank (Mantel-Cox) test. * p≤0.05, *** p≤0.0.001.
Figure 56:
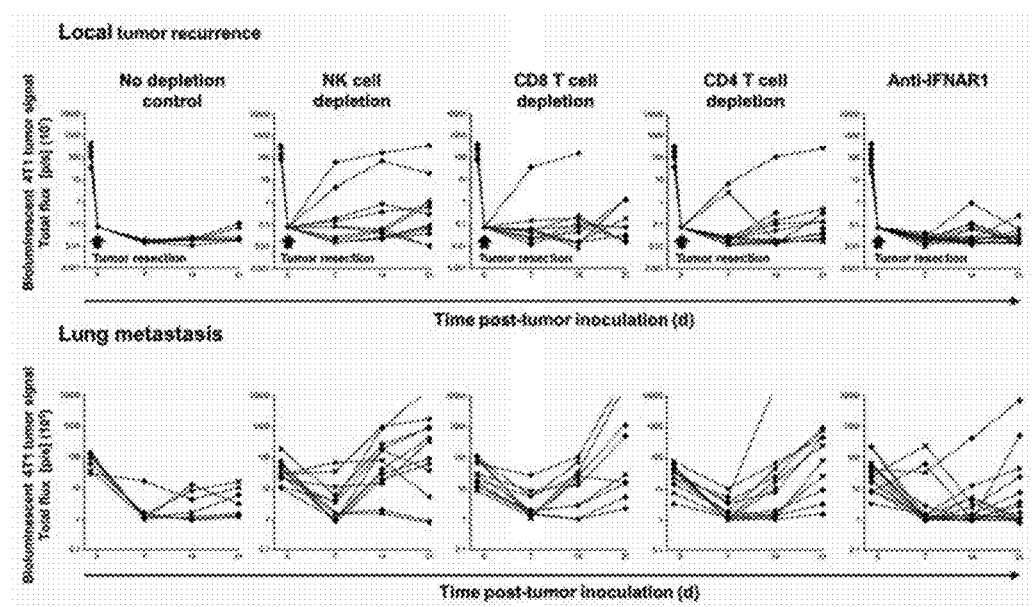
FIG. 56 is a series of graphs showing the total flux of bioluminescent 4T1-Luc2 cells after administration of exemplary drug delivery device 1 from the experiments described in FIG. 54. Data for individual mice are shown for tumors that recurred locally or metastasized to the lung following the treatments shown.

Experiments were also performed to discern which cells and pathways underlie the enhanced antitumor immune response upon sustained local release of the immunotherapy. The tumor inoculation and resection procedure described above was repeated, but—in addition to placing device 1 in the resection site—NK cells, CD8+ T cells, or CD4+ T cells were depleted (FIG. 53) or type I interferon signaling was inhibited by neutralizing interferon alpha receptor 1 (IFNAR1), IVIS imaging indicated that NK cells, CD8+ T cells, CD4+ T cells, and type 1 interferon signaling are all useful in preventing tumor recurrence and metastasis (FIGS. 54 and 56). The most apparent difference between the groups was the involvement of NK cells in the rejection of metastases in the first week post-surgery. As before, the recurrence observed by IVIS imaging corresponded to an impact on long-term benefit; mice in all groups whose innate or adaptive immune system was compromised exhibited reduced survival after sustained release of the triple combination (device 1) in the perioperative setting (FIG. 55).

Figure 57A:
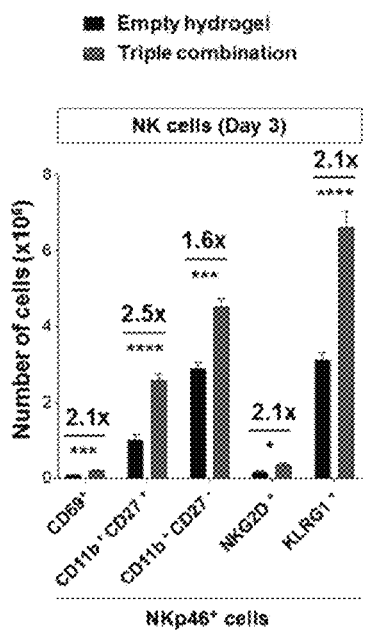
FIGS. 57A-57F are a series of graphs showing that sustained local release of 2′-3′-cGAMP, IL-15sa, and anti-PD-1 increases the number of innate and adaptive antitumor immune cells and cytokines. Tumors were resected from mice 10 days after orthotopic inoculation of 4T1-Luc2 cells, and device 1 was placed in the resection site. Spleens were recovered from mice 3 or 14 days after surgery for flow cytometry analysis, and blood was recovered from mice 14 days after surgery for cytokine analysis.
Figure 57B:
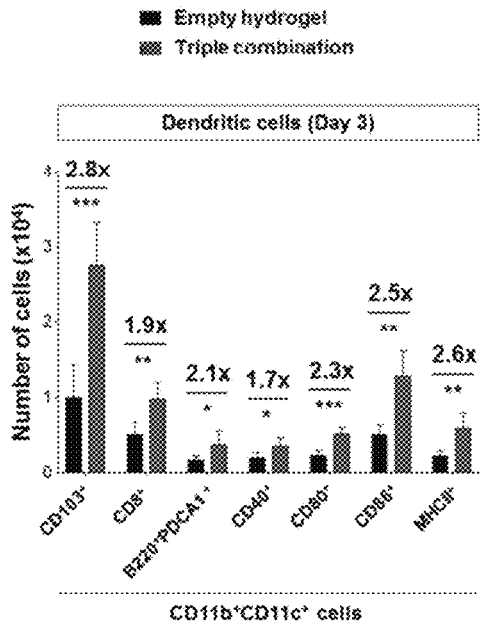

To dissect the cellular and molecular changes among immune cell subsets following treatment with device 1, the composition, activation status, and function of leukocytes in the spleen were assessed. Spleens were recovered from mice 3 or 14 days after surgery for flow cytometry analysis. For the early time point, the innate arm of the immune system was evaluated, particularly NK cells and dendritic cells. The number of activated NK cells, both high effector (CD11b+CD27+) and terminal effector (CD11b+CD27−), was increased following sustained release of the triple combination of device 1, as was the number of NK cells expressing NKG2D and KLRG1 (FIG. 57A). Similarly, the number of dendritic cells was increased, including the CD103+ class of dendritic cells that is useful for the production of robust antitumor immunity and the B220+PDCA1+ class of plasmacytoid dendritic cells that are known to produce large amounts of type I interferons (FIG. 57B). The dendritic cells expressed the co-stimulatory molecules CD40, CD80, and CD86, indicating that they had been activated.

Figure 57C:
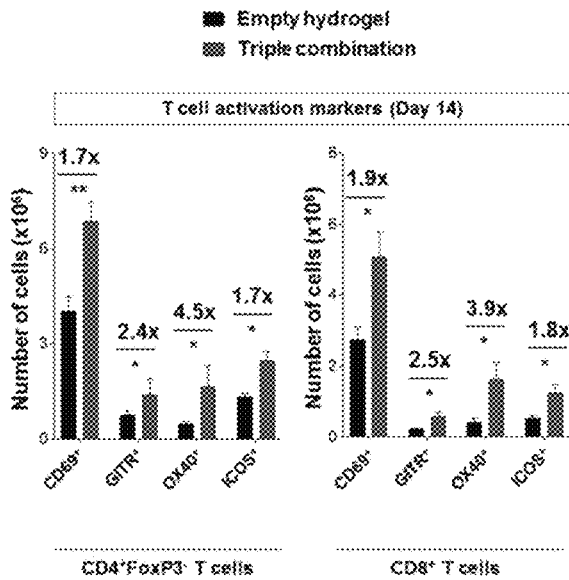
Figure 57D:
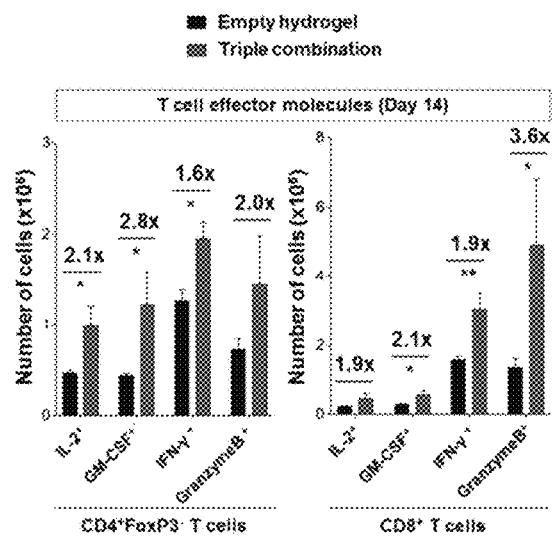
Figure 57E:
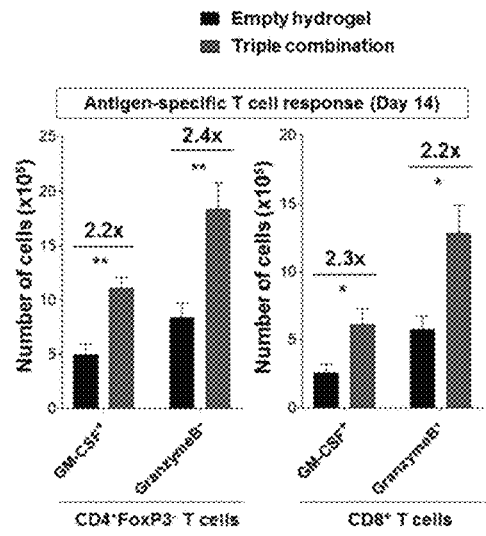

These dendritic cells induced a strong adaptive antitumor response, as evidenced by the T cell compartment 14 days post-surgery. Increased numbers of CD4+FoxP3− T cells and CD8+ T cells that express markers of activation, including CD69, GITR, OX40, and ICOS, were detected (FIG. 57C). Treatment with device 1 also increased the proportion of T cells expressing the pro-inflammatory cytokines IL-2, GM-CSF, and IFN-γ as well as the cytolytic molecule granzyme B relative to treatment with empty hydrogels (FIG. 57D). To confirm that the T cells functionally recognized tumor-associated antigens, splenocytes isolated from the treatment and control groups were re-stimulated with GWEPDDNPI, an immunodominant peptide of survivin (amino acids 66-74) expressed by 4T1 cells. Enhanced numbers of both CD4+FoxP3− T cells and CD8+ T cells that expressed GM-CSF and granzyme B were observed (FIG. 57E). These data confirm the breadth, robustness, and specificity of the systemic antitumor immune response induced by perioperative delivery of device 1.

Figure 59:
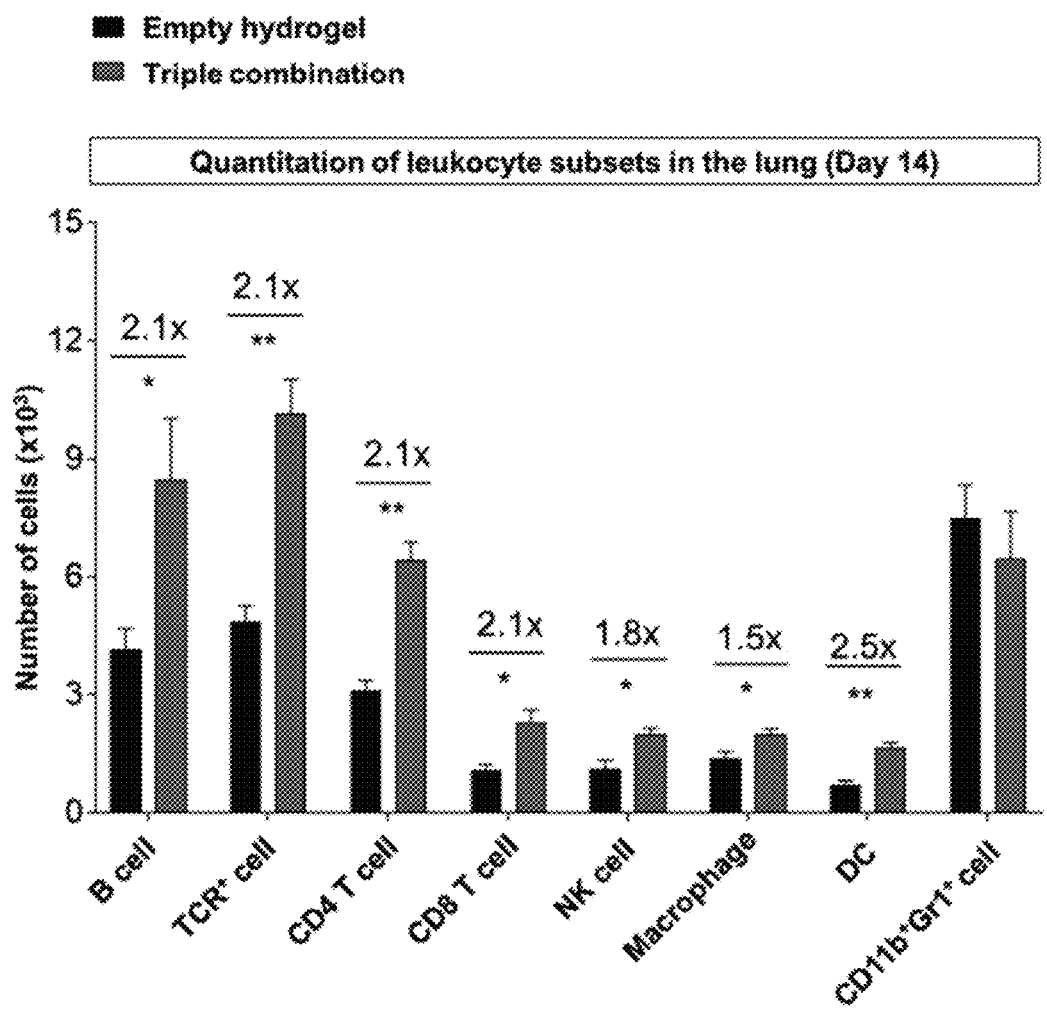
FIG. 59 is a graph showing that sustained local release of 2′-3′-cGAMP, IL-15sa, and anti-PD-1 increased the numbers of several leukocyte subsets in the lung. Lungs were recovered on day 14 post-surgery of the experiment described in FIGS. 57A-57F, and single-cell suspensions were prepared for flow cytometry. Data are presented as mean±SEM. * p≤0.05, ** p≤0.01.

Given the ability of the therapy to eliminate metastases that had already developed in the lungs, the composition of leukocytes in lungs recovered 14 days after surgery were also inspected. Elevated numbers of B cells, CD4+ T cells, CD8+ T cells, NK cells, macrophages, and dendritic cells were detected among mice treated with device 1 (FIG. 59). While these data do not suggest a particular mechanism that is responsible for eradication of metastases, they again support the notion that sustained release of the therapeutic agents described herein promotes a broad systemic antitumor immune response.

Figure 57F:
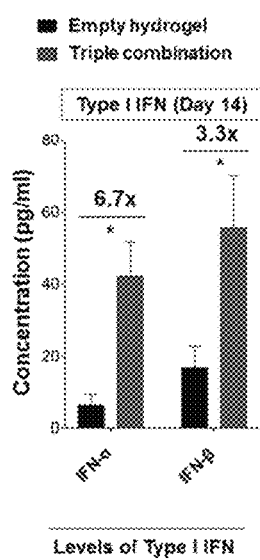
Figure 58:
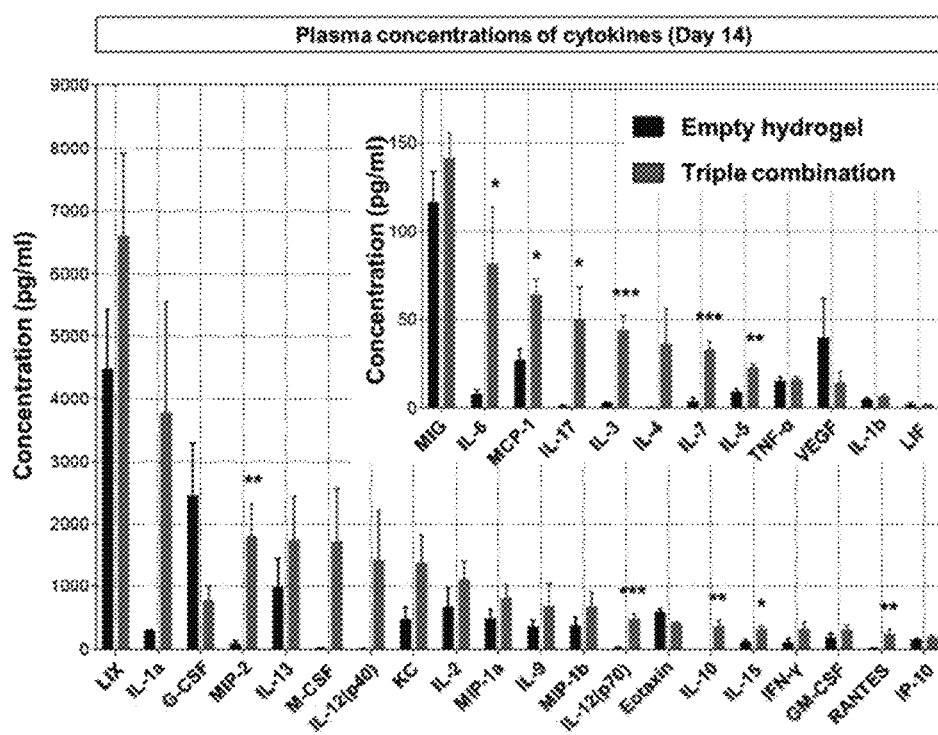
FIG. 58 is a graph showing that elevated concentrations of cytokines were observed in plasma collected on day 14 after surgery for the experiment described in FIGS. 57A-57F. Levels of a panel of cytokines are shown. Data were generated by multiplexing laser bead technology. Statistics were calculated using a two-tailed unpaired t-test. Data are presented as mean±SEM. * p≤0.05,  p≤0.01, * p≤0.001, **** p≤0.0001.

To gain insights into the soluble factors that are associated with the activation of innate and adaptive immune cells, the levels of cytokines in peripheral blood were measured. On day 14 post-surgery, plasma was collected and subsequently analyzed by multiplexing laser bead technology. Consistent with the loss of efficacy following neutralization of IFNAR1, it was observed that levels of both IFN-α and IFN-β were markedly elevated following treatment with hydrogel containing the triple combination relative to empty hydrogel (FIG. 57F). The levels of several other soluble mediators of immunity were also noticeably increased, including IL-12, IL-3, and IL-7 as well as the chemokines CXCL2, CCL2, and CCL5 (FIG. 58). These results indicate an expansive induction of antitumor immunity.

Figure 60:
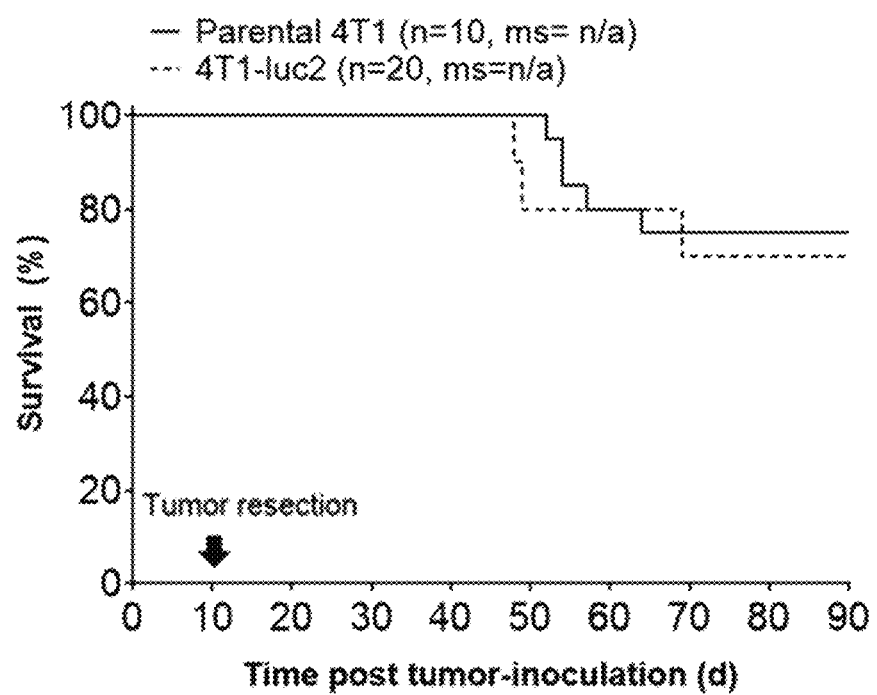
FIG. 60 is a Kaplan-Meier curve demonstrating the efficacy of exemplary drug delivery device 1 against parental 4T1. (lacking the luc2 transgene) is comparable to the efficacy of exemplary drug delivery device 1 against 4T1-luc2 in mice with tumors originating from 4T1-Luc2 syngeneic breast cancer cells. The number of mice per group (n) and median survival (ms) are listed.

Efficacy experiments were also performed and demonstrated that the triple combination of device 1 was effective in female BALB/cJ mice inoculated orthotopically with parental 4T1 breast cancer cells (FIG. 60). Importantly, these cells lack the Luc2 transgene.

Figure 61:
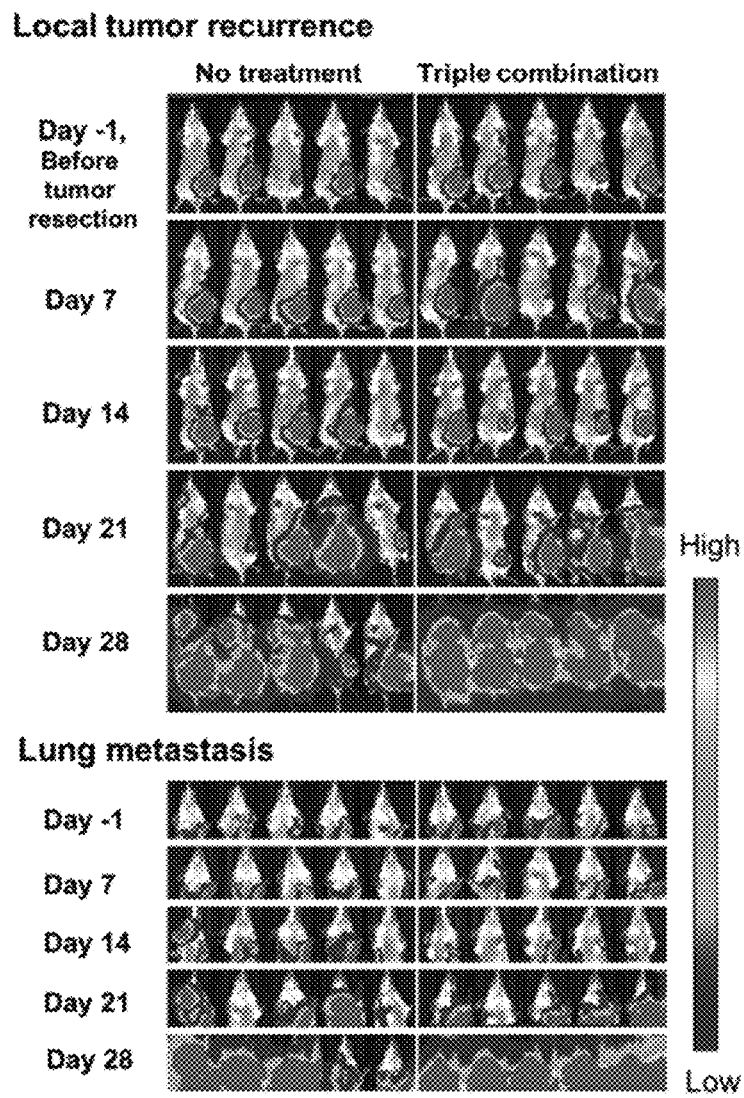
FIG. 61 shows images of individual mice after implantation of exemplary drug delivery device 1 following inoculation of tumors originating from 4T1-Luc2 syngeneic breast cancer cells in comparison to untreated mice. The tumors were not resected and the devices were implanted peritumorally. The images show the appearance/disappearance of tumor over a 4-week period.
Figure 62:
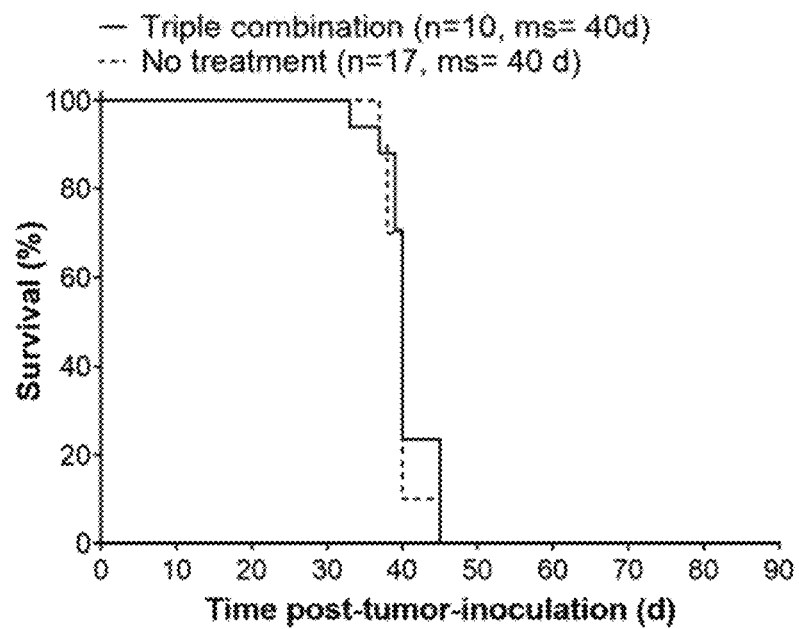
FIG. 62 shows a Kaplan-Meier curve for all groups of the experiment described in FIG. 61. The number of mice per group (n) and median survival (ms) are listed.
Figure 62:
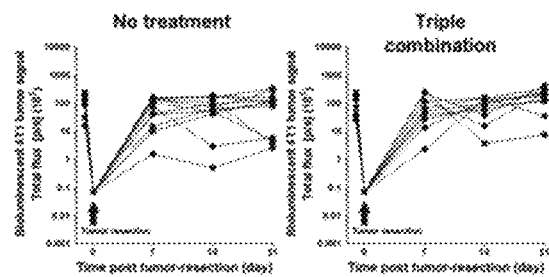
Figure 62:
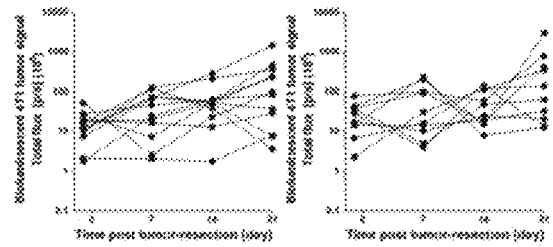

Efficacy experiments also demonstrated that intraoperative placement of the drug delivery device (e.g., device 1) is required for therapeutic benefit. Efficacy is lost if the tumor is not surgically removed, even if hydrogel is placed peri-tumorally (FIGS. 61 and 62).

Figure 63:
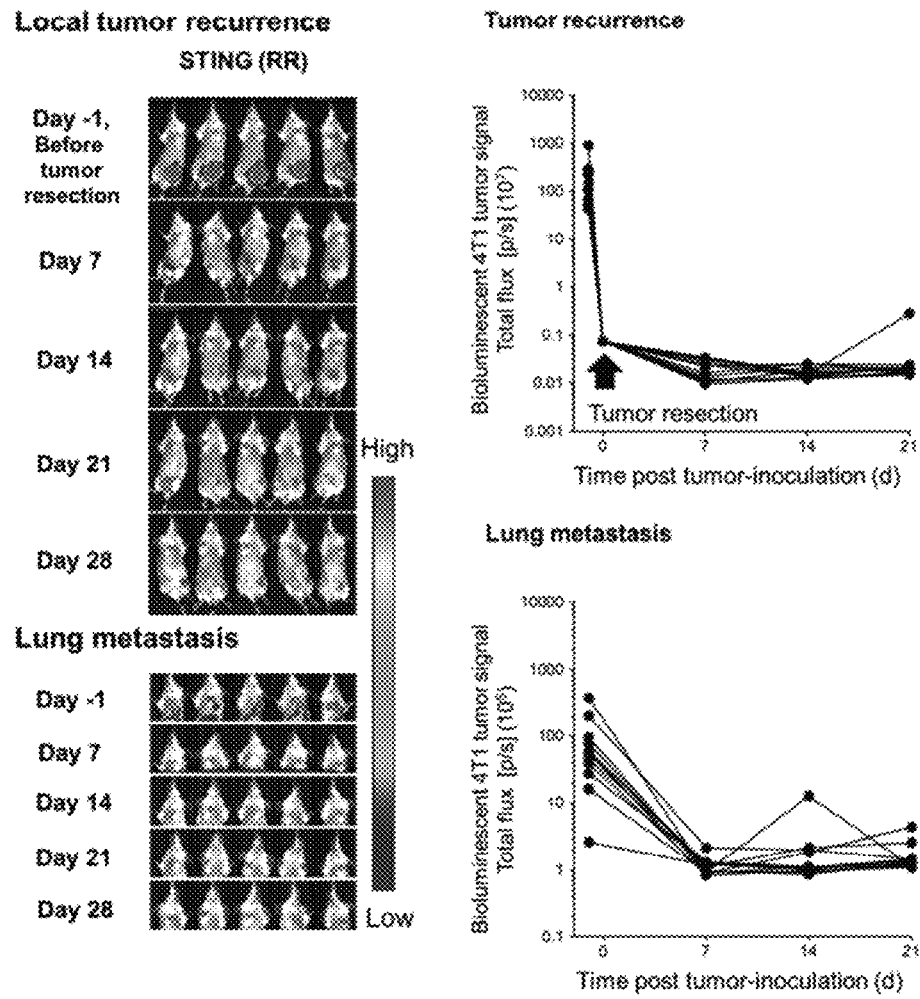
FIG. 63 shows images of individual mice after implantation of exemplary drug delivery device 21 following inoculation of tumors originating from 4T1-Luc2 syngeneic breast cancer cells. The images show the appearance/disappearance of tumor over a 4-week period.
Figure 64:
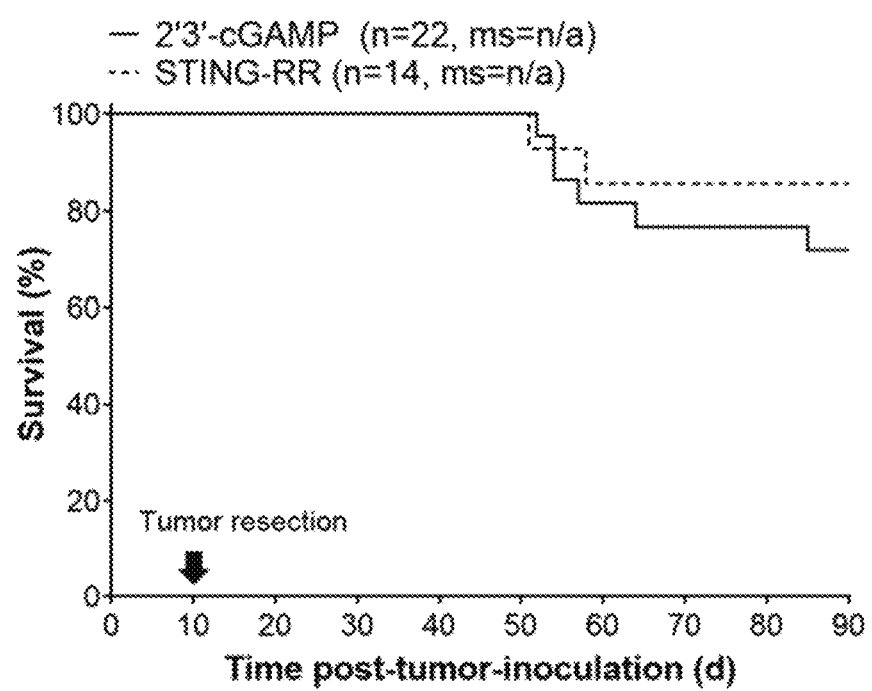
FIG. 64 shows a Kaplan-Meier curve for mice after implantation of exemplary drug delivery device 21 in comparison to exemplary drug delivery device 1 following inoculation of tumors originating from 4T1-Luc2 syngeneic breast cancer cells. The number of mice per group (n) and median survival (ms) are listed.

Additional STING agonists were also effective as a component of the drug delivery device. Device 21, which incorporated the STING agonist 2′,3′-c-di-AM(PS)2 (Rp, Rp) (also referred to as STING-RR herein) with IL-15sa and anti-PD-1 antibody, was efficacious in female BALB/cJ mice inoculated orthotopically with 4T1-Luc2 breast cancer cells (FIGS. 63 and 64).

Figure 72:
FIG. 72 shows images of individual mice after implantation of exemplary drug delivery devices 27 (150 µg each of anti-PD-1 antibody and anti-CTLA4 antibody), 28 (50 µg resiquimod+150 µg each of anti-PD-1 antibody and anti-CTLA4 antibody), 29 (300 µg M-TriDAP), 30 (200 µg lenalidomide wherein lenalidomide was dissolved in water for formation of the device), and 30 (200 µg lenalidomide wherein lenalidomide was dissolved in DMSO for formation of the device) following inoculation of tumors originating from 4T1-Luc2 syngeneic breast cancer cells. The images show the appearance/disappearance of tumor over a 4-week period. The upper images monitor the site of resection (local tumor recurrence) while the lower images show lung metastasis.
Figure 73:
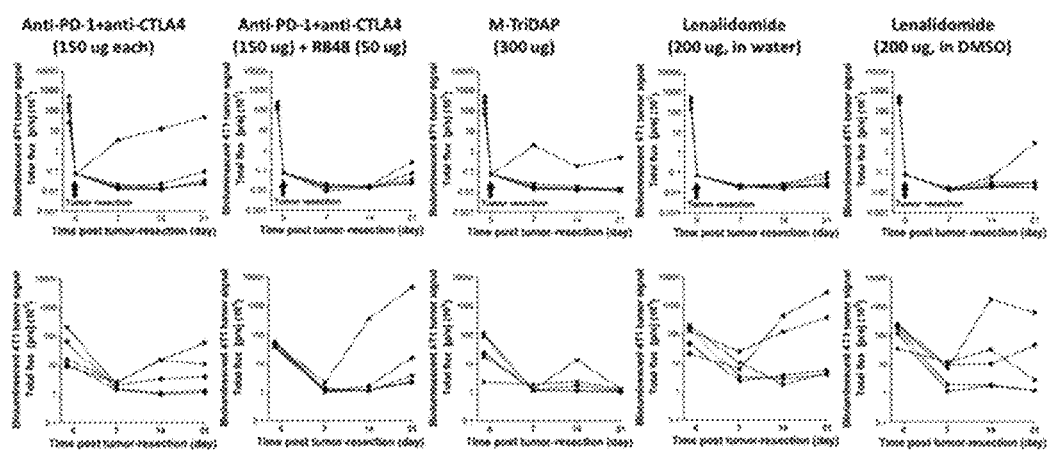
FIG. 73 is a series of graphs showing the total flux of bioluminescent 4T1-Luc2 cells after administration of the exemplary drug delivery devices described in FIG. 72. The upper images show the site of resection (local tumor recurrence) while the lower images show lung metastasis.

Additional combinations of therapeutic agents were incorporated in exemplary drug delivery devices 27 (150 μg each of anti-PD-1 antibody and anti-CTLA4 antibody) and 28 (50 μg resiquimod+150 μg each of anti-PD-1 antibody and anti-CTLA4 antibody). Both of these devices also demonstrated the ability to prevent tumor recurrence and metastasis following tumor resection and implantation in female BALB/cJ mice inoculated orthotopically with 4T1-Luc2 breast cancer cells in their fourth mammary fat pad (FIGS. 72 and 73).

Example 7. Sustained Local Release of Exemplary Monotherapeutic Drug Delivery Devices Prevents Tumor Relapse and Metastasis Several drug delivery devices with a single therapeutic agent were prepared and evaluated. Female BALB/cJ mice were inoculated orthotopically with 4T1-Luc2 breast cancer cells in their fourth mammary fat pad. The devices were implanted intraoperatively in tumor resection sites of the mice as described above. The therapeutic agents/devices evaluated included: 2′,3′-cGAMP (50 μg, 100 μg) in drug delivery device 7; STING-RR (50 μg) in drug delivery device 23; STING-RR (100 μg) in a drug delivery device wherein the cross-linked hyaluronic acid was replaced with alginate; resiquimod (50 μg, 100 μg, 200 μg) in drug delivery device 22 wherein resiquimod was dissolved in water for formation of the device; resiquimod (200 μg) in drug delivery device 22 wherein resiquimod was dissolved in DMSO for formation of the device; IL-15sa (3 μg) in drug delivery device 5; anti-PD-1 antibody (300 μg) in drug delivery device 4; IFN-α (15 μg) in drug delivery device 24; IFN-β (3 μg) in drug delivery device 25; IFN-γ (30 μg) in drug delivery device 26; M-TriDAP (300 μg) in drug delivery device 29; lenalidomide (200 μg) in drug delivery device 30 wherein lenalidomide was dissolved in water for formation of the device; and lenalidomide (200 μg) in drug delivery device 30 wherein lenalidomide was dissolved in DMSO for formation of the device.

The results demonstrated that the monotherapeutic devices can provide efficacy, although a range of effectiveness was observed (FIGS. 66-73). The use of alginate as the hydrogel confirms that immunotherapy released from hydrogels derived from other biomaterials can also confer efficacy. The use of DMSO in formulation of device 22 also showed that organic solvents (e.g., DMSO) may not negatively impact the efficacy of the device. Overall, a wide variety of therapeutic agents and devices provided good efficacy.

Figure 74:
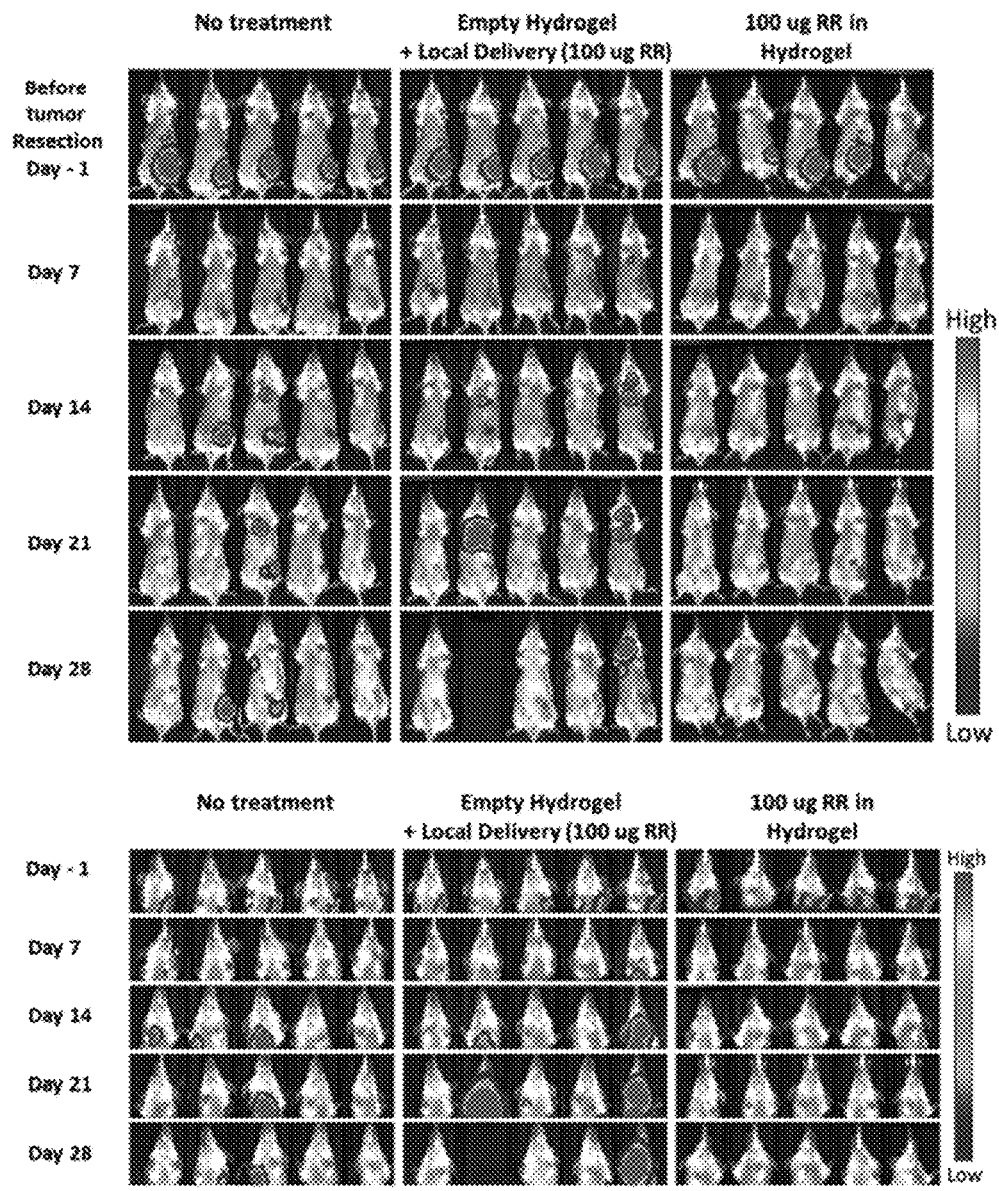
FIG. 74 shows images of individual mice after implantation of exemplary drug delivery devices 23 (100 µg STING-RR) or 8 (hydrogel 4) following inoculation of tumors originating from 4T1-Luc2 syngeneic breast cancer cells. Device 8 was implanted in combination with local administration of STING-RR (100 µg). A control group was also evaluated wherein no treatment was administered after tumor resection. The images show the appearance/disappearance of tumor over a 4-week period. The upper images monitor the site of resection (local tumor recurrence) while the lower images show lung metastasis.
Figure 75:
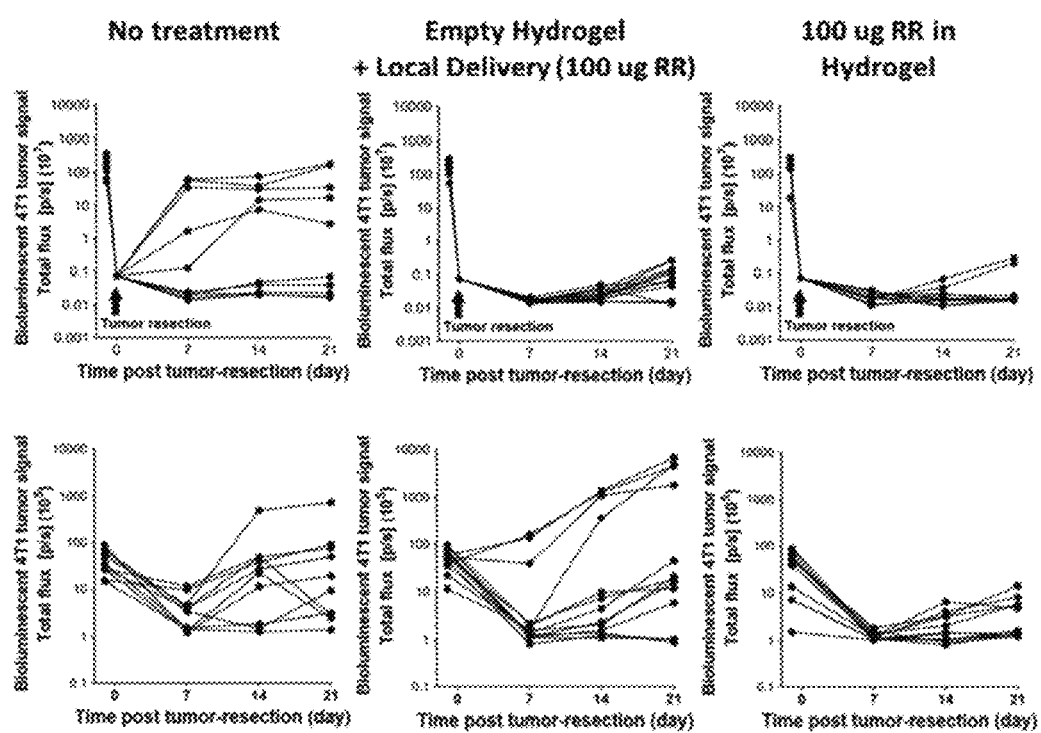
FIG. 75 is a series of graphs showing the total flux of bioluminescent 4T1-Luc2 cells after administration of the exemplary drug delivery devices described in FIG. 74. The upper images show the site of resection (local tumor recurrence) while the lower images show lung metastasis.
Figure 78:
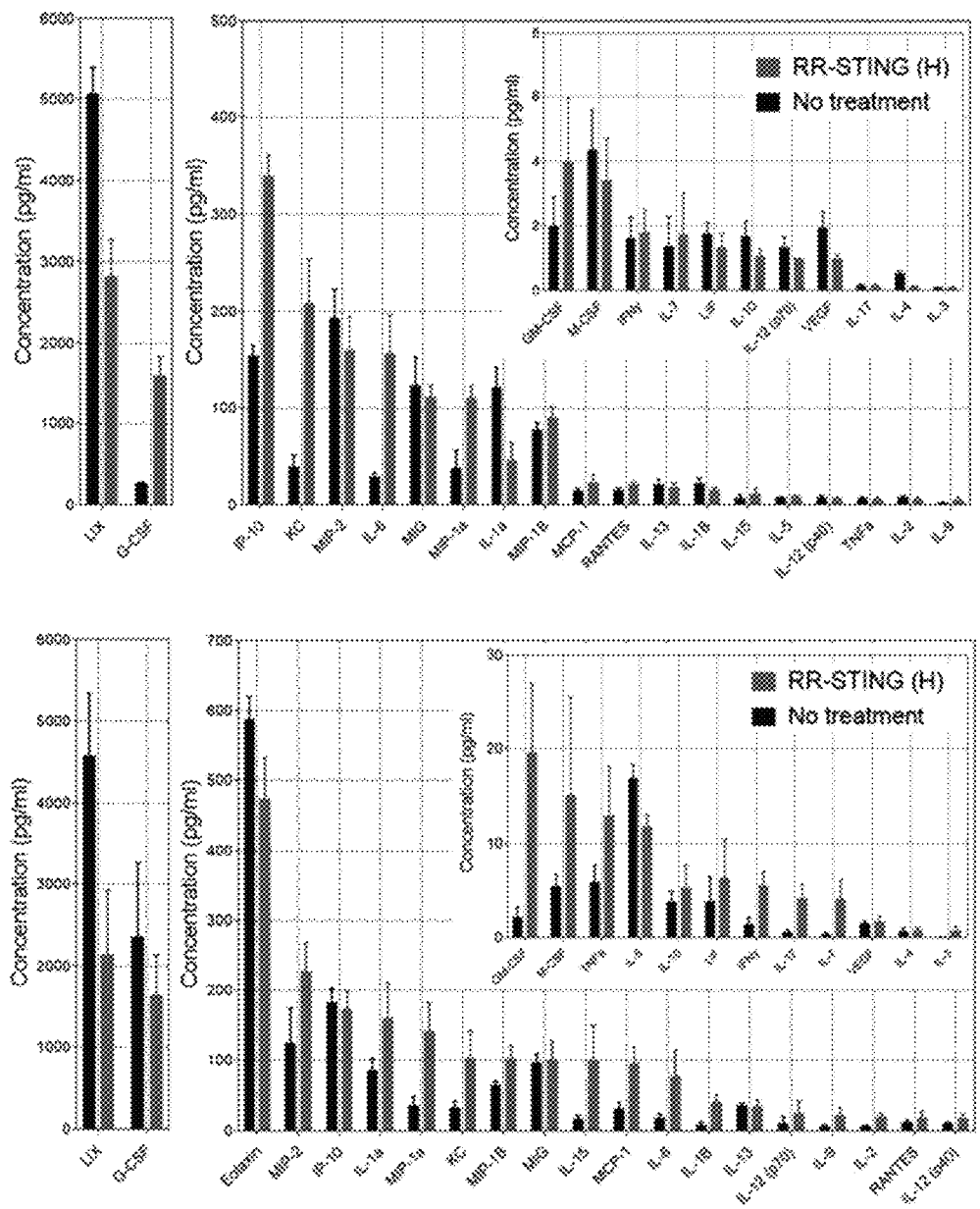
FIG. 78 is a series of graphs showing that sustained local release of STING-RR increases the levels of cytokines in the blood. Tumors were resected from mice 11) days after orthotopic inoculation of 4T1-Luc2 cells, and device 23 was placed in the resection site. For cytokine analysis, blood was recovered from the mice 3 days (upper graph) or 14 days (lower graph) after surgery.

Device 23 comprising 2′,3′-c-di-AM(PS)2 (Rp,Rp) (STING-RR) was further evaluated. Sustained perioperative release of STING-RR (100 μg) from scaffolds placed in tumor resection sites conferred greater prevention of local tumor recurrence and distal metastasis than local delivery of the STING agonist (FIGS. 74 and 75). Sustained release of STING-RR from device 23 also alters the level of cytokines in the blood (FIG. 78).

Figure 76:
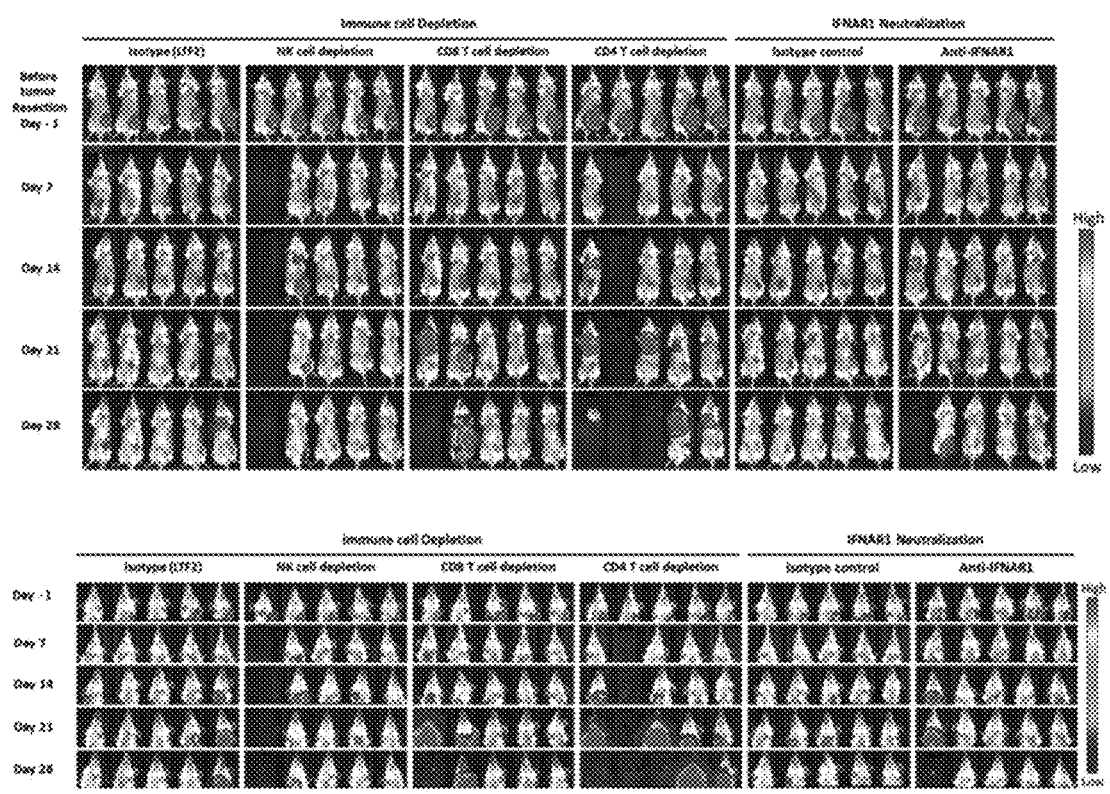
FIG. 76 shows images of individual mice after implantation of exemplary drug delivery device 23 following inoculation and resection of tumors originating from 4T1-Luc2 syngeneic breast cancer cells. The images show the appearance/disappearance of tumor over a 4-week period among mice depleted of NK cells, CD8+ T cells, or CD4+ T cells; or mice in which innate immune signaling (IFNAR1) was inhibited. The upper images monitor the site of resection (local tumor recurrence) while the lower images show lung metastasis.
Figure 77:
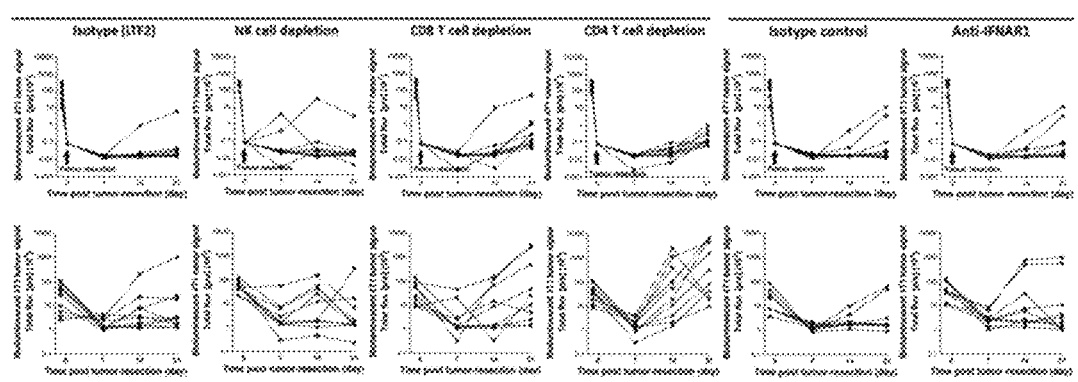
FIG. 77 is a series of graphs showing the total flux of bioluminescent 4T1-Luc2 cells after administration of the exemplary drug delivery devices described in FIG. 76. The upper images show the site of resection (local tumor recurrence) while the lower images show lung metastasis.

The tumor inoculation and resection procedure described above was repeated. In addition to placing device 23 in the resection site, NK cells, CD8+ T cells, or CD4+ T cells were depleted or type I interferon signaling was inhibited by neutralizing interferon alpha receptor 1 (IFNAR1). IVIS imaging indicated that NK cells, CD8+ T cells, CD4+ T cells, and type I interferon signaling are all useful in preventing tumor recurrence and metastasis (FIGS. 76 and 77), suggesting that both innate and adaptive arms of the immune system are useful for the efficacy observed with administration of STING-RR. Interestingly, CD4+ T cells appear to be more heavily involved in the therapeutic efficacy of STING- RR monotherapy than of the triple combination of 2′,3′-cGAMP, IL-15sa, and anti-PD-1.

Example 8. Extended Local Release of Agonists of Innate Immunity Prevents Tumor Relapse and Metastasis Having confirmed that the release of these immunomodulatory compounds could be extended locally in vivo, it was an aim to evaluate the utility of such extended delivery in the therapeutic setting. Female BALB/cJ mice were inoculated orthotopically with 4T1-Luc2 breast cancer cells in their fourth mammary fat pad. Nine days later, the mice were imaged by bioluminescent IVIS imaging, which confirmed that the size of the tumors was consistent across animals and enabled randomization into groups. On day 10 post-tumor inoculation, tumors (~100 mm$^3$) were resected, and a device (3 (1500 µg celecoxib), 18, 19, 22, 23, 30, or 31) was placed in the tumor resection site. Tumor burden was monitored weekly by IVIS imaging, and it was confirmed that local tumor recurrence was prevented most effectively when an agonist of innate immunity (STING-RR or R848) was administered via the hydrogel (FIG. 83A).

The STING agonist STING-RR induces production of Ifn-β by tumor-resident dendritic cells, which is required for spontaneous tumor-initiated T cell priming. This molecule has not been investigated in the absence of intact primary tumors to date. R848 is a TLR7/8 agonist that induces expression of type I interferon and co-stimulatory molecules by plasmacytoid dendritic cells as well as phenotypic maturation of conventional dendritic cells. It is typically used as a vaccine adjuvant or as a topical gel for treatment of viral or neoplastic skin lesions but has similarly not previously been examined in settings other than intratumoral injection or topical application.

Figure 83A:
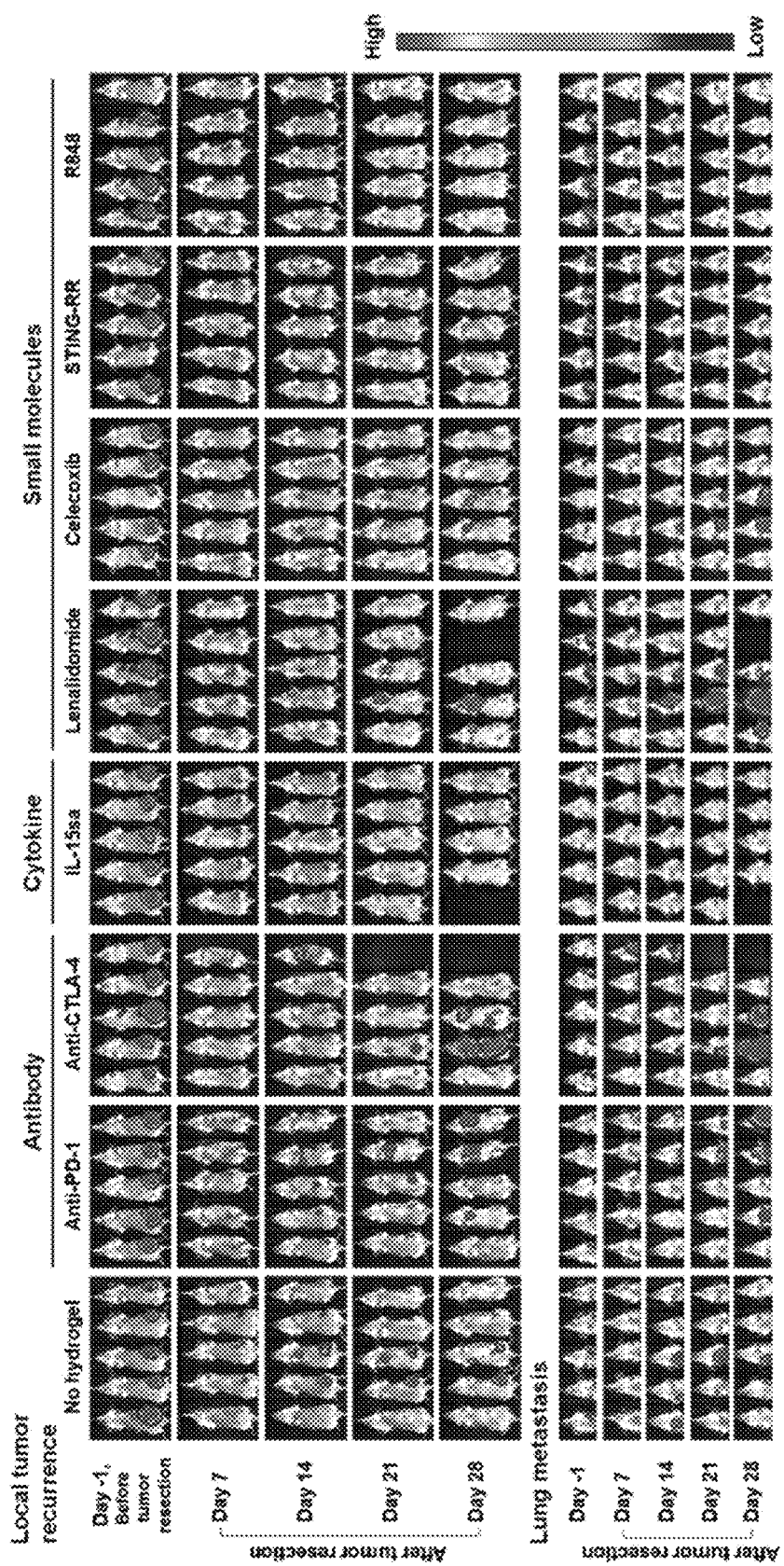
Figure 83B:
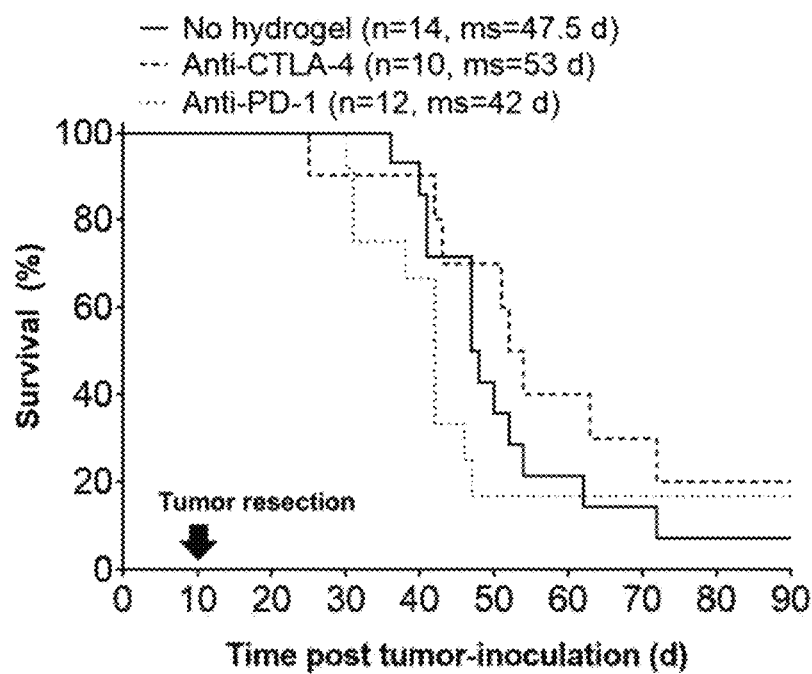
Figure 83C:
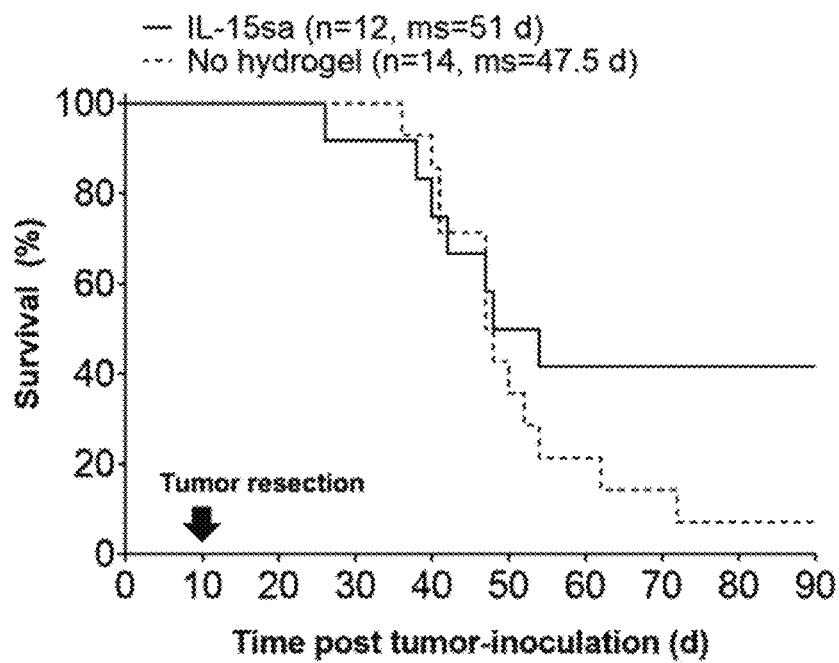
Figure 83D:
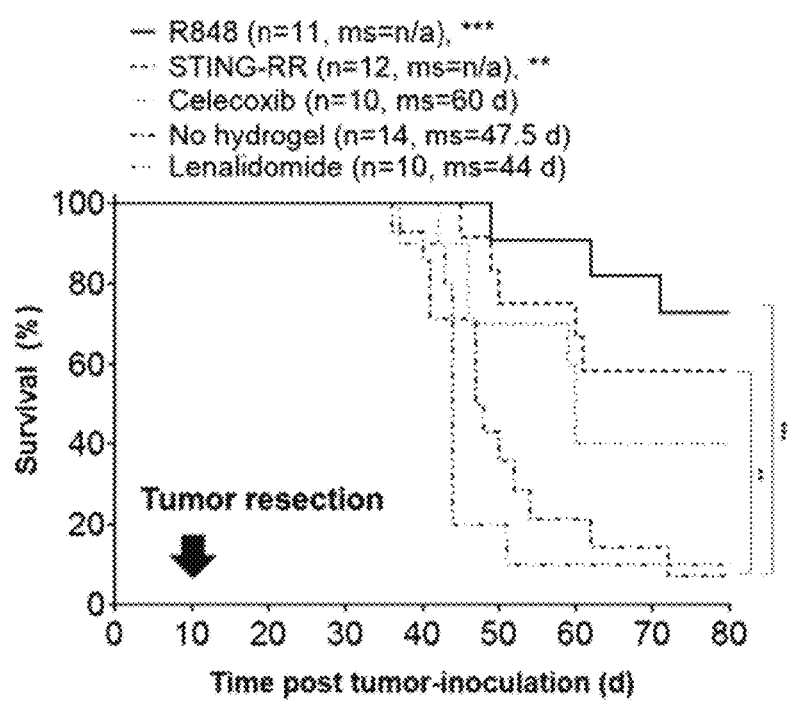

Notably, lung metastases had already been established by the time of surgery, and extended local release of an agonist of innate immunity was again the lone condition that eradicated the existing metastatic lesions (FIG. 83A). The IVIS imaging provided a meaningful proxy for long-term survival, as only the hydrogel loaded with one of the agonists of innate immunity conferred durable survival benefit to a majority of mice (FIGS. 83B-83D). These data indicate that activating the adaptive immune system (via immune checkpoint blockade or immunomodulatory imide drug (iMiD)) or inhibiting immunosuppressive myeloid cells (celecoxib) is insufficient to confer efficacy in the perioperative setting as monotherapy. IL-15sa, which is a highly potent complex of IL-15 and IL-15Rα sushi domain that significantly expands NK cells and CD8$^+$ T cells, confers a modest benefit, suggesting that driving proliferation of effector cells is less important than stimulating upstream cells that produce type I interferons.

Figure 84A:
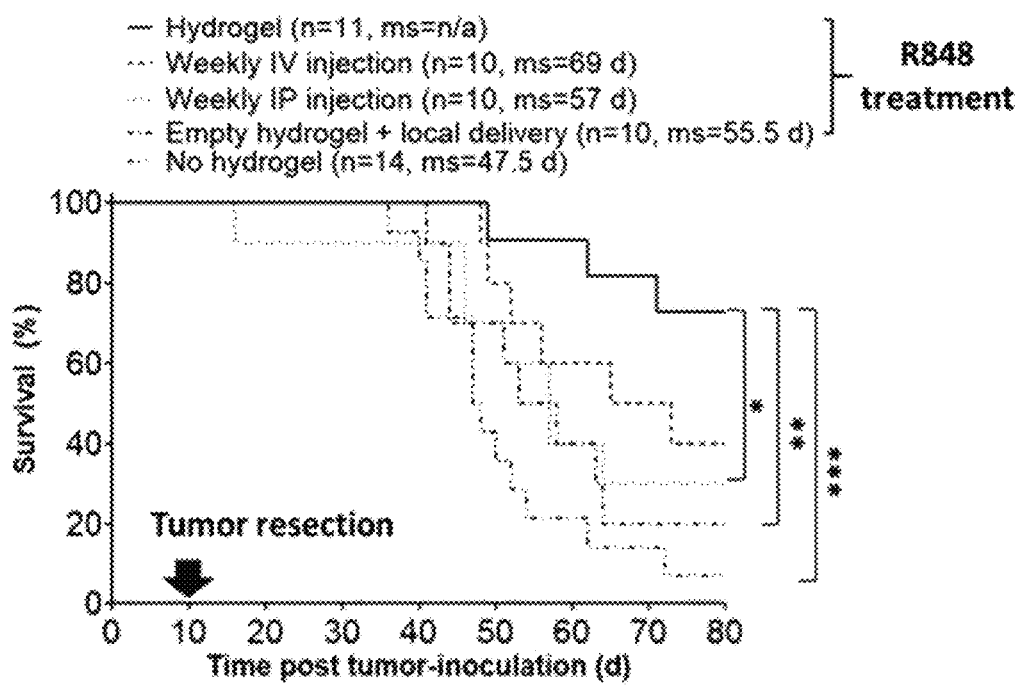
FIGS. 84A-84F show agonists of innate immunity are effective only when released locally from the hydrogel. Tumors were resected from mice 10 days after orthotopic inoculation of 4T1-Luc2 cells (see FIGS. 84A-84B).
Figure 84B:
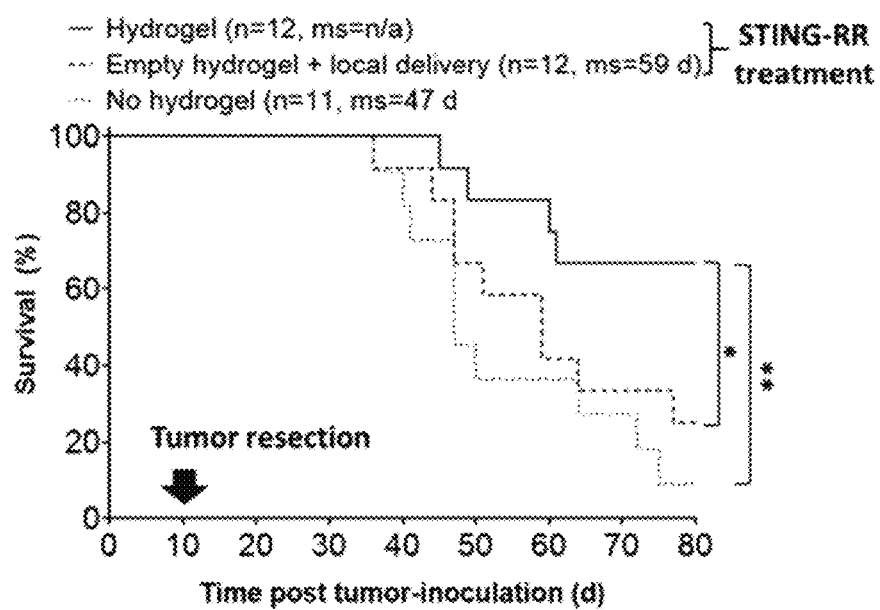
Figure 85A:
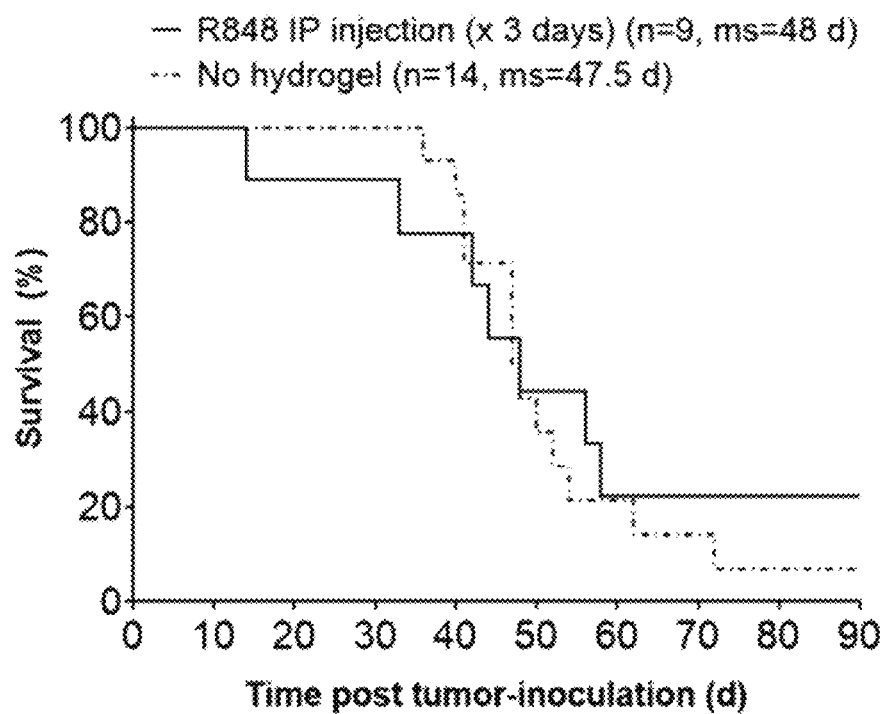
FIGS. 85A-85B show that multiple systemic administrations of R848 fail to confer robust survival benefit and are much less well tolerated than R848 released from the hydrogel. Tumors were resected from mice 10 clays after orthotopic inoculation of 4T1-Luc2 cells.
Figure 85B:
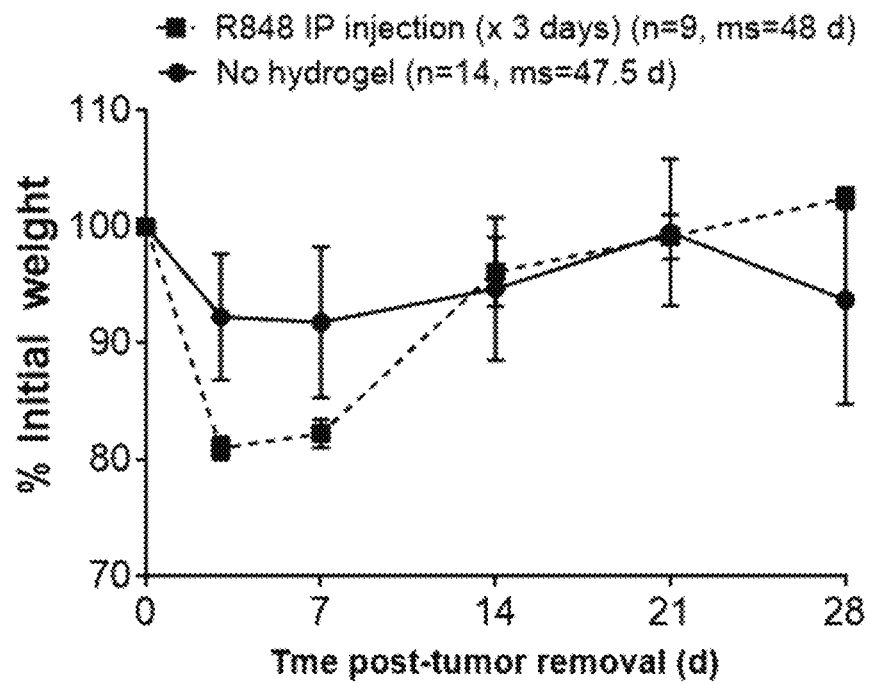
Figure 86:
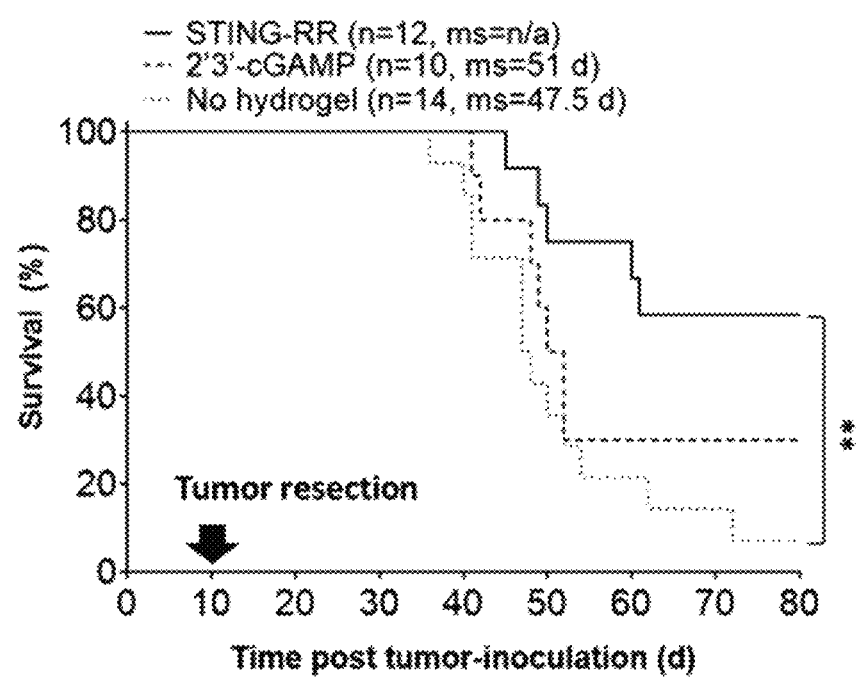
FIG. 86 shows that STING-RR confers superior efficacy to 2'3'-cGAMP for a given loaded dose upon extended release from a hydrogel (device 23 or 7 (100 μg S)) in the perioperative setting. Tumors were resected from mice 10 days after orthotopic inoculation of 4T1-Luc2 cells. A Kaplan-Meier curve illustrates relative survival benefit. The number of mice per group (n) and median survival (ms) are listed. The experiment was performed with biological replicates at least three times. Statistics were calculated relative to no hydrogel using the Log-rank (Mantel-Cox) test.  $p \leq 0.01$
Figure 97:
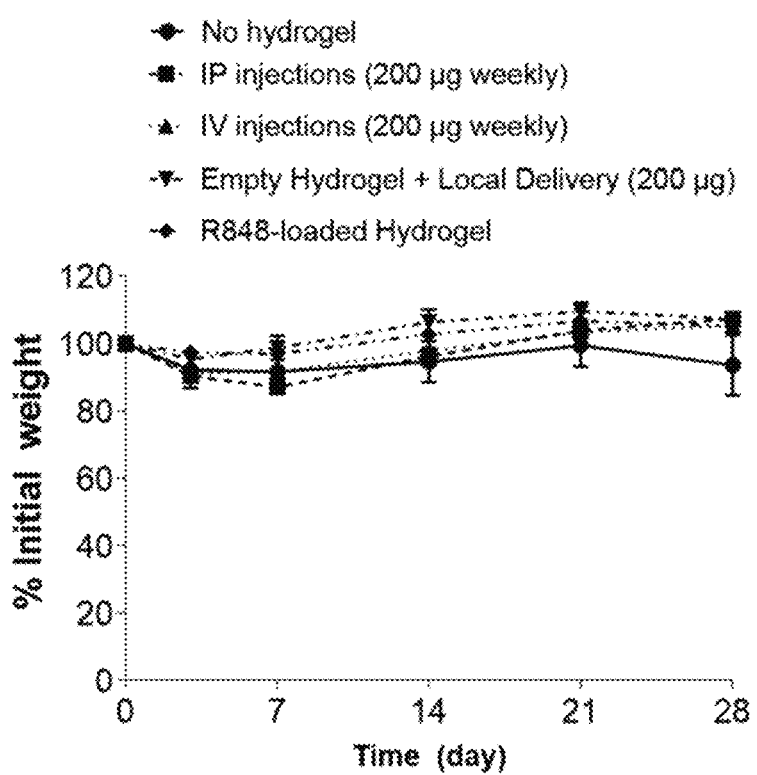
FIG. 97 shows that the extended local release of agonists of innate immunity is very well tolerated. None of the conditions listed impact the weight of mice longitudinally upon administration of R848 (device 22). The weight loss observed in the first week is related to the stress of the surgery itself, as it is observed in all groups, including the no hydrogel and empty hydrogel negative controls. Data are presented as mean±SD (sample sizes for each group are provided in FIG. 2d, performed with biological replicates at least three times).

Example 9. Agonists of Innate Immunity are Effective Only when Released Locally from the Hydrogel To confirm that extended release from the hydrogel was useful for the observed efficacy, various additional modes of administration of the agonists of innate immunity were compared. For treatment with device 22 (200 µg R848), in addition to a no hydrogel control, the following groups were evaluated: hydrogel (single dose), weekly intravenous injection (20 µg R848), weekly intraperitoneal injection (200 µg R848), and local delivery in solution (single dose 200 µg R848) in conjunction with placement of an empty hydrogel (FIG. 84A). The survival benefit was observed only when R848 was loaded in the hydrogel. To ensure that efficacy afforded by delivery of R848 in solution was not missed owing to the fact that weekly administration was too long of a window between doses, daily intraperitoneal injections were performed for three consecutive days. Multiple systemic administrations of R848 failed to confer robust survival benefit (FIG. 85A), despite resulting in dramatic weight loss (FIG. 85B)—whereas R848 released from the hydrogel was well tolerated (FIG. 97). Similarly, for treatment with STING-RR (device 23)—which is considerably more potent than its natural analog 2'3'-cGAMP (device 7 (100 µg S); FIG. 86)—delivery via hydrogel was required to induce durable survival benefit among a majority of mice (FIG. 84B and FIG. 74).

Figure 84C:
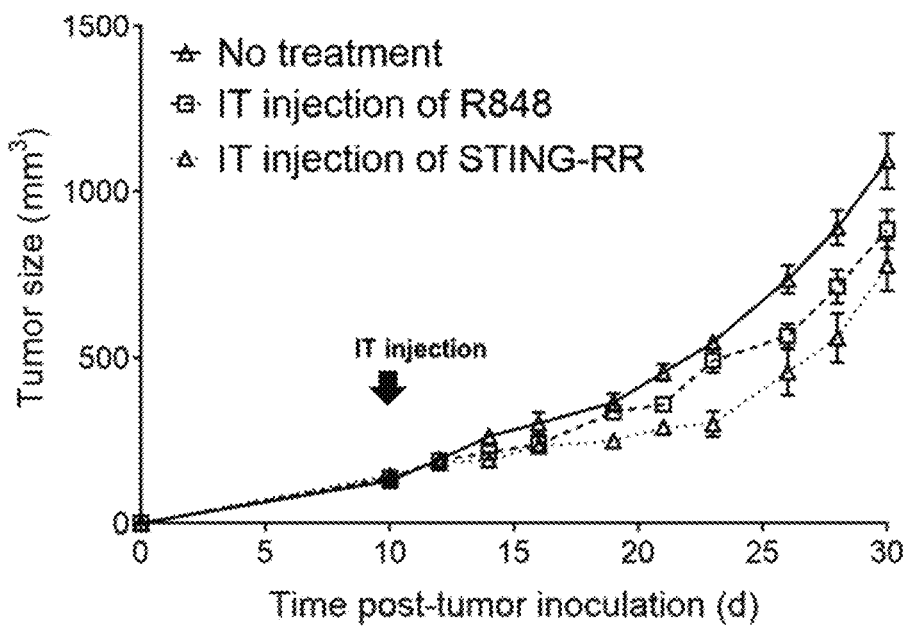
Figure 84D:
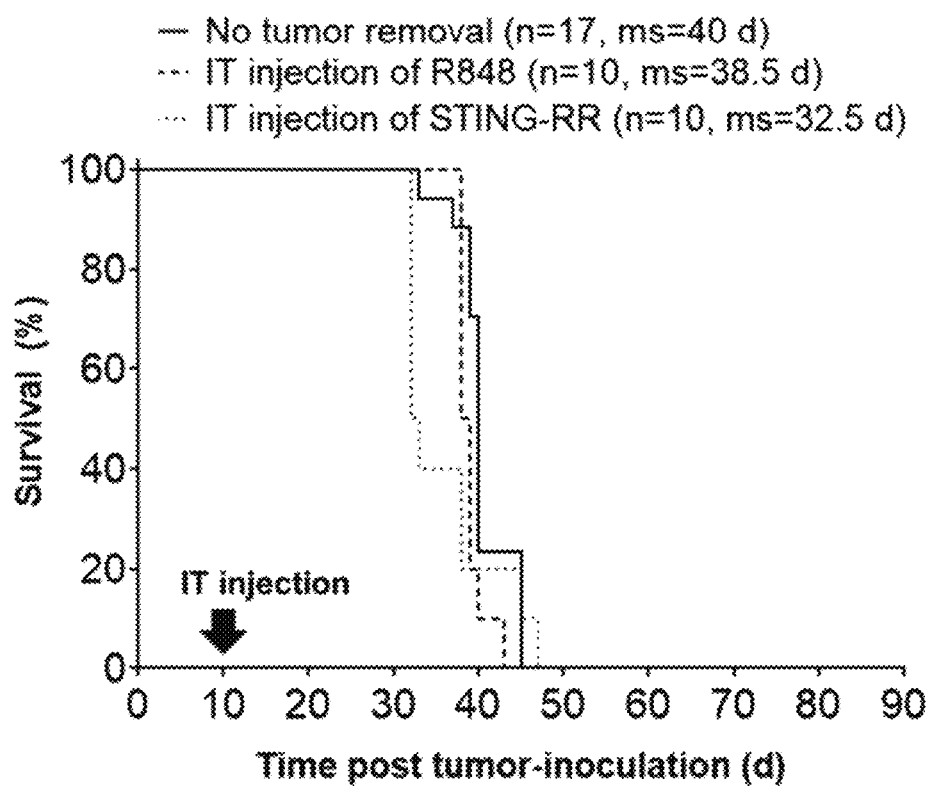
Figure 87:
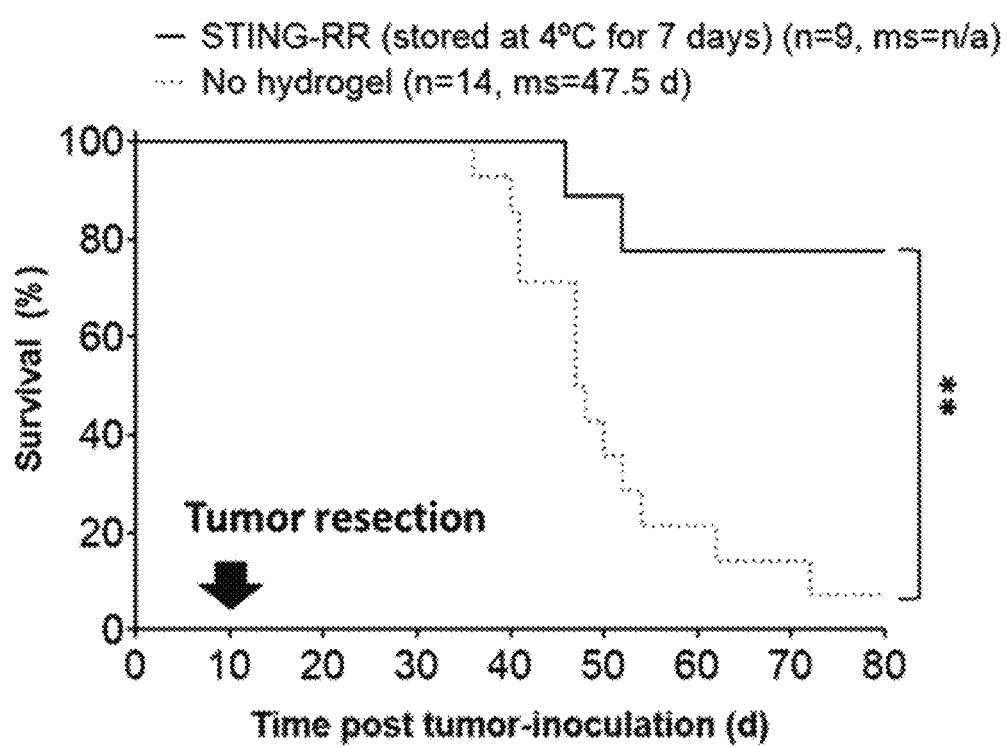
FIG. 87 shows that the efficacy of STING-RR loaded in a hydrogel is retained following refrigerated storage for one week at 4° C. Tumors were resected from mice 10 days after orthotopic inoculation of 4T1-Luc2 cells. A Kaplan-Meier curve is shown for no hydrogel, a hydrogel loaded with STING-RR (device 23), or a hydrogel loaded with STING-RR that had been stored at 4° C. for seven days. The number of mice per group (n) and median survival (ms) are listed. The experiment was performed with biological replicates at least three times. Statistics were calculated relative to no hydrogel using the Log-rank (Mantel-Cox) test.  $p \leq 0.01$

Notably, perioperative delivery of R848 or STING-RR from a hydrogel was superior to intratumoral (IT) injection of either compound, which did not prolong survival (FIGS. 84C-84D). This finding is noteworthy, because cyclic dinucleotide STING agonists are currently being administered intratumorally in clinical trials; perioperative administration may yield superior results and is not limited to superficially accessible lesions. To demonstrate utility for the context of clinical translation, it was validated that the efficacy of STING-RR loaded in a hydrogel is retained following one week of refrigerated storage at 4° C. (device 23; FIG. 87).

Figure 88A:
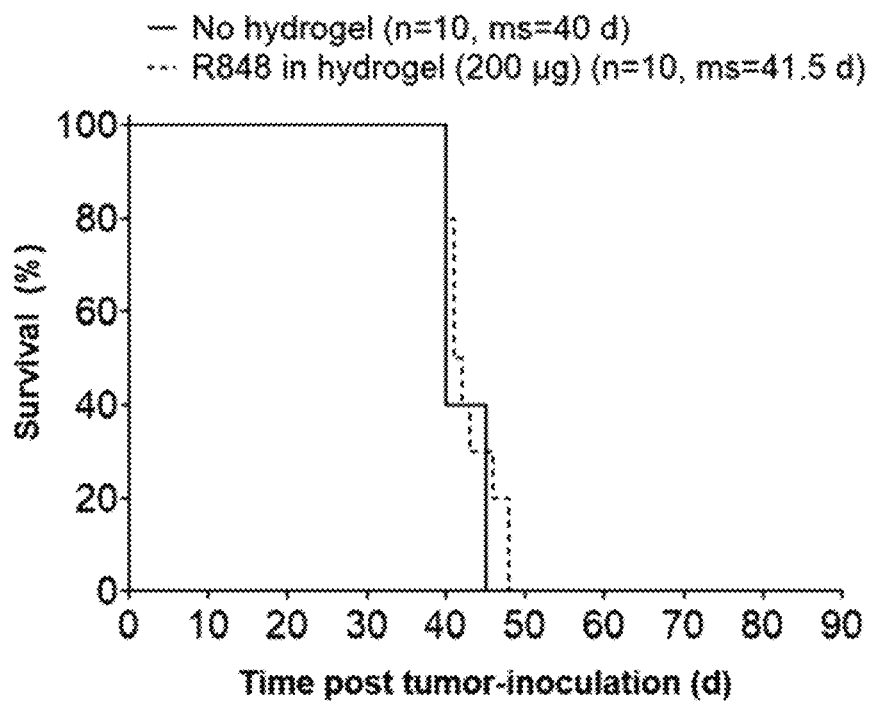
FIGS. 88A-88B show that intraoperative placement of the immunotherapy-loaded hydrogel into the tumor resection site is required for therapeutic benefit. Local release of an agonist of innate immunity (as monotherapy) from a hydrogel does not confer therapeutic efficacy in the absence of tumor removal, even if the hydrogel is placed peritumorally. Hydrogels loaded with R848 (device 22) (FIG. 88A) or STING-RR (device 23) (FIG. 88B) were placed peritumorally 10 days after orthotopic inoculation of 4T1-Luc2 cells. A Kaplan-Meier curve is shown for the control and treatment groups. The number of mice per group (n) and median survival (ms) are listed. The experiment was performed with biological replicates at least three times.
Figure 88B:
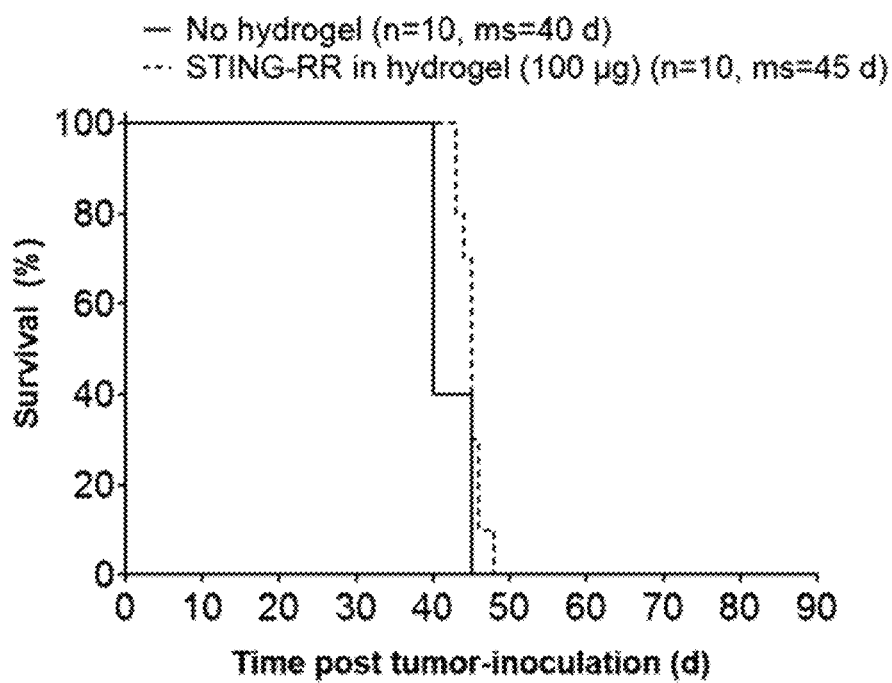

In certain embodiments, intraoperative placement of the immunotherapy-loaded hydrogel is required for therapeutic benefit. Placement of hydrogels loaded with either R848 (device 22) or STING-RR (device 23) adjacent to non-resected tumors produced no survival benefit (FIGS. 88A-88B), supporting the notion that the intervention is modifying the post-surgical resection microenvironment rather than treating an established tumor. Collectively, these results underscore the usefulness of having extended local release of the immunomodulatory payloads in the tumor resection site relative to administration of the compounds in solution, whether systemically, locally into the resection site, or directly into the tumor.

Figure 84E:
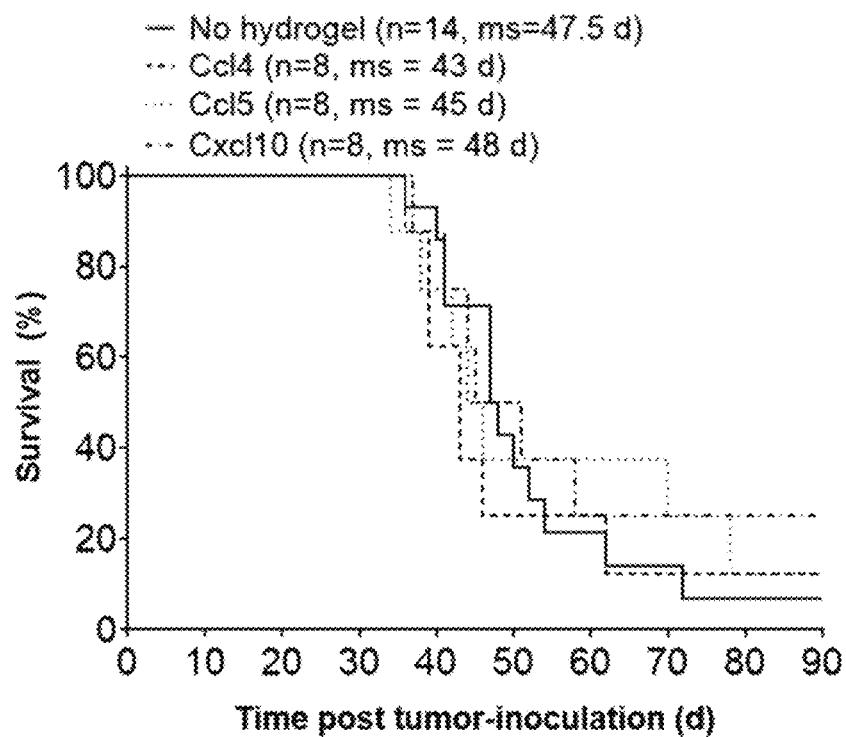
Figure 84F:
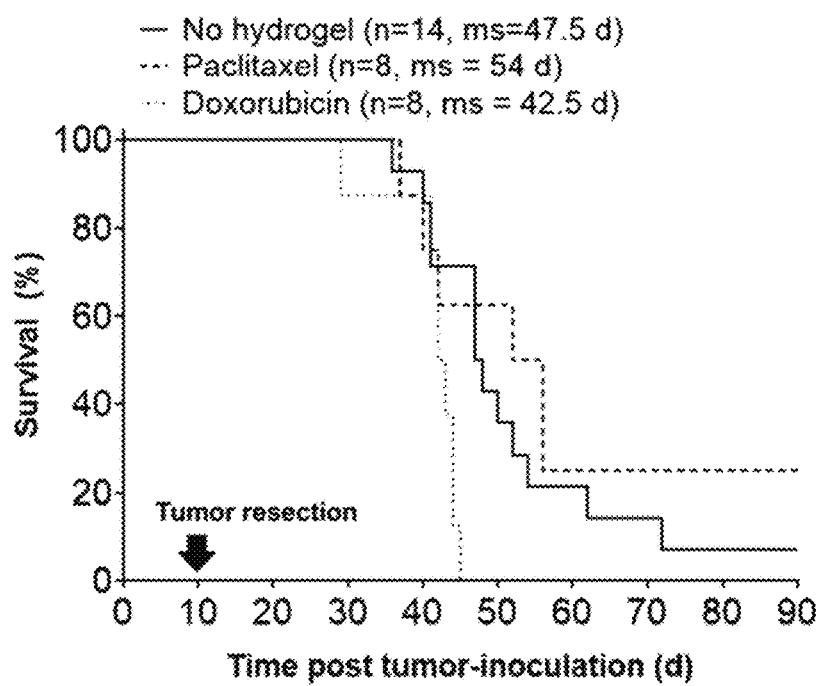
Figure 89:
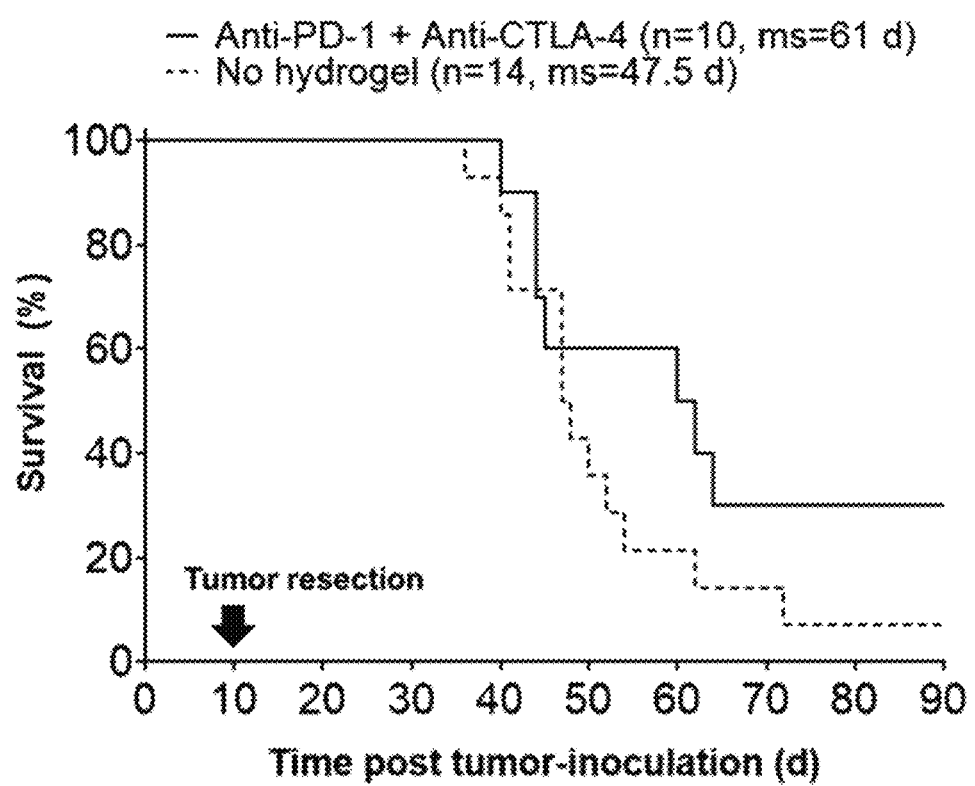
FIG. 89 shows that extended local release of combination immune checkpoint blockade confers limited survival benefit. Tumors were resected from mice 10 days after orthotopic inoculation of 4T1-Luc2 cells. A Kaplan-Meier curve is shown for no hydrogel or a hydrogel loaded with anti-PD-1 and anti-CTLA-4 (device 27 loaded with 300 μg of each antibody). The number of mice per group (n) and median survival (ms) are listed. The experiment was performed with biological replicates at least three times.

To evaluate immune stimulation versus leukocyte recruitment, hydrogels were loaded with chemokines known to be central to mediating antitumor immunity: Ccl4, Ccl5, and Cxcl10 (devices 32-34). Ccl4 is critical to recruitment of CD103$^+$ dendritic cells, while CCL5 and CXCL10 recruit T cells and are upregulated in DNA damage response-deficient breast tumors, which exhibit constitutive activation of the STING pathway. Interestingly, none of the chemokines conferred survival benefit (FIG. 84E), nor did combination immune checkpoint blockade of anti-PD-1 and anti-CTLA-4 (device 27 (300 µg each antibody); FIG. 89). Similarly, neither paclitaxel (device 35) nor doxorubicin (device 36) loaded in hydrogels produced efficacy (FIG. 84F), despite the fact that doxorubicin has been reported to induce immunogenic cell death that leads to cancer cell-autonomous production of type I interferons. Together, these data suggest that direct agonism of innate immune cells—leading to production of a sufficient level of type I interferon and/or other maturation-related phenotypic determinants such as expression of co-stimulatory molecules—may be a requirement for achieving curative outcomes in a majority of treated mice.

Figure 90A:
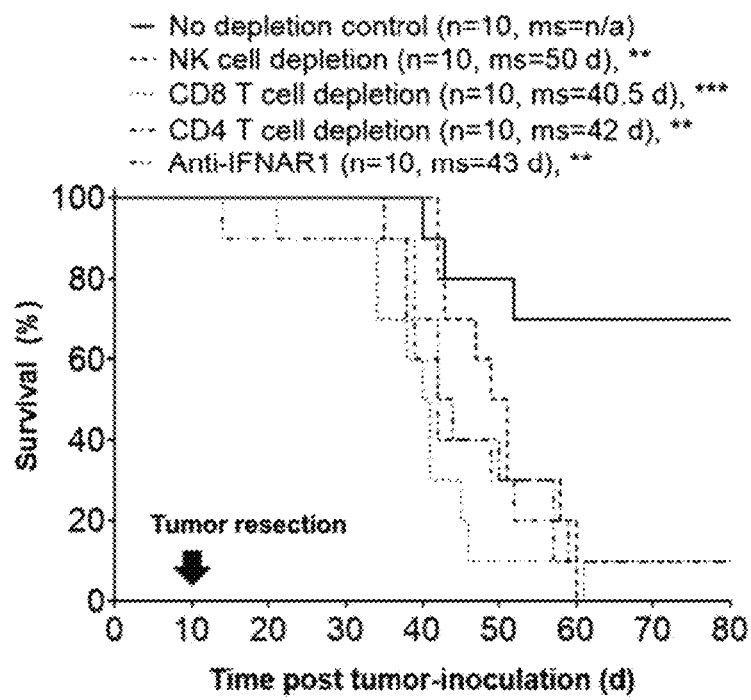
FIGS. 90A-90B show that both the innate and adaptive arms of the immune system are critical to the observed efficacy. Tumors were resected from mice 10 days after orthotopic inoculation of 4T1-Luc2 cells, and device 22 (R848) (FIG. 90A) or device 23 (STING-RR) (FIG. 90B) were placed in the resection site. Specific immune cell subsets (NK cells, $CD8^+$ T cells, or $CD4^+$ T cells) were depleted or innate immune signaling (IFNAR1) was inhibited in order to explore their relative contribution to the observed efficacy. Kaplan-Meier curves are shown for all groups described. The number of mice per group (n) and median survival (ms) are listed. The experiment was performed with biological replicates at least three times. Statistics were calculated relative to the group treated with hydrogel containing the indicated agonist of innate immunity and treated with PBS (no depletion control) using the Log-rank (Mantel-Cox) test. * $p \leq 0.05$,  $p \leq 0.01$ * $p \leq 0.001$.
Figure 90B:
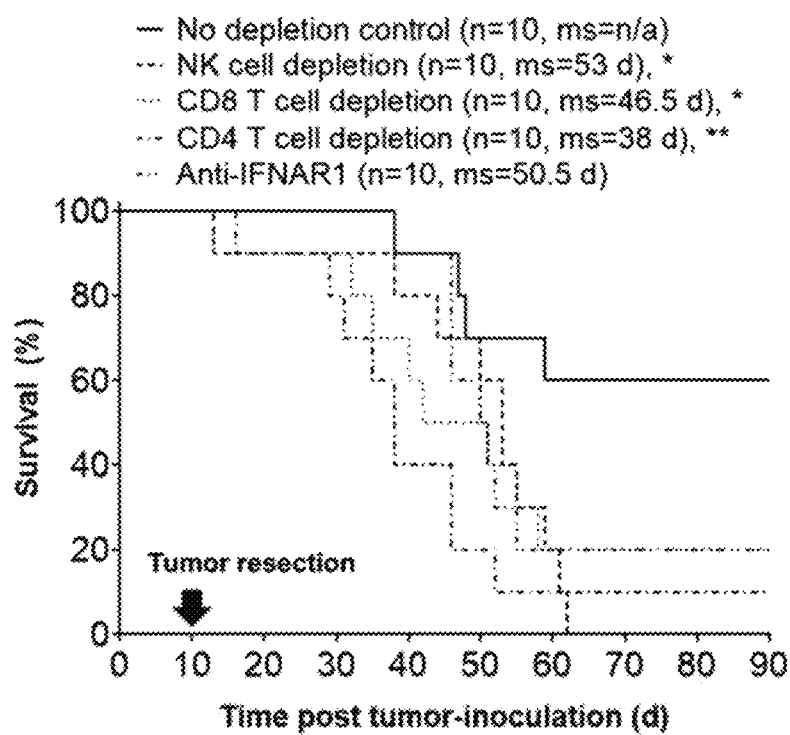

Example 10. Activation of Both Innate and Adaptive Arms of the Immune System are Useful for the Observed Efficacy While R848 and STING-RR activate innate immune cells, it was sought to discern whether there were particular downstream cells or pathways underlying the enhanced antitumor immune response upon extended local release of these compounds. To this end, the tumor inoculation and resection procedure described above was repeated, but—in addition to placing a hydrogel loaded with R848 or STING-RR in the resection site—NK cells, CD8⁺ T cells, or CD4⁺ T cells were depleted (FIG. 53) or type I interferon signaling was inhibited by neutralizing interferon alpha receptor 1 (IFNAR1). Survival studies indicated that NK cells, CD8⁺ T cells, CD4⁺ T cells, and type I interferon signaling are all useful to prevent tumor recurrence and metastasis. Mice in all groups whose innate or adaptive immune system was compromised exhibited reduced survival after extended release of an agonist of innate immunity in the perioperative setting (FIGS. 90A-90B).

Figure 91A:
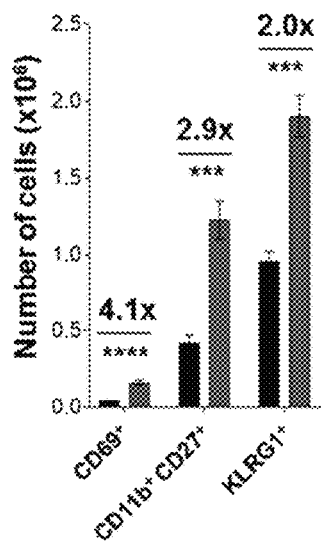
FIGS. 91A-91G show that the extended local release of R848 increases the number of innate and adaptive antitumor immune cells and cytokines. Tumors were resected from mice 10 days after orthotopic inoculation of 4T1-Luc2 cells, and device 22 was placed in the resection site. Spleens were recovered from mice 3 and 14 days after surgery for flow cytometry analysis, and blood was recovered from mice 1.5 hours, 6 hours, 3 days, and 14 days after surgery for cytokine analysis.
Figure 91B:
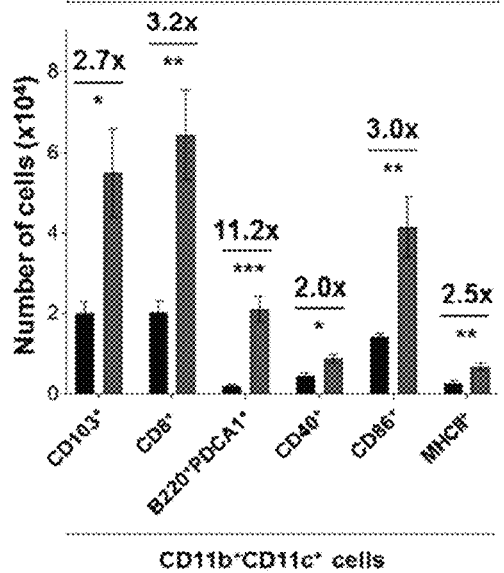
Figure 92A:
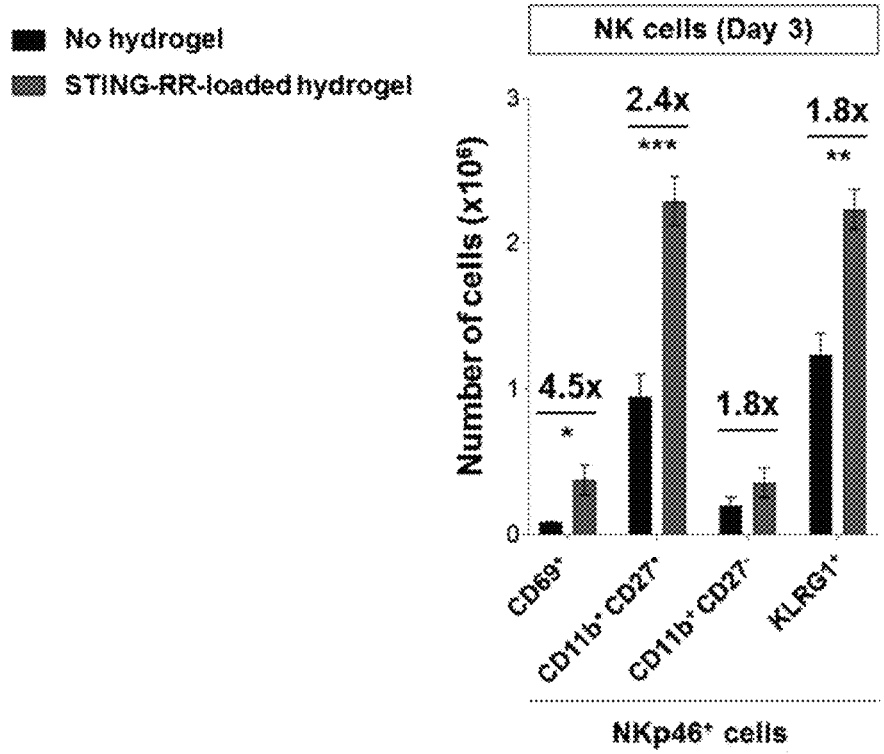
FIGS. 92A-92B show that the extended local release of STING-RR increases the number of innate immune cells. Tumors were resected from mice 10 days after orthotopic inoculation of 4T1-Luc2 cells, and device 23 was placed in the resection site. Spleens were recovered from mice 3 days after surgery for flow cytometry analysis. Increased numbers of leukocytes with activated and effector phenotypes are observed. Quantitation of flow cytometry gating of subsets of NK cells (FIG. 92A) and dendritic cells (FIG. 92B) is shown.
Figure 92B:
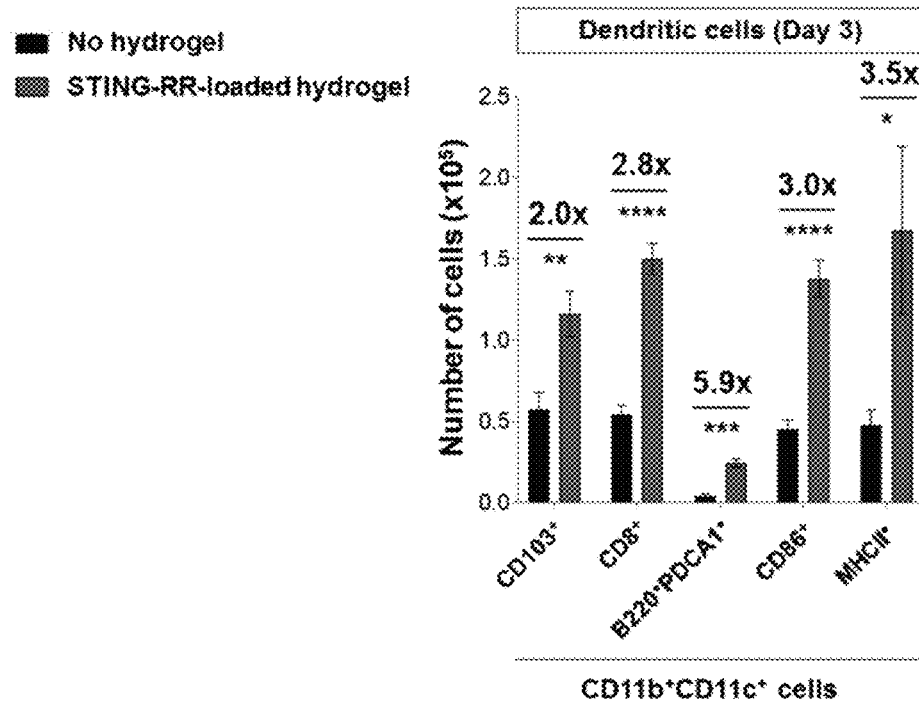

To dissect the cellular and molecular changes among immune cell subsets following localized release of R848, the composition, activation status, and function of leukocytes in the spleen were assessed. Spleens were recovered from mice 3 and 14 days after surgery for flow cytometry analysis. For the early time point the "priming phase"—focus was on the innate arm of the immune system, particularly NK cells and dendritic cells. The number of activated (CD69⁺, KLRG1⁺) as well as high effector (CD11b⁺CD27⁺) NK cells was increased following treatment with R848 (device 22; FIG. 91A). Elevated numbers of CD8⁺ and CD103⁺ dendritic cells, which are crucial to cross-presentation and the production of robust antitumor immunity, as well as B220⁺ PDCA1⁺ plasmacytoid dendritic cells, which produce large amounts of type I interferons, were similarly observed (FIG. 91B). Following exposure to R848, more dendritic cells expressed the co-stimulatory molecules CD40 and CD86 as well as MHC II, indicating that they had been activated. Similar findings were observed for NK cells and dendritic cells isolated from mice treated with hydrogels containing STING-RR (device 23; FIGS. 92A-92B), supporting the usefulness of activating innate immunity to the observed therapeutic efficacy.

Figure 91C:
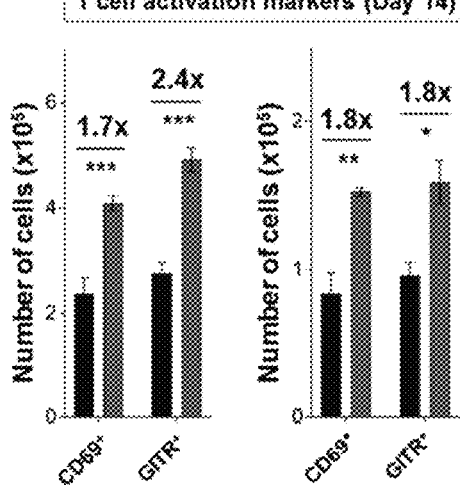
Figure 91D:
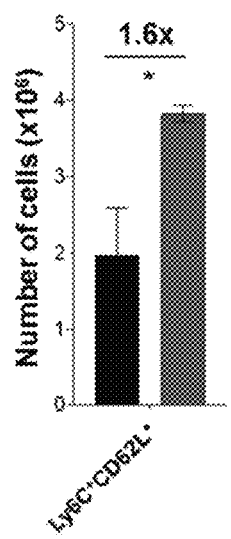
Figure 91E:
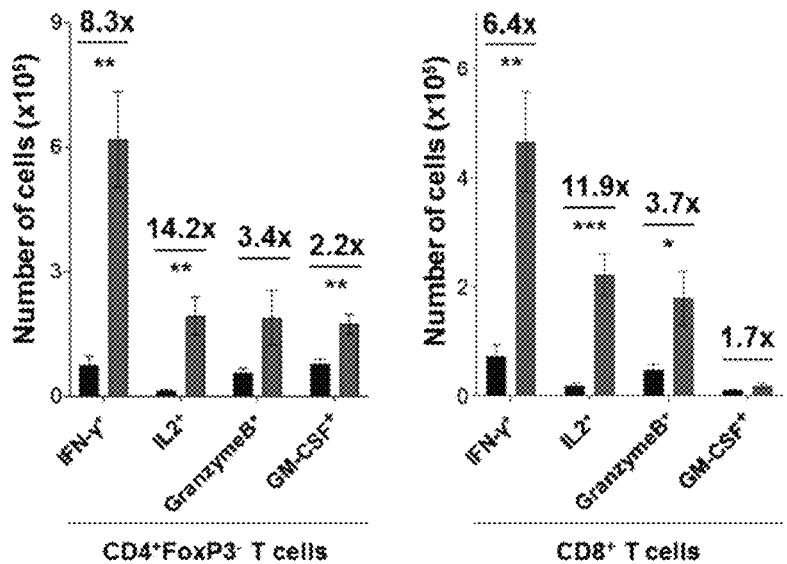

These dendritic cells induced a strong adaptive antitumor response, as evidenced by the T cell compartment 14 days post-surgery. Increased numbers of CD4⁺FoxP3⁻ T cells and CD8⁺ T cells that express markers of activation, including CD69 and GITR were detected (FIG. 91C). Systemic immunity is required for effective cancer immunotherapy, and an increase in the number of central memory-like CD8⁺ T cells that co-express Ly6C and CD62L, (FIG. 91D) was confirmed, which have been shown to become more prevalent with effective therapy. To assess whether the inhibition of tumor recurrence and lung metastasis upon implantation of R848-loaded hydrogels is associated with systemic expansion of tumor antigen-specific CD8⁺ T cells, splenocytes were re-stimulated that were isolated from the treatment and control groups with SPSYVYHQF, an immunodominant peptide of Murine leukemia virus envelope glycoprotein gp70 (amino acids 423-431), which is expressed by 4T1 cells. The proportion of T cells expressing the pro-inflammatory cytokines IFN-γ, IL-2, and GM-CSF as well as the cytolytic molecule granzyme B was increased among mice treated with hydrogels containing R848 (FIG. 91E). These data confirm the breadth, robustness, and specificity of the systemic antitumor immune response induced by perioperative delivery of a hydrogel loaded with R848 (device 22).

Figure 93A:
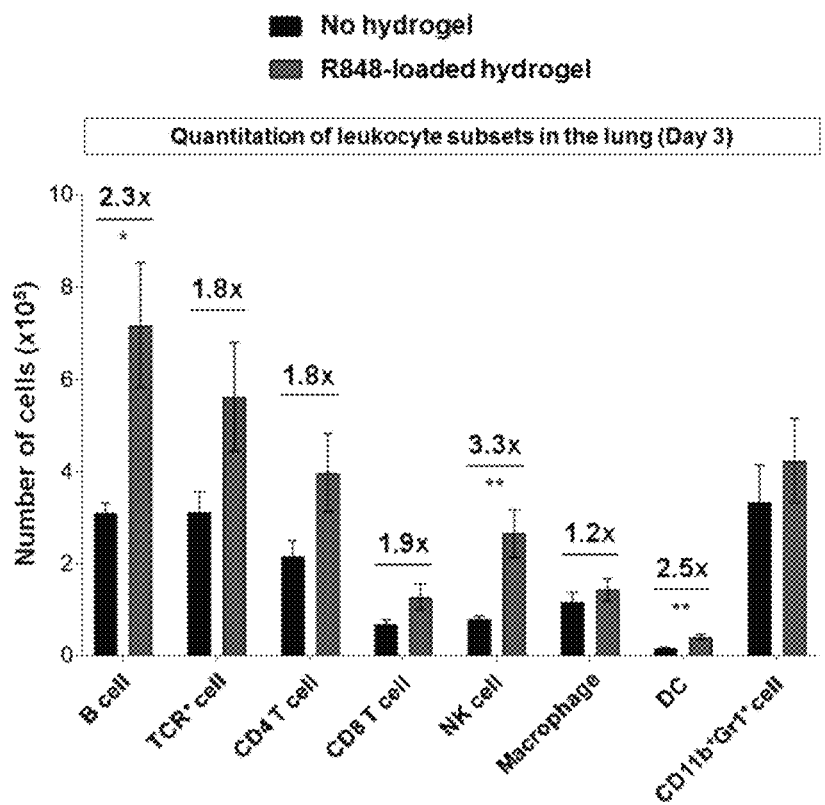
FIGS. 93A-93B show that the extended local release of R848 increases the numbers of several leukocyte subsets in the lung. Tumors were resected from mice 10 days after orthotopic inoculation of 4T1-Luc2 cells, and device 22 was placed in the resection site. Lungs were recovered on days 3 (FIG. 93A) and 14 (FIG. 93B) post-surgery, and single-cell suspensions were prepared for flow cytometry. Data are presented as mean±SEM. * $p \leq 0.05$, ** $p \leq 0.01$.
Figure 93B:
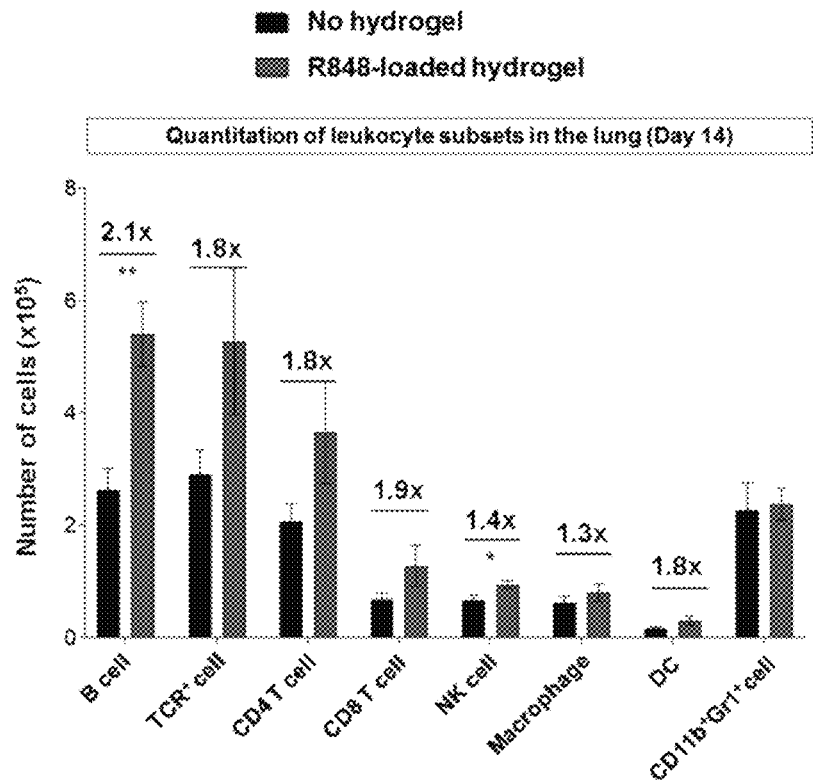

Given the ability of the therapy to eliminate metastases that had already developed in the lungs, the composition of leukocytes in lungs recovered 3 and 14 days after surgery were also inspected. Elevated numbers of B cells, T cells, NK cells, and dendritic cells were detected among mice treated with R848-loaded hydrogels (device 22; FIGS. 93A-93B). While these data do not suggest a particular mechanism that is responsible for eradication of metastases, they again support the notion that extended release of R848 promotes a broad systemic antitumor immune response.

Figure 91F:
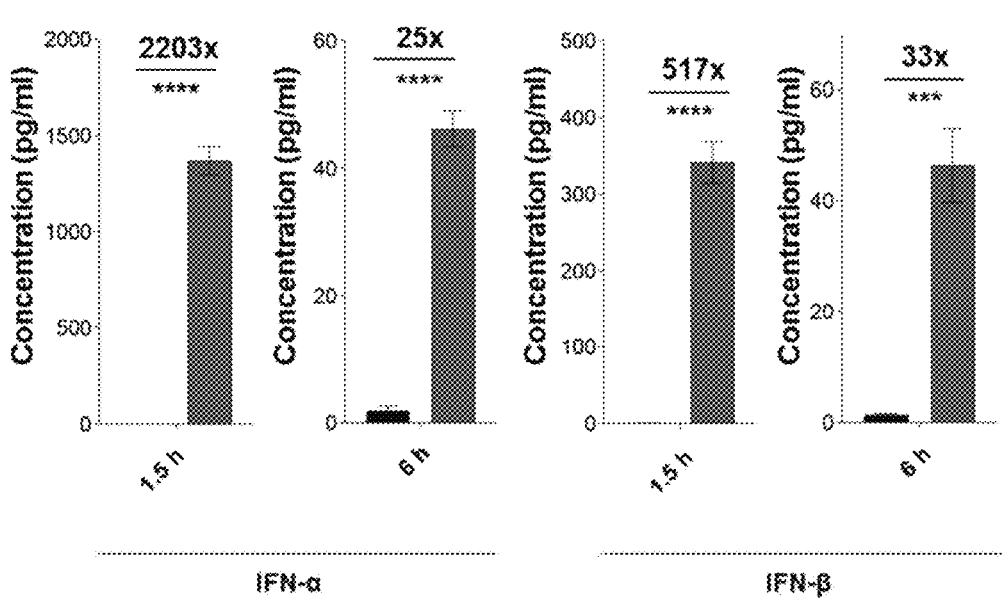
Figure 91G:
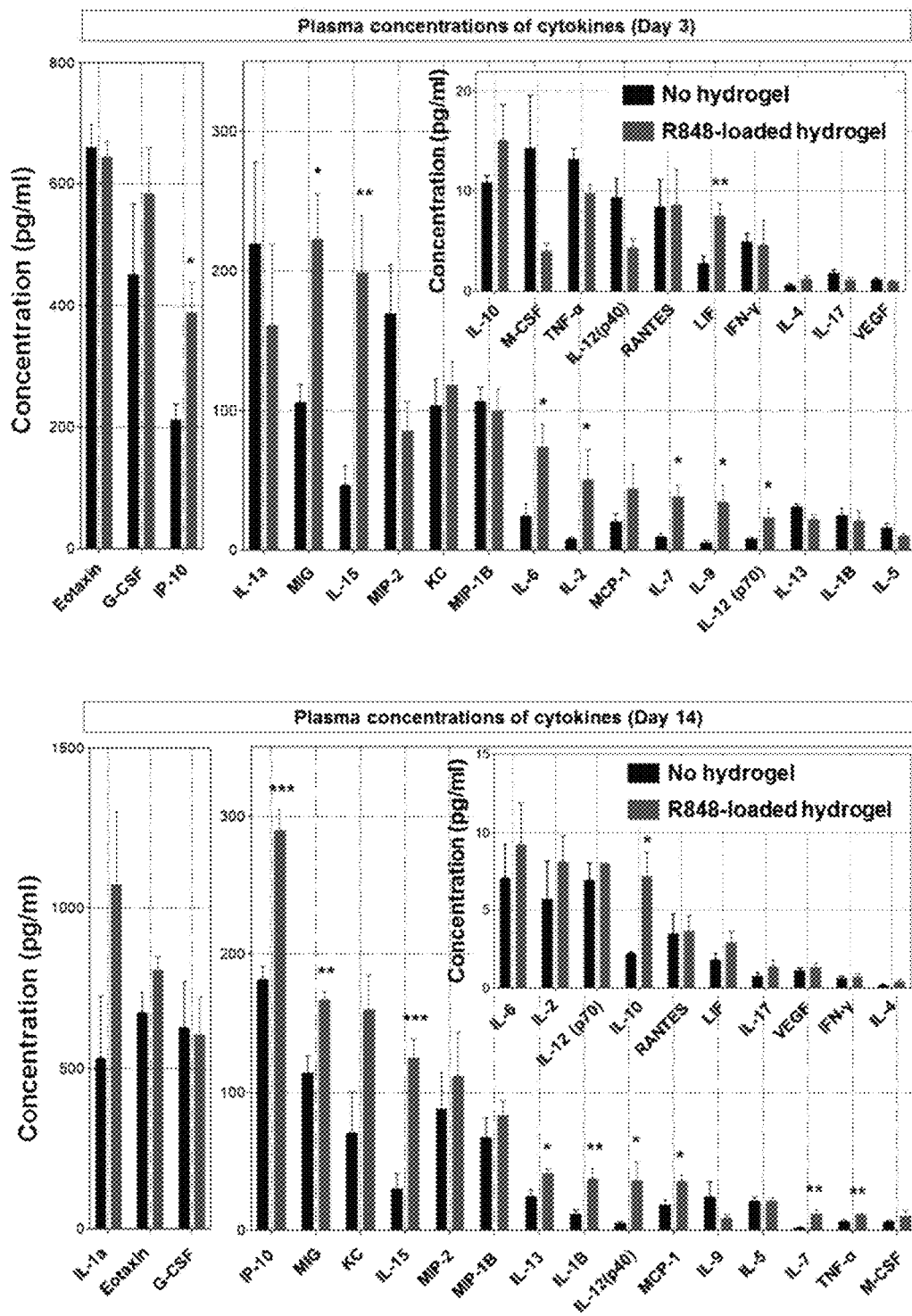
Figure 94A:
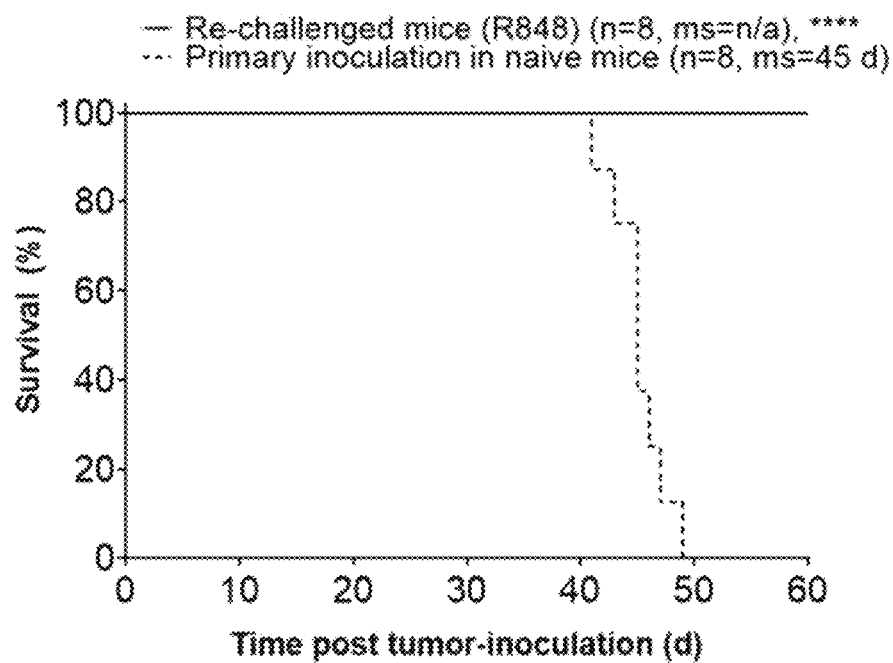
FIGS. 94A-94B show that the induction of an adaptive antitumor memory response is confirmed by rejection of 4T1-Luc2 cells inoculated as re-challenge. A Kaplan-Meier curve illustrates that 100% of nave mice succumb to the lethal challenge, whereas 100% of the mice that had achieved durable survival benefit following treatment with hydrogels loaded with R848 (FIG. 94A) or STING-RR (FIG. 94B) survive the re-challenge. The number of mice per group (n) and median survival (ms) are listed. The experiment was performed once with biological replicates. Statistics were calculated relative to the re-challenged mice using the Log-rank (Mantel-Cox). * $p \leq 0.001$, ** $p \leq 0.0001$.

To gain insights into the soluble factors that are associated with the activation of innate and adaptive immune cells, the levels of cytokines in peripheral blood were measured. At multiple time points post-surgery, plasma was collected and subsequently analyzed by multiplexing laser bead technology. Consistent with the loss of efficacy following neutralization of IFNAR1, it was observed that levels of both Ifn-α and Ifn-β were markedly elevated following treatment with hydrogel containing R848 (device 22) relative to no hydrogel (FIG. 91F). The levels of several other soluble mediators of immunity were also noticeably increased, including CXCL10 (IP-10), CXCL9 (MIG), and IL-15 (FIG. 91G and Table 4). Together, these results indicate an expansive induction of antitumor immunity. Indeed, the induction of a memory response was confirmed by re-challenging the surviving mice, 100% of which rejected the freshly inoculated 4T1-Luc2 cells (FIG. 94A).

Figure 94B:
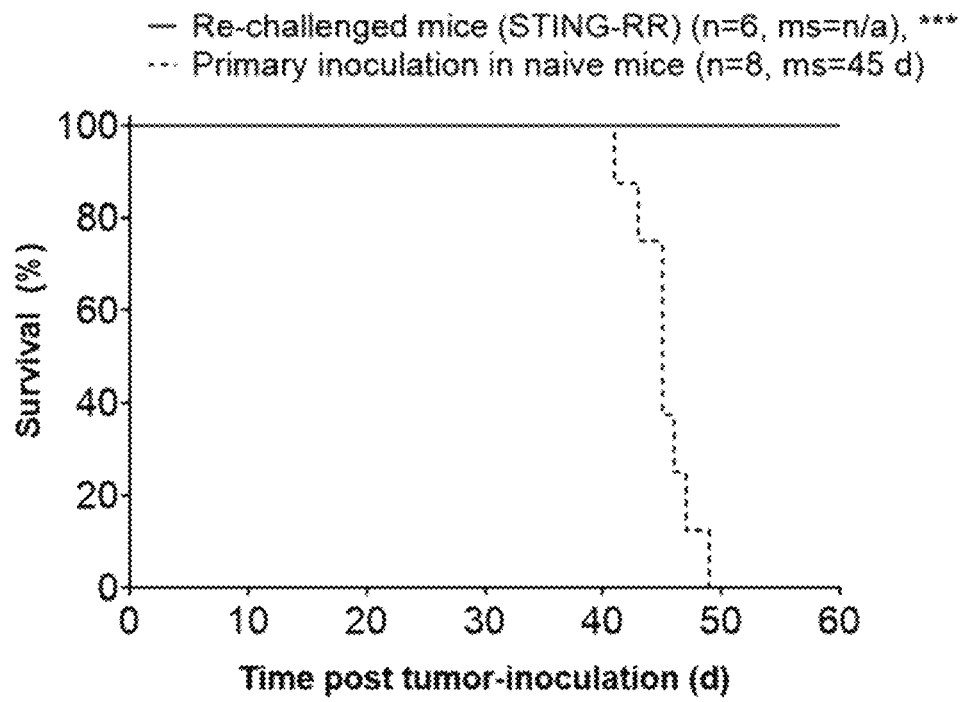

Similar results were achieved with evaluation of STING-RR (device 23) (Table 5) in analogous procedures (FIG. 94B).

TABLE 4

Quantitation and statistics for a panel of cytokines measured in plasma recovered 3 days and 14 days after surgery (device 22 vs no hydrogel) are shown. These data are presented graphically in FIG. 91G.

| | No hydrogel | | R848-loaded hydrogel | | Fold | |
|---|---|---|---|---|---|---|
| | Average | Std. Error | Average | Std. Error | increase | Statistics |
| Day 3 | | | | | | |
| Eotaxin | 661.63 | 82.44 | 643.60 | 82.10 | 0.97 | 0.6972 ns |
| G-CSF | 451.86 | 257.44 | 584.47 | 202.75 | 1.29 | 0.338 ns |
| IP-10 | 211.36 | 66.06 | 388.75 | 150.95 | 1.84 | 0.0151 * |
| IL-1a | 219.46 | 141.46 | 161.58 | 152.67 | 0.74 | 0.4929 ns |
| MIG | 105.80 | 31.77 | 222.49 | 96.73 | 2.10 | 0.0112 * |
| IL-15 | 47.00 | 32.86 | 198.73 | 108.56 | 4.23 | 0.0056 ** |
| MIP-2 | 169.50 | 77.69 | 85.29 | 56.56 | 0.50 | 0.0506 ns |
| KC | 103.62 | 37.54 | 118.12 | 50.57 | 1.14 | 0.606 ns |
| MIP-1B | 106.70 | 24.57 | 99.91 | 46.55 | 0.94 | 0.7447 ns |
| IL-6 | 24.64 | 21.84 | 73.98 | 38.72 | 3.00 | 0.0187 * |
| IL-2 | 8.33 | 2.69 | 51.05 | 46.23 | 6.13 | 0.0463 * |
| MCP-1 | 21.09 | 13.64 | 44.49 | 38.07 | 2.11 | 0.1906 ns |

TABLE 4-continued

Quantitation and statistics for a panel of cytokines measured in plasma recovered 3 days and 14 days after surgery (device 22 vs no hydrogel) are shown. These data are presented graphically in FIG. 91G.

|  | No hydrogel | | R848-loaded hydrogel | | Fold | | |
|---|---|---|---|---|---|---|---|
|  | Average | Std. Error | Average | Std. Error | increase | Statistics | |
| IL-7 | 9.68 | 5.44 | 38.56 | 24.46 | 3.98 | 0.0124 | * |
| IL-9 | 5.22 | 5.10 | 34.79 | 26.68 | 6.67 | 0.0229 | * |
| IL-12 (p70) | 8.27 | 2.70 | 23.69 | 16.09 | 2.86 | 0.0392 | * |
| IL-13 | 31.57 | 4.95 | 22.72 | 10.06 | 0.72 | 0.0615 | ns |
| IL-1B | 25.37 | 12.54 | 21.38 | 17.73 | 0.84 | 0.6606 | ns |
| IL-5 | 16.38 | 8.02 | 10.21 | 4.36 | 0.62 | 0.0872 | ns |
| IL-10 | 10.81 | 1.76 | 15.17 | 10.01 | 1.40 | 0.3052 | ns |
| M-CSF | 14.37 | 10.47 | 4.06 | 2.35 | 0.28 | 0.0161 | * |
| TNF-α | 13.15 | 2.84 | 9.76 | 2.53 | 0.74 | 0.0281 | * |
| IL-12(p40) | 9.37 | 4.64 | 4.37 | 2.21 | 0.47 | 0.032 | * |
| RANTES | 8.40 | 5.51 | 8.60 | 9.97 | 1.02 | 0.97 | ns |
| LIF | 2.84 | 1.69 | 7.58 | 3.08 | 2.66 | 0.005 | ** |
| IFN-γ | 4.97 | 2.05 | 4.66 | 6.54 | 0.94 | 0.9126 | ns |
| IL-4 | 0.61 | 0.37 | 1.25 | 0.86 | 2.04 | 0.1224 | ns |
| IL-17 | 1.85 | 0.72 | 1.13 | 0.83 | 0.61 | 0.1407 | ns |
| VEGF | 1.22 | 0.33 | 1.00 | 0.25 | 0.82 | 0.1558 | ns |
| Day 14 | | | | | | | |
| IL-1a | 533.12 | 431.99 | 1072.61 | 459.88 | 2.01 | 0.1035 | ns |
| Eotaxin | 675.67 | 124.36 | 806.71 | 94.20 | 1.19 | 0.106 | ns |
| G-CSF | 627.79 | 285.67 | 606.01 | 204.61 | 0.97 | 0.913 | ns |
| IP-10 | 181.67 | 16.25 | 290.02 | 33.29 | 1.60 | 0.0006 | *** |
| MIG | 114.38 | 26.87 | 167.19 | 12.53 | 1.46 | 0.0026 | ** |
| KC | 70.23 | 67.43 | 159.87 | 49.92 | 2.28 | 0.0529 | ns |
| IL-15 | 30.62 | 22.92 | 124.85 | 23.30 | 4.09 | 0.0005 | *** |
| MIP-2 | 88.42 | 44.76 | 112.01 | 62.98 | 1.27 | 0.5944 | ns |
| MIP-1B | 66.92 | 32.77 | 83.05 | 24.67 | 1.24 | 0.3999 | ns |
| IL-13 | 24.70 | 10.74 | 41.19 | 6.15 | 1.67 | 0.0223 | * |
| IL-1B | 12.15 | 6.52 | 37.37 | 14.00 | 3.08 | 0.0062 | ** |
| IL-12(p40) | 5.41 | 1.88 | 35.81 | 23.83 | 6.62 | 0.0238 | * |
| MCP-1 | 18.62 | 7.20 | 35.68 | 8.90 | 1.91 | 0.0124 | * |
| IL-9 | 24.51 | 18.66 | 9.14 | 4.90 | 0.37 | 0.163 | ns |
| IL-5 | 21.37 | 6.45 | 21.47 | 4.55 | 1.00 | 0.9789 | ns |
| IL-7 | 1.93 | 1.29 | 11.78 | 4.99 | 6.12 | 0.0033 | ** |
| TNF-α | 6.63 | 2.36 | 11.65 | 1.83 | 1.76 | 0.0038 | ** |
| M-CSF | 6.23 | 2.99 | 10.65 | 6.52 | 1.71 | 0.2321 | ns |
| IL-6 | 7.06 | 3.80 | 9.25 | 4.61 | 1.31 | 0.5482 | ns |
| IL-2 | 5.68 | 4.20 | 8.09 | 2.98 | 1.42 | 0.4482 | ns |
| IL-12 (p70) | 6.91 | 2.44 | 8.00 | 0.00 | 1.16 | 0.4468 | ns |
| IL-10 | 2.24 | 0.14 | 7.13 | 2.77 | 3.18 | 0.0226 | * |
| RANTES | 3.50 | 2.43 | 3.87 | 1.62 | 1.05 | 0.9204 | ns |
| LIF | 1.83 | 0.89 | 2.93 | 1.29 | 1.60 | 0.1932 | ns |
| IL-17 | 0.78 | 0.48 | 1.38 | 0.72 | 1.77 | 0.1938 | ns |
| VEGF | 1.13 | 0.37 | 1.34 | 0.52 | 1.19 | 0.4925 | ns |
| IFN-γ | 0.65 | 0.23 | 0.72 | 0.48 | 1.10 | 0.8239 | ns |
| IL-4 | 0.20 | 0.09 | 0.41 | 0.23 | 2.11 | 0.0926 | ns | ns = not significant
* $p \leq 0.05$,
** $p \leq 0.01$,
*** $p \leq 0.001$

TABLE 5

Figure 104A:
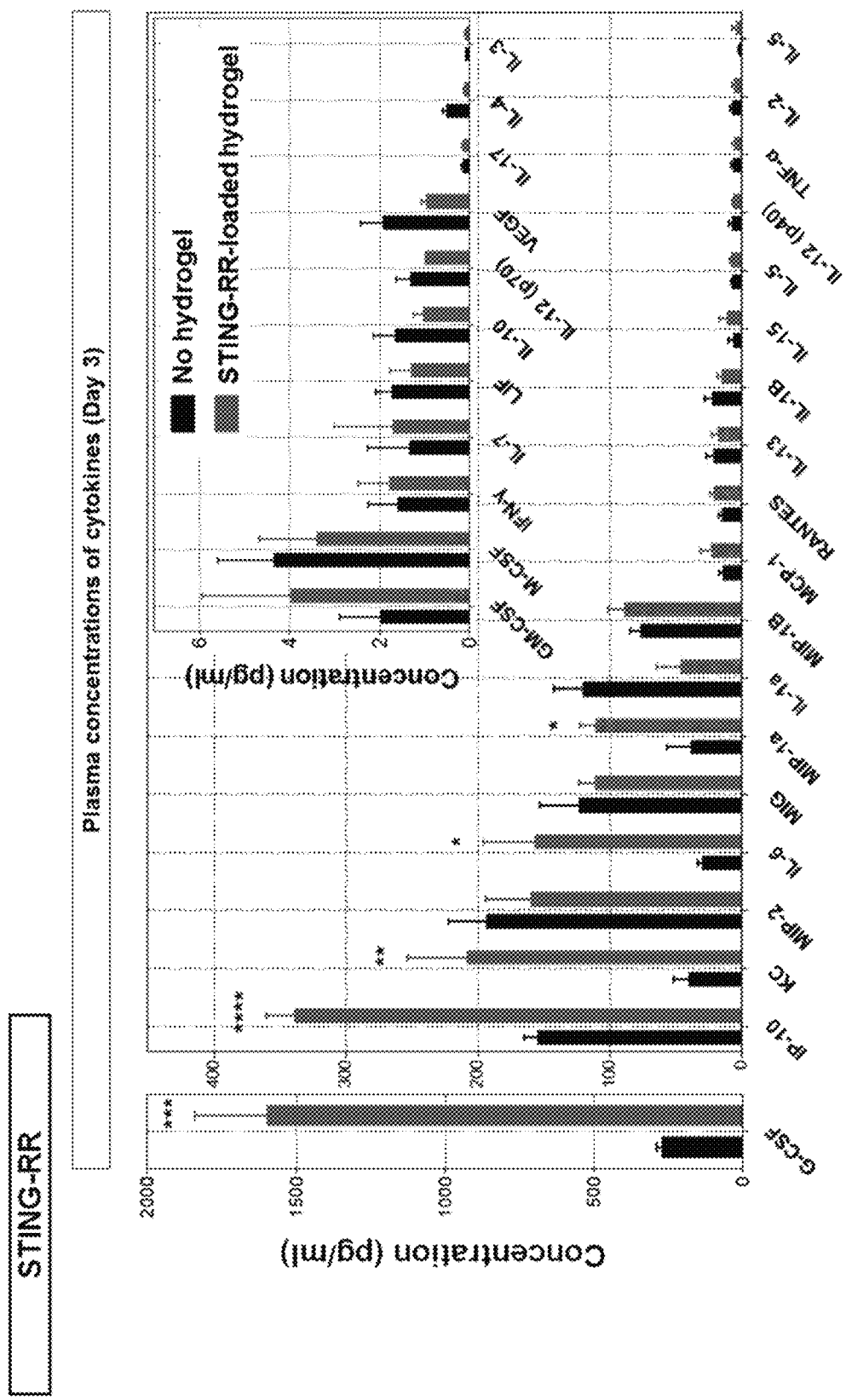
FIGS. 104A-104B show that the extended local release of STING-RR increases the levels of cytokines in the blood. Tumors were resected from mice 10 days after orthotopic inoculation of 4T1-Luc2 cells, and device 23 was placed in the resection site. Elevated concentrations of cytokines are observed in plasma collected at 3 days (FIG. 104A) and 14 days (FIG. 104B) after surgery. Levels of a panel of cytokines are shown. Data were generated by multiplexing laser bead technology. The experiment was performed once with n=5 biological replicates. Statistics were calculated using a two-sided unpaired t-test. Data are presented as mean± SEM. * p≤0.05,  p≤0.01, * p≤0.001, **** p≤0.0001.
Figure 104B:
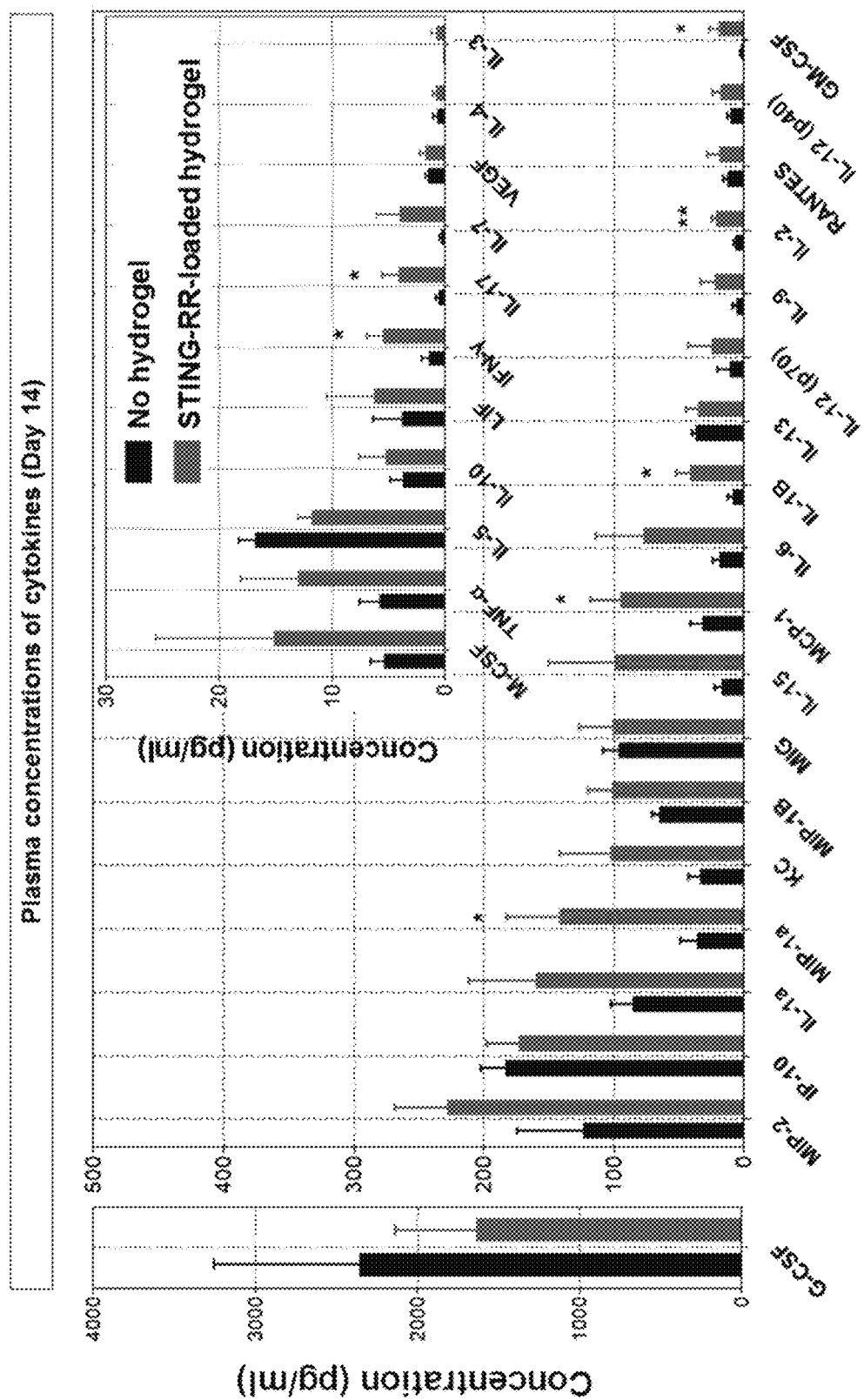
Figure 105:
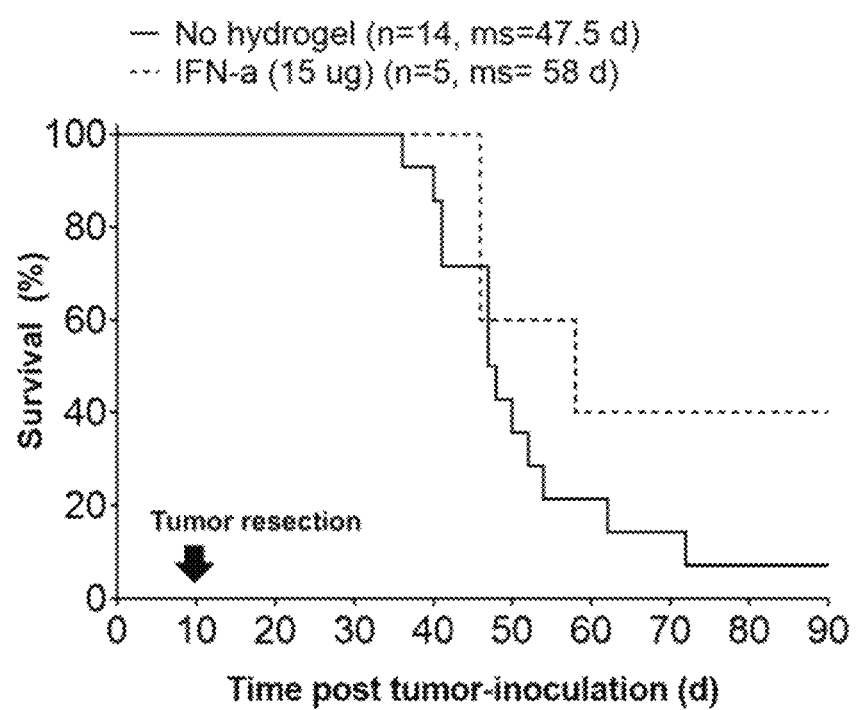
FIG. 105 shows a Kaplan-Meier curve demonstrating survival benefit for Ifn-α (device 24) versus no hydrogel. The number of mice per group (n) and median survival (ms) are listed.

Quantitation and statistics for a panel of cytokines measured in plasma recovered 3 days and 14 days after surgery (device 23 vs no hydrogel) are shown. These data are presented graphically in FIGS. 104A-104B.

|  | No hydrogel | | STING-RR-loaded hydrogel | | Fold | | |
|---|---|---|---|---|---|---|---|
|  | Average | Std. Error | Average | Std. Error | increase | Statistics | |
| Day 3 | | | | | | | |
| G-CSF | 273.962 | 15.47037 | 1600.81 | 240.4479 | 5.843183 | 0.0008 | *** |
| IP-10 | 154.93 | 10.14809 | 339.6383 | 21.18998 | 2.192205 | <0.0001 | **** |
| KC | 40.426 | 11.74889 | 208.685 | 45.26506 | 5.162148 | 0.0094 | ** |
| MIP-2 | 193.63 | 29.05612 | 160.294 | 30.39366 | 0.827837 | 0.4772 | ns |
| IL-6 | 29.996 | 3.934154 | 156.9333 | 39.31508 | 5.231809 | 0.0173 | * |
| MIG | 123.564 | 29.79537 | 111.615 | 11.92762 | 0.903297 | 0.6993 | ns |

TABLE 5-continued

Quantitation and statistics for a panel of cytokines measured in plasma recovered 3 days and 14 days after surgery (device 23 vs no hydrogel) are shown. These data are presented graphically in FIGS. 104A-104B.

|  | No hydrogel | | STING-RR-loaded hydrogel | | Fold | |
|---|---|---|---|---|---|---|
|  | Average | Std. Error | Average | Std. Error | increase | Statistics |
| MIP-1a | 38.816 | 18.19764 | 111.056 | 10.66939 | 2.861088 | 0.0105 * |
| IL-1a | 121.02 | 21.82695 | 46.54333 | 18.09235 | 0.384592 | 0.0264 * |
| MIP-1B | 77.062 | 7.705941 | 89.38 | 12.01979 | 1.159845 | 0.4327 ns |
| MCP-1 | 14.714 | 2.805587 | 23.6275 | 6.215258 | 1.605784 | 0.2868 ns |
| RANTES | 15.686 | 2.202321 | 21.69 | 2.672533 | 1.382762 | 0.1261 ns |
| IL-13 | 21.796 | 5.573219 | 18.462 | 4.162021 | 0.847036 | 0.6583 ns |
| IL-1B | 22.736 | 5.705969 | 15.59833 | 2.967572 | 0.686063 | 0.2725 ns |
| IL-15 | 6.905 | 3.110188 | 11.928 | 4.929974 | 1.727444 | 0.4963 ns |
| IL-5 | 7.858 | 0.422343 | 8.115 | 1.455286 | 1.032706 | 0.8799 ns |
| IL-12 (p40) | 7.288 | 2.588707 | 6.493333 | 1.170213 | 0.890962 | 0.7728 ns |
| TNFa | 6.716 | 1.386862 | 6.013333 | 1.685186 | 0.895374 | 0.7614 ns |
| IL-2 | 7.36 | 1.73482 | 5.901667 | 1.763501 | 0.801857 | 0.5741 ns |
| IL-9 | 2.18 | 0.767717 | 4.803333 | 2.764254 | 2.203364 | 0.4242 ns |
| GM-CSF | 1.9775 | 0.789861 | 3.978333 | 1.964859 | 2.011799 | 0.4569 ns |
| M-CSF | 4.35 | 1.238051 | 3.41 | 1.267972 | 0.783908 | 0.6127 ns |
| IFN$\gamma$ | 1.608 | 0.649334 | 1.791667 | 0.696709 | 1.114221 | 0.8537 ns |
| IL-7 | 1.3425 | 0.807592 | 1.716 | 1.162431 | 1.278212 | 0.831 ns |
| LIF | 1.735 | 0.31254 | 1.31 | 0.409566 | 0.755043 | 0.5073 ns |
| IL-10 | 1.67 | 0.475016 | 1.036 | 0.203442 | 0.620359 | 0.2631 ns |
| IL-12 (p70) | 1.3225 | 0.279293 | 1 | 0 | 0.756144 | 0.2924 ns |
| VEGF | 1.936 | 0.497037 | 0.966667 | 0.120407 | 0.499311 | 0.0682 ns |
| IL-17 | 0.155 | 0.027726 | 0.15 | 0.022361 | 0.967742 | 0.8978 ns |
| IL-4 | 0.528 | 0.080833 | 0.118333 | 0.021042 | 0.224116 | 0.0005 *** |
| IL-3 | 0.1 | 0 | 0.096667 | 0.013081 | 0.966667 | 0.8229 ns |
| Day 14 | | | | | | |
| G-CSF | 2362.936 | 800.065 | 1635.592 | 448.6133 | 0.692186 | 0.4983 ns |
| MIP-2 | 124.0033 | 50.46225 | 228.1467 | 40.40126 | 1.839843 | 0.1382 ns |
| IP-10 | 183.0183 | 19.29988 | 172.8533 | 24.79856 | 0.944459 | 0.753 ns |
| IL-1a | 85.456 | 15.29279 | 160.14 | 51.06685 | 1.873947 | 0.2339 ns |
| MIP-1a | 36.265 | 12.89418 | 142.082 | 36.28055 | 3.917882 | 0.0247 * |
| KC | 33.56 | 9.18097 | 102.525 | 39.18123 | 3.054976 | 0.1173 ns |
| MIP-1B | 65.13833 | 5.3508 | 101.5383 | 18.63475 | 1.558811 | 0.0899 ns |
| MIG | 96.665 | 11.87218 | 101.235 | 25.64208 | 1.047277 | 0.8747 ns |
| IL-15 | 17.16 | 5.356666 | 99.33 | 45.45023 | 5.788462 | 0.1094 ns |
| MCP-1 | 31.715 | 9.553609 | 95.25 | 20.68909 | 3.003311 | 0.0238 * |
| IL-6 | 18.81 | 5.385726 | 77.118 | 33.15454 | 4.099841 | 0.1204 ns |
| IL-1B | 8.68 | 3.79157 | 41.70167 | 10.26284 | 4.804339 | 0.0129 * |
| IL-13 | 38.93667 | 3.132075 | 35.23667 | 9.574537 | 0.953975 | 0.8694 ns |
| IL-12 (p70) | 10.98333 | 9.470848 | 25.038 | 15.94554 | 2.279636 | 0.4828 ns |
| IL-9 | 5.811667 | 2.937091 | 22.355 | 11.13385 | 3.846573 | 0.1813 ns |
| IL-2 | 6.7 | 1.366016 | 20.96 | 3.657102 | 3.128358 | 0.006 ** |
| RANTES | 12.63 | 3.377399 | 18.57667 | 9.657804 | 1.470837 | 0.574 ns |
| IL-12 (p40) | 10.44167 | 2.295441 | 17.83667 | 6.479352 | 1.70822 | 0.307 ns |
| GM-CSF | 2.076 | 0.962404 | 19.5875 | 5.789398 | 9.435212 | 0.0343 * |
| M-CSF | 5.356667 | 1.297281 | 15.125 | 10.46318 | 2.823584 | 0.376 ns |
| TNFa | 5.798333 | 1.815099 | 12.97833 | 5.08964 | 2.238287 | 0.2135 ns |
| IL-5 | 16.8 | 1.453242 | 11.81833 | 1.20244 | 0.703472 | 0.0247 * |
| IL-10 | 3.72 | 1.143028 | 5.214 | 2.145074 | 1.401613 | 0.5559 ns |
| LIF | 3.82 | 2.59544 | 6.288333 | 4.212638 | 1.646161 | 0.6287 ns |
| IFN$\gamma$ | 1.401667 | 0.652367 | 5.4525 | 1.171087 | 3.890012 | 0.0232 * |
| IL-17 | 0.578333 | 0.254105 | 4.1 | 1.472044 | 7.089337 | 0.0401 * |
| IL-7 | 0.36 | 0.143108 | 4.012 | 1.852504 | 11.14444 | 0.1168 ns |
| VEGF | 1.533333 | 0.206812 | 1.701667 | 0.524445 | 1.109783 | 0.7714 ns |
| IL-4 | 0.696667 | 0.350244 | 0.825 | 0.253965 | 1.184211 | 0.7728 ns |
| IL-3 | 0.1 | 6.21E−18 | 0.741667 | 0.45289 | 7.416667 | 0.1869 ns |

Example 11. Safety Studies

Figure 79:
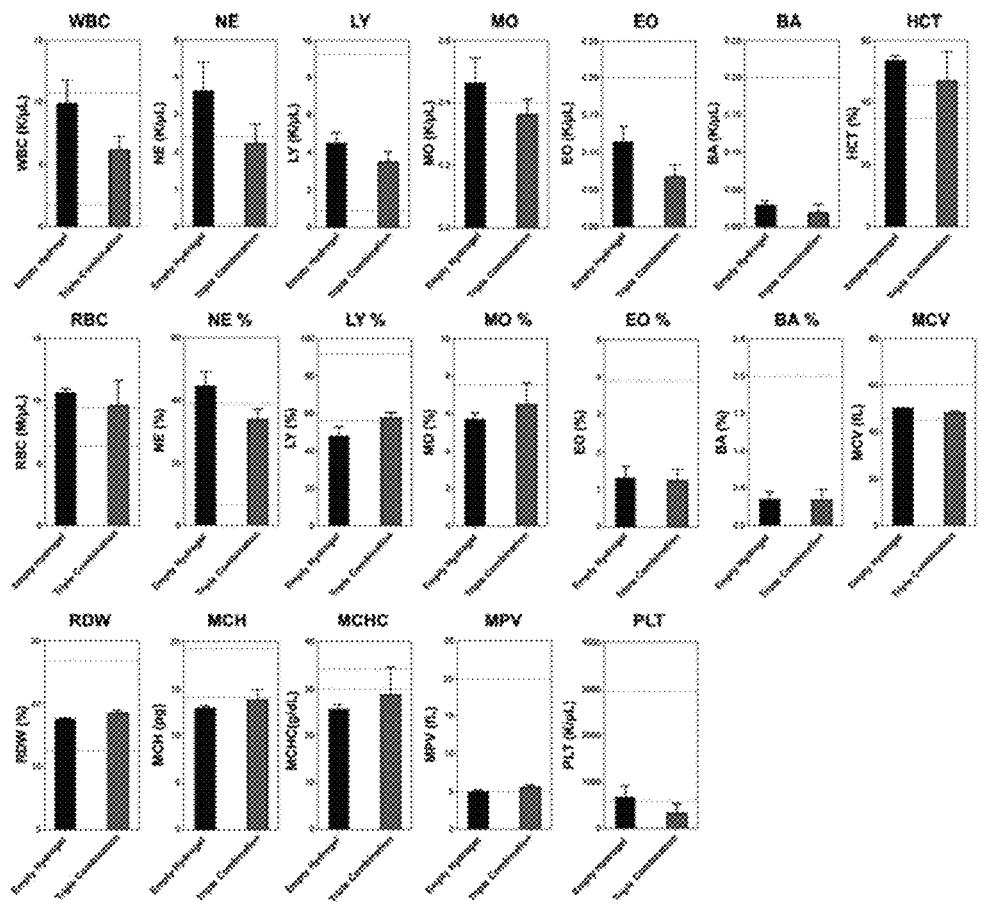
FIG. 79 is a series of graphs showing that sustained local release of 2′-3′-cGAMP, IL-15sa, and anti-PD-1 (device 1) did not alter the composition of blood. Blood was recovered on day 14 post-surgery after device 1 was placed in the resection site, WBC, white blood cells; NE, neutrophils; LY, lymphocytes; MO, monocytes; eosinophils; BA, basophils; HCT, hematocrit; RBC, red blood cells; MCV, mean corpuscular volume; RDW, red blood cell distribution width; MCH, mean corpuscular hemoglobin; MOW, mean corpuscular hemoglobin concentration; MPV, mean platelet volume; PLT, platelets. Data are presented as mean±SEM. Dashed lines indicate established normal ranges.

The safety of the hydrogel (hydrogel 4; device 8) as well as hydrogels loaded with therapeutic agents (e.g., exemplary devices 1, 2, 9, 10) was confirmed. Fifteen days after tumor resection and placement of the empty or loaded scaffolds, serum was collected and subjected to a blood panel analysis. The composition of the blood was unaffected by the triple combination released from device 1 (FIG. 79). The lack of any systemic toxicity was confirmed by a lack of changes in liver enzymes (AST, ACT, and BUN) in the blood (FIG. 80A) across treatment groups. Similarly, body weight was consistent across all groups tested, with the sole decrease being observed transiently after surgery, as expected (FIG. 80B).

Figure 81:
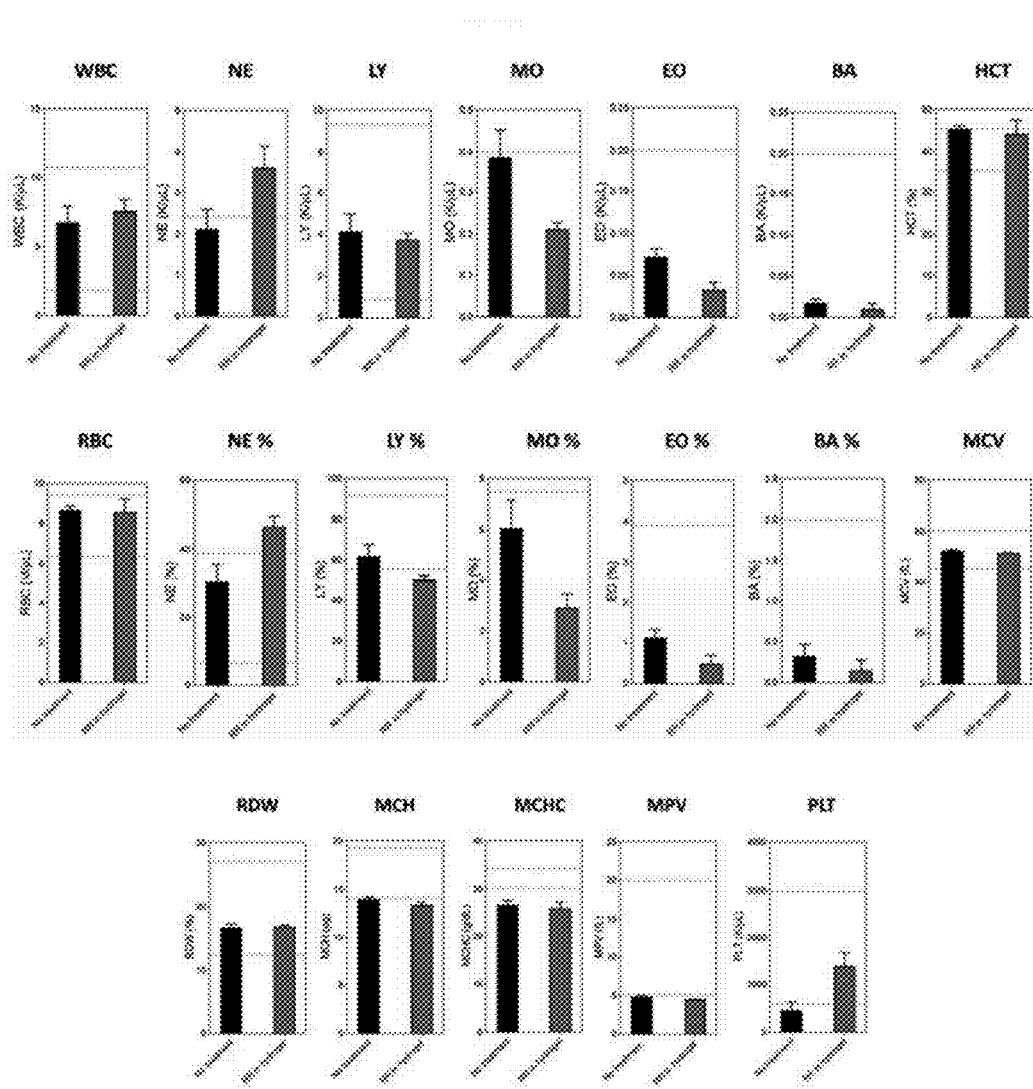
FIG. 81 is a series of graphs showing that sustained local release of STING-RR (device 23) did not alter the composition of blood. Blood was recovered on day 14 post-surgery after device 23 was placed in the resection site. WBC, white blood cells; NE, neutrophils; LY, lymphocytes; MO, monocytes; EO, eosinophils; BA, basophils; HCT, hematocrit; RBC, red blood cells; MCV, mean corpuscular volume; RDW, red blood cell distribution width; MCH, mean corpuscular hemoglobin; MCHC, mean corpuscular hemoglobin concentration; MPV, mean platelet volume; PLT, platelets. Data are presented as mean±SEM. Dashed lines indicate established normal ranges.
Figure 82A:
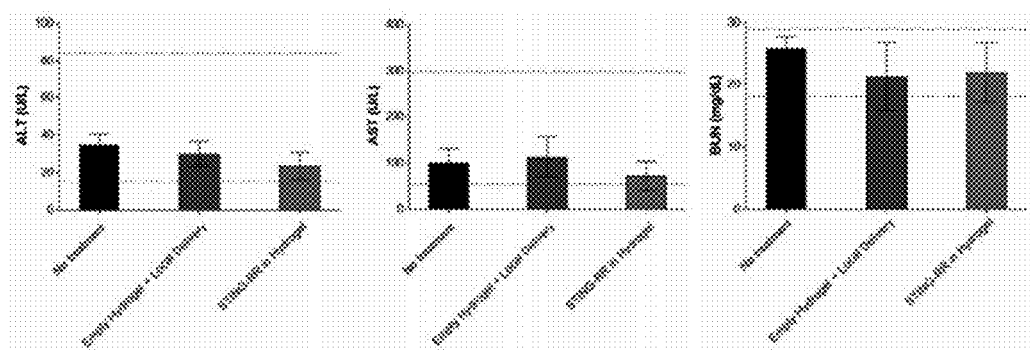
Figure 82B:
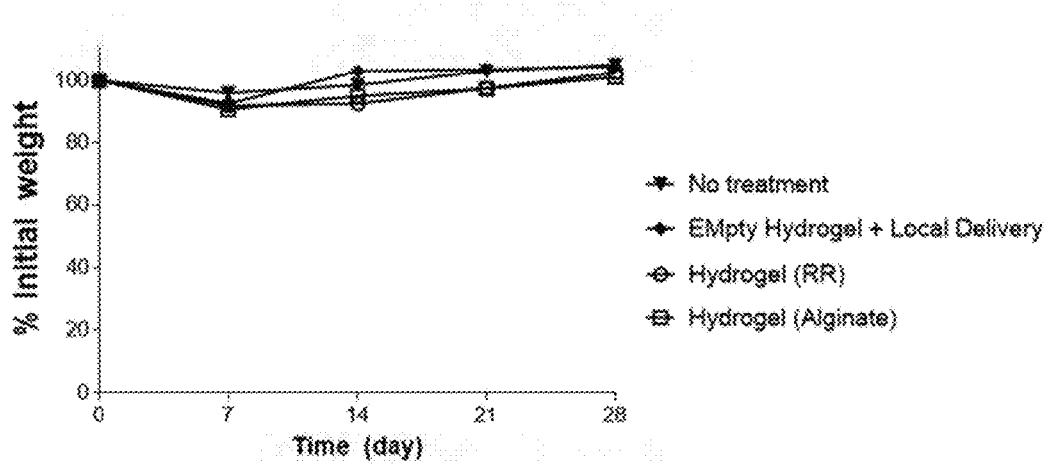

In similar fashion, the safety of device 23 and administration of STING-RR was demonstrated. Repeating the experiments described above for devices 1, 2, 8, 9, 10, the composition of the blood was unaffected by treatment with device 23 (FIG. 81). In this experiment, a solution containing STING-RR was administered locally in conjunction with the placement of device 8. The lack of systemic toxicity was also confirmed by a lack of changes in liver enzymes (AST, ACT, and BUN) in the blood (FIG. 81). Body weight was consistent across several groups tested in addition to mice treated with device 23, including alginate as the hydrogel, with the sole decrease being observed in the first week after surgery, as expected (FIG. 82).

Figure 95A:
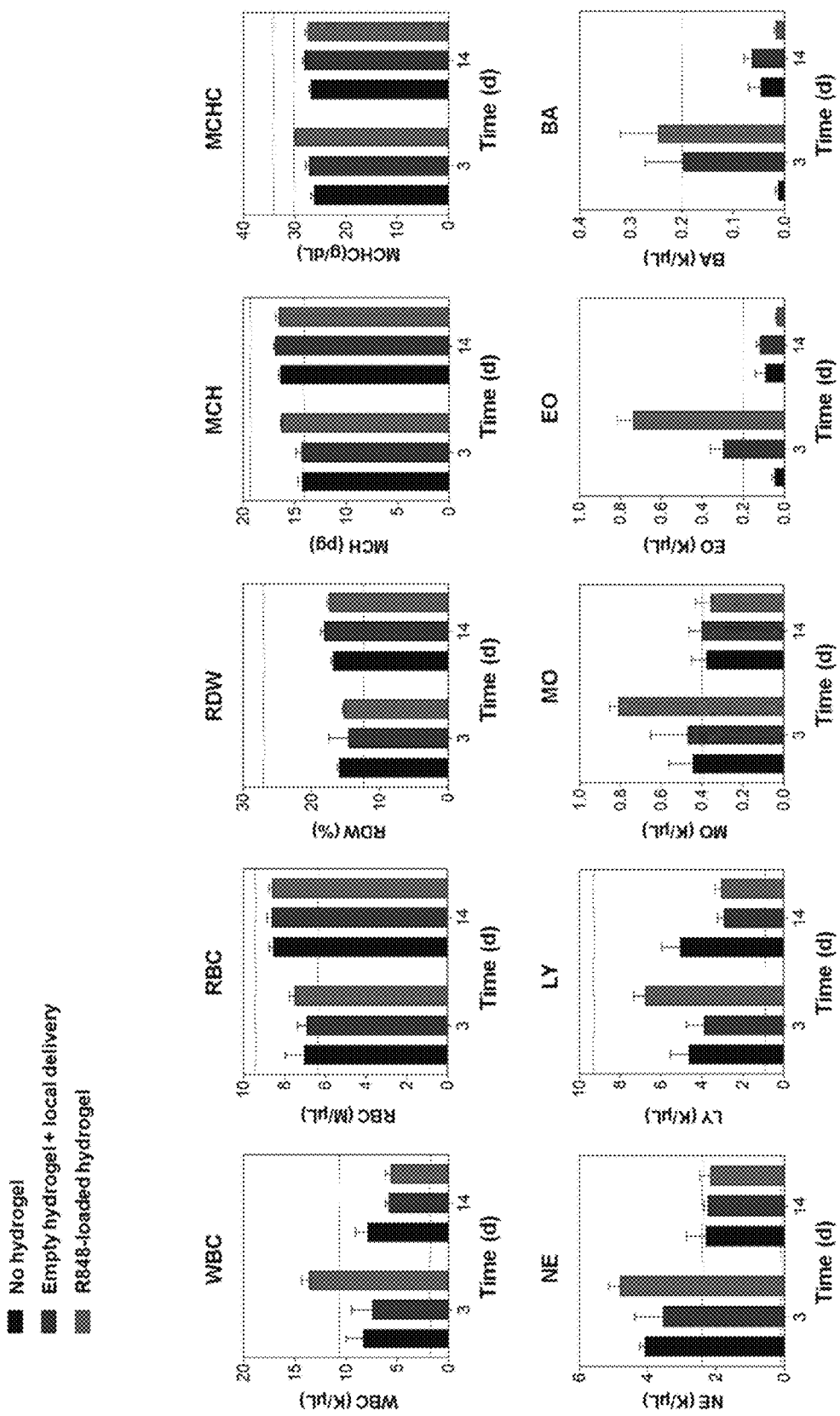
FIGS. 95A-95B show that the extended local release of agonists of innate immunity does not alter the composition of blood. Blood was recovered on days 3 and 14 post-surgery for treatment with R848 (device 22) (FIG. 95A) or STING-RR (device 23) (FIG. 95B). WBC, white blood cells; NE, neutrophils; LY, lymphocytes; MO, monocytes; EO, eosinophils; BA, basophils; HCT, hematocrit; RBC, red blood cells; MCV, mean corpuscular volume; RDW, red blood cell distribution width; MCH, mean corpuscular hemoglobin; MCHC, mean corpuscular hemoglobin concentration; MPV, mean platelet volume; PLT, platelets. The experiment was performed once with n=5 biological replicates. Statistics were calculated using a two-sided unpaired t-test. Data are presented as mean±SEM. Dashed lines indicate established normal ranges.
Figure 95A:
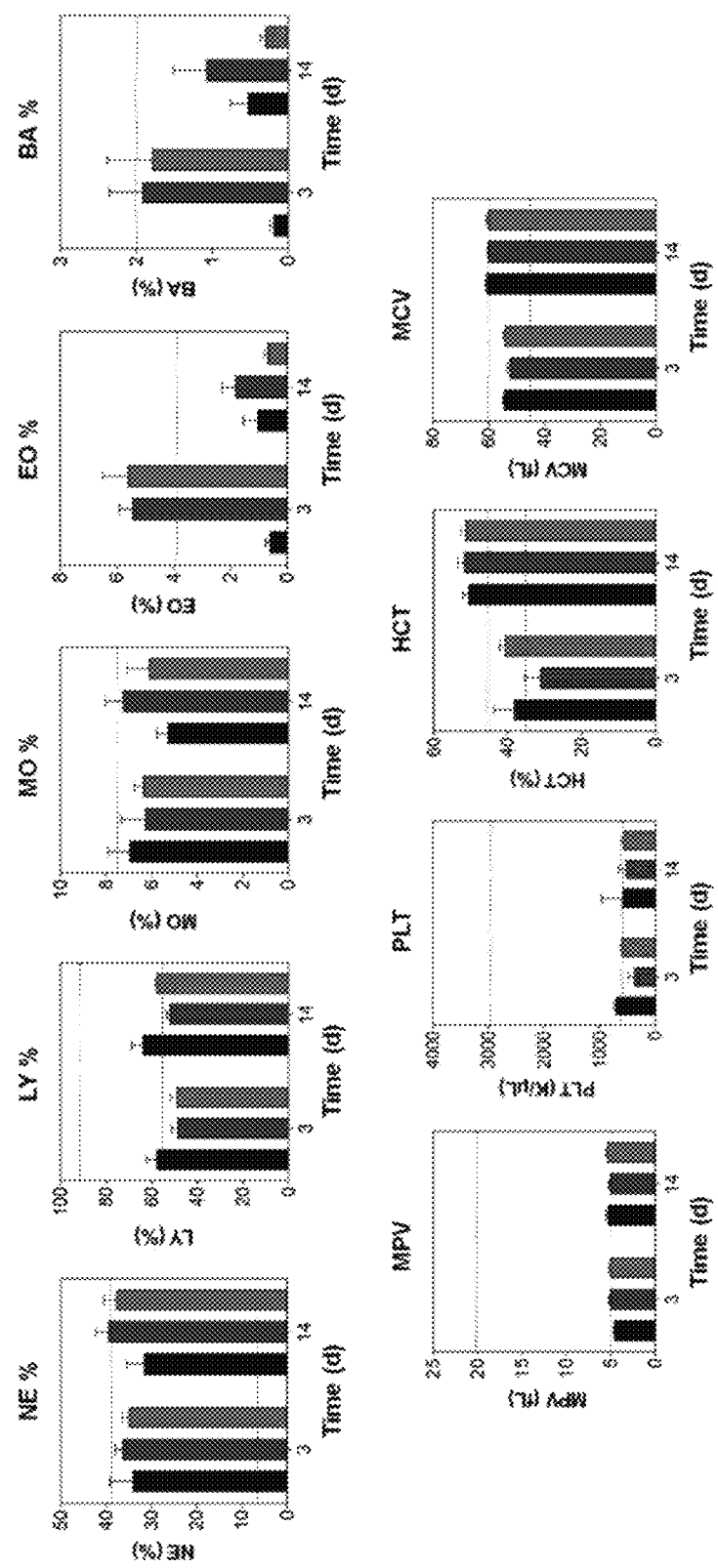
Figure 95B:
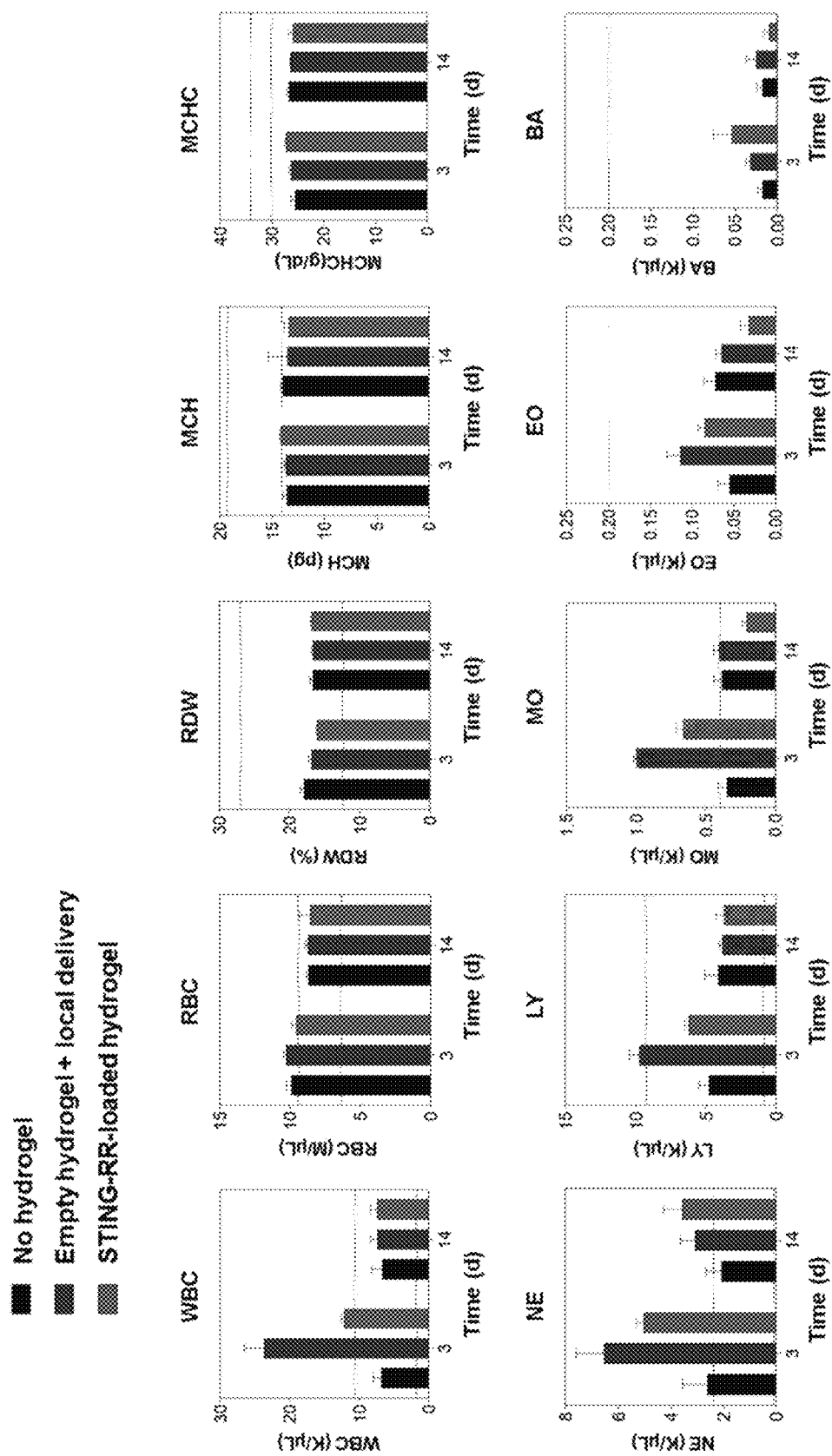
Figure 95B:
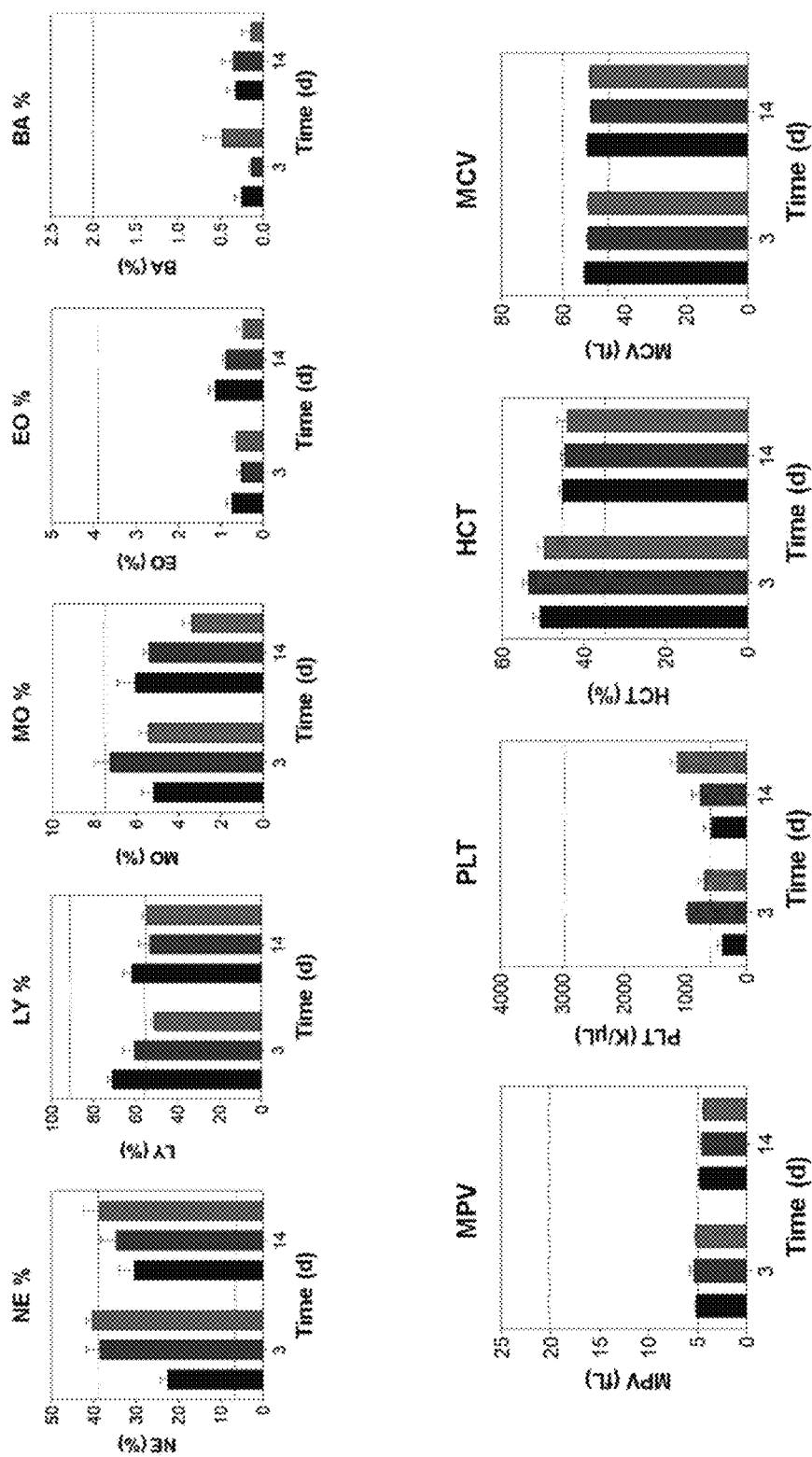
Figure 96A:
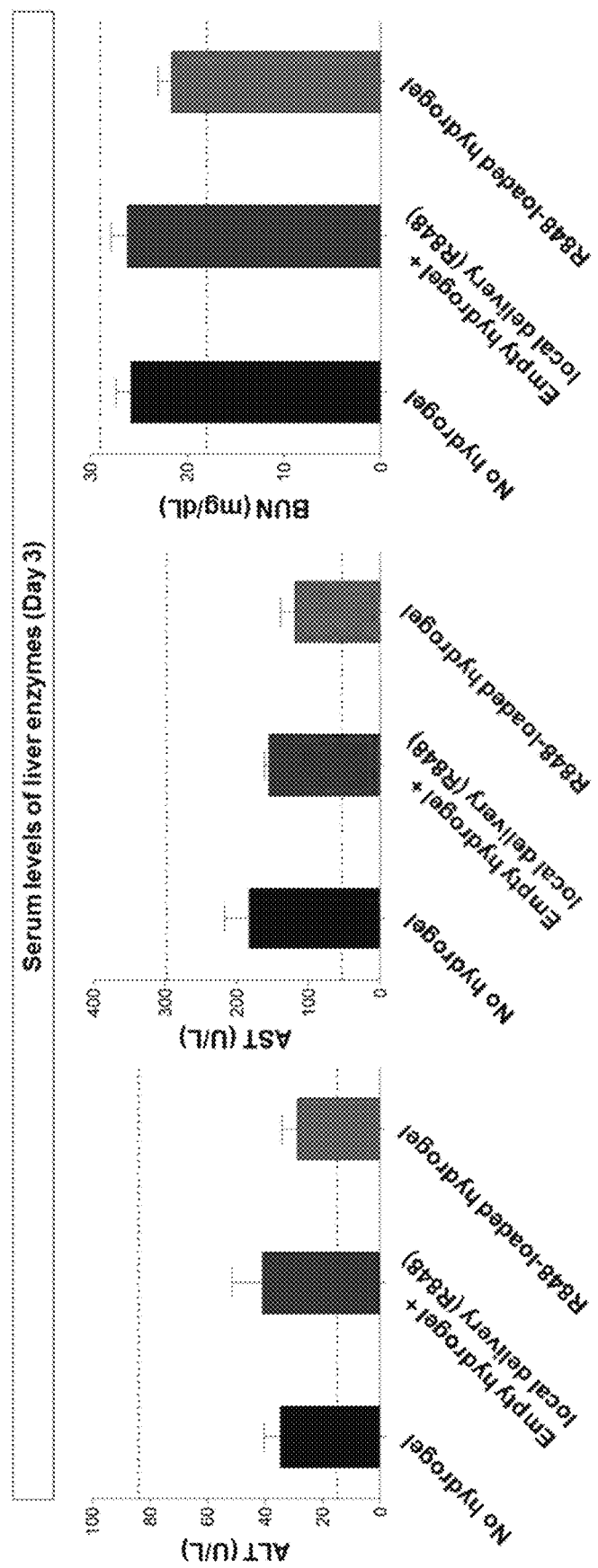
FIGS. 96A-96B show that the extended local release of agonists of innate immunity is safe. None of the conditions listed impact the levels of liver enzymes measured 3 days post-surgery (R848, device 22) (FIG. 96A) or 15 days post-surgery (STING-RR, device 23) (FIG. 96B). Data are presented as mean±SD (n=6+ per group, performed twice as biological replicates). Dashed lines indicate established normal ranges.
Figure 96B:
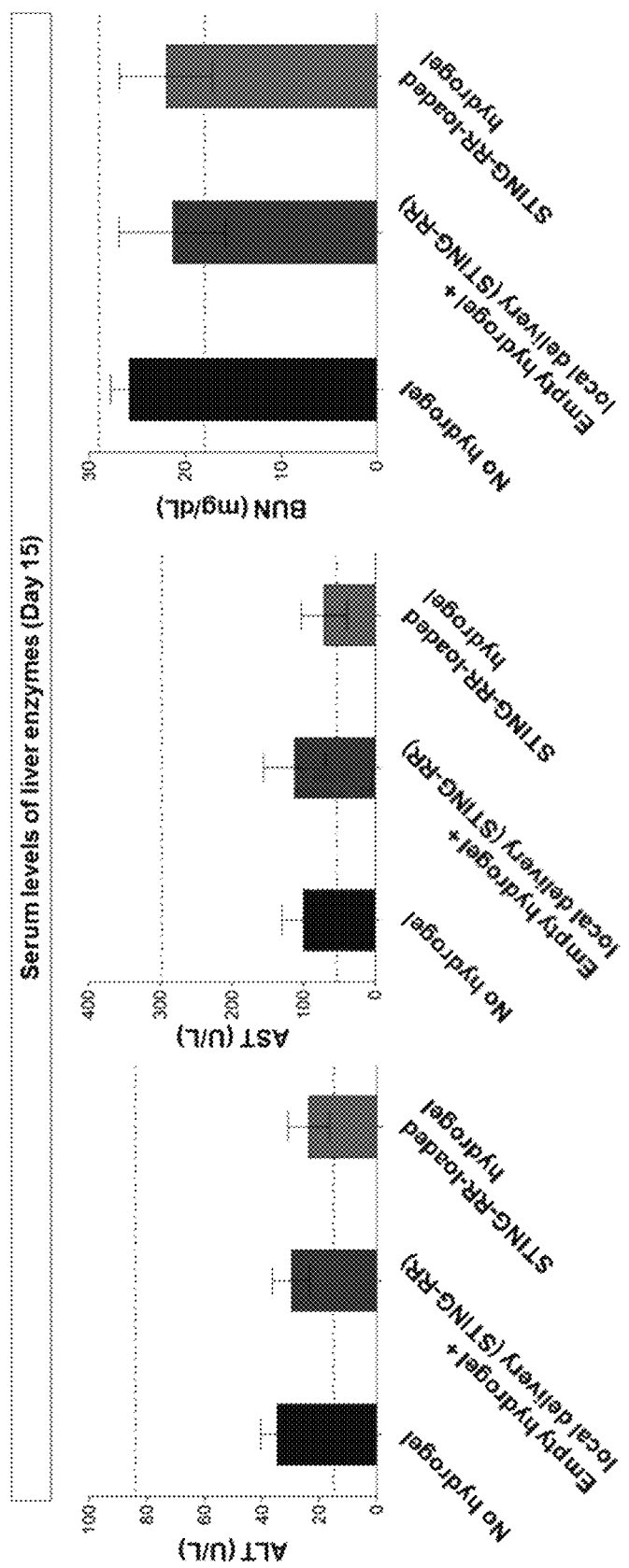

Additional safety studies were performed with R884 and STING-RR. Three or 14 days after tumor resection and placement of no hydrogel, an empty hydrogel plus local delivery of drug (200 µg R848 or 100 µg STING-RR), or a hydrogel loaded with drug (device 22 or 23), serum was collected and subjected to a blood panel analysis. The composition of the blood was unaffected by the treatments (FIGS. 95A-95B). The lack of any systemic toxicity was confirmed by a lack of changes in liver enzymes (AST, ACT, and BUN) in the blood (FIGS. 96A-96B) across treatment groups. Similarly, body weight was consistent across all groups tested, with the sole decrease being observed transiently after surgery, as expected (FIG. 97).

Figure 98:
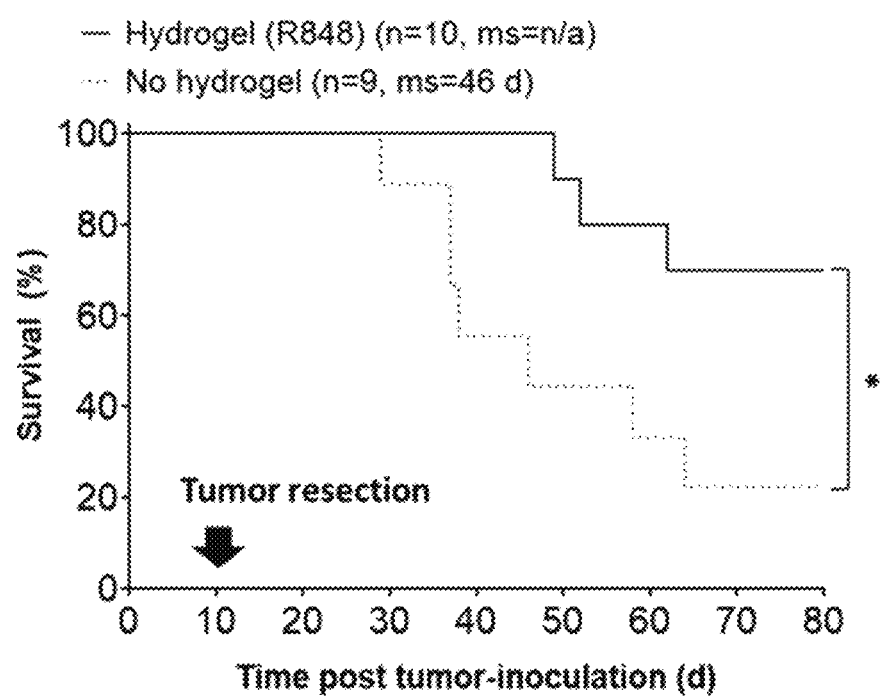
FIG. 98 shows that the response of parental 4T1 cells to R848 released locally from a hydrogel is similar to that of 4T1 cells that express Luc2. A Kaplan-Meier curve of female BALB/cJ mice inoculated orthotopically with wild-type 4T1 cells that received either no hydrogel or a hydrogel loaded with R848 (device 22). These data are similar to those presented in FIG. 84A, which involves 4T1-Luc2 cells. The number of mice per group (n) and median survival (ms) are listed. The experiment was performed with biological replicates at least three times. Statistics were calculated relative to no hydrogel using the Log-rank (Mantel-Cox). * p≤0.05.
Figure 99A:
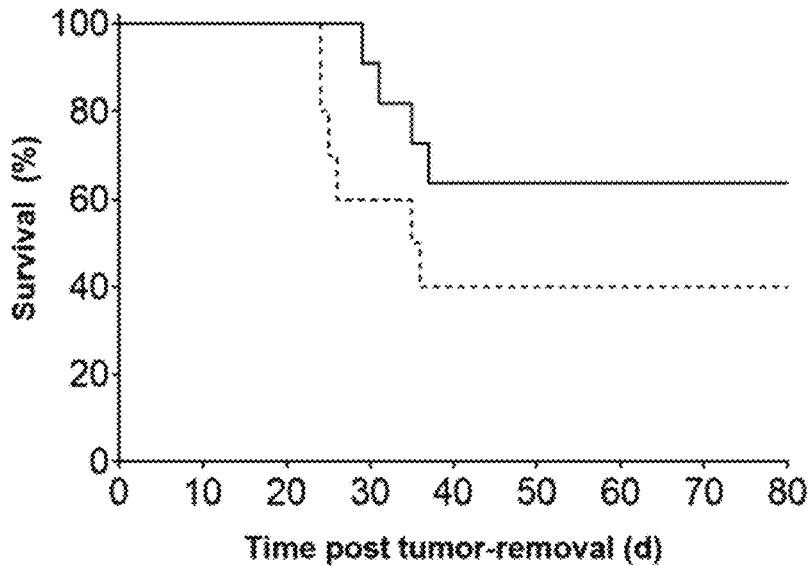
FIGS. 99A-99C show that localized release of perioperative immunotherapy is efficacious in additional models of spontaneous metastasis. Tumors were resected from mice when tumor volumes reached ~600 mm3 after subcutaneous inoculation of B16-BL6 melanoma cells (FIG. 99A) or LLC lung carcinoma cells (FIGS. 99B-99C).
Figure 99B:
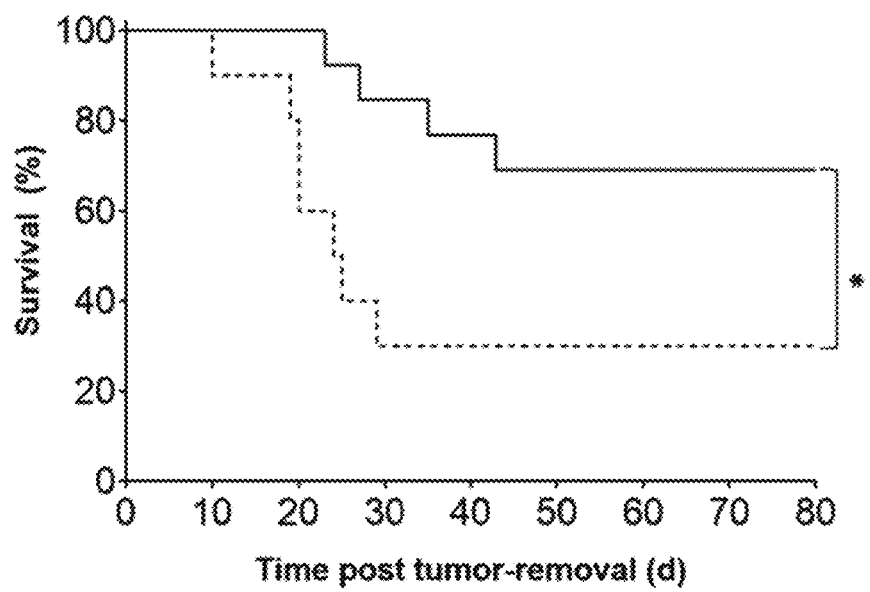
Figure 99C:
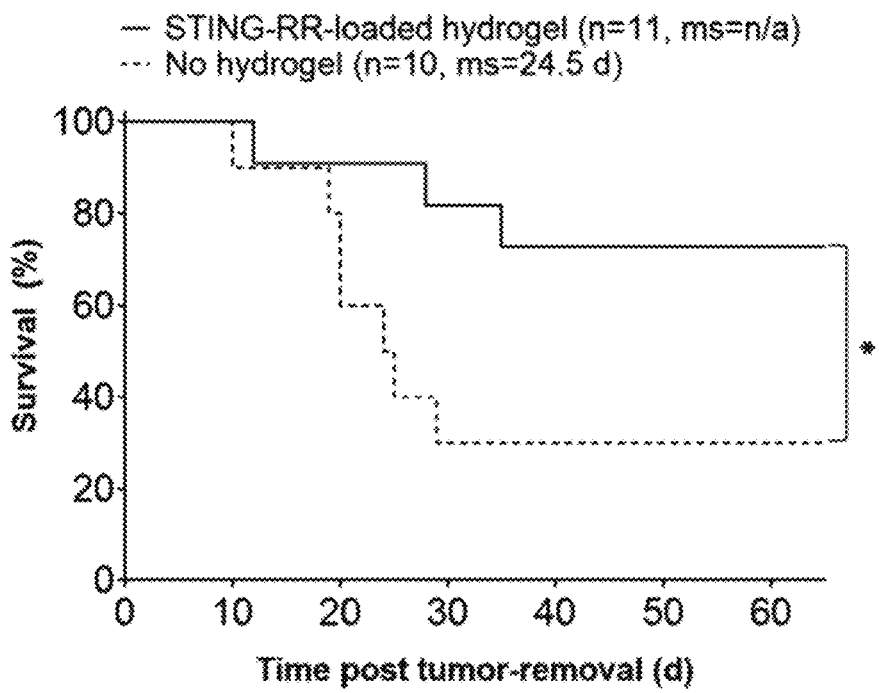

Example 12. Efficacy is Confirmed in Additional Models of Spontaneous Metastasis The broad utility of extended localized release of perioperative immunotherapy was also demonstrated. In addition to confirming that the parental 4T1 cell line is as responsive as 4T1-Luc2 cells to R848-loaded hydrogels (device 22; FIG. 98), as previously reported, C57BL/6J mice were inoculated subcutaneously with B16-BL6 melanoma cells or LLC lung carcinoma cells, which also spontaneously metastasize to the lung. When tumor volumes reached ~600 $mm^3$, tumors were surgically resected. Again, long-term survival benefit was observed among mice receiving hydrogels loaded with R848 (device 22) or STING-RR (device 23) (FIGS. 99A-99C).

Figure 99D:
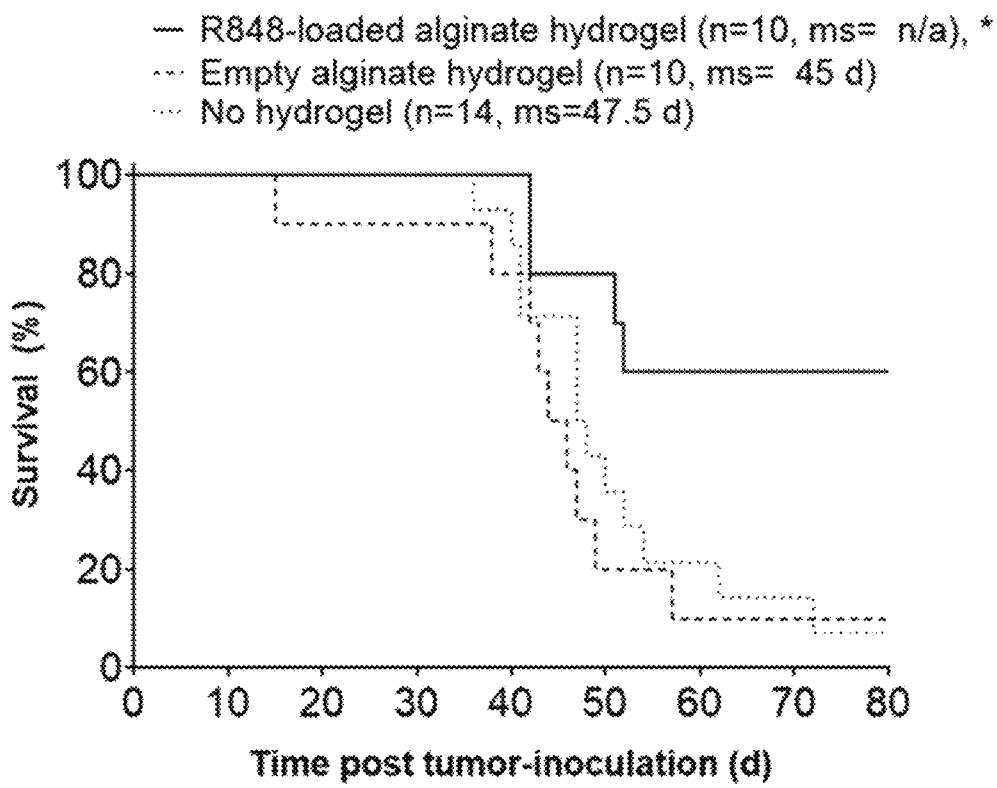
FIG. 99D shows that additional biomaterials can be used to achieve extended local release of immunotherapy in the perioperative setting, resulting in meaningful survival benefit.
Figure 100:
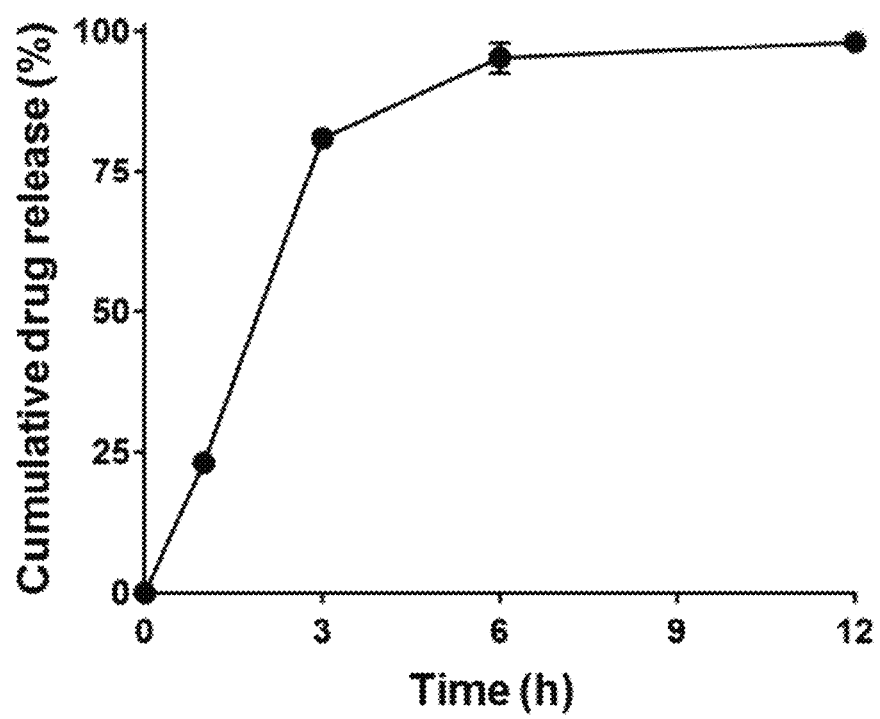
FIG. 100 shows that a hydrogel scaffold derived from alginate extends the release of R848 in vitro. Scaffolds were placed in PBS (pH 7.4), and drug release was measured using HPLC. The experiment was performed with biological replicates (n=4+) three times. Data are presented as mean±SD.
Figure 101:
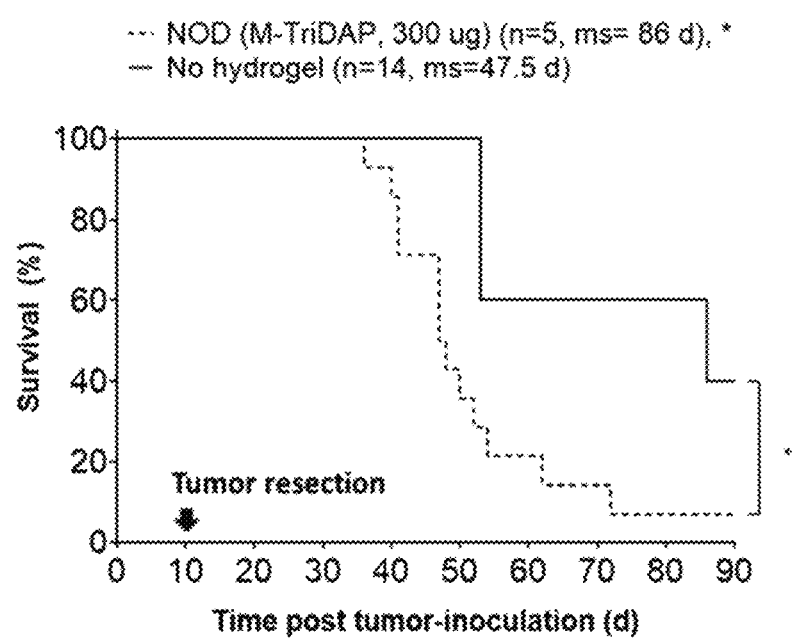
FIG. 101 shows a Kaplan-Meier curve demonstrating survival benefit for the NOD1/NOD2 agonist M-TriDAP (device 29) versus no hydrogel. The number of mice per group (n) and median survival (ms) are listed. Statistics were calculated relative to the group treated with hydrogel containing triple combination using the Log-rank (Mantel-Cox) test. * p≤0.05.
Figure 102A:
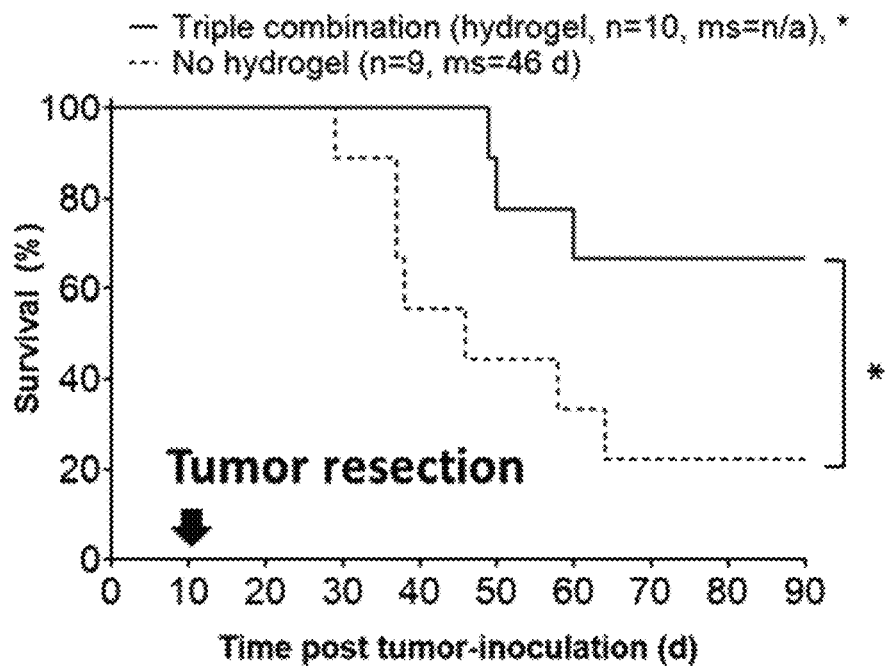
FIGS. 102A-102C show that localized release of perioperative immunotherapy is efficacious in additional models of spontaneous metastasis. Tumors were resected from mice 10 days after orthotopic inoculation of parental 4T1 breast carcinoma cells (FIG. 102A), when tumor volumes reached ~600 mm$^3$ after subcutaneous inoculation of B16-BL6 melanoma cells (FIG. 102B), or when tumor volumes reached ~600 mm3 after subcutaneous inoculation of LLC lung carcinoma cells (FIG. 102C).
Figure 102B:
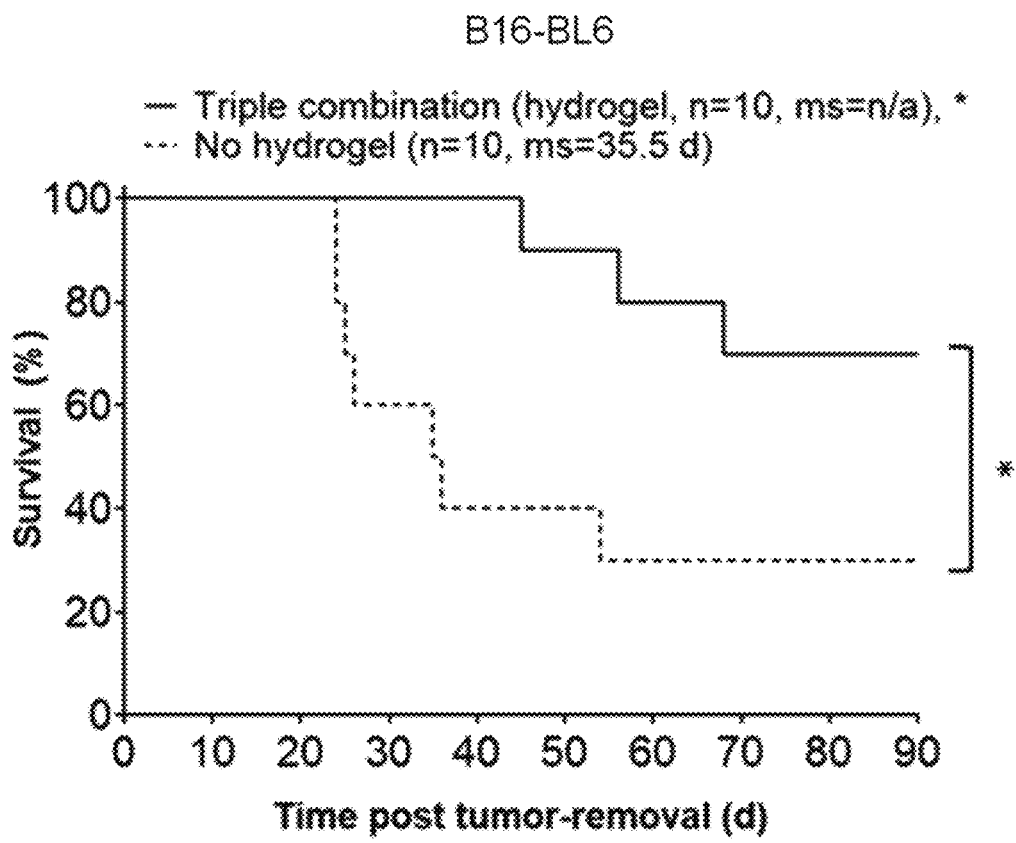
Figure 102C:
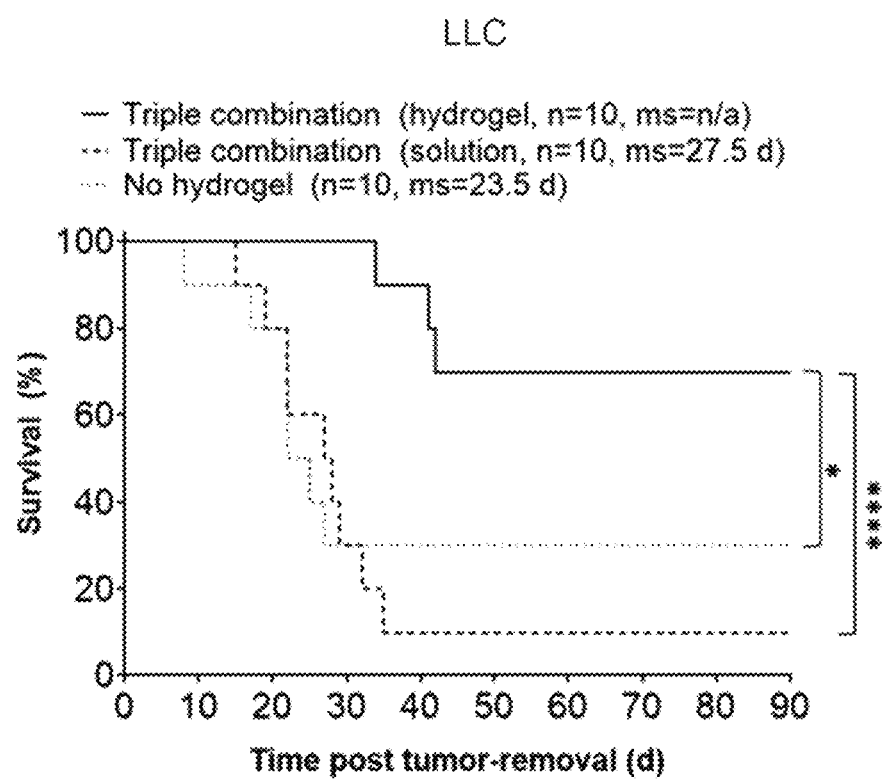
Figure 103A:
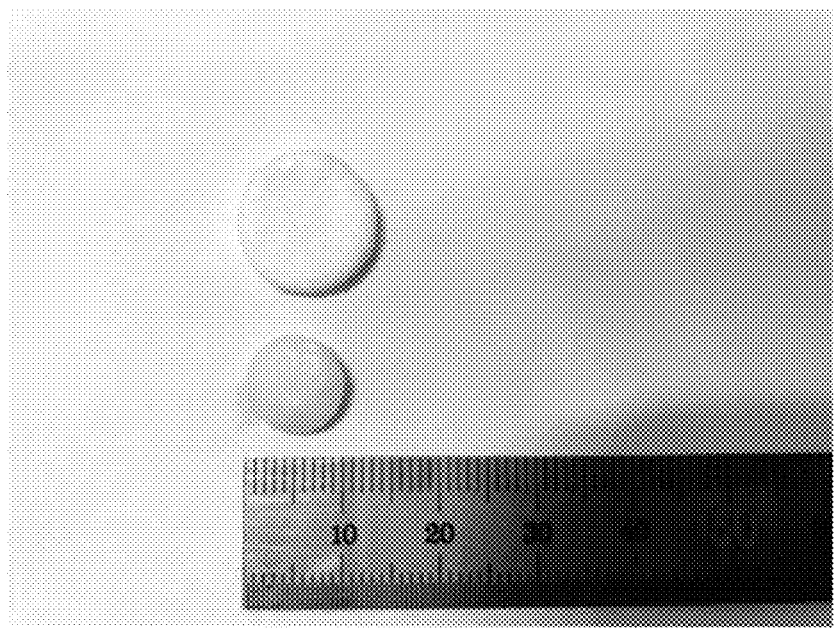
FIGS. 103A-103C show that for a given loaded dose of R848, hydrogels (derived from cross-linked hyaluronic acid or alginate) confer superior survival benefit to poly(lactic-co-glycolic acid) (PLGA) scaffolds. For a loaded dose of 200 μg R848, the majority of R848 must be released within hours in order to confer efficacy.
Figure 103B:
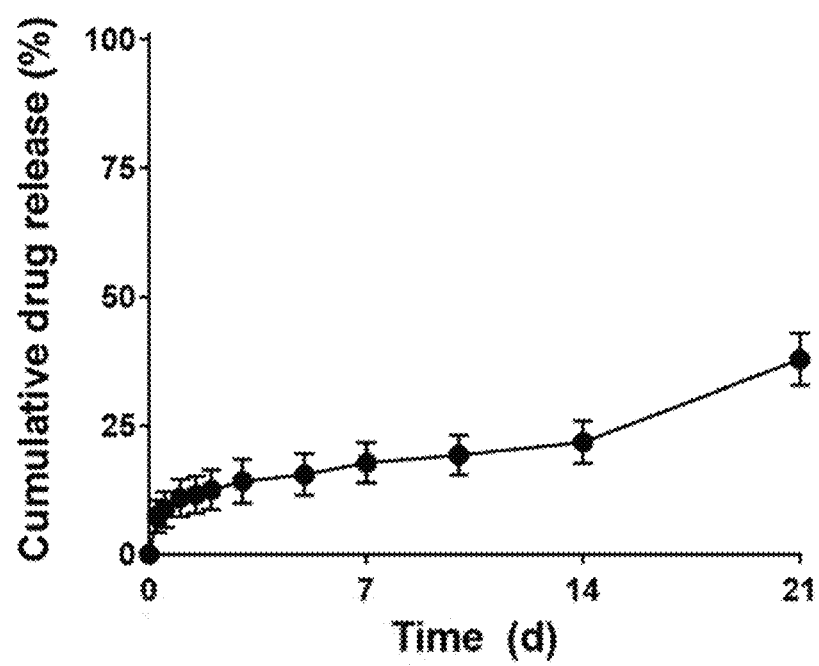
Figure 103C:
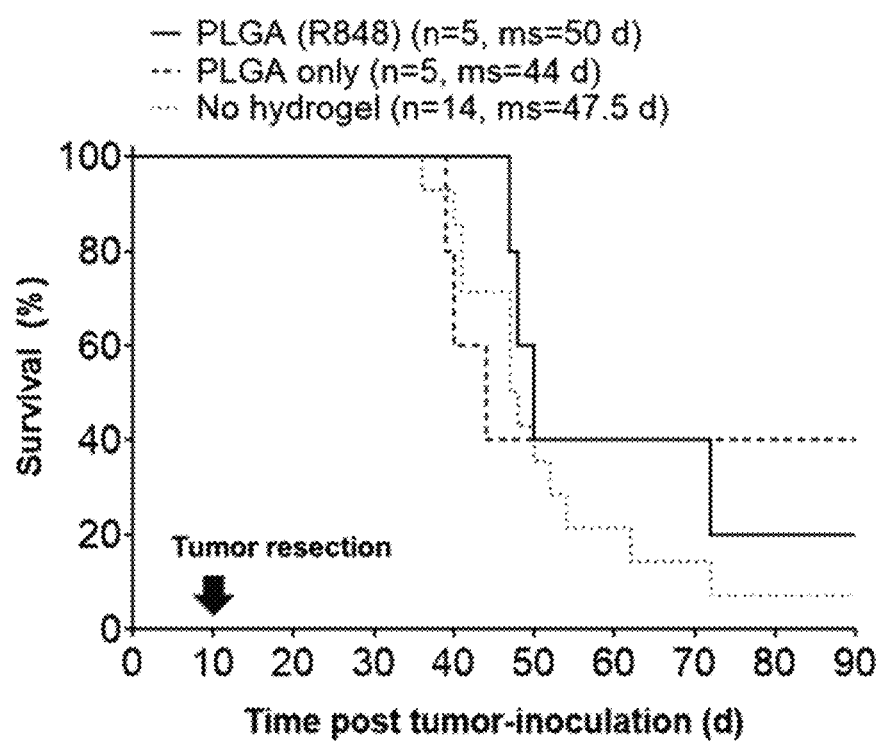

Additionally, hydrogels were generated from alginate, which were ionically cross-linked with calcium chloride, to establish that extended localized release of an agonist of innate immunity can be achieved using additional biomaterials. The alginate-based hydrogel exhibited a similar in vitro release profile of R848 to that of the hyaluronic acid-based hydrogel (FIG. 100) and conferred similar survival benefit (FIG. 99D).

TABLE 6

Antibodies used for flow cytometry experiments.

|  | Protein | Color | Clone | Vender |
|---|---|---|---|---|
| 1 | CD45 | BV785 | 30-F11 | Biolegend |
| 2 | TCR | BV510 | H57-597 | Biolegend |
| 3 | CD4 | BV605 | GK1.5 | Biolegend |
| 4 | CD8 (alpha) | BV650 | 53-6.7 | Biolegend |
| 5 | NK cell (NKp45) | PE | 29A1.4 | Biolegend |
| 6 | CD11b | BV421 | M1/70 | Biolegend |
| 7 | CD11b | BV785 | M1/70 | Biolegend |
| 8 | CD11c | PerCP/Cy5.5 | N418 | Biolegend |
| 9 | CD19 | APC/Cy7 | 6D5 | Biolegend |
| 10 | F4/80 | PE/Cy7 | BM8 | Biolegend |
| 11 | GR1 | FITC | RB6-8C5 | Biolegend |
| 12 | CD25 | BV786 | PC61 | Biolegend |
| 13 | CD69 | PerCP/Cy5.5 | H1.2F3 | Biolegend |
| 14 | CD62L | APC/Cy7 | MEL-14 | Biolegend |
| 15 | GITR | PerCP/Cy5.5 | DTA-1 | Biolegend |
| 16 | Ly-6C | FITC | HK1.4 | Biolegend |
| 17 | CD27 | BV650 | LG.3A10 | BD Biosciences |
| 18 | KLRG1 | BV605 | 2F1/KLRG1 | Biolegend |
| 19 | CD40 | PE/Cy7 | 23-3 | Biolegend |
| 20 | CD86 | BV510 | GL-1 | Biolegend |
| 21 | MHC2 | FITC | 39-10-8 | Biolegend |
| 22 | PDCA1 | PE | 129C1 | Biolegend |
| 23 | CD103 | BV605 | 2E7 | Biolegend |
| 24 | B220 | APC/Cy7 | RA3-6B2 | Biolegend |
| 25 | FoxP3 | APC | FJK-16s | eBioscience |
| 26 | FoxP3 | PE | MF-14 | Biolegend |
| 27 | IFNgamma | BV421 | XMG1.2 | Biolegend |
| 28 | IL2 | PE/Cy7 | JES6-5H4 | Biolegend |
| 29 | Grazyme B | FITC | NGZB | eBioscience |
| 30 | GM-CSF | PerCP/Cy5.5 | MP1-22E9 | Biolegend |

The data described herein demonstrate that extended release of immunotherapy from a hydrogel placed in a tumor resection site can prevent local tumor recurrence and induce systemic antitumor immunity that eradicates existing metastases. Such a therapy may be advantageous over existing therapies, including neoadjuvant immunotherapy, which has been shown to be superior to adjuvant immunotherapy. Without being bound by any theory, it is thought that this relative benefit is owing to the fact that the presence of tumor antigen is important to expansion of tumor-reactive T cells. The data herein, however, show that immunotherapy can be effective in the absence of gross residual tumor antigen.

Surgery can reduce primary resistance to immunotherapy by removing cancer cell-intrinsic mechanisms of resistance. Moreover, it can remove cancer cell-extrinsic factors that promote primary and adaptive resistance, such as immunosuppressive regulatory cells that are often found in high numbers in the tumor microenvironment. While it is generally thought that earlier treatment with immunotherapy would be beneficial, side effects following systemic administration have limited such studies to date, and localized therapy is expected to reduce such toxicity. Intraoperative placement of a scaffold also obviates the need to optimize the scheduling of immunotherapy administration, which will be required in the neoadjuvant setting and may be particularly challenging for combination therapies.

The perioperative setting represents a high-leverage time point, as surgical stress causes acute immunosuppression that must be overcome to prevent recurrence and dissemination. Converting the perioperative period from a pronounced augmenter of metastatic progression to a window of opportunity for halting and/or eradicating residual disease is expected to improve long-term survival rates.

Surgery has been implicated in promoting metastasis, which accounts for 90% of cancer-related mortality. Specifically, the wound-healing response allows for dissemination of cancer cells and awakening of dormant micrometastases through the induction of transient immunosuppression, which, as described herein, may be counteracted in the intraoperative setting. Scaffolds (e.g., compositions and devices of the present disclosure) can be used to control drug delivery in a spatiotemporal manner. Focusing the action of therapy at the site of disease concentrates the drugs on the cells of interest, improving efficacy and reducing systemic toxicity relative to systemic administration. Notably, sustained release of small molecules and/or biologics from the scaffold described herein conferred superior efficacy to local delivery of the same therapy in solution.

Taken together, the present disclosure provides compositions and devices that achieve extended local release of an agonist of innate immunity following surgical resection of a tumor in order to prevent local tumor recurrence and clear established distal metastases. The resultant impact on the immune system is broad, as evidenced by cellular and molecular analyses of systemic leukocyte populations. Unlike previous approaches, this intervention does not require the loading of exogenous tumor antigen or tumor-reactive 'T' cells in order to be effective. The data suggest that intraoperative placement of scaffolds containing immunotherapy is worthy of clinical investigation, and the off-the-shelf scaffold described herein does not require patient-by-patient customization.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in have verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, A of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating cancer comprising a step of: intraoperative administration at a tumor resection site of a subject suffering from cancer: an effective amount of a combination of a biomaterial and a Toll-like receptor (TLR) 7 and/or TLR8 (TLR7/8) agonist, wherein the biomaterial is or comprises hyaluronic acid.

2. The method of claim 1, wherein the biomaterial is characterized by a storage modulus of about 500 Pa to about 3000 Pa.

3. The method of claim 1, wherein the step of administration does not involve adoptive transfer of T cells to the subject.

4. The method of claim 1, wherein the step of administration does not involve administration of a tumor antigen to the subject.

5. The method of claim 1, wherein the step of administration does not involve administration of a microparticle to the subject.

6. The method of claim 1, wherein the biomaterial is or comprises a hydrogel.

7. The method of claim 1, wherein the biomaterial is or comprises a crosslinked hyaluronic acid.

8. The method of claim 7, wherein the biomaterial is or comprises a hyaluronic acid crosslinked with a polyethylene glycol crosslinker.

9. The method of claim 1, wherein the TLR7/8 agonist is or comprises imiquimod and/or resiquimod (R848).

10. The method of claim 1, wherein the combination further comprises an activator of innate and/or adaptive immunity, and/or a cytokine that modulates T cells, natural killer (NK) cells, monocytes, and/or dendritic cells.

11. The method of claim 1, wherein the combination further comprises a cytokine that modulates T cells, NK cells, monocytes, and/or dendritic cells, and the cytokine is selected from an IL-15 superagonist, IFN-α, IFN-β, IFN-γ, and combinations thereof.

12. The method of claim 1, wherein the combination further comprises a COX2 inhibitor.

13. The method of claim 1, wherein the combination further comprises a chemotherapeutic agent for use as an immunomodulatory agent but not as a cytotoxic agent.

14. The method of claim 1, wherein the combination further comprises a NOD1/2 agonist.

15. The method of claim 1, wherein the combination further comprises an anti-PD-1 antibody.

16. The method of claim 1, wherein the combination further comprises an anti-CD137 antibody.

17. The method of claim 1, wherein the biomaterial forms a matrix or depot and the TLR7/8 agonist is within the biomaterial.

18. The method of claim 17, wherein the TLR7/8 agonist is released by diffusion through the biomaterial.

19. The method of claim 1, wherein the biomaterial is biodegradable in vivo.

20. The method of claim 1, wherein the biomaterial is characterized in that, when tested in vitro by placing a combination of a biomaterial and resiquimod (R848) in PBS (pH 7.4), less than 100% of the resiquimod (R848) is released within 3 hours from the biomaterial.

21. The method of claim 1, wherein the biomaterial is characterized in that, when tested in vivo by implanting the combination at a mammary fat pad of a mouse subject, less than or equal to 50% of the TLR7/8 agonist is released in vivo 8 hours after the implantation.

22. The method of claim 1, wherein the biomaterial is characterized in that it extends release of the TLR7/8 agonist so that, when assessed at 24 hours after administration, more TLR7/8 agonist is present in the tumor resection site than is observed when the TLR7/8 agonist is administered in solution.

23. The method of claim 1, wherein the administration is by implantation.

24. The method of claim 1, wherein the administration is by injection.

25. The method of claim 24, wherein the administration comprises injecting one or more precursor components of the biomaterial and permitting the biomaterial to form at the site.

26. The method of claim 1, wherein the tumor resection site is characterized by absence of gross residual tumor antigen.

27. The method of claim 1, wherein the cancer is metastatic cancer.

28. The method of claim 27, further comprising a step of monitoring at least one metastatic site in the subject after the administration.

* * * * *